United States Patent [19]
Corey et al.

[11] Patent Number: 5,721,362
[45] Date of Patent: Feb. 24, 1998

[54] PROCESS FOR PRODUCING ECTEINASCIDIN COMPOUNDS

[75] Inventors: Elias J. Corey, Cambridge, Mass.; David Gin, Urbana, Ill.

[73] Assignee: President and Fellows of Harvard College, Cambridge, Mass.

[21] Appl. No.: 715,541

[22] Filed: Sep. 18, 1996

[51] Int. Cl.$^6$ ................................................. C07D 515/22
[52] U.S. Cl. .......................... 540/466; 540/453; 540/454; 544/99; 544/338; 549/437; 560/29
[58] Field of Search ............................... 540/466, 453, 540/454; 549/437; 544/99, 338

[56] References Cited

U.S. PATENT DOCUMENTS

| | | | |
|---|---|---|---|
| 5,089,273 | 2/1992 | Rinehart et al. | 424/520 |
| 5,149,804 | 9/1992 | Rinehart et al. | 540/466 |
| 5,256,663 | 10/1993 | Rinehart et al. | 514/250 |
| 5,478,932 | 12/1995 | Rinehart et al. | 540/466 |

OTHER PUBLICATIONS

Corey, E.J. J. Am. Chem. Soc. vol. 118 pp. 9202–9203, 1996.
Rinehart, et al. *Journal of National Products*, 1990, "Bioactive Compounds from Aquatic and Terrestrial Sources", vol. 53, pp. 771.
Rinehart et al. *Pure and Appl. Chem.*, 1990, "Biologically active natural products", vol. 62, pp. 1277.
Rinehart, et al. *J. Org. Chem.* 1990, "Ecteinascidins 729, 743, 745, 759A, 759B, and 770: Potent Antitumor Agents from the Caribbean Tunicate *Ecteinascidia turbinata*", vol. 55, pp. 4512.
Wright et al. *J. Org. Chem.* 1990, "Antitumor Tetrahydroisoquinoline Alkaloids from the Colonial Ascidian *Ecteinascidia turbinata*", vol. 55, pp. 4508.
Sakai et al. *Proc. Natl. Acad. Sci. USA* 1992, "Additional antitumor ecteinascidins from a Caribbean tunicate: Crystal structures and activities in vivo", vol. 89, 11456.
Science 1994, "Chemical Prospectors Scour the Seas for Promising Drugs", vol. 266, pp. 1324.
Koenig, K.E. *Asymmetric Synthesis*. ed. Morrison, Academic Press, Inc., Orlando, FL, vol. 5, 1985, p. 71.
Barton, et al. *J. Chem Soc. Perkin Trans.* 1, 1982, "Synthesis and Properties of a Series of Sterically Hindered Guanidine Bases", pp. 2085.
Fukuyama et al. *J. Am Chem Soc.*, 1982, "Stereocontrolled Total Synthesis of (+)–Saframycin B", vol. 104, pp. 4957.
Fukuyama et al. *J. Am Chem Soc.*, 1990, "Total Synthesis of (+)–Saframycin A", vol. 112, p. 3712.
Saito, et al. *J. Org. Chem.* 1989, "Synthesis of Saframycins. Preparation of a Key Tricyclic Lactam Intermediate to Saframycin A", vol. 54, 5391.
Still, et al. *J. Org. Chem.* 1978, "Rapid Chromatographic Technique for Preparative Separations with Moderate Resolution", vol. 43, p. 2923.
Kofron, W.G.; Baclawski, L. M., *J. Org. Chem.*, 1976, vol. 41, 1879.

*Primary Examiner*—Donald G. Daus
*Attorney, Agent, or Firm*—Ernest V. Linek

[57] ABSTRACT

The present invention is directed to a synthetic process for the formation of ecteinascidin compounds and related structures, such as the saframycins. In one particularly preferred embodiment, the present invention provides a synthetic route for the formation of ecteinascidin 743 (1),

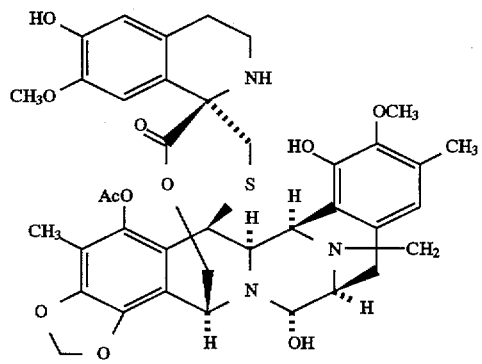

an exceedingly potent and rare marine-derived antitumor agent which is slated for clinical trials. The process of this invention is enantio- and stereocontrolled, convergent and short. Also disclosed are novel process intermediates, useful not only in the total synthesis of ecteinascidin 743, but also other known ecteinascidin compounds, including derivatives and analogs thereof.

32 Claims, No Drawings

PROCESS FOR PRODUCING ECTEINASCIDIN COMPOUNDS

STATEMENT OF GOVERNMENT SUPPORT

This invention was supported in part by funding from the National Institutes of Health and the National Science Foundation. Accordingly, the Government of the United States may have certain rights in this invention.

SUMMARY OF THE INVENTION

The present invention is directed to a synthetic process for the formation of ecteinascidin compounds and related structures, such as the saframycins. In one particularly preferred embodiment, the present invention provides a synthetic route for the formation of ecteinascidin 743 (1),[1]

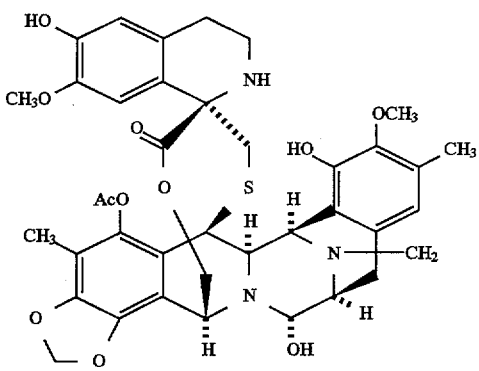

an exceedingly potent and rare marine-derived antitumor agent which is slated for clinical trials when adequate quantities become available.[2,3] This process is enantio- and stereocontrolled, convergent and short. The preferred embodiment of the synthetic process of the present invention is best represented in the following Scheme I:

Scheme I
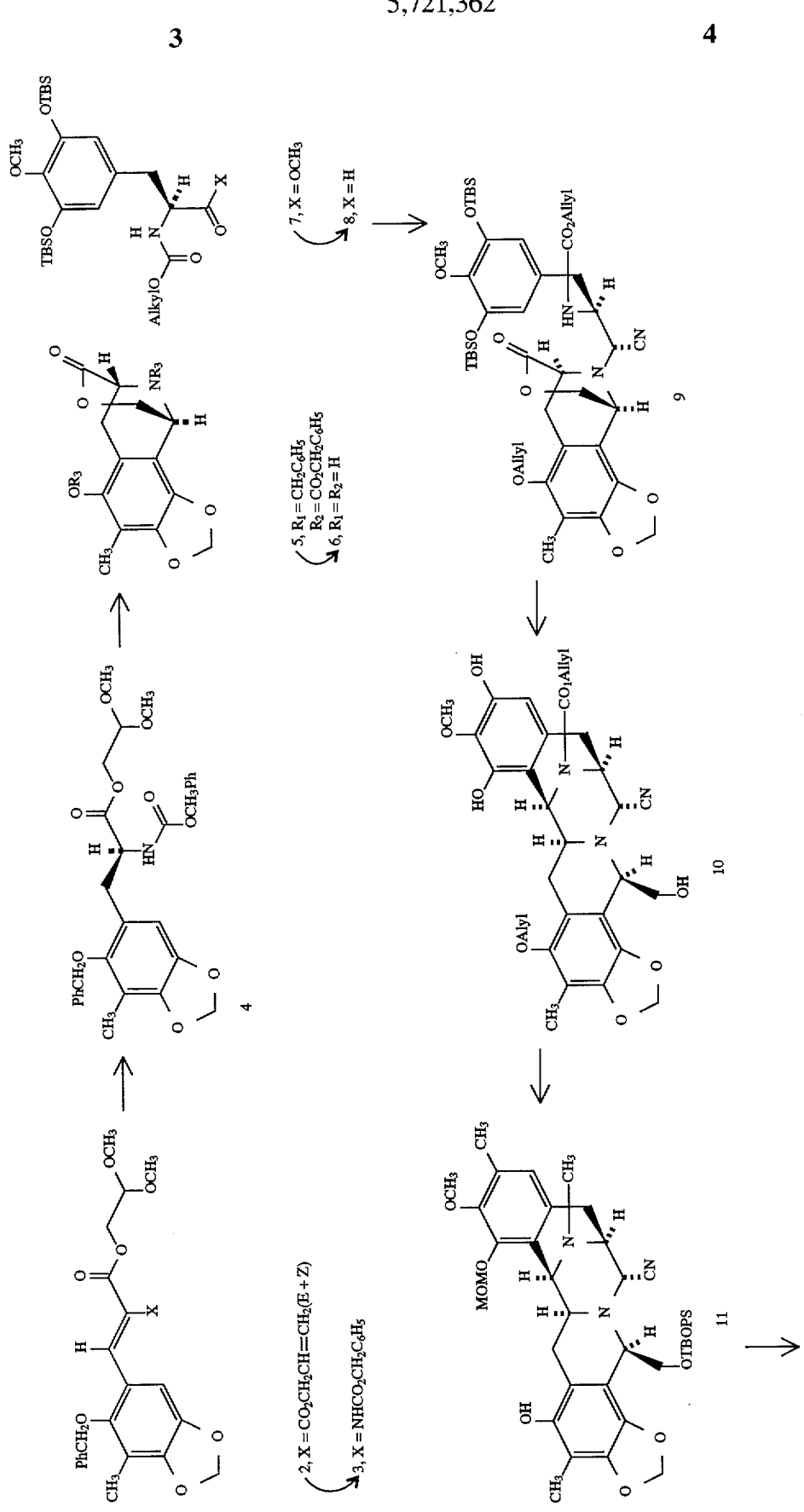

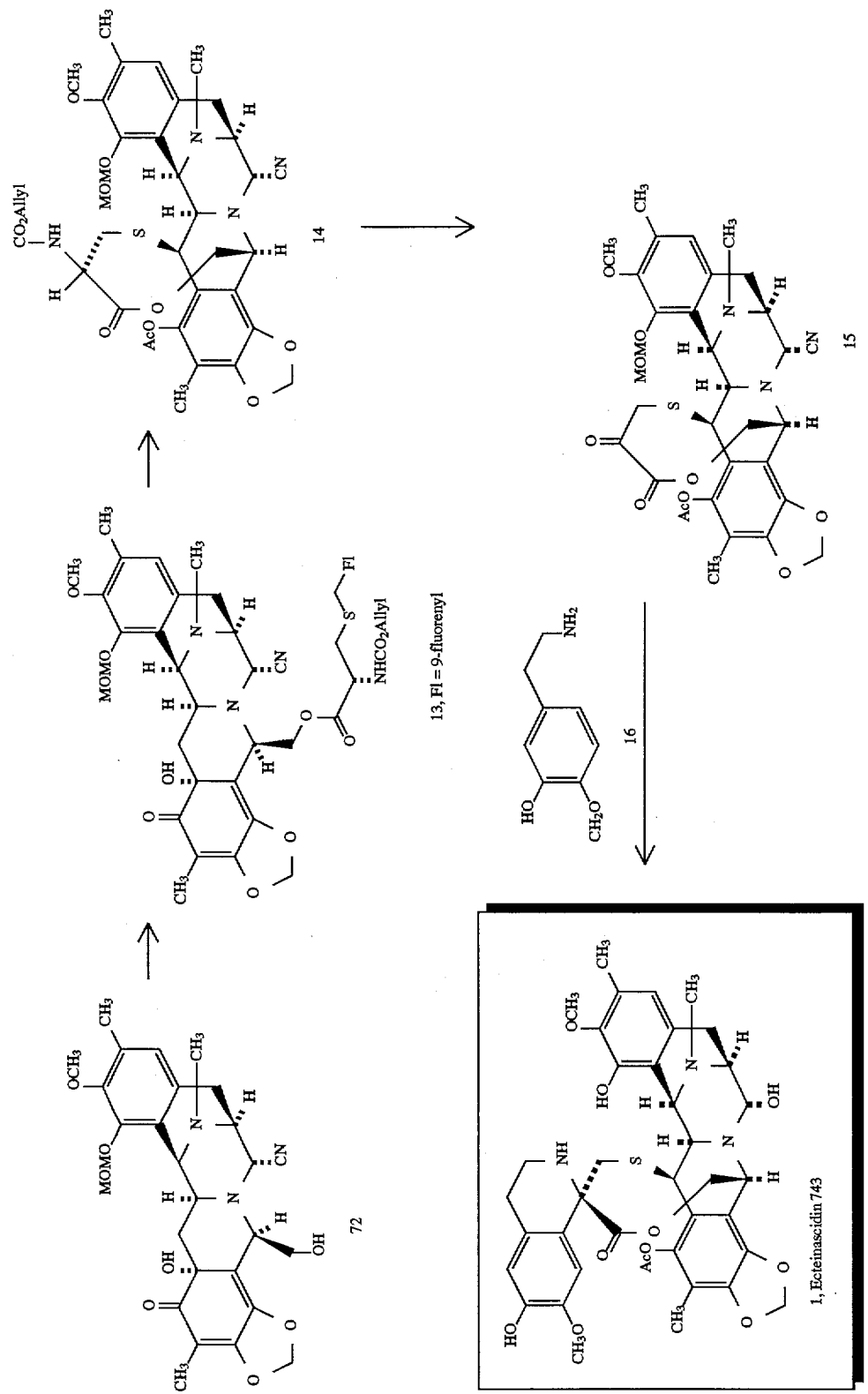

As shown above in Scheme I, the preferred process for the synthetic formation of ecteinascidin 743 comprises the sequential steps of:

(a) forming an α,β-unsaturated malonic ester of Formula 2, as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, by selective allyl ester cleavage, Curtius rearrangement, and reaction of the intermediate isocyanate with benzyl alcohol;

(c) converting the compound of Formula 3 into the compound of Formula 4 by catalytic hydrogenation over Rh(COD)R,R-DIPAMP$^+$BF$_4^-$;

(d) converting the compound of Formula 4 into the compound of Formula 5 by acetal cleavage, wherein isolation and exposure of the resulting aldehyde to BF$_3$.Et$_2$O and 4 Å mol sieves yields the bridged lactone compound of Formula 5;

(e) converting the bridged lactone compound of Formula 5 to the free amino phenol compound of Formula 6 by hydrogenolysis over 10% Pd-C;

(f) forming the protected α-amino ester compound of Formula 7 by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 by reduction;

(h) combining the compounds of Formulae 6 and 8 to afford the key monobridged pentacyclic intermediate of Formula 10, as follows:

reacting the compounds of Formulae 6 and 8 to give a coupled phenolic α-amino nitrile, followed by O-allylation to give the allyl ether compound of Formula 9;

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 by an internal Mannich bisannulation;

(i) converting the pentacycle compound of Formula 10 to the compound of Formula 11 by the selective trifluoromethanesulfonation of the least hindered phenolic hydroxyl; followed by (1) selective silylation of the primary hydroxyl; (2) protection of the remaining phenolic group as the methoxymethyl ether; (3) double deallylation; (4) reductive N-methylation; and (5) replacement of CF$_3$SO$_3$ by CH$_3$;

(j) Oxidizing the phenol compound of Formula 11 effected position-selective angular hydroxylation to give after desilylation the dihydroxy dienone compound of Formula 12;

(k) forming the compound of Formula 13 by esterifying the primary hydroxyl function of the compound of Formula 12 with (S)-N-allyloxycarbonyl-S-(9-fluorenylmethyl)cysteine;

(l) transforming the compound of Formula 13 to the bridged lactone compound of Formula 14 by;

(1) first reacting the compound of Formula 13 with an in situ generated Swern reagent; (2) followed by the formation of the exendo quinone methide, (3) destruction of the excess Swern reagent; (4) addition of excess N-tert-butyl-N',N''-tetramethylguanidine to generate the 10-membered lactone bridge; and (5) addition of excess Ac$_2$O to acetylate the resulting phenoxide group;

(m) cleaving the N-allyloxycarbonyl group of the compound of Formula 14 and oxidizing the resulting α-amino lactone to the corresponding α-keto lactone by transamination thereby forming the compound of Formula 15;

(n) stereospecifically forming spiro tetrahydroisoquinoline compound by reacting the compound of Formula 15 with 2-3-hydroxy-4-methoxyphenylethylamine;

(o) followed by methoxymethyl cleavage (yielding Et 770) followed by the replacement of CN by HO to form the compound of Formula 1, ecteinascidin 743.

In addition to the preferred process of Scheme I, the present invention also provides novel intermediate compounds useful for the synthesis of known ecteinascidin compounds, as well as analogs and derivatives of said compounds. These novel intermediates include the following compounds:

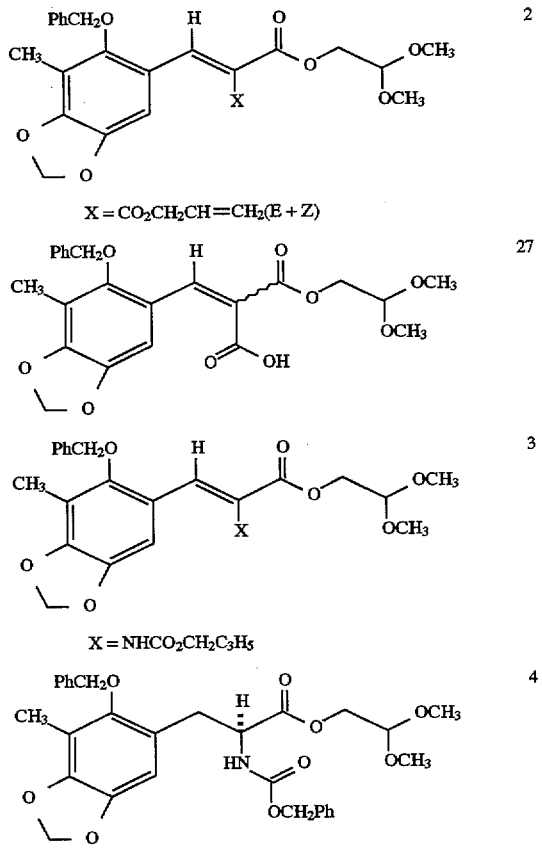

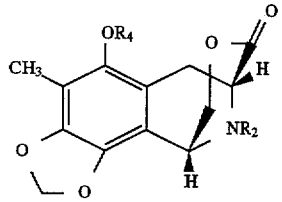
R1 = CH2C6H5
R2 = CO2CH2C6H5
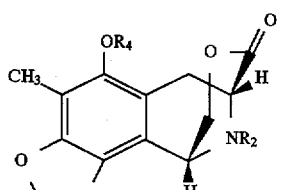
R1 = R2 = H
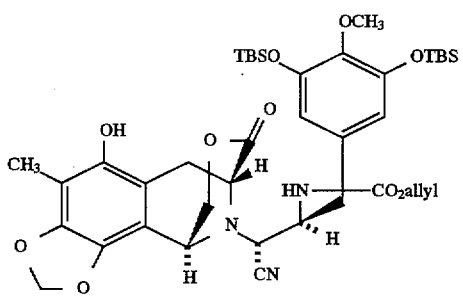
37
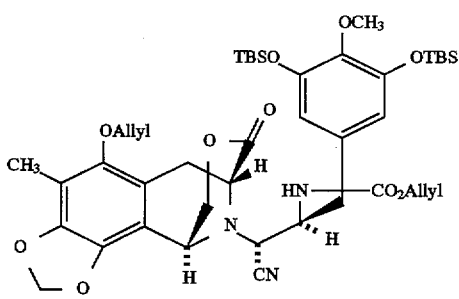
9
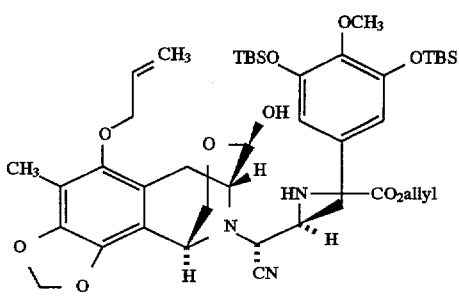
38
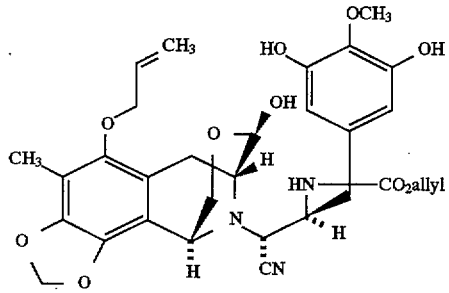
39
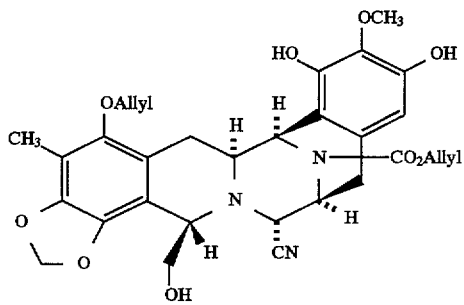
10
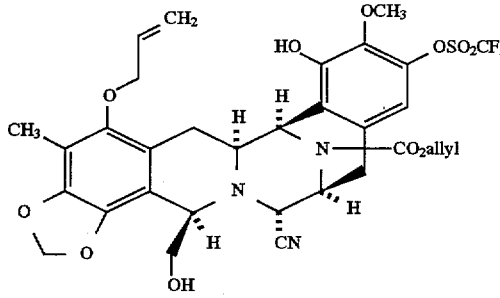
40
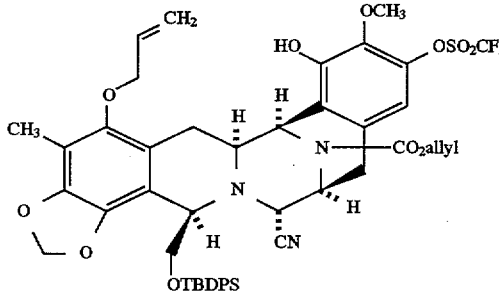
41
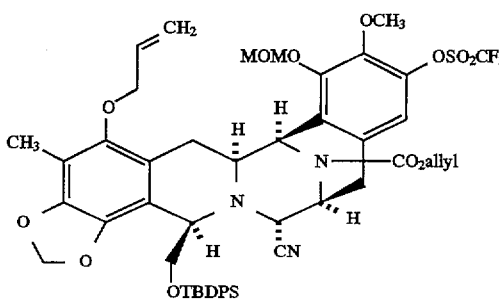
42

11
-continued
43
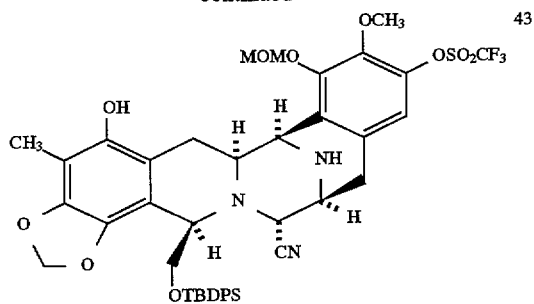
44
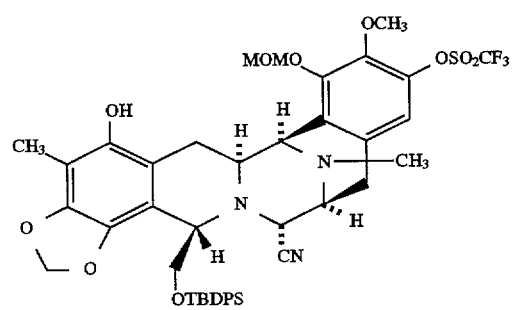
11
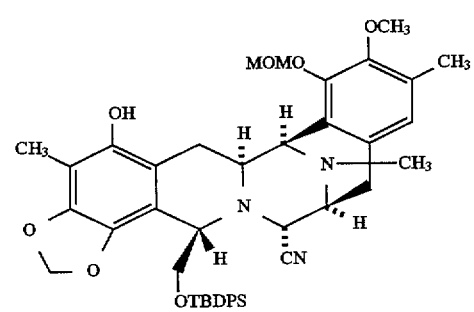
45
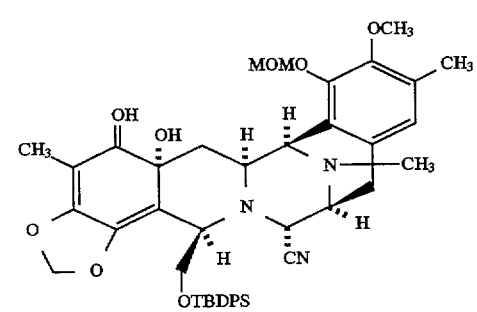
12
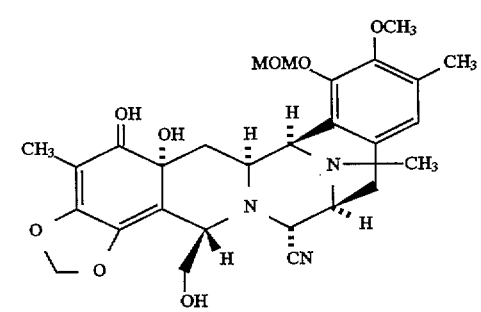
12
-continued
13
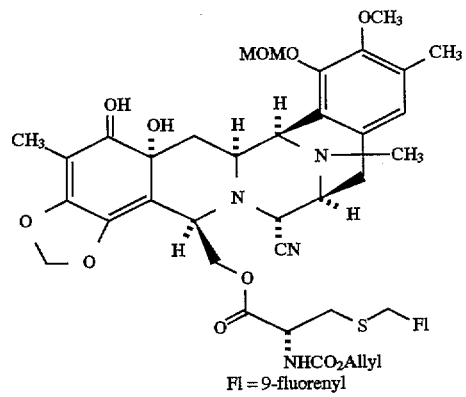
Fl = 9-fluorenyl
14
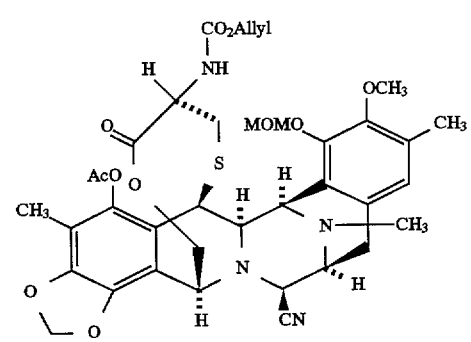
47
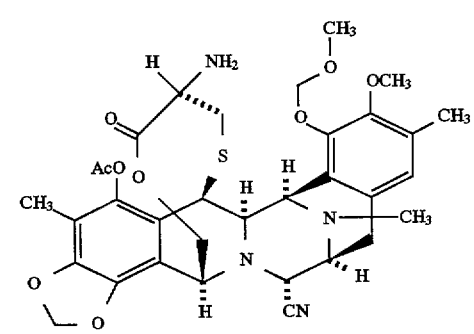
15
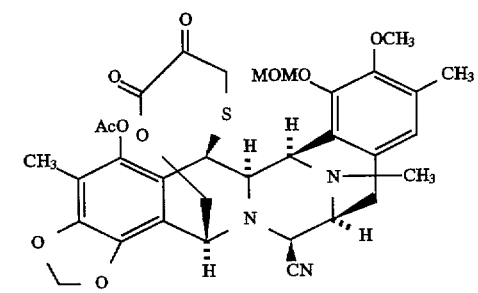

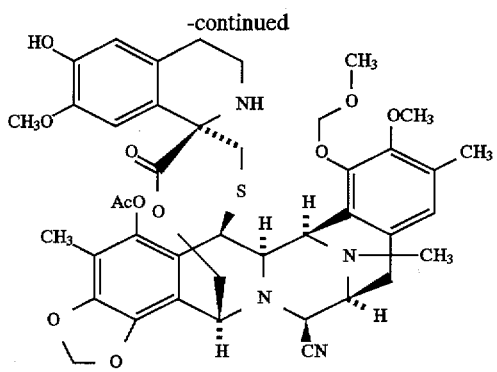

DETAILED DESCRIPTION OF THE PREFERRED EMBODIMENTS

The preferred process of the present invention is illustrated in Scheme I. As shown therein, and as discussed in greater detail in the examples which follow below, this process was conducted as follows:

The α,β-unsaturated malonic ester 2, was prepared as a mixture of E and Z isomers from 2-benzyloxy-3-methyl-4,5-methylenedioxy-benzaldehyde[4a] and allyl 2,2-dimethoxyethyl malonate[4b] (2 equiv of piperidine and 4 equiv of acetic acid in $C_6H_6$ or $C_7H_8$ at 23° C. for 18 h; 99%), was subjected to selective allyl ester cleavage ($Et_3N$—HCOOH, cat. Pd(PPh$_3$)$_4$, 23° C., 4 h; 94% yield), Curtius rearrangement (1.2 equiv of (PhO)$_2$P(O)N$_3$, 4 equiv of Et$_3$N, in C$_7$H$_8$ containing 4 Å mol sieves at 70° C. for 2 h) and reaction of the intermediate isocyanate with benzyl alcohol at 23° C. for 1 hour to form 3 stereospecifically (93% yield).[5]

Hydrogenation of 3 at 3 atm with Rh(COD)R,R-DIPAMP]$^+$BF$_4^-$ as catalyst at 230 C. for 16 h afforded 4 in 97% yield and 96% ee.[6] Acetal cleavage of 4 (10 equiv BF$_3$.Et$_2$O and 10 equiv of H$_2$O in CH$_2$Cl$_2$ at 0° C. for 10 min), isolation and exposure of the resulting aldehyde to BF$_3$.Et$_2$O (17 equiv) and 4 Å mol sieves in CH$_2$Cl$_2$ at 23° C. for 18 h gave the bridged lactone 5 in 73% yield.[7]

Hydrogenolysis of 5 (1 atm H$_2$, 10% Pd-C, EtOAc, 23° C., 6 h) produced the free amino phenol 6 in 100% yield. The protected α-amino ester 7 was synthesized by an analogous route, starting with 3,5-bis-tert-butyl-dimethylsilyloxy-4-methoxybenzaldehyde and methyl hydrogen malonate, and then reduced (2 equiv of diisobutylaluminum hydride in CH$_2$Cl$_2$ at –78° C. for 1 h) to give the chiral aldehyde 8 (>90% yield).

The next stage of the synthesis, which involved the combination of the building blocks 6 and 8 and subsequent elaboration to construct the key monobridged pentacyclic intermediate 10, commenced with the reaction of 6 and 8 in HOAc containing 25 equiv of KCN at 23° C. for 18 h to give a coupled phenolic α-amino nitrile (61%) and subsequent O-allylation to give allyl ether 9 in 87% yield (2 equiv of Cs$_2$CO$_3$ and 5 equiv allyl bromide in DMF at 23° C. for 1 h). Starting with intermediate 10, it is believed that all known ecteinasicin compounds can be synthetically prepared, as well as analogs and derivatives thereof.

Treatment of 9 with 1.2 equiv of diisobutylaluminum hydride in toluene at –78° C. for 5 h effected the selective conversion of the lactone function to a lactol which was desilylated by exposure to excess KF.2H$_2$O in CH$_3$OH at 23° C. for 20 min and cyclized to pentacycle 10 by internal Mannich bisannulation with 20 equiv of CH$_3$SO$_3$H in CH$_2$Cl$_2$ in the presence of 3 Å mol sieves at 23° C. for 5 h (55% overall from 9).

Selective trifluoromethane-sulfonation of the least hindered phenolic hydroxyl (5 equiv of Tf$_2$NPh, Et$_3$N, 4,4-dimethylaminopyridine (DMAP) in CH$_2$Cl$_2$ at 23° C. for 6 h; 72% yield) was followed by (1) selective silylation of the primary hydroxyl (excess tert-butyldiphenylsilyl chloride-DMAP in CH$_2$Cl$_2$ at 23° C. for 13 h; 89%), (2) protection of the remaining phenolic group as the methoxymethyl ether (MeOCH$_2$Br and i-Pr$_2$NEt in CH$_2$Cl$_2$ at 23° C. for 20 min; 92%), (3) double deallylation (Bu$_3$SnH, cat. Cl$_2$Pd(Ph$_3$)$_2$, excess HOAc in CH$_2$Cl$_2$ at 23° C. for 15 min; 100%), (4) reductive N-methylation (excess formalin, NaBH$_3$CN, HOAc in CH$_3$CN at 23° C. for 30 min; 95%), and (5) replacement of CF$_3$SO$_3$ by CH$_3$ (excess Me$_4$Sn, Cl$_2$Pd (Ph$_3$P)$_2$, LiCl, DMF, 80° C. 2 h) to give 11 in 83% yield.

Oxidation of the phenol 11 with 1.1 equiv of (PhSeO)$_2$O in CH$_2$Cl$_2$ at 23° C. for 15 min effected position-selective angular hydroxylation to give after desilylation (2 equiv of Bu$_4$NF in THF at 23° C. for 10 min) the dihydroxy dienone 12 (75% from 11).

The last three rings of ecteinascidin 743, the 10-membered lactone bridge and the spiro tetrahydroisoquinoline subunit, were then added in the final stage of the synthesis of 1 by the following sequence of reactions:

The primary hydroxyl function of 12 was esterified with (S)-N-allyloxycarbonyl-S-(9-fluorenylmethyl)cysteine using 5 equiv of 1-(3-dimethylaminopropyl)-3-ethyl-carbodiimide.HCl and 5 equiv of DMAP in CH$_2$Cl$_2$ at 23° C. for 30 min to form 13 (91%) which was then transformed in one flask to the bridged lactone in 79% overall yield by the operations: (1) reaction of 13 with the in situ generated Swern reagent from excess triflic anhydride and DMSO at –40° C. for 30 min,[8a] (2) addition of i-Pr$_2$NEt and warming to 0° C. for 30 min to form the exendo quinone methide,[8b] (3) quenching with tert-butyl alcohol (to destroy excess Swern reagent), (4) addition of excess N-tert-butyl-N',N''-tetramethylguanidine[9] to convert the 9-fluorenylmethyl thiolether to the thiolate ion and to promote nucleophilic addition of sulfur to the quinone methide to generate the 10-membered lactone bridge, and (5) addition of excess Ac$_2$O to acetylate the resulting phenoxide group. The N-allyloxycarbonyl group of 14 was cleaved (excess Bu$_3$SnH, HOAc and cat. Cl$_2$Pd(PPh$_3$)$_2$ in CH$_2$Cl$_2$ at 23° C. for 5 min; 84%) and the resulting a-amino lactone was oxidized to the corresponding α-keto lactone by transamination with the methiodide of pyridine-4-carboxaldehyde, DBU, and DMF in CH$_2$Cl$_2$ at 23° C. for 40 min to give 15 (70%). Reaction of 15 with 2-3-hydroxy-4-methoxyphenylethylamine (16) in EtOH in the presence of silica gel at 23° C. generated the spiro tetrahydroisoquinoline stereospecifically (82%) which was then subjected to methoxymethyl cleavage (4:1:1 CF$_3$CO$_2$H—H$_2$O-THF at 23° C. for 9 h) and replacement of CN by HO (AgNO$_3$ in CH$_3$CN—H$_2$O at 23° C. for 11 h) to form in high yield ecteinascidin 743 (1), identical in all respects with an authentic sample.[10]

The synthetic process of the present invention provides access not only to 1 but also to a host of other members of the ecteinascidin family and analogs, as well as to related simpler structures such as the saframycins.[11] The preparation and characterization of the novel intermediates described above are described in detail below in the Examples.

The present invention will be further illustrated with reference to the following examples which aid in the understanding of the present invention, but which are not to be construed as limitations thereof.

EXAMPLES

General Procedures.

All reactions were performed in flame-dried round bottom or modified Schlenk (Kjeldahl shape) flasks fitted with rubber septa under a positive pressure of argon, unless otherwise noted. Air- and moisture-sensitive liquids and solutions were transferred via syringe or stainless steel cannula. Where necessary (so noted), solutions were deoxygenated by alternate evacuation/argon flush cycles (greater than three iterations). Organic solutions were concentrated by rotary evaporation below 30° C. at ca. 25 Torr. Flash column chromatography was performed as described by Still et al. employing 230–400 mesh silica gel.[12] Thin-layer chromatography (analytical and preparative) was performed using glass plates pre-coated to a depth of 0.25 mm with 230–400 mesh silica gel impregnated with a fluorescent indicator (254 nm).

Materials.

Commercial reagents and solvents were used as received with the following exceptions. Tetrahydrofuran and ethyl ether were distilled from sodium benzophenone ketyl. Dichloromethane, hexanes, N,N-diisopropyl-ethylamine, diisopropylamine, triethylamine, pyridine, toluene, benzene, TMEDA, piperidine, and acetonitrile were distilled from calcium hydride at 760 Torr. The molarity of n-butyllithium solutions was determined by titration using diphenylacetic acid as an indicator (average of three determinations).[13]

Instrumentation.

Infrared (IR) spectra were obtained using a Nicolet 5ZDX FT-IR spectrophotometer referenced to a polystyrene standard. Data are presented as follows: frequency of absorption ($cm^{-1}$), and intensity of absorption (s=strong, m=medium, w=weak). Proton and carbon-13 nuclear magnetic resonance ($^1H$ NMR or $^{13}C$ NMR) spectra were recorded with a Bruker AM500 (500 MHz), a Bruker AM400 (400 MHz), or a Bruker AM300 (300 MHz) NMR spectrometer; chemical shifts are expressed in parts per million (d scale) downfield from tetramethylsilane and are referenced to residual protium in the NMR solvent ($CHCl_3$: d 7.26, $C_6HD_5$: d 7.20, $CDHCl_2$: d 5.38, $CD_3COCD_2H$: d 2.04, $CD_2HOD$: d 3.30). Data are presented as follows: chemical shift, multiplicity (s=singlet, d=doublet, t=quartet, m=multiplet and/or multiple resonances), integration, coupling constant in Hertz (Hz), and assignment. Chiral high performance liquid chromatography (HPLC) was conducted with an Isco 2350 equipped with the specified column (see below). Melting points were recorded with a Fisher-Johns melting point apparatus and are uncorrected.

The following schemes 2–7, illustrate the examples which follow:

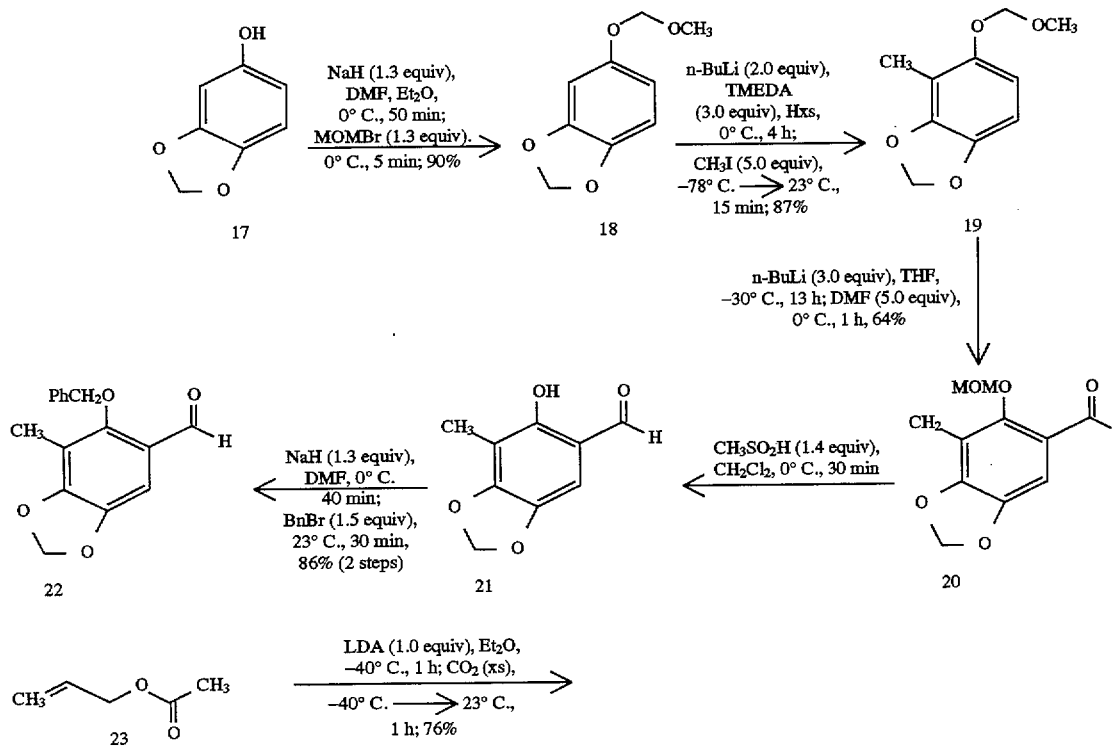

Scheme 2-Left Fragment

-continued
Scheme 2-Left Fragment
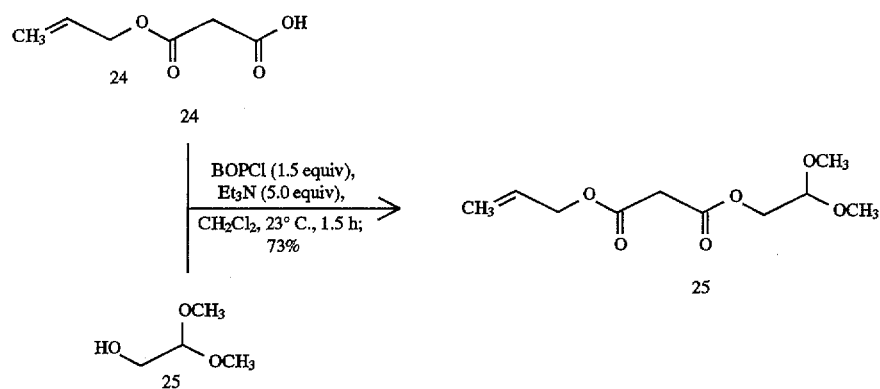
Scheme 3-Left Fragment II
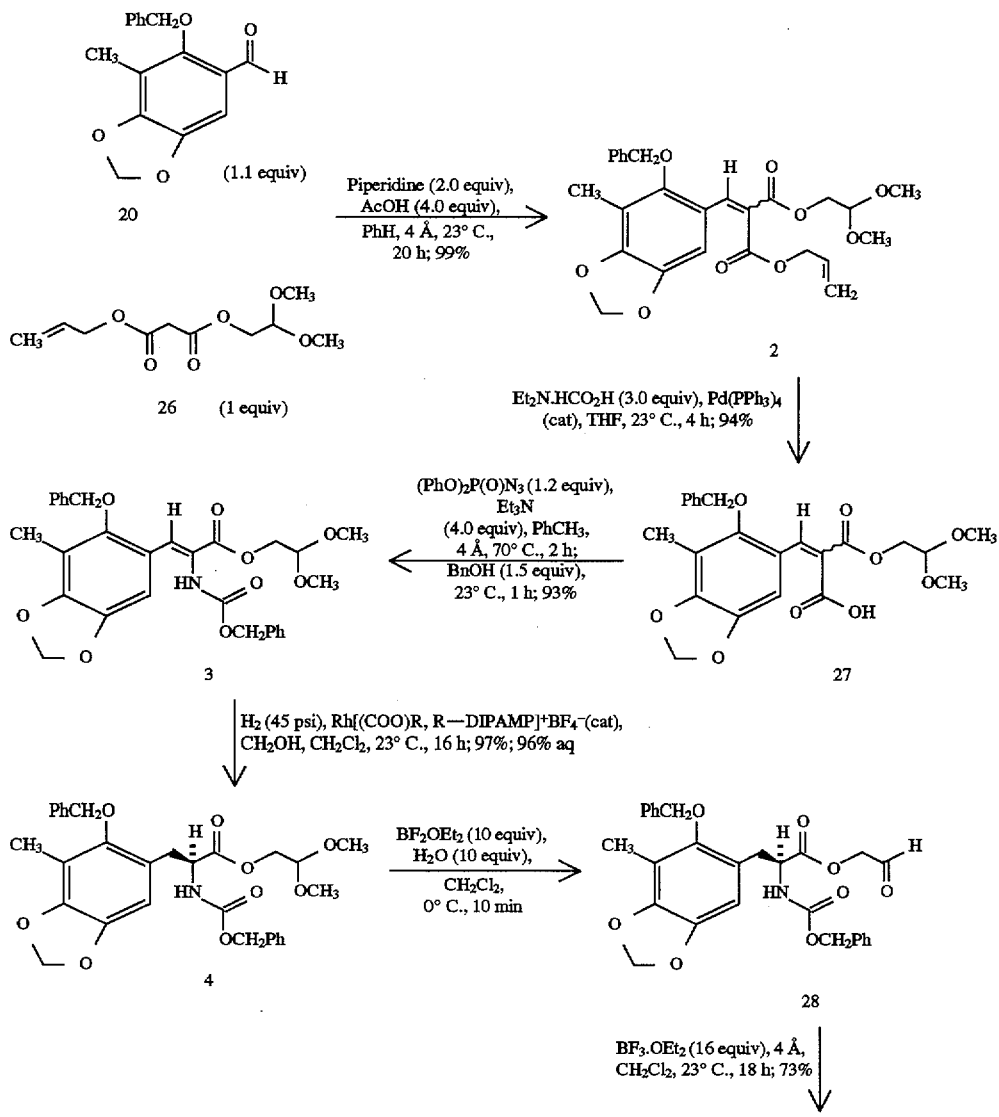

Scheme 3-Left Fragment II
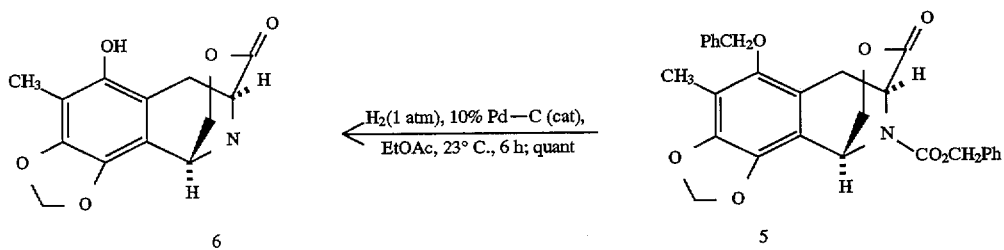
Scheme 4-Right Fragment
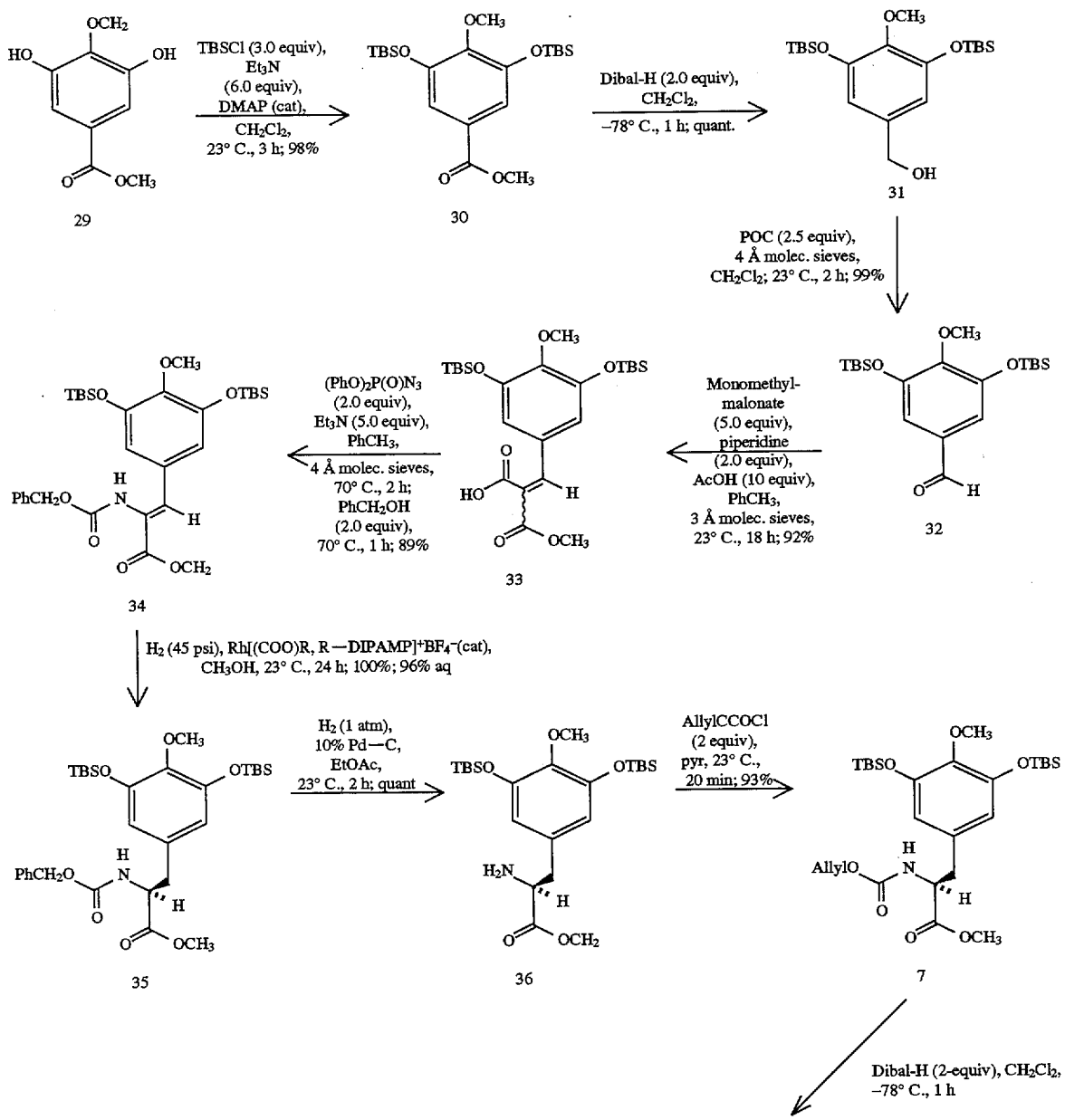

-continued
Scheme 4-Right Fragment
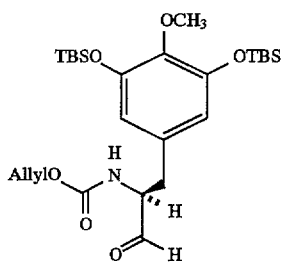
Scheme 5-Pentacycle I
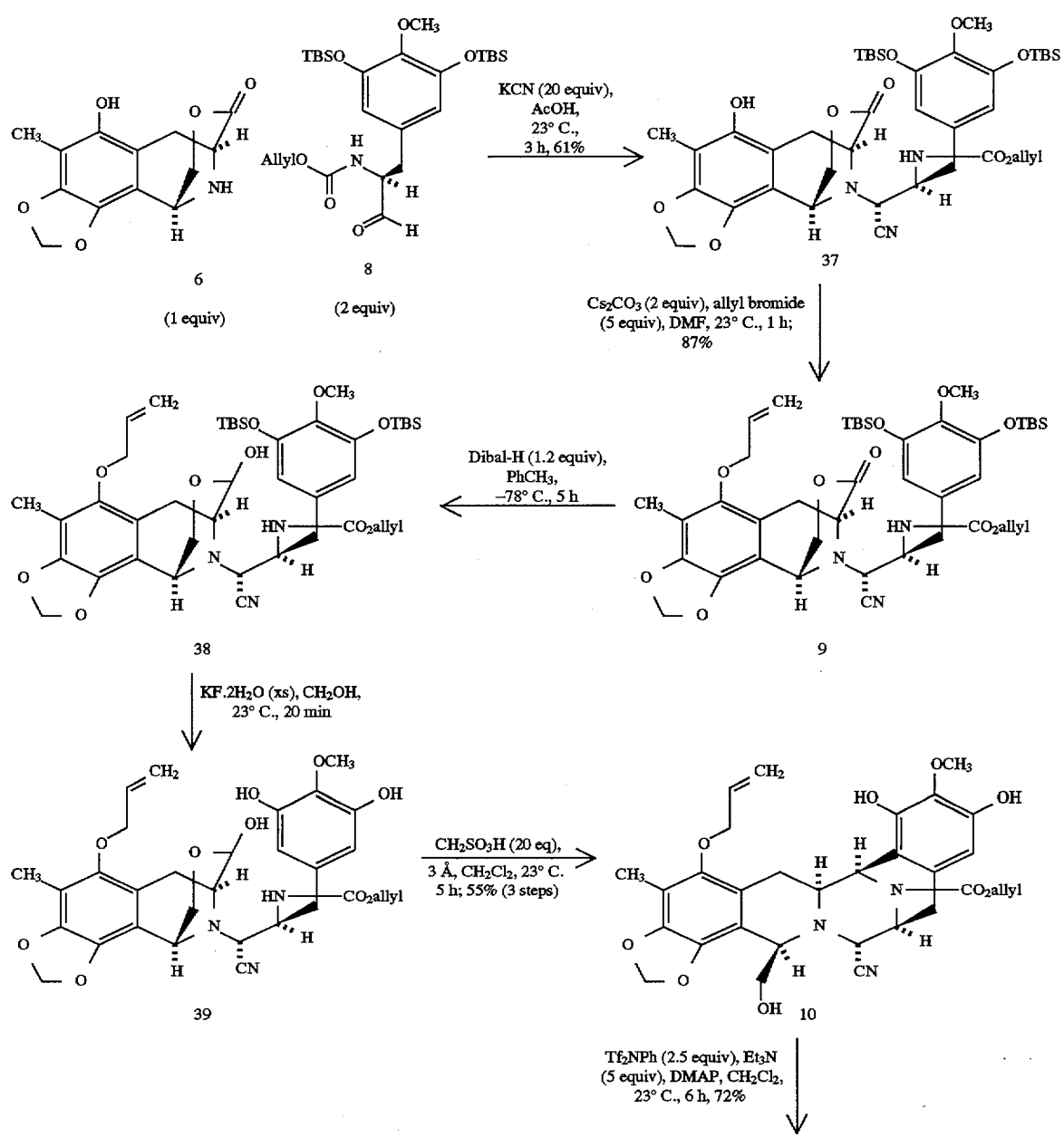

Scheme 5-Pentacycle I
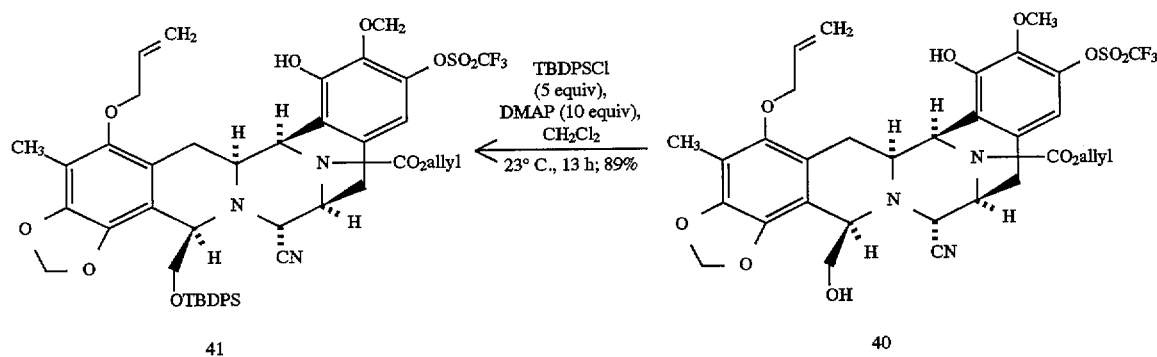
Scheme 6 - Pentacycle II
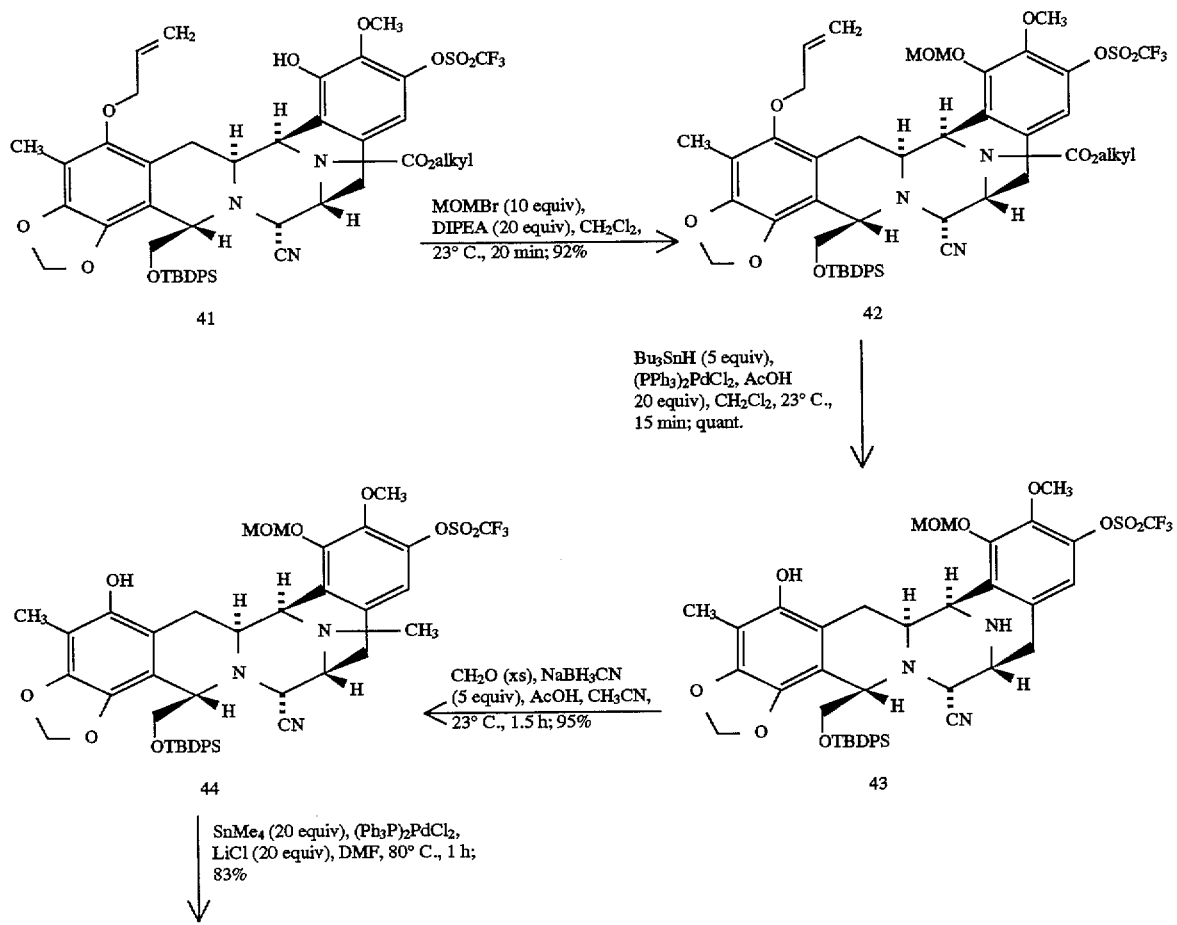

Scheme 6 - Pentacycle II
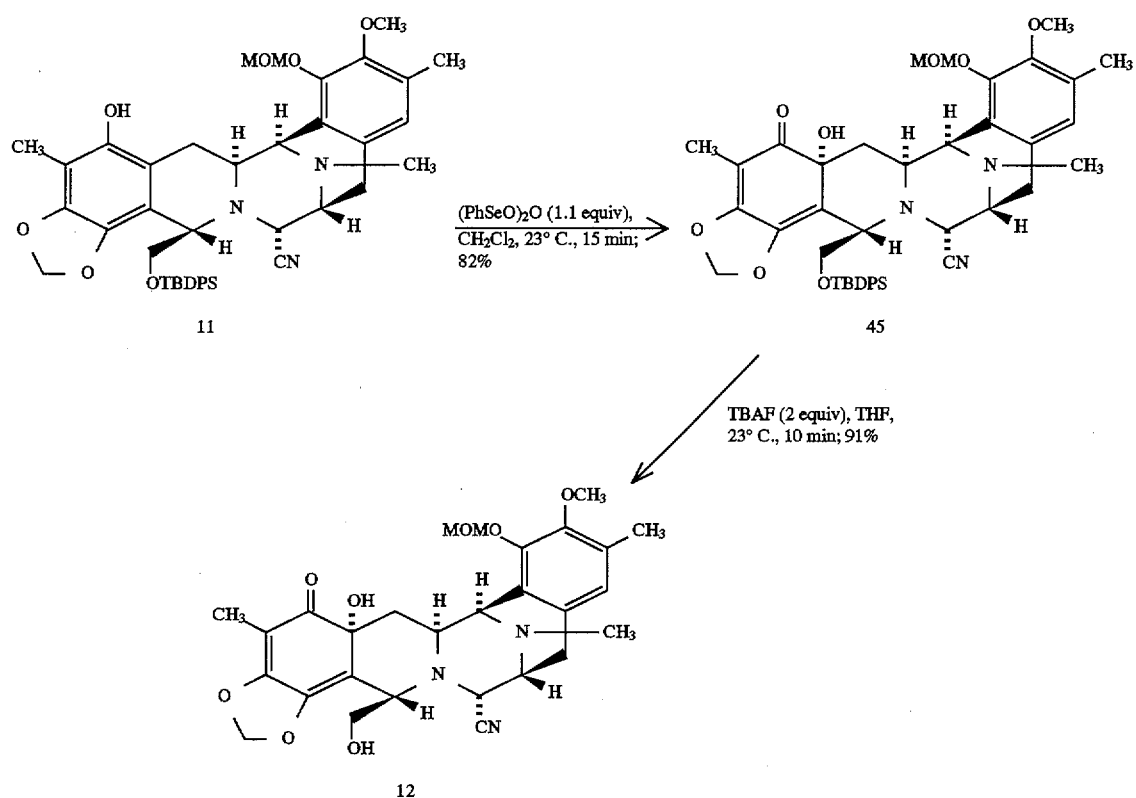
Scheme 7 - Final Steps
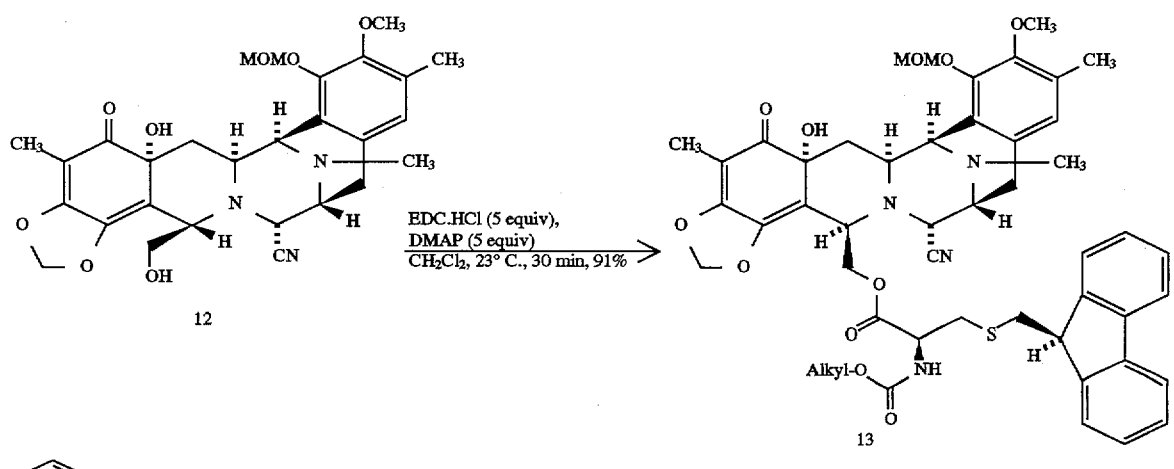
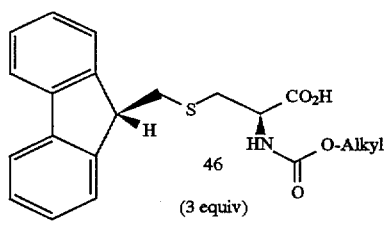

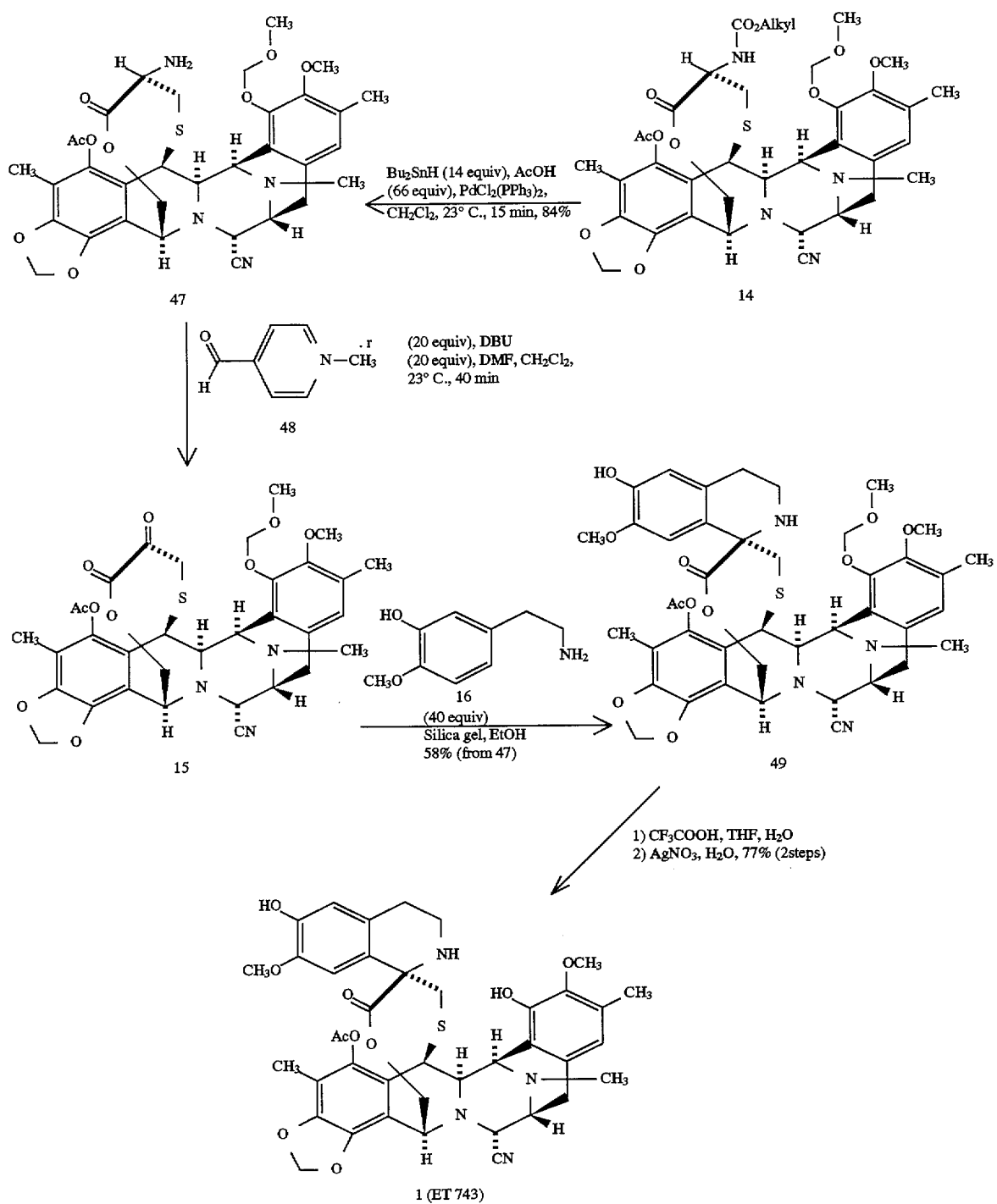

Left Fragment

Example 1

Methoxymethyl Ether 18:

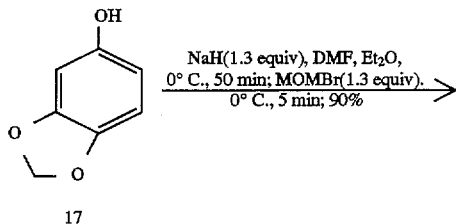

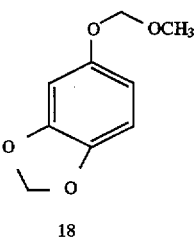

To a solution of 17 (10.2 g, 74.3 mmol, 1 equiv) in a mixture of ethyl ether and DMF (4:1 (v/v), 100 mL) at 0° C. was added a suspension of sodium hydride in mineral oil (57% (w/w), 4.07 g, 96.6 mmol, 1.3 equiv). The resulting suspension was stirred at 0° C. for 35 min, and then bromomethylmethyl ether (7.89 mL, 96.6 mmol, 1.3 equiv) was added dropwise. The suspension was stirred at 0° C. for 5 min and then at 23° C. for 1 h before the excess sodium hydride was neutralized with the slow addition of methyl alcohol (5 mL) at 0° C. The solution was partitioned between ethyl acetate (500 mL) and water (300 mL), and the organic phase was then washed with saturated aqueous sodium chloride solution (200 mL), dried (sodium sulfate), and concentrated. The residue was purified by flash column chromatography (7% ethyl acetate in hexanes) to afford 18 (13.1 g, 90%) as a colorless oil. $R_f$ 0.32 (10% ethyl acetate in hexanes); $^1$H NMR (500 MHz, CDCl$_3$) d 6.70 (d, 1H, J=8.4 Hz, ArH), 6.62 (d, 1H, J=2.4 Hz, ArH), 6.49 (dd, 1H, J=8.4, 2.4 Hz, ArH), 5.91 (s, 2H, ArOCH$_2$OAr), 5.10 (s, 2H, MOM CH$_2$), 3.50 (s, 3H, OCH$_3$); $^{13}$C NMR (100 MHz, CDCl$_3$) d 152.5, 148.1, 142.5, 108.5, 108.0, 101.1, 99.7, 95.5, 60.3, 55.8, 14.1; IR (neat film) 2990 (m), 2847 (m), 2827 (m), 1632 (m), 1611 (m), 1502 (s), 1486 (s), 1451 (m), 1245 (s), 1213 (s), 1152 (s), 1069 (s), 1004 (s), 922 (s) cm$^{-1}$; HRMS (EI$^+$) m/z: calcd for C$_9$H$_{10}$O$_4$ (M$^+$) 182.0578, found 182.0582.

Example 2

Methoxymethyl Ether 19:

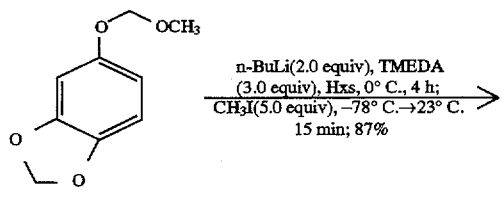

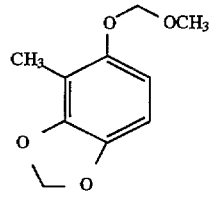

To a solution of 18 (6.76 g, 37.1 mmol, 1 equiv) and tetramethylethylenediamine (16.8 mL, 111 mmol, 3.0 equiv) in hexanes (70 mL) at 0° C. was added dropwise a solution of n-butyllithium (1.55M in hexanes, 72.0 mL, 74.2 mmol, 2.0 equiv), and the resulting yellow suspension was stirred at 0° C. for 2.5 h. A solution of iodomethane (11.5 mL, 186 mmol, 5.0 equiv) in diethyl ether (12 mL) was added dropwise at 0° C., and the resulting slurry was stirred at 23° C. for 1 h before it was quenched with the slow addition of water (10 mL). The reaction mixture was diluted with diethyl ether (500 mL), the product solution was washed sequentially with water (50 mL) and saturated aqueous sodium chloride solution (50 mL), and then was dried (sodium sulfate) and concentrated. The residue was purified by flash column chromatography (gradient elution: 2%→3% ethyl acetate in hexanes) to afford 19 (6.32 g, 87%) as a pale yellow oil. $R_f$ 0.31 (10% ethyl acetate in hexanes); $^1$H NMR (500 MHz, CDCl$_3$) d 6.57 (d, 1H, J=8.5 Hz, ArH), 6.51 (d, 1H, J=8.5 Hz, ArH), 5.91 (s, 2H, ArOCH$_2$OAr), 5.11 (s, 2H, MOM CH$_2$), 3.49 (s, 3H, OCH$_3$), 2.14 (s, 3H, ArCH$_3$); $^{13}$C NMR (126 MHz, CDCl$_3$) d 151.0, 146.6, 141.9, 110.7, 106.7, 104.8, 100.9, 95.7, 56.0, 8.9; IR (neat film) 2928 (w), 1479 (s), 1468 (s), 1242 (s), 1155 (m), 1103 (s), 1068 (s), 1020 (m), 988 (m), 793 (w) cm$^{-1}$; HRMS (EI$^+$) m/z: calcd for C$_{10}$H$_{12}$O$_4$ (M$^+$) 196.0735, found 196.0729.

Example 3

Aldehyde 20:

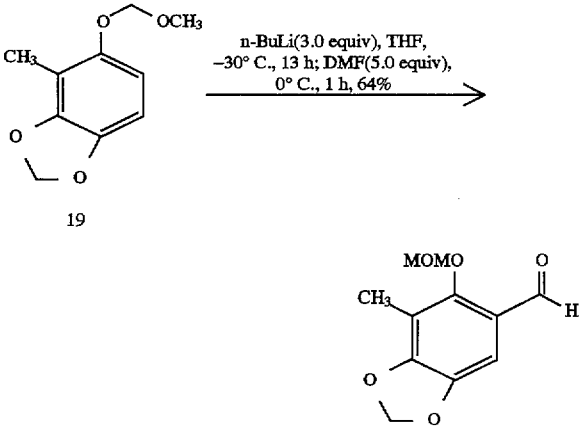

To a solution of 19 (7.50 g 38.3 mmol, 1 equiv) in a 1:1 (v/v) mixture of diethyl ether and hexanes (70 mL) at 0° C. was added dropwise a solution of n-butyllithium (1.50M in hexanes, 77.0 mL, 115 mmol, 3.0 equiv). The reaction mixture was allowed to warm to 23° C. and was stirred at this temperature for 5 h. The yellow suspension was cooled to −10° C., and N,N-dimethylformamide (14.7 mL, 191 mmol, 5.0 equiv) then was added. The resulting solution was stirred at −10° C. for 1 h. Excess base was neutralized by the slow addition of glacial acetic acid (10 mL) at −10° C., and the resulting suspension was stirred at 23° C. for 5 min. The reaction mixture was diluted with ethyl acetate (500 mL), and the product solution was washed sequentially with saturated aqueous sodium bicarbonate solution (400 mL), water (400 mL), and saturated sodium chloride solution (300 mL). The organic phase was dried (sodium sulfate) and concentrated, and the product 20 was crystallized from 10% ethyl acetate in hexanes (4.05 g). The mother liquor was purified by flash column chromatography (15% ethyl acetate in hexanes) to afford additional 20 (1.35 g) (64% total) as a pale yellow solid (mp 91.5° C.). $R_f$ 0.22 (ethyl acetate in hexanes); $^1$H NMR (400 MHz, CDCl$_3$) d 10.15 (s 1H, CHO), 7.13 (s, 1H, ArH), 6.03 (s, 2H, ArOCH$_2$OAr), 5.03 (s, 2H, MOM CH$_2$), 3.59 (s, 3H, OCH$_3$), 2.19 (s, 3H, ArCH$_3$); $^{13}$C NMR (100 MHz, CDCl$_3$) d 189.0, 157.0, 152.4, 144.2, 123.8, 113.7, 103.3, 102.1, 101.3, 58.0, 9.4; IR (neat film) 2925 (w), 1670 (s), 1614 (w), 1473 (m), 1452 (m), 1399 (m), 1280 (m), 1155 (m), 1059 (m), 935 (s), 927 (s), 860 (m) cm$^{-1}$; HRMS (EI$^+$) m/z: calcd for C$_{11}$H$_{12}$O$_5$ (M$^+$) 224.0684, found 224.0684.

Example 4

Aldehyde 22:

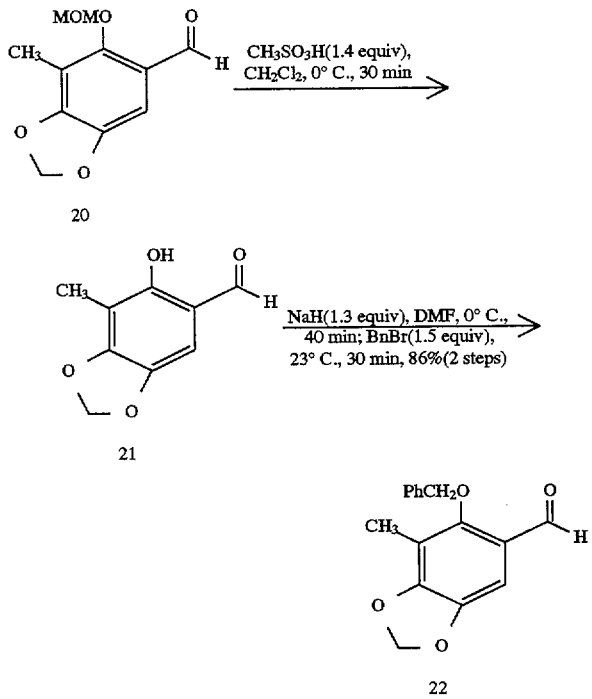

To a solution of 20 (3.70 g, 16.5 mmol, 1 equiv) in dichloromethane (50 mL) and water (1.0 mL) at 0° C. was added methanesulfonic acid (1.50 mL, 22.5 mmol, 1.4 equiv). The reaction mixture was then neutralized with saturated aqueous sodium bicarbonate solution (50 mL) at 0° C., and the resulting mixture was partitioned between saturated aqueous sodium bicarbonate solution (400 mL) and dichloromethane (3×200 mL). The combined organic layers were dried (sodium sulfate) and concentrated to afford 21 as a crude intermediate. To a solution of 21 in N,N-dimethylformamide (16.0 mL) at 0° C. was added a suspension of sodium hydride in mineral oil (57% (w/w), 903 mg, 21.5 mmol, 1.3 equiv), and the resulting suspension was stirred at 0° C. for 40 min. Benzyl bromide (2.94 mL, 24.8 mmol, 1.5 equiv) was added to the reaction mixture at 0° C., and the resulting suspension was stirred at 23° C. for 30 min. Excess base was neutralized by the slow addition of methanol (2.0 mL) at 0° C., and the reaction mixture was diluted with ethyl acetate (250 mL). The product solution was washed sequentially with water (200 mL) and saturated aqueous sodium chloride solution (200 mL), then was dried (sodium sulfate) and concentrated. The residue was purified by flash column chromatography (10% ethyl acetate in hexanes) to afford 22 (3.85 g, 86%) as a viscous syrup. $R_f$ 0.18 (10% ethyl acetate in hexanes); $^1$H NMR (400 MHz, CDCl$_3$) d 10.08 (s, 1H, CHO), 7.40 (m, 5H, Bn ArH), 7.12 (s, 1H, ArH), 6.04 (s, 2H, ArOCH$_2$OAr), 4.93 (s, 2H, Bn CH$_2$), 1.60 (s, 3H, ArCH$_3$); $^{13}$C NMR (100 MHz, CDCl$_3$) d 188.5, 158.3, 152.6, 144.1, 135.7, 128.7, 128.3, 123.6, 113.8, 103.2, 102.1, 78.5, 11.8, 9.1; IR (neat film) 2923 (w), 1674 (s), 1612 (w), 1470 (m), 1420 (m), 1375 (m), 1352 (m), 1278 (s), 1170 (m), 1096 (s), 1069 (m) cm$^{-1}$; HRMS (EI$^+$) m/z: calcd for C$_{16}$H$_{14}$O$_4$ (M$^+$) 270.0892, found 270.0892.

Example 5

Monoallylmalonate 24:

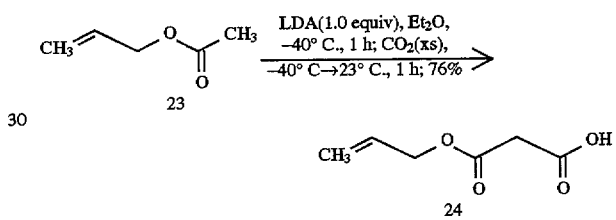

A solution of n-butyllithium (1.56M in hexanes, 19.2 mL, 30.0 mmol, 1.0 equiv) was added to a solution of diisopropylamine (5.47 mL, 39.0 mmol, 1.3 equiv) in ethyl ether (30.0 mL) at −78° C. The reaction flask was transferred briefly to an ice bath (10 min), and then was recooled to −78° C. Allyl acetate 23 (3.23 mL, 30.0 mmol, 1 equiv) was added to the cold solution of lithium diisopropylamide, and the resulting solution was stirred at −40° C. for 1 h. The reaction mixture was cooled to −78° C. and excess solid carbon dioxide was added to the reaction mixture before it was allowed to warm to 23° C. over a 1 h period. The turbid solution was diluted with water (100 mL) and was washed with ethyl ether (3×50 mL). The aqueous layer was acidified at 0° C. to pH=2 with the slow addition of concentrated hydrochloric acid and then was extracted with ethyl acetate (3×50 mL). The combined organic layers were dried (sodium sulfate) and concentrated to afford crude acid 24 (3.35 g, 76%) as a pale yellow oil, which was used without further purification. $^1$H NMR (400 MHz, CDCl$_3$) d 5.92 (m, 1H, CH$_2$=CH—), 5.36 (m, 1H, CH$_2$=CH—), 5.27 (m, 1H, CH$_2$=CH—), 4.68 (dt, 2H, J=5.7, ~1 Hz, CH$_2$=CHCH$_2$—), 3.48 (s, 2H, CH$_2$); IR (neat film) 3300–2400 (m), 1744 (s), 1322 (m), 1156 (m) cm$^{-1}$.

Example 6

Allyl-2,2-dimethoxyethyl Malonate 26:

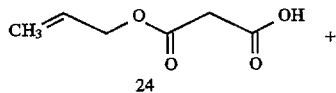

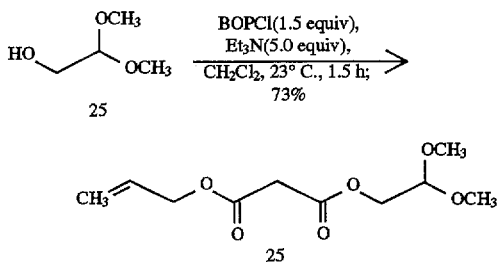

To a solution of acid 24 (7.50 g, 52.0 mmol, 1 equiv), 2,2-dimethoxyethanol (25) (5.50 g, 52.0 mmol, 1.0 equiv), and triethylamine (36.0, 258 mmol, 5.0 equiv) in dichoromethane (100 mL) was added solid BOPCl (20.0 mg, 78.7 mmol, 1.5 equiv), and the resulting slurry was stirred at 23° C. for 1 h. The reaction mixture was filtered, the filtrate was diluted with ethyl acetate (400 mL), and the product solution was washed sequentially with water (2×300 mL) and saturated aqueous sodium chloride solution (300 mL). The organic layer was dried (sodium sulfate) and concentrated, and the residue was purified by flash column chromatography (gradient elution: 20–33% ethyl acetate in hexanes) to afford 26 (8.81 g, 73%) as a colorless liquid. $R_f$ 0.26 (25% ethyl acetate in hexanes); $^1$H NMR (300 MHz, $CDCl_3$) d 5.91 (m, 1H, $CH_2$=CH—), 5.34 (m, 1H, $CH_2$=CH—), 5.26 (m, 1H, $CH_2$=CH), 4.64 (dt, 2H, J=5.6, ~1 Hz, $CH_2$=$CHCH_2$), 4.58 (t, 1H, J=5.3 Hz, $CH(OCH_3)_2$), 4.17 (d, 2H, J=5.3 Hz, $CH_2CH(OCH_3)_2$), 3.46 (s, 2H, $CH_2$), 3.39 (s, 6H, $OCH_3$); $^{13}$C NMR (100 MHz, $CDCl_3$) d 166.0, 165.9, 131.5, 118.7, 101.0, 66.0, 63.8, 53.9, 41.2; FTIR (neat film) 2955 (m), 1757 (s), 1738 (s), 1447 (m), 1412 (m), 1367 (s), 1340 (s), 1323 (s), 1276 (s), 1193 (s), 1134 (s), 1102 (s), 1078 (s), 1046 (s) $cm^{-1}$; HRMS ($CI^+$) m/z: Calcd for $C_{10}H_{20}NO_6$ $(M+NH_4)^+$ 250.1291, found 250.1296.

Example 7

α,β-Unsaturated Diester 2:

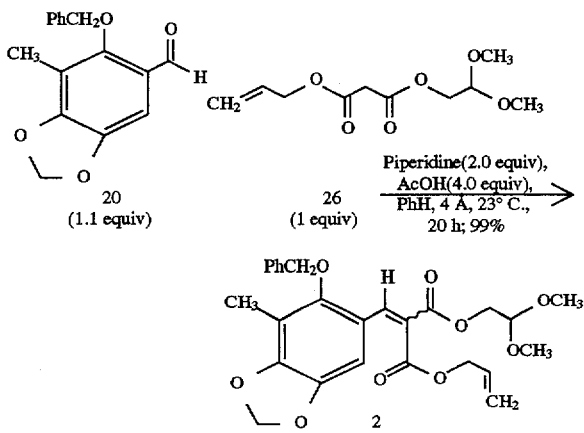

To a mixture of aldehyde 20 (3.84 g, 14.2 mmol, 1.1 equiv), 26 (3.00 g, 12.9 mmol, 1 equiv), piperidine (2.80 mL, 28.4 mmol, 2.0 equiv), and crushed activated 4 Å molecular sieves (~6 g) in benzene (40 mL) was added dropwise glacial acetic acid (3.25 mL, 56.8 mmol, 4.0 equiv), and the resulting suspension was stirred at 23° C. for 18 h. The reaction was filtered, and the filtrate was concentrated. The residue was purified by flash column chroma- tography (gradient elution: 20→33% ethyl acetate in hexanes) to afford 2 (6.20 g, 99%) as an inseparable mixture of E/Z isomers (1.3:1). $R_f$ 0.62 (10% ethyl ether in dichloromethane); $^1$H NMR (500 MHz, $CDCl_3$) d major isomer: 8.07 (s, 1H, ArCH), 7.38 (m, 5H, Ph-H), 6.83 (s, 1H, ArH), 5.98 (s, 2H, $ArOCH_2OAr$), 5.75 (m, 1H, $CH_2$=CH), 5.34 (m, 1H, $CH_2$=CH), 5.24 (m, 1H, $CH_2$=CH), 4.77 (s, 2H, Bn $CH_2$), 4.72 (m, 2H, $CH_2$=$CHCH_2$), 4.64 (t, 1H, J=5.6 Hz, $CH(OCH_3)_2$), 4.32 (d, 2H, J=5.6 Hz, $CH_2CH(OCH_3)_2$), 3.41 (s, 6H, $OCH_3$), 2.16 (s, 3H, $ArCH_3$), minor isomer: 8.06 (s, 1H, ArCH), 7.38 (m, 5H, Ph-H), 6.76 (s, 1H, ArH), 5.98 (s, 2H, $ArOCH_2OAr$), 5.73 (m, 1H, $CH_2$=CH), 5.38 (m, 1H, $CH_2$=CH), 5.28 (m, 1H, $CH_2$=CH), 4.77 (s, 2H, Bn $CH_2$), 4.78 (m, 2H, $CH_2$=$CHCH_2$), 4.59 (t, 1H, J=5.6 Hz, $CH(OCH_3)_2$), 4.23 (d, 2H, J=5.6 Hz, $CH_2CH(OCH_3)_2$), 3.40 (s, 6H, $OCH_3$), 2.16 (s, 3H, $ArCH_3$); $^{13}$C NMR (100 MHz, $CDCl_3$) d 166.3, 166.2, 163.9, 163.8, 153.5, 149.5, 143.6, 139.1, 139.0, 136.3, 131.8, 131.4, 128.6, 128.4, 123.6, 119.4, 119.1, 118.2, 114.1, 104.7, 104.6, 101.7, 101.2, 101.0, 77.5, 77.4, 66.2, 65.8, 63.9, 63.8, 53.9, 53.8, 14.1, 9.3; IR (neat film) 2928 (w), 1732 (s), 1609 (m), 1476 (m), 1423 (m), 1243 (s), 1217 (s), 1186 (s), 1096 (s), 1079 (s) $cm^{-1}$; HRMS ($FAB^+$) m/z: calcd for $C_{26}H_{28}O_9Na$ $(MNa^+)$ 507.1631, found 507.1640.

Example 8

α,β-Unsaturated Acid 27:

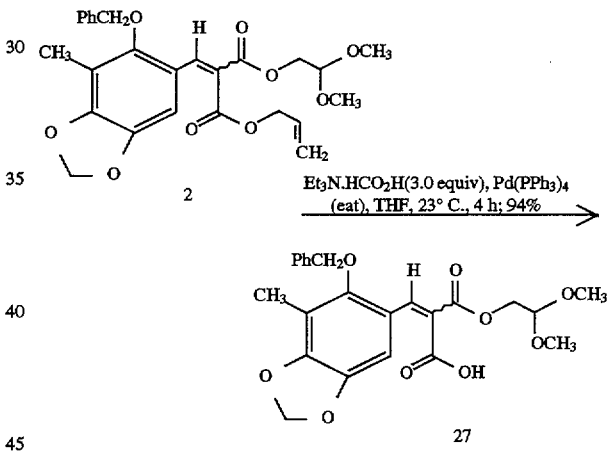

To solution of 2 (6.20 g, 12.8 mmol, 1 equiv) in tetrahydrofuran (30 mL) was added sequentially a solution of triethylammonium formate (1M in tetrahydrofuran, 38.4 mL, 38.4 mmol, 3.0 equiv) and solid tetrakis-(triphenylphosphine)palladium (120 mg), and the resulting solution was stirred at 23° C. for 4 h. All volatiles were removed in vacuo, and the residue was purified by flash column chromatography (10% methyl alcohol in dichloromethane) to yield the yellow oil 27 (5.33 g 94%) as a mixture of E/Z isomers (4:1). $R_f$ 0.21 (10% methyl alcohol in dichloromethane); $^1$H NMR (500 MHz, $CDCl_3$) d major isomer: 8.19 (s, 1H, ArCH), 7.40 (m, 5H, Ph-H), 6.82 (s, 1H, ArH), 6.00 (s, 2H, $ArOCH_2OAr$), 4.78 (s, 2H, Bn $CH_2$), 4.61 (t, 1H, J=5.8 Hz, $CH(OCH_3)_2$), 4.29 (d, 2H, J=5.8 Hz, $CO_2CH_2$), 3.40 (s, 6H, $OCH_3$), 2.15 (s, 3H, $ArCH_3$), minor isomer: 8.21 (s, 1H, ArCH), 7.40 (m, 5H, Ph-H), 7.13 (s, 1H, ArH), 5.96 (s, 2H, $ArOCH_2OAr$), 4.78 (s, 2H, Bn $CH_2$), 4.59 (t, 1H, J=5.8 Hz, $CH(OCH_3)_2$), 4.24 (d, 2H, J=5.8 Hz, $CO_2CH_2$), 3.38 (s, 6H, $OCH_3$), 2.15 (s, 3H, $ArCH_3$); $^{13}$C NMR (100 MHz, $CDCl_3$) d 169.3, 168.9, 166.3, 164.8, 153.8, 149.9, 143.6, 143.5, 141.6, 141.4, 136.1, 135.9, 128.7, 128.5, 128.4, 128.3, 122.0, 121.5, 119.2, 119.1, 114.0, 113.8, 105.2, 104.7, 101.7, 101.0, 100.9, 77.6, 77.5, 63.9, 63.7, 53.9, 53.8, 53.3, 50.3, 9.2; IR (neat film) 3500–2500 (m), 2958 (m), 1735 (s), 1701 (s), 1608 (m), 1476 (s), 1423 (s), 1258 (s), 1218 (m), 1188 (s), 1135 (m), 1096 (s) cm$^{-1}$; MS (EI$^+$) m/z: 444 (M$^+$).

Example 9

Benzyl Carbamate 3:

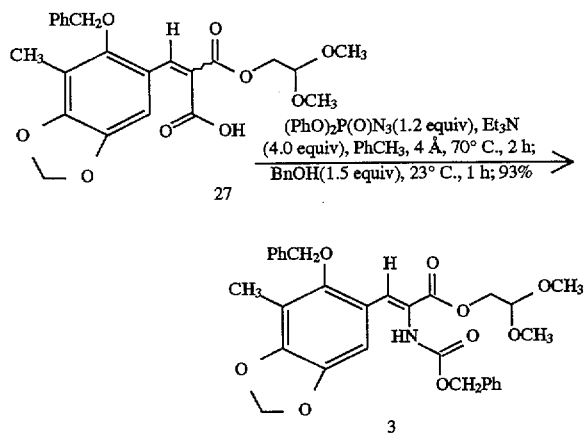

To a mixture of 27 (5.32 g, 11.2 mmol, 1 equiv), triethylamine (6.24 mL, 44.8 mmol, 4.0 equiv), and crushed, activated 4 Å molecular sieves (~20 g) in toluene (53 mL) was added diphenylphosphoryl azide (3.10 mL, 14.4 mmol, 1.2 equiv), and the resulting suspension was heated to 70° C. for 2 h. The reaction mixture was cooled to 23° C., and benzyl alcohol (1.73 mL, 16.8 mmol, 1.5 equiv) was then added. The suspension was stirred at 23° C. for 1 h, filtered, and the filtrate was concentrated. The residue was purified by flash column chromatography (gradient elution: 20→50% ethyl acetate in hexanes) to afford 3 (5.90 g, 93%) as a pale yellow solid (mp 102°–103° C.). R$_f$ 0.25 (33% ethyl acetate in hexanes); $^1$H NMR (400 MHz, CDCl$_3$) d 7.40 (m, 1H, Ph-H & ArCH), 6.92 (s, 1H, ArH), 6.70 (s (br), 1H, NH), 5.99 (s, 2H, ArOCH$_2$OAr), 5.10 (s, 2H, Cbz CH$_2$), 4.70 (m (br), 2H, Bn CH$_2$), 4.58 (t (br), 1H, J=unres, CH(OCH$_3$)$_2$), 4.23 (d (br), 2H, J=unres, CO$_2$CH$_2$CH), 3.39 (s, 6H, OCH$_3$), 2.18 (s, 3H, ArCH$_3$), Z configuration verified by 5.8% NOE of Ar-H upon irradiation of N—H; $^{13}$C NMR (100 MHz, CDCl$_3$) d 165.0, 151.7, 148.1, 143.4, 136.3, 135.9, 128.6, 128.5, 128.4, 128.3, 128.1, 126.3, 123.6, 120.1, 113.9, 105.0, 101.5, 101.1, 67.3, 64.0, 53.9, 9.4; IR (neat film) 3350 (w, br), 2940 (w), 1718 (s), 1498 (m), 1473 (m), 1423 (m), 1247 (s), 1193 (s), 1130 (m), 1094 (s), 1069 (m) cm$^{-1}$; HRMS (FAB$^+$) m/z: calcd for C$_{30}$H$_{31}$NO$_9$Na (MNa$^+$) 572.1896, found 572.1909.

Example 10

Protected Amino Acid 4:

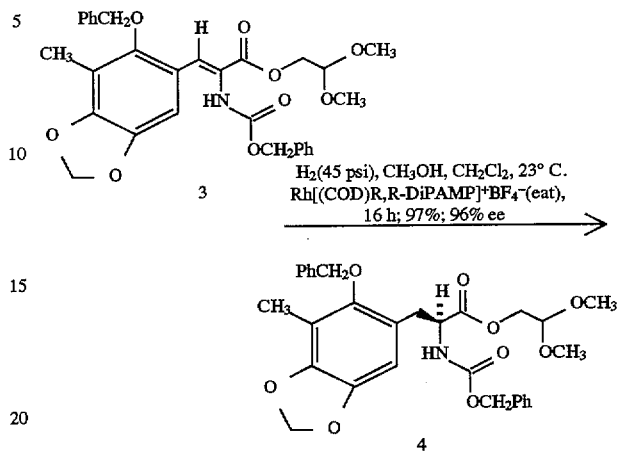

A solution of 3 (800 mg, 1.46 mmol, 1 equiv) and Rh[(COD)R,R-DiPAMP]$^+$BF$_4^-$ (20 mg) in a mixture of methyl alcohol and dichloromethane (10:1 (v/v), 11.0 mL) was placed in a high pressure Parr reactor and was purged with hydrogen gas (5×50 psi). The reaction mixture was sealed under hydrogen (50 psi) and was stirred at 23° C. for 16 h. The solution was concentrated, and the residue was purified by flash column chromatography (gradient elution: 33→50% ethyl acetate in hexanes) to yield 4 (774 mg, 97%) as a white solid (mp 93.5°–94.0° C.). R$_f$ 0.25 (33% ethyl acetate in hexanes); ee: 96% (HPLC Chiracel OD, 10% isopropyl alcohol in hexanes); [a]$_D^{23}$=1.9° (c=0.67, CH$_2$Cl$_2$); $^1$H NMR (500 MHz, CDCl$_3$) d 7.36 (m, 10H, Ph-H), 6.50 (s, 1H, ArH), 5.92 (s, 2H, ArOCH$_2$OAr), 5.75 (d, 1H, J=7.8 Hz, NH), 5.03 (s, 2H, Cbz CH$_2$), 4.76 (s, 2H, Bn CH$_2$), 4.53 (m, 1H, CHCO$_2$), 4.46 (t, 1H, J=5.6 Hz, CH(OCH$_3$)$_2$), 4.09 (m, 2H, CO$_2$CH$_2$CH), 3.35 (s, 6H, OCH$_3$), 3.06 (dd, 1H, J=4.7, 13.4 Hz, ArCH$_2$), 2.94 (dd, 1H, J=7.6, 13.4 Hz, ArCH$_2$), 2.20 (s, 3H, ArCH$_3$); $^{13}$C NMR (126 MHz, CDCl$_3$) d 171.3, 155.8, 150.5, 146.2, 143.3, 136.8, 136.5, 128.5, 128.4, 128.1, 127.9, 127.8, 121.2, 113.6, 107.1, 101.2, 101.1, 75.4, 66.6, 63.6, 55.2, 53.9, 53.8, 32.7, 9.7; IR (neat film) 3390 (w), 2949 (w), 1724 (s), 1500 (m), 1476 (s), 1213 (m), 1034 (m), 1091 (s), 1027 (m) cm$^{-1}$; HRMS (EI$^+$) m/z: Calcd for C$_{30}$H$_{33}$NO$_9$ (M$^+$) 551.2153, found 551.2159.

Example 11

Aldehyde 28:

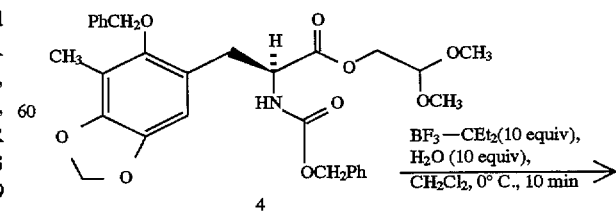

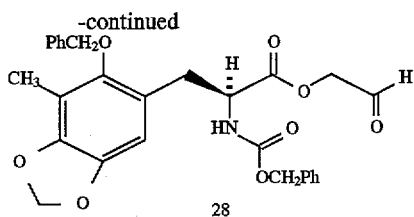

To a solution of 4 (175 mg, 0.318 mmol, 1 equiv) and water (57 mL, 3.18 mmol, 10.0 equiv) in dichloromethane (10.0 mL) at 0° C. was added boron trifluoride etherate (392 mL, 3.18 mmol, 10.0 equiv), and the resulting solution was stirred at this temperature for 10 min. The Lewis acid was neutralized with the slow addition of saturated aqueous sodium bicarbonate solution (10.0 mL), and the resulting mixture was then partitioned between saturated aqueous sodium bicarbonate solution (80 mL) and dichloromethane (40 mL). The aqueous phase was extracted further with ethyl acetate (2×50 mL), and the combined organic layers were dried (sodium sulfate) and concentrated to afford crude aldehyde 28 of sufficient purity. $R_f$ 0.24 (50% ethyl acetate in hexanes); $^1$H NMR (500 MHz, CDCl$_3$) d 9.44 (s, 1H, CHO), 7.32 (m, 10H, Ph-H), 6.50 (s, 1H, ArH), 5.95 (s, 2H, ArOCH$_2$OAr), 5.72 (d, 1H, J=7.4 Hz, NH), 5.07 (d, 1H, J=10.7 Hz, Cbz CH$_2$), 5.02 (d, 1H, J=10.7 Hz, Cbz CH$_2$), 4.78 (d, 1H, J=10.2 Bn CH$_2$), 4.74 (d, 1H, J=10.2 Bn CH$_2$), 4.58 (m, 1H, CHCO$_2$), 4.53 (d, 1H, J=16.8 Hz, CH$_2$CHO), 4.48 (d, 1H, J=16.8 Hz, CH$_2$CHO), 3.04 (m, 2H, ArCH$_2$), 2.20 (s, 3H, ArCH$_3$); IR (neat film) 3353 (w, br), 2913 (w), 1724 (s), 1476 (m), 1254 (m), 1215 (m), 1184 (m), 1090 (s), 1063 (m), 1027 (m) cm$^{-1}$.

Example 12

Lactone 5:

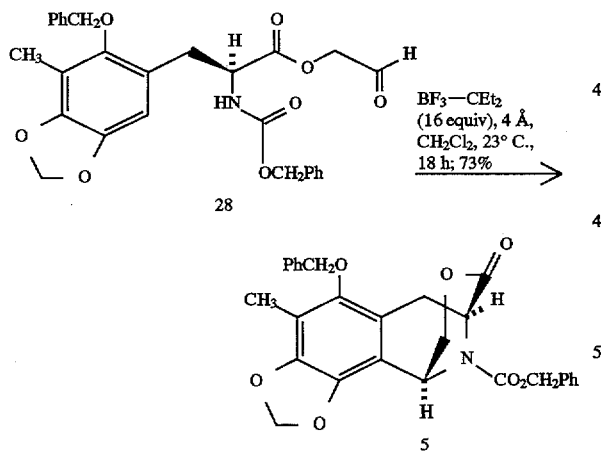

Borontrifluoride etherate (640 mL, 5.20 mmol, 16.4 equiv) was added to a mixture of crude aldehyde 28 (0.318 mmol, 1 equiv) and crushed, activated 4 Å molecular sieves (2.8 g) in dichloromethane (32 mL) at 0° C., and the resulting suspension was stirred at 23° C. for 18 h. The reaction mixture was quenched by the addition of saturated aqueous sodium bicarbonate solution (100 mL), and the mixture was partitioned. The aqueous layer was further extracted with ethyl acetate (3×50 mL), and the combined organic layers were dried (sodium sulfate) and concentrated. The residue was purified by flash column chromatography (gradient elution: 0→5% ethyl acetate in dichloromethane) to afford 5 (113 mg, 73%) as a white solid (mp 53°–55° C.). $R_f$ 10.19 (dichloromethane); $[\alpha]_D^{23}$ –9.8° (c=0.40, CH$_2$Cl$_2$); $^1$H NMR (500 MHz, CDCl$_3$, 55° C.) d 7.38 (m, 10H, Ph-H), 6.00 (s, 1H, ArOCH$_2$OAr), 5.97 (s, 1H, ArOCH$_2$OAr), 5.49 (m (br), 1H, ArCH), 5.19 (m, 3H, Cbz CH$_2$ & CHCO$_2$), 4.72 (m, 3H, Bn CH$_2$ & CO$_2$CH$_2$), 4.43 (d, 1H, J=10.4 Hz, CO$_2$CH$_2$), 3.18 (m, 1H, ArCH$_2$), 2.98 (m, 1H, ArCH$_2$), 2.18 (s, 3H, ArCH$_3$); $^{13}$C NMR (100 MHz, CDCl$_3$) d 167.8, 153.1, 149.9, 145.3, 139.3, 136.8, 135.4, 128.5, 128.4, 128.3, 128.1, 127.6, 118.5, 118.1, 114.0, 113.8, 111.5, 101.6, 74.6, 73.4, 67.9, 52.8, 52.1, 45.4, 44.5, 28.1, 27.6, 9.3; IR (neat film) 2920 (w), 1747 (s), 1710 (s), 1455 (s), 1432 (s), 1321 (m), 1299 (s), 1230 (m), 1163 (m), 1096 (s), 1058 (m), 1042 (m) cm$^{-1}$; HRMS (EI$^+$) m/z: calcd for C$_{28}$H$_{25}$NO$_7$ (M$^+$) 487.1629, found 487.1628.

Example 13

Aminophenol 6:

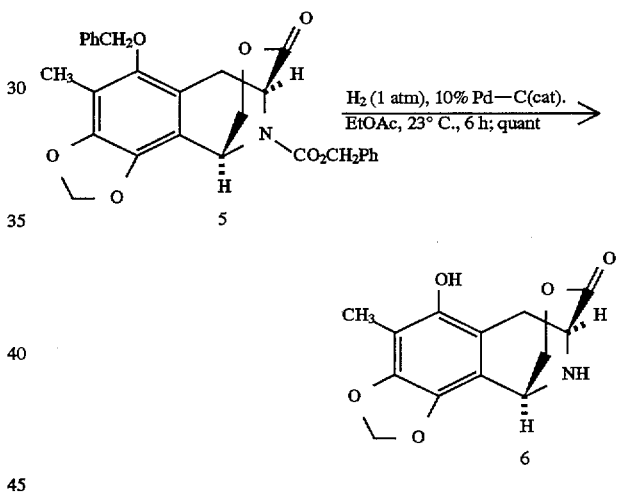

A mixture of lactone 5 (240 mg, 0.493 mmol, 1 equiv) and 10% palladium on carbon (20 mg) in ethyl acetate (10.0 mL) was stirred under 1 atm of hydrogen at 23° C. for 6 h. The reaction mixture was filtered, and the filtrate was concentrated to afford 6 (131 mg, quant) as a colorless film. $R_f$ 0.20 (ethyl acetate); $^1$HNMR (400 MHz, CDCl$_3$) d 5.94 (d, 1H, J~1 Hz, OCH$_2$O), 5.91 (d, 1H, J~1 Hz, OCH$_2$O), 4.76 (dd, 1H, J=3.7, 10.6 Hz, CH$_2$O$_2$C), 4.43 (d, 1H, J=10.6 Hz, CH$_2$O$_2$C), 4.38 (d, 1H, J=3.7 Hz, ArCH), 4.29 (d (br), 1H, J=6.2 Hz, CHCO$_2$), 3.00 (dd, 1H, J=1.1, 16.9 Hz, ArCH$_2$), 2.91 (dd, 1H, J=6.2, 16.9 Hz, ArCH$_2$); FTIR (neat film) 3360 (w, br), 2951 (w), 1731 (s), 1461 (s), 1432 (s), 1241 (m), 1117 (m), 1096 (s), 1076 (m), 1048 (s), 1025 (m) cm$^{-1}$; HRMS (EI$^+$) m/z: Calcd for C$_{13}$H$_{13}$NO$_5$ (M$^+$) 263.0794, found 263.0802.

39

Right Fragment

Example 14

Acid 33:

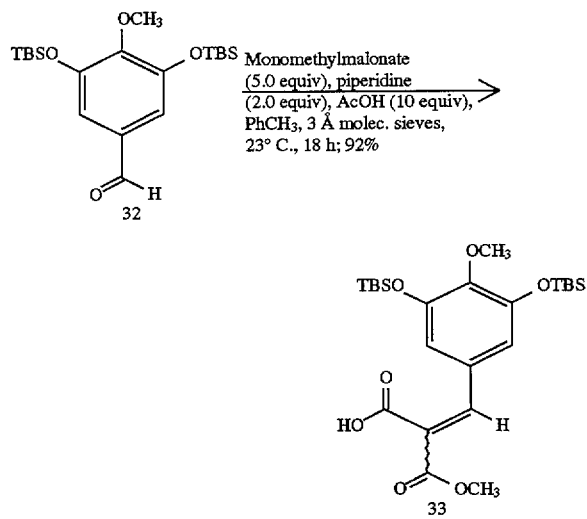

Piperidine (1.01 mL, 10.2 mmol, 2.0 equiv) was added to a suspension of 32 (2.02 g, 5.10 mmol, 1 equiv), monomethyl malonate (3.01 g, 25.5 mmol, 5.0 equiv), acetic acid (2.92 mL, 51.0 mmol, 10.0 equiv), and crushed, activated 3 Å molecular sieves (~12 g) in toluene (25.0 mL), and the resulting suspension was stirred at 23° C. for 18 h. The reaction mixture was filtered, washing well with ethyl acetate (100 mL). The filtrate was concentrated, and the residue was purified by flash column chromatography (4% methyl alcohol in dichloromethane) to give acid 33 (2.32 g, 92%) as an inseparable mixture of E/Z isomers. $R_f$ 0.42 (10% methyl alcohol in dichloromethane); $^1$H NMR (500 MHz, CDCl$_3$) d (major isomer) 7.71 (s, 1H, ArCH), 6.83 (s, 2H, ArH), 3.90 (s, 3H, OCH$_3$), 3.75 (s, 3H, OCH$_3$), 1.00 (s, 18H, t-butyl), 0.18 (s, 12H, SiCH$_3$), d (minor isomer) 7.71 (s, 1H, ArCH), 6.65 (s, 2H, ArH), 3.81 (s, 3H, OCH$_3$), 3.77 (s, 3H, OCH$_3$), 1.00 (s, 18H, t-butyl), 0.18 (s, 12H, SiCH$_3$); $^{13}$C NMR (126 MHz, CDCl$_3$) d 169.9, 165.3, 150.0, 145.8, 144.5, 127.4, 122.5, 116.8, 60.0, 52.8, 25.6, 18.2, −4.7; IR (neat film) 3600–2600 (m, br), 2955 (s), 1741 (s), 1713 (s), 1569 (s), 1493 (s), 1253 (s), 1219 (m), 1096 (s), 864 (s) cm$^{-1}$; HRMS (FAB$^-$) m/z: Calcd for C$_{24}$H$_{39}$O$_7$Si$_2$ (M—H$^-$) 495.2234, found 495.2253.

Example 15

Benzyl Carbamate 34:

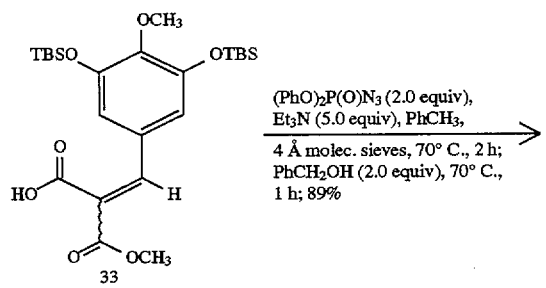

40

-continued

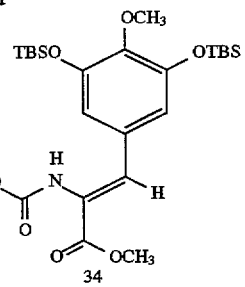

To a suspension of 33 (3.35 g, 6.75 mmol, 1 equiv), triethylamine (4.71 mL, 33.8 mmol, 5.0 equiv), and crushed, activated 3 Å molecular sieves (~15 g) in toluene (50 mL) was added diphenylphosphoryl azide (2.90 mL, 13.5 mmol, 2.0 equiv), and the resulting suspension was heated at 70° C. for 2 h. Benzyl alcohol (1.40 mL, 13.5 mmol, 2.0 equiv) then was added to the reaction mixture, and the suspension was stirred at 70° C. for 1 h. The reaction was filtered, washing well with ethyl acetate (100 mL), and the filtrate was concentrated. The residue was purified by flash column chromatography (10% ethyl acetate in hexane) to afford 34 as a pale yellow oil (3.62 g, 89%). $R_f$ 0.53 (25% ethyl acetate in hexane); $^1$H NMR (500 MHz, CDCl$_3$) d 7.34 (m, 5H, Cbz ArH), 7.18 (s, 1H, ArCH), 6.77 (s, 2H, ArH), 6.14 (s (br), 1H, NH), 5.13 (s, 2H, Cbz CH$_2$), 3.81 (s (br), 3H, OCH$_3$), 3.75 (s, 3H, OCH$_3$), 1.00 (s, 18H, t-butyl), 0.16 (s, 12H, SiCH$_3$), Z configuration verified by 11.6% NOE of ArH's upon irradiation of NH; $^{13}$C NMR (100 MHz, CDCl$_3$) d 165.8, 149.8, 144.4, 135.8, 132.5, 130.0, 128.5, 128.4, 128.2, 126.1, 123.4, 120.2, 116.4, 67.6, 60.0, 52.5, 25.7, 18.3, −4.7; IR (neat film) 3500 (w, br), 2951 (m), 1723 (s), 1567 (m), 1493 (s), 1424 (m), 1289 (s), 1259 (s), 1122 (s), 1006 (w), 829 (s) cm$^{-1}$; HRMS (FAB$^+$) m/z: Calcd for C$_{31}$H$_{48}$NO$_7$Si$_2$ (MH$^+$) 602.2969, found 602.2993.

Example 16

Protected Amino Acid 35:

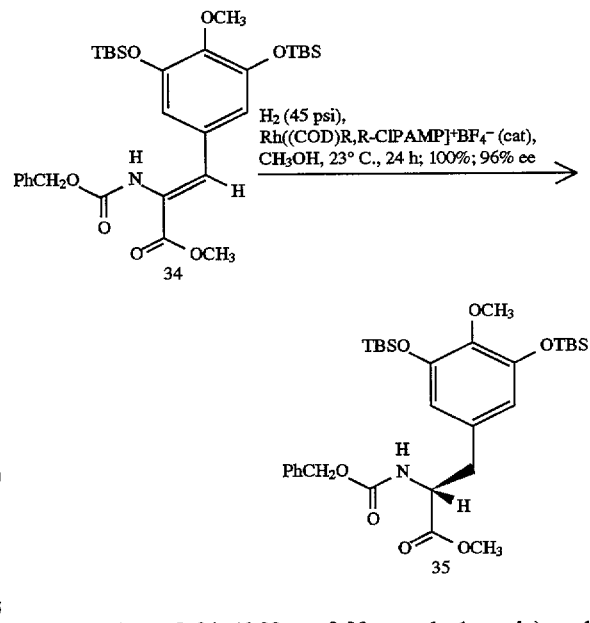

A solution of 34 (6.00 g, 9.98 mmol, 1 equiv) and Rh[(COD)R,R-DiPAMP]$^+$BF$_4^-$ (75 mg) in a mixture of methyl alcohol and dichloromethane (10:1 (v/v), 110 mL) was placed in a high pressure Parr reactor and was purged with hydrogen gas (5×50 psi). The reaction mixture was sealed under hydrogen (50 psi) and was stirred at 23° C. for 24 h. The solution was concentrated, and the residue was purified by flash column chromatography (2.5% ethyl acetate in dichloromethane) to yield 35 (6.01 g, quant) as a colorless viscous oil. $R_f$ 0.41 (20% ethyl acetate in hexane); ee: 96% (HPLC ChirlPak AD, 1% isopropyl alcohol in hexanes); $[a]_D^{23}$ +30.5° (c=0.40, $CH_2Cl_2$); $^1H$ NMR (400 MHz, $CDCl_3$) d 7.32 (m, 5H, Cbz ArH), 6.23 (s, 2H, ArH), 5.18 (d, 1H, J=8.0 Hz, NH), 5.12 (d, 1H, J=12.3 Hz, Cbz $CH_2$), 5.07 (d, 1H, J=12.3 Hz, Cbz $CH_2$), 4.59 (m, 1H, $ArCH_2CH$), 3.72 (s, 3H, $OCH_3$), 3.68 (s, 3H, $OCH_3$), 2.95 (d, 2H, J=5.3 Hz, $ArCH_2$), 0.98 (s, 18H, t-butyl), 0.15 (s, 12H, $SiCH_3$); $^{13}C$ NMR (100 MHz, $CDCl_3$) d 171.9, 155.6, 149.8, 1.42.1, 136.2, 130.5, 128.5, 128.1, 115.6, 67.0, 59.9, 54.5, 52.2, 37.6, 25.7, 18.3, −4.7; IR (neat film) 3350 (w, br), 2931 (m), 2858 (w), 1728 (s), 1577 (m), 1496 (s), 1434 (s), 1360 (m), 1253 (s), 1230 (s), 1209 (m), 1091 (s), 831 (s) $cm^{-1}$; HRMS ($FAB^+$) m/z: Calcd for $C_{31}H_{50}NO_7Si_2$ ($MH^+$) 604.3126, found 604.3103.

Example 17

Amino Ester 36:

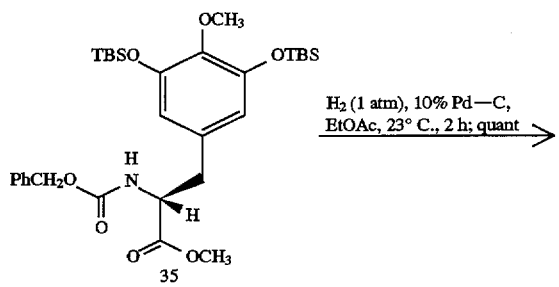

A solution of 35 (1.00 g, 1.66 mmol, 1 equiv) and 10% palladium on activated charcoal (50 mg) in ethyl acetate (40 mL) was stirred under 1 atm of hydrogen gas at 23° C. for 2 h. The reaction mixture was gravity filtered, and the filtrate was concentrated to afford 36 (780 mg, quant) as a viscous oil. $R_f$ 0.38 (50% ethyl acetate in hexane); $[a]_D^{23}$ +5.7° (c=0.70, $CH_2Cl_2$); $^1H$ NMR (500 MHz, $CDCl_3$) d 6.35 (s, 2H, ArH), 3.71 (s, 3H, $OCH_3$), 3.69 (s, 3H, $OCH_3$), 3.67 (dd, 1H, J=5.4, 7.9 Hz, $CHCO_2CH_3$), 2.92 (dd, 1H, J=5.4, 13.5 Hz, $ArCH_2$), 2.71 (dd, 1H, J=7.9, 13.5 Hz, $ArCH_2$), 1.00 (s, 9H, t-butyl), 0.19 (s, 6H, $Si(CH_3)_2$); $^{13}C$ NMR (100 MHz, $CDCl_3$) d 175.2, 149.6, 141.7, 132.1, 115.5, 59.8, 55.6, 51.9, 40.5, 25.6, −4.7; FTIR (neat film) 2955 (m), 2930 (m), 2858 (m), 1743 (s), 1577 (s), 1495 (m), 1433 (m), 1356 (m), 1252 (m), 1229 (m), 1087 (s), 858 (s) $cm^{-1}$; HRMS ($FAB^+$) m/z: Calcd for $C_{23}H_{43}NO_5Si_2Na$ ($MNa^+$) 492.2578, Found 492.2580.

Example 18

Allyl Carbamate 7:

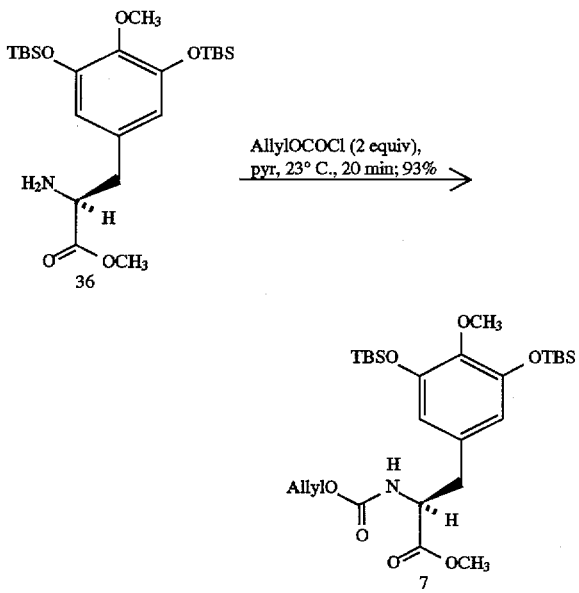

To a solution of 36 (780 mg, 1.66 mmol, 1 equiv) in pyridine (8 mL) at 0° C. was added dropwise allylchloroformate (352 mL, 3.32 mmol, 2.0 equiv), and the reaction was stirred at 23° C. for 20 min. The mixture was concentrated at 23° C. and the residue was partitioned between water (50 mL) and dichloromethane (3×25 mL). The combined organic layers was dried (sodium sulfate) and concentrated, and the residue was purified by flash column chromatography (15% ethyl acetate in hexane) to give 7 (856 mg, 93%) as a colorless oil. $R_f$ 0.37 (20% ethyl acetate in hexane); $[a]_D^{23}$ +26.2° (c=0.40, $CH_2Cl_2$); $^1HNMR$ (400 MHz, $CDCl_3$) d 6.28 (s, 2H, ArH), 5.89 (m, 1H, vinyl H), 5.28 (d, 1H, J=17.3 Hz, vinyl H), 5.20 (d, 1H, J=10.5 Hz, vinyl H), 5.14 (d, 1H, J=7.9 Hz, NH), 4.35 (m, 3H, allylic $CH_2$ and $CHCOCH_3$), 3.73 (s, 3H, $OCH_3$), 3.69 (s, 3H, $OCH_3$), 2.94 (d, 2H, J=9.4 Hz, $ArCH_2$), 1.00 (s, 9H, t-butyl), 0.19 (s, 6H, $Si(CH_3)_2$); $^{13}C$ NMR (100 MHz, $CDCl_3$) d 171.9, 149.8, 132.6, 130.6, 117.8, 115.6, 65.8, 59.9, 54.5, 52.3, 37.5, 25.7, 18.3, −4.7; FTIR (neat film) 3280 (w, br), 2955 (s), 2931 (s), 2858 (s), 1737 (s), 1716 (s), 1578 (s), 1519 (s), 1472 (s), 1361 (m), 1253 (s), 1229 (s), 1207 (m), 1092 (s), 1011 (m), 832 (s) $cm^{-1}$; HRMS ($FAB^+$) m/z: Calcd for $C_{27}H_{47}NO_7Si_2Na$ ($MNa^+$) 576.2789, Found 576.2777.

Example 19

Aldehyde 8:

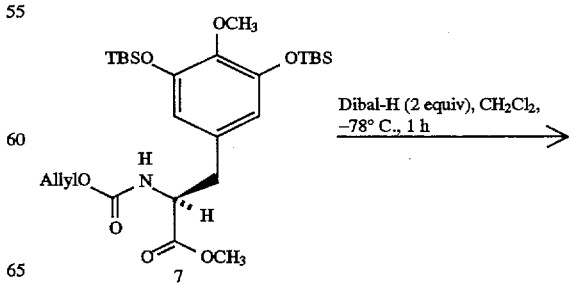

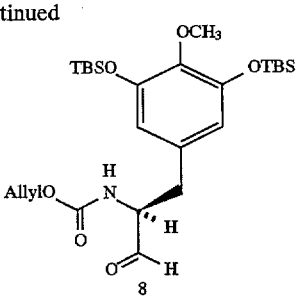

To a solution of 7 (850 mg, 1.54 mmol, 1 equiv) in dichloromethane (85 mL) at −78° C. was added diisobutylaluminun hydride (1.5M in toluene, 2.05 mL, 3.08 mmol, 2.0 equiv), and the reaction mixture was stirred at −78° C. for 1 h. Excess reducing agent was quenched by the sequential addition of methyl alcohol (700 mL), sodium sulfate decahydrate (~5 g), and celite (~2 g). The mixture was stirred at 23° C. for 1 h, and was then filtered through a pad of celite. The filtrate was concentrated and the residue was dissolved in diethyl ether (150 mL). The solution was again filtered through a pad of celite, and the filtrate was concentrated to give the crude aldehyde 8, which was used immediately without further purification in the coupling reaction with 6. $R_f$ 0.33 (25% ethyl acetate in hexanes); $^1$H NMR crude product (400 MHz, CDCl$_3$) d 9.61 (s, 1H, CHO), 6.28 (s, 2H, ArH), 5.90 (m, 1H, vinyl H), 5.30 (dd, 1H, J=1.2, 17.2 Hz, vinyl H), 5.21 (m, 2H, vinyl H, NH), 4.58 (m, 2H, allyl H), 4.41 (m, 1H, CHCHO), 3.70 (s, 3H, OCH$_3$), 3.01 (dd, 1H, J=6.0, 14.4 Hz, ArCH$_2$), 2.94 (dd, 1H, J=6.8, 14.4 Hz, ArCH$_2$), 0.99 (s, 18H, Si-t-butyl), 0.15 (s, 12H, SiCH$_3$).

Synthesis of the Pentacycle

Example 21

Aminonitrile 37:

To a solution of amine 6 (123 mg, 0.467 mmol, 1 equiv) and crude aldehyde 8 (489 mg, 0.935 mmol, 2.0 equiv) in glacial acetic acid (5 mL) was added solid potassium cyanide (608 mg, 9.35 mmol, 20 equiv), and the resulting mixture was stirred at 23° C. for 1 h. The reaction mixture was diluted with ethyl acetate (80 mL) and was washed sequentially with saturated aqueous sodium bicarbonate solution (3×60 mL) and saturated aqueous sodium chloride solution (60 mL). The organic layer was dried (sodium sulfate) and concentrated, and the residue was purified by flash column chromatography (gradient elution: 15%→20% ethyl acetate in hexane) to afford 37 (159 mg) and its aminonitrile epimer (67 mg) in separate fractions (61% total). 37: $R_f$ 0.19 (25% ethyl acetate in hexane); $[a]_D^{23}$ −36.8(c=1.30, CH$_2$Cl$_2$); $^1$HNMR (400 MHz, CDCl$_3$) d (multiple and broadened resonances due to carbamate rotamers at 23° C.) 6.34 (s, ArH), 6.32 (s, ArH), 6.30 (s, ArH), 5.98–5.80 (m, vinyl H and OCH$_2$O), 5.33 (m), 5.28 (m), 5.23 (m), 5.2–4.8 (m (br)), 4.63 (m), 4.57 (m), 4.45 (m (br)), 4.40–4.25 (m) 4.10 (m (br)), 3.93 (m (br)), 3.70 (s, OCH$_3$), 3.61 (s, OCH$_3$), 2.13 (s, ArCH$_3$), 2.08 (s, ArCH$_3$), 1.00 (s, t-butyl), 0.99 (s, t-butyl), 0.19 (s, Si(CH$_3$)$_2$), 0.11 (s, Si(CH$_3$); $^{13}$C NMR (100 MHz, CDCl$_3$) d 171.3, 169.7, 169.2, 156.1, 155.5, 150.1, 150.0, 146.3, 145.1, 142.2, 142.0, 137.9, 132.3, 132.1, 131.3, 130.7, 118.1, 117.9, 117.8, 115.9, 115.5, 115.4, 115.2, 115.0, 110.1, 109.7, 108.9, 107.3, 101.4, 101.3, 73.7, 73.4, 66.0, 60.4, 59.9, 59.8, 57.1, 57.0, 55.2, 55.0, 52.0, 50.7, 47.9, 46.7, 38.2, 35.1, 31.6, 25.7, 22.9, 22.6, 22.0, 21.0, 18.3, 14.1, 8.7, 8.6, −4.7, −4.8; FTIR (neat film) 3300 (m, br), 2955 (s), 2932 (s), 2858 (s), 1727 (s), 1712 (s), 1578 (m), 1495 (m), 1434 (s), 1360 (m), 1255 (s), 1233 (s), 1095 (s), 1043 (m), 1009 (s), 860 (s), 832 (s) cm$^{-1}$; HRMS (FAB$^+$) m/z: Calcd for C$_{40}$H$_{58}$N$_3$O$_{10}$Si$_2$ (MH$^+$) 796.3661, Found 796.3636.

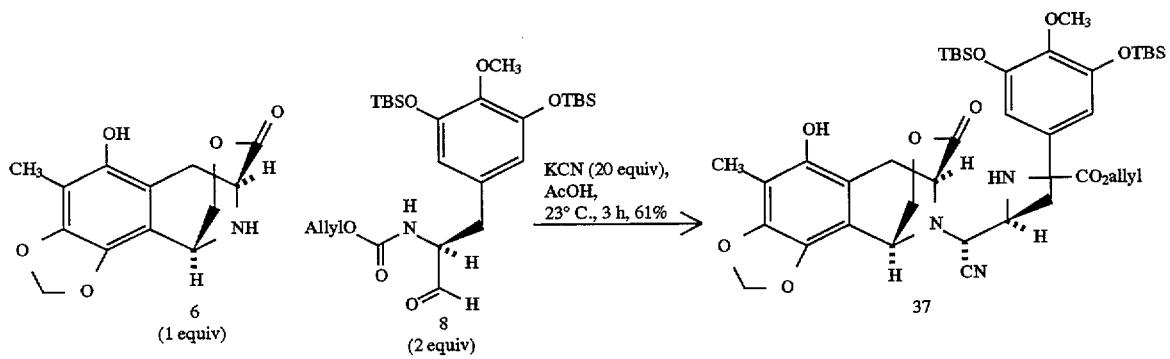

Example 22

Allyl Ether 9:

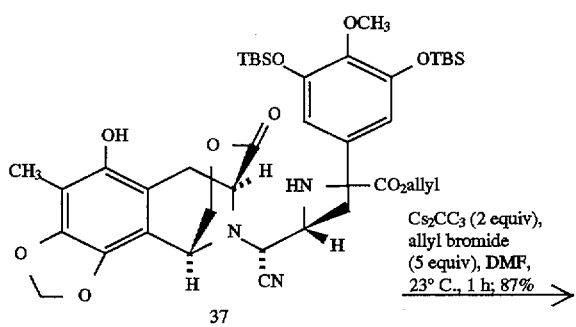

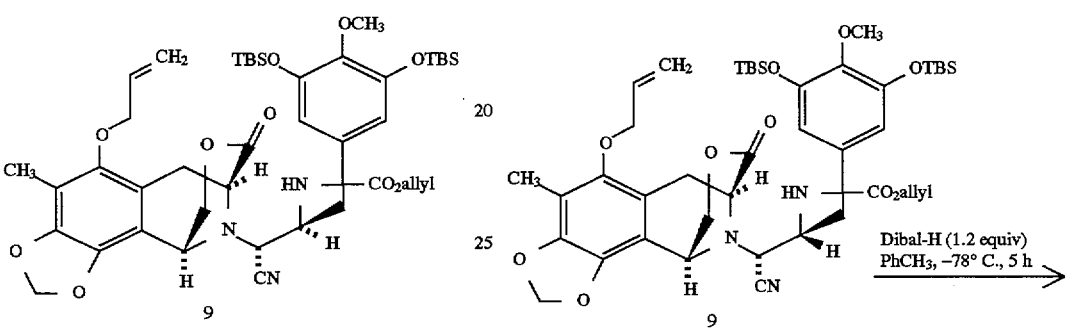

To a solution of aminonitrile 37 (986 mg, 1.24 mmol, 1 equiv) in DMF (10 mL) was added sequentially time-dried cesium carbonate (809 mg, 2.78 mmol, 2.0 equiv) and allyl bromide (537 mL, 6.20 mmol, 5.0 equiv), and the mixture was stirred at 23° C. for 1 h. Excess base was neutralized with the addition of acetic acid (4 mL), and the mixture was then partitioned between saturated aqueous sodium bicarbonate solution (100 mL) and dichloromethane (2×50 mL), The aqueous layer was further extracted with ethyl acetate (2×50 mL). The combined organic layers were dried (sodium sulfate) and concentrated, and the residue was purified by flash column chromatography (20% ethyl acetate in hexane) to afford 9 (901 mg, 87%) as a colorless film. $R_f$ 0.41 (25% ethyl acetate in hexane); $[a]_D^{23}$ −40.0° (c=0.53, $CH_2Cl_2$); $^1HNMR$ (500 MHz, $CDCl_3$) d (multiple and broadened resonances due to carbamate rotamers at 23° C.) 6.32 (s, ArH), 6.29 (s, ArH), 6.1–5.7 (m, vinyl H and $OCH_2O$), 5.41 (m, vinyl H), 5.29 (m, vinyl H), 5.31 (m, vinyl H), 5.30–5.10 (m), 4.93 (m (br)), 4.79 (m (br)), 4.70–4.05 (m), 3.91 (m (br)), 3.70 (s, $OCH_3$), 3.60 (s, $OCH_3$), 3.42 (m), 3.19 (m), 3.04–2.89 (m), 2.64 (m), 2.17 (s, $ArCH_3$), 2.10 (s, $ArCH_3$), 1.01 (s, t-butyl), 0.98 (s, t-butyl), 0.18 (s, $Si(CH_3)_2$), 0.11 (s, $Si(CH_3)_2$); $^{13}C$ NMR (100 MHz, $CDCl_3$) d 169.3, 168.8, 156.1, 155.4, 150.1, 150.0, 149.9, 149.7, 145.4, 145.3, 142.2, 142.0, 140.4, 140.2, 133.4, 133.3, 132.4, 132.1, 131.3, 130.8, 118.1, 117.9, 117.6, 117.5, 117.1, 116.0, 115.4, 115.2, 115.0, 114.1, 113.8, 109.8, 109.2, 101.7, 101.6, 73.6, 73.5, 73.2, 66.0, 59.9, 59.8, 57.2, 56.9, 55.3, 54.9, 53.4, 52.1, 50.6, 48.2, 46.8, 38.1, 35.13, 25.7, 25.6, 23.5, 22.5, 18.3, 9.4, 9.3, −4.7, −4.8; FTIR (neat film) 3300 (w, br), 2955 (m), 2932 (s), 2858 (m), 1727 (s), 1577 (m), 1494 (m), 1461 (s), 1434 (m), 1253 (s), 1232 (s), 1095 (s), 1043 (m), 1009 (m), 860 (m), 832 (s) $cm^{-1}$; HRMS ($FAB^+$) m/z: Calcd for $C_{43}H_{61}N_3O_{10}Si_2Na$ ($MNa^+$) 858.3793, found 858.3820.

Example 23

Triol 10:

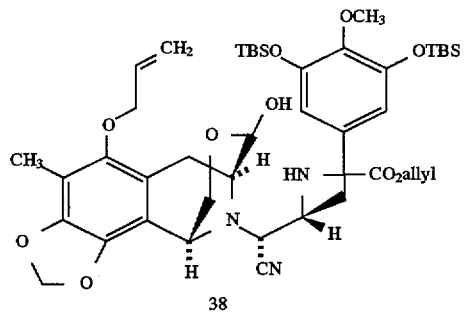

To a solution of 9 (390 mg, 0.467 mmol, 1 equiv) in a solution of toluene (50 mL) at −78° C. was added a solution of diisobutylaluminum hydride (1.5M in toluene, 374 mL, 0.560 mmol, 1.2 equiv), and the resulting solution was stirred at −78° C. for 5 h. Excess reducing agent was quenched by the slow sequential addition of methyl alcohol (500 mL), sodium sulfate decahydrate (~5 g), and celite at −78° C. The suspension was stirred at 23° C. for 1 h before it was filtered through a pad of celite. The filtrate was concentrated, and the residue (38) was dissolved in methyl alcohol (4 mL).

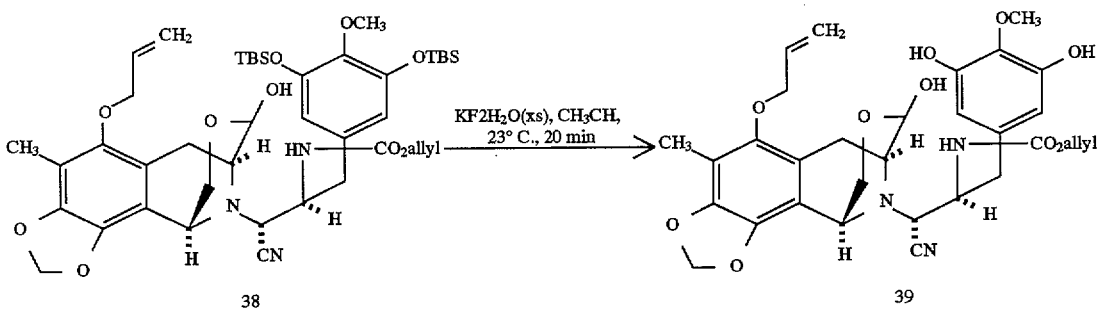

To this solution was added potassium fluoride dihydrate (250 mg, 2.66 mmol, 5.7 equiv), and the reaction was stirred at 23° C. for 20 min. The mixture was partitioned between dichoromethane (50 mL) and 80% saturated aqueous sodium chloride solution (80 mL), and the aqueous phase was further extracted with ethyl acetate (2×50 mL). The combined organic layers were dried (sodium sulfate) and concentrated, and the residue (39) was dissolved in dichloromethane (100 mL).

acetate in hexane); $[\alpha]_D^{23}$ −4.4° (c=0.48, $CH_2Cl_2$); $^1HNMR$ (500 MHz, $CDCl_3$) d (multiple and broadened resonances due to carbamate rotamers at 23° C.) 6.32 (s, 1H, ArH), 6.31 (s, 1H, ArH), 6.29 (m, 1H, vinyl H), 5.90 (m, vinyl H, $OCH_2O$), 5.60 (s (br), ArOH), 5.50 (s(br), ArOH), 5.42 (m, 1H), 5.39 (m, 1H), 5.32–5.17 (m), 4.91 (m, 1H), 4.83 (m, 1H), 4.62 (m), 4.20 (m), 4.31 (m, 1H), 3.97 (m, 2H), 3.83 (s, 3H, $OCH_3$), 3.82 (s, 3H, $OCH_3$), 3.66–3.20 (m), 2.74 (m, 1H, $ArCH_2$), 2.12 (s, 3H, $ArCH_3$), 0.87 (m, 1H, $ArCH_2$); $^{13}C$

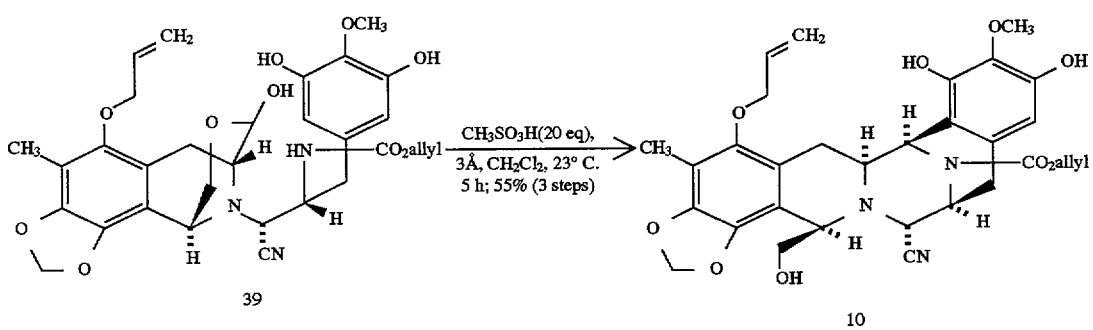

To this solution was added crushed, flamed 3 Å molecular sieves (6.20 g) followed by methanesulfonic acid (531 mL, 8.21 mmol, 20 equiv), and the suspension was stirred at 23° C. for 5 h. Excess acid was quenched by the addition of pyridine (1.32 mL, 16.4 mmol, 40 equiv), and the mixture was suction filtered, washing well 10% isopropyl alcohol in dichloromethane (4×20 mL). The product solution was washed with saturated aqueous sodium chloride solution (150 mL), and the aqueous layer was further extracted with ethyl acetate (2×100 mL) The combined organic layers were dried (sodium sulfate) and concentrated, and the residue was purified by flash column chromatography (gradient elution: 60%→100% ethyl acetate in hexane) to afford triol 10 (152 mg, 55%, 3 steps) as a colorless oil. $R_f$ 0.23 (66% ethyl NMR (100 MHz, $CDCl_3$) d 171.3, 154.4, 153.9, 148.7, 148.6, 148.4, 146.2, 145.9, 145.5, 144.6, 144.5, 139.0, 133.7, 133.6, 132.6, 132.3, 132.0, 130.8, 130.4, 121.3, 120.6, 120.4, 118.8, 118.0, 117.9, 117.8, 117.5, 117.2, 116.3, 116.1, 115.9, 113.7, 112.5, 113.3, 112.1, 107.7, 107.2, 106.6, 101.2, 74.4, 74.1, 66.8, 66.5, 64.3, 60.9, 60.4, 59.0, 58.9, 58.2, 56.6, 52.9, 51.4, 49.8, 49.4, 48.9, 46.6, 31.0, 30.6, 30.4, 25.9, 21.0, 14.1, 9.3; FTIR (neat film) 3300 (m, br), 2902 (m), 1686 (s), 1460 (s), 1432 (s), 1372 (m), 1328 (m), 1291 (m), 1264 (w), 1106 (s), 1064 (m), 1027 (m), 954 (m) $cm^{-1}$; HRMS ($FAB^+$) m/z: Calcd for $C_{31}H_{33}N_3O_9Na$ ($MNa^+$) 614.2114, found 614.2133.

Example 24

Aryl Triflate 40:

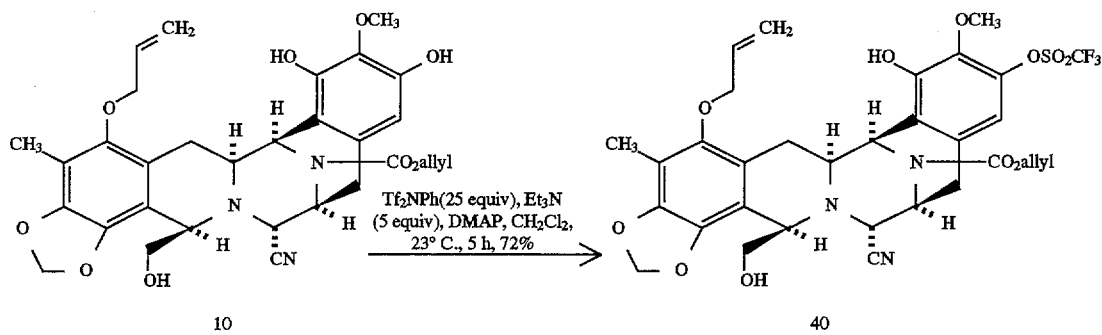

To a solution of 10 (150 mg, 0.253 mmol, 1 equiv) and triethylamine (177 mL, 1.27 mmol, 5.0 equiv) in dichloromethane (15 mL) was added sequentially Example 25

Silyl Ether 41:

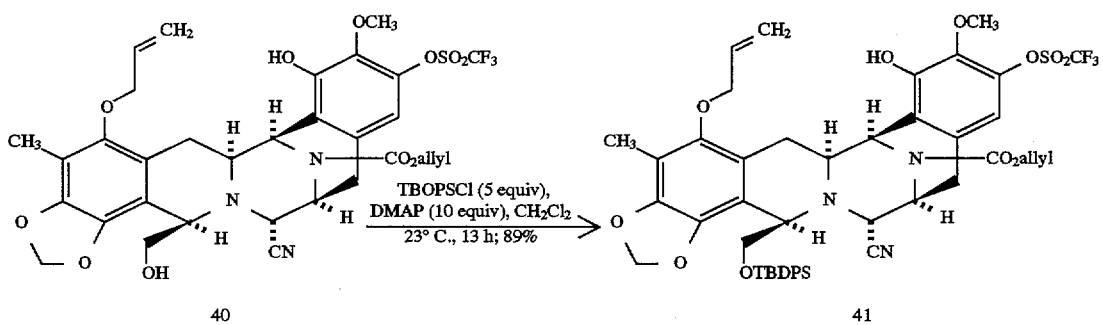

N-phenyltriflimide (227 mg, 0.634 mmol, 2.5 equiv) and DMAP (1 mg), and the reaction was stirred at 23° C. for 6.5 h. Excess base was neutralized by the addition of acetic acid (145 mL, 2.53 mmol, 10 equiv) followed by pyridine (306 mL, 3.79 mmol, 15 equiv). The mixture was partitioned between dichloromethane (50 mL) and saturated aqueous sodium chloride solution (80 mL), and the aqueous layer was further extracted with ethyl acetate (2×50 mL). The combined organic layers were dried (sodium sulfate) and concentrated, and the residue was purified by flash column chromatography (60% ethyl acetate in hexane) to afford 40 (132 mg, 72%) as a colorless film. $R_f$ 0.44 (50% ethyl acetate in hexane); $[a]_D^{23}$ +32.3° (c=0.60, $CH_2Cl_2$); $^1$HNMR (500 MHz, $CDCl_3$) d (signals broadened due to carbamate rotamers at 23° C.) 6.65 (s, 1H, ArH), 6.10 (m, 1H, vinyl H), 5.92 (m, vinyl H and $OCH_2O$), 5.68 (s, ArOH), 5.57 (s (br)), 5.40 (m), 5.26 (m, vinyl H), 4.93 (m), 4.87 (m), 4.63 (m), 4.21 (m), 3.98 (m), 3.92 (s, 3H, $OCH_3$), 3.7–3.4 (m), 3.30 (m), 2.86 (m), 2.13 (s, 3H, $ArCH_3$), 1.81 (m, 1H, ArCH); $^{13}$C NMR (126 MHz, $CDCl_3$) d 154.1, 153.9, 148.7, 148.5, 147.2, 146.6, 144.8, 144.7, 141.1, 140.9, 139.1, 138.9, 136.9, 136.7, 134.2, 133.7, 132.2, 132.1, 131.7, 129.4, 127.1, 123.2, 122.3, 121.3, 121.2, 120.1, 119.9, 119.8, 118.2, 17.6, 117.5, 117.2, 116.2, 116.1, 112.8, 112.7, 112.3, 112.2, 112.1, 101.2, 74.4, 66.9, 66.7, 65.6, 65.4, 61.9, 59.5, 59.4, 58.5, 56.5, 49.7, 49.2, 48.9, 48.3, 30.9, 30.3, 25.9, 14.1, 9.3; FTIR (neat film): 3350 (w, br), 2928 (w), 1694 (s), 1685 (s), 1451 (s), 1422 (s), 1319 (m), 1257 (s), 1214 (s), 1138 (s), 1102 (s), 1026 (s), 989 (m) cm$^{-1}$; HRMS (FAB$^+$) m/z: Calcd for $C_{32}H_{32}F_3N_3O_{11}SNa$ (MNa$^+$) 746.1607, found 746.1616.

To a solution of 41 (90 mg, 0.124 mmol, 1 equiv) and DMAP (152 mg, 1.24 mmol, 10 equiv) in dichloromethane (10 mL) was added t-butyldiphenylsilylchloride (162 mL, 0.622 mmol, 5.0 equiv), and the solution was stirred at 23° C. for 13 h. The excess base was quenched by the addition of acetic acid (150 mL), and the mixture was partitioned between water (50 mL), and dichloromethane (3×30 mL). The combined organic layers were dried (sodium sulfate) and concentrated, and the residue was purified by flash column chromatography (gradient elution: 25%→50% ethyl acetate in hexane) to afford 41 (106 mg, 89%) as a colorless glassy solid. $R_f$ 0.66 (50% ethyl acetate in hexane); $[a]_D^{23}$ +45.2° (c=1.00, $CH_2Cl_2$); $^1$HNMR (500 MHz, $CDCl_3$) d (multiple and broadened resonances due to carbamate rotamers at 23° C.) 5.70 (m, 1H, ArH), 7.56 (m, ArH), 7.45–7.15 (m, ArH), 6.58 (m, 1H, ArH), 6.06 (m, 1H, vinyl H), 5.90 (m, 1H, vinyl H), 5.80 (s, 1H, $OCH_2O$), 5.13 (m, 2H, ArOH and $OCH_2O$), 5.4–5.1 (m), 4.92 (m), 4.83 (m), 4.61 (m), 4.20 (m), 4.09 (m), 3.92 (s, 3H, $OCH_3$), 3.7–3.2 (m), 2.98 (m, 1H, ArCH), 2.11 (s, 3H, $ArCH_3$), 1.90 (m, 1H, ArCH), 1.01 (s, t-butyl), 1.00 (s, t-butyl); $^{13}$C NMR (126 MHz, $CDCl_3$) d 171.2, 154.2, 148.6, 148.5, 147.4, 146.7, 144.6, 144.4, 141.3, 141.2, 139.3, 139.1, 136.6, 136.4, 135.7, 135.3, 134.8, 133.8, 133.0, 132.5, 132.4, 129.8, 129.7, 127.7, 122.2, 122.1, 120.5, 120.4, 119.9, 118.2, 117.6, 117.5, 117.3, 117.2, 116.9, 116.7, 112.7, 112.4, 112.1, 111.8, 101.0, 74.4, 69.3, 68.8, 66.8, 66.5, 65.3, 61.9, 60.5, 60.4, 60.3, 59.3, 56.6, 49.8, 49.2, 48.9, 48.3, 31.6, 30.7, 30.0, 26.8, 26.5, 26.2, 26.1, 22.6, 21.0, 19.0, 14.2, 14.1, 9.3, 9.2; FTIR (neat film) 3350 (w, br), 2951 (m), 1694 (s), 1458 (m), 1451 (s), 1425 (s), 1317 (m), 1257 (m), 1214 (s), 1139 (s), 1110 (s), 1038 (m), 989 (m), 824 (m) cm$^{-1}$; HRMS (FAB$^+$) m/z: Calcd for $C_{48}H_{50}F_3N_3O_{11}SSiNa$ (MNa$^+$) 984.2785, found 984.2771.

Example 26

Methoxymethyl Ether 42:

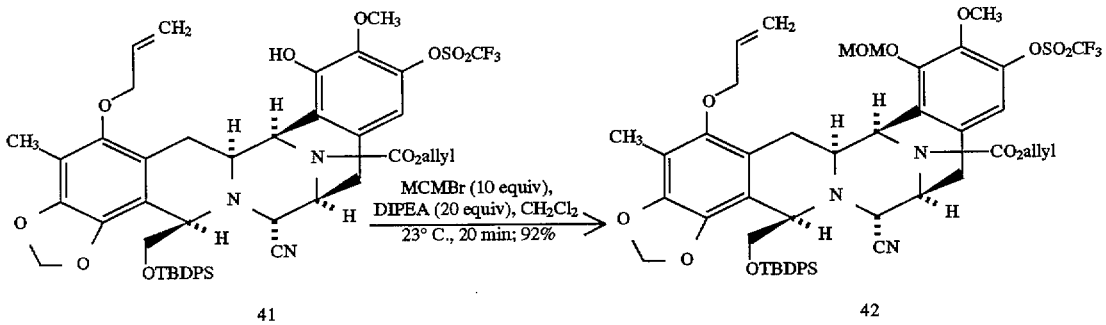

To a solution of 41 (94 mg, 0.0978 mmol, 1 equiv) and diisopropylethylamine (340 mL, 1.96 mmol, 20 equiv) in dichloromethane (6 mL) at 0° C. was added bromomethylmethyl ether (80 mL, 0.978 mmol, 10 equiv), and the solution was stirred at 23° C. for 20 min. After the reaction was quenched with methyl alcohol (100 mL), the mixture was partitioned between saturated aqueous sodium bicarbonate solution (30 mL), and dichloromethane (2×30 mL), and the combined organic layers were dried (sodium sulfate) and concentrated. The residue was purified by flash column chromatography (25% ethyl acetate in hexane) to afford 42 (90 mg, 92%) as a colorless film. $R_f$ 0.66 (50% ethyl acetate in hexane); $[a]_D^{23}$ +57.0 (c=1.0, $CH_2Cl_2$); $^1$HNMR (400 MHz, $CDCl_3$) d (multiple and broadened resonances due to carbamate rotamers at 23° C.) 7.6–7.1 (m, 10H, ArH), 6.74 (s, 1H, ArH), 6.10 (m, 1H, vinyl H), 5.93 (m, 1H, vinyl H), 5.81 (s, 1H, $OCH_2O$), 5.65 (s, 1H, $OCH_2O$), 5.45–5.13 (m, vinyl H, and $OCH_2O$), 4.91 (m, 1H), 4.69 (m, 1H), 4.59 (m, 2H), 4.16 (m, 2H), 4.07 (m, 1H), 3.87 (m, 3H, $OCH_3$), 3.73–3.60 (m, 4H, $OCH_3$ and CHOSi), 3.4–3.2 (m, 3H, CHOSi and ArCH), 2.97 (m, 1H, $ArCH_2$), 2.12 (s, 3H, $ArCH_3$), 1.83 (m, 1H, $ArCH_2$), 0.97 (m, 9H, t-butyl); $^{13}$C NMR (100 MHz, $CDCl_3$) d 154.1, 153.9, 148.5, 147.9, 144.6, 142.6, 142.4, 142.1, 139.3, 139.2, 135.7, 135.3, 134.8, 133.7, 132.9, 132.5, 132.4, 132.3, 129.8, 128.8, 128.7, 127.7, 120.3, 120.1, 118.5, 118.1, 117.5, 117.1, 116.7, 116.6, 116.5, 112.5, 112.4, 112.0, 111.8, 101.1, 99.7, 74.2, 69.2, 68.8, 67.0, 66.7, 61.1, 60.4, 60.2, 59.2, 58.4, 58.1, 56.5, 50.2, 49.3, 49.2, 48.3, 30.7, 30.1, 29.7, 26.8, 26.1, 26.0, 19.0, 9.2; FTIR (neat film) 2959 (m), 1709 (s), 1426 (s), 1315 (m), 1253 (m), 1213 (s), 1140 (s), 1110 (s), 1066 (s), 1015 (s), 987 (s), 921 (s), 825 (m) $cm^{-1}$; MS ($FAB^+$) m/z: Calcd for $C_{50}H_{54}F_3N_3O_{12}SSiNa$ ($MNa^+$) 1028, found 1028.

Example 27

Aminophenol 43:

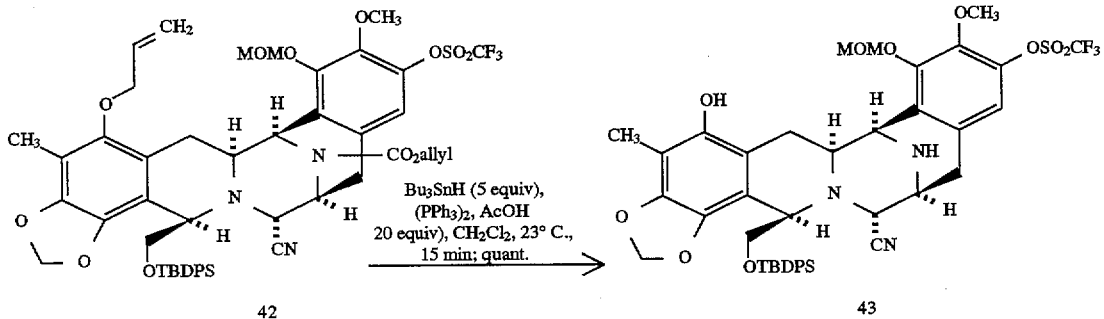

To a solution of 42 (90 mg, 0.0895 mmol, 1 equiv), acetic acid (102 mL, 1.79 mmol, 20 equiv), and dichloro-bis (triphenylphosphine)palladium (5 mg) in dichloro-methane (5 mL) was added tributyltin hydride (120 mL, 0.448 mmol, 5.0 equiv), and the yellow/brown solution was stirred at 23° C. for 15 min. The mixture was loaded onto a silica gel column, and the product was purified by flash column chromatography (gradient elution: 50% ethyl acetate in hexane→100% ethyl acetate) to afford 43 (79 mg, quant) as a colorless film. $R_f$ 0.30 (50% ethyl acetate in hexane); $[a]_D^{23}$ +34.0 (c=1.0, $CH_2Cl_2$); $^1$HNMR (500 MHz, $CDCl_3$) d 7.59 (d, 2H, J=9.4 Hz, ArH), 7.5–7.2 (m, 8H, ArH), 6.76 (s, 1H, ArH), 5.75 (s, 1H, $OCH_2O$), 5.61 (s, 1H, $OCH_2O$), 5.39 (d, 1H, J=5.3 Hz, $OCH_2O$), 5.22 (d, 1H, J=5.3 Hz, $OCH_2O$), 5.14 (s, 1H, ArOH), 4.60 (d, 1H, J=1.1 Hz, ArCH), 4.49 (d, 1H, J=2.3 Hz, CHCN), 4.07 (m, 1H, ArCH), 3.85 (s, 3H, $OCH_3$), 3.70 (s, 3H, $OCH_3$), 3.75–3.40 (m (br)), 3.35 (dd, 1H, J=7.6, 10.2 Hz, CHOSi), 3.28 (dd, 1H, J=~1, 10.2 Hz, CHOSi), 3.13 (m, 2H, $ArCH_2$), 2.94 (d, 1H, J=15.9 Hz, $ArCH_2$), 2.07 (s, 3H, $ArCH_3$), 1.77 (dd, 1H, J=11.0, 13.6 Hz, $ArCH_2$), 0.95 (s, 9H, t-butyl); $^{13}$C NMR (100 MHz, $CDCl_3$) d 171.2, 148.4, 145.2, 144.5, 142.0, 141.2, 136.6, 135.6, 135.3, 133.0, 132.9, 132.6, 130.8, 129.7, 127.6, 120.2, 117.9, 117.1, 116.5, 112.4, 111.7, 106.0, 100.6, 99.9, 77.2, 69.2, 61.3, 61.2, 60.4, 59.5, 58.1, 56.8, 49.8, 49.2, 31.0, 26.7, 26.2, 21.0, 19.0, 14.1, 8.7; FTIR (neat film) 3400 (w, br), 2929 (m), 1488 (m), 1460 (m), 1426 (s), 1250 (m), 1213 (s), 1158 (m), 1140 (s), 1105 (s), 1034 (m), 1011 (m), 982 (m), 915 (m), 824 (m) $cm^{-1}$; HRMS ($FAB^+$) m/z: Calcd for $C_{43}H_{47}F_3N_3O_{10}SSiNa$ ($MNa^+$) 882.2704, found 882.2694.

Example 28

Phenol 44:

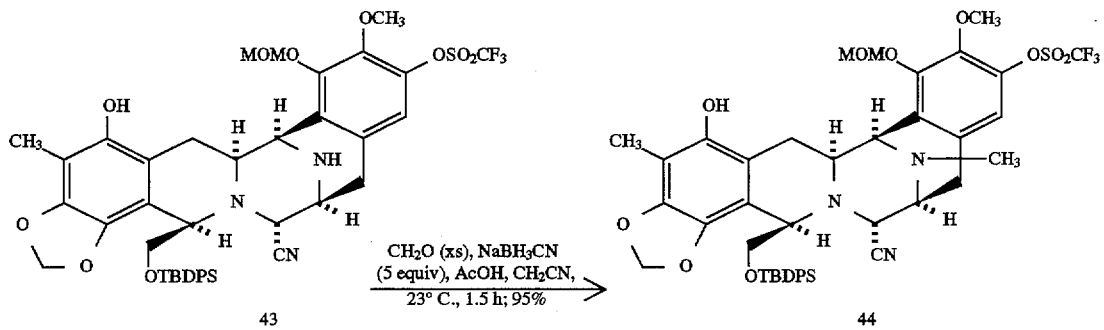

To a solution of 43 (79 mg, 0.0896 mmol, 1 equiv) and formalin solution (600 mL) in acetonitrile (6 mL) was added solid sodium cyanoborohydride (17 mg, 0.269 mmol, 5.0 equiv), and the solution was stirred at 23° C. for 30 min. Acetic acid (102 mL, 1.79 mmol, 20 equiv) was added and the reaction was stirred at 23° C. for a further 1.5 h. The mixture was partitioned between saturated aqueous sodium bicarbonate solution (40 mL) and dichloromethane (30 mL), and the aqueous layer was further extracted with ethyl acetate (2×30 mL). The combined organic layers were dried (sodium sulfate) and concentrated, and the residue was purified by flash column chromatography (gradient elution: 33%→50% ethyl acetate in hexane) to afford 44 (76 mg, 95%) as a colorless film. $R_f$ 0.60 (50% ethyl acetate in hexane); $[a]_D^{23}$ +33.5 (c=1.0, $CH_2Cl_2$); $^1$HNMR (500 MHz, CDCl3) d 7.59 (m, 2H, ArH), 7.46–7.22 (m, 8H, ArH), 6.74 (s, 1H, ArH), 5.74 (d, 1H, J=1.5 Hz, $OCH_2O$), 5.60 (d, 1H, J=1.5 Hz, $OCH_2O$), 5.35 (d, 1H, J=5.7 Hz, $OCH_2O$), 5.21 (d, 1H, J=5.7 Hz, $OCH_2O$), 5.01 (s, 1H, ArOH), 4.89 (m, 1H), 4.60 (d, 1H, J=3.0 Hz), 4.25 (m, 1H), 4.11 (m, 1H), 3.86 (s, 3H, $OCH_3$), 3.67 (s, 3H, $OCH_3$), 3.39–3.30 (m, 3H), 3.09 (dd, 1H, J=2.6, 15.2 Hz, $ArCH_2$), 3.01 (dd, 1H, J=7.3, 18.2 Hz, $ArCH_2$), 2.74 (d, 1H, J=18.2 Hz, $ArCH_2$), 2.30 (s, 3H, $NCH_3$), 2.05 (s, 3H, $ArCH_3$), 1.79 (dd, 1H, J=11.3, 15.2 Hz, $ArCH_2$), 0.97 (s, 9H, t-butyl); $^{13}$C NMR (100 MHz, CDCl$_3$) d 150.1, 145.1, 144.4, 141.8, 141.7, 136.7, 135.7, 135.3, 133.0, 132.6, 132.2, 129.7, 127.6, 126.8, 120.3, 118.3, 118.0, 117.1, 116.0, 112.5, 111.9, 106.1, 100.7, 99.9, 77.2, 69.3, 61.6, 61.3, 58.9, 58.2, 56.9, 56.8, 55.0, 48.7, 41.6, 26.7, 25.8, 25.6, 19.0, 14.1, 8.7; FTIR (neat film) 3400 (w, br), 2932 (m), 1466 (m), 1426 (s), 1249 (m), 1213 (s), 1156 (s), 1140 (s), 1107 (s), 1063 (m), 1035 (m), 1013 (s), 992 (s), 976 (s), 958 (m), 934 (m) cm$^{-1}$; HRMS (FAB$^+$) m/z: Calcd for $C_{44}H_{49}F_3N_3O_{10}SSi$ (MH$^+$) 896.2860, found 896.2872.

Example 29

Phenol 11:

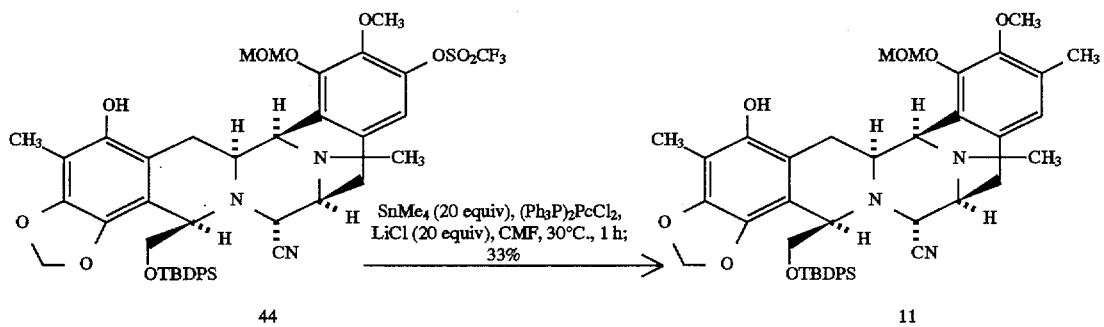

To a solution of 44 (17 mg, 0.0190 mmol, 1 equiv), lithium chloride (16 mg, 0.380 mmol, 20 equiv), and dichlorobis(triphenylphosphine)palladium (1 mg) in DMF (0.5 mL) was added tetramethyl tin (53 mL, 0.380 mmol, 20 equiv), and the brown solution was stirred at 80° C. for 2 h. The reaction mixture was partitioned between water (30 mL) and dichloromethane (2×20 mL). The aqueous layer was further extracted with ethyl acetate (2×20 mL), and the combined organic layers were dried (sodium sulfate) and concentrated. The product was purified by flash column chromatography (gradient elution: 33%→50% ethyl acetate in hexane) to afford 11 (14 mg, 96) as a colorless film. $R_f$ 0.27 (20% ethyl acetate in benzene); $[a]_D^{23}$ +11.2 (c=0.55, $CH_2Cl_2$); $^1$HNMR (400 MHz, CDCl$_3$) d 7.56 (m, 2H, ArH), 7.41–7.25 (m, 8H, ArH), 6.67 (s, 1H, ArH), 5.72 (d, 1H, J=1.0 Hz, $OCH_2O$), 5.58 (d, 1H, J=1.0 Hz, $OCH_2O$), 5.51 (s, 1H, ArOH), 5.38 (d, 1H, J=5.7 Hz, $OCH_2O$), 5.16 (d, 1H, J=5.7 Hz, $OCH_2O$), 4.57 (d, 1H, J=2.9 Hz), 4.21 (m, 1H), 4.09 (m, 1H), 3.72 (s, 3H, $OCH_3$), 3.71 (s, 3H, OCH), 3.68 (dd, 1H, J=2.1, 10.4 Hz), 3.38–3.26 (m, 3H), 3.11 (dd, 1H, J=2.5, 15.7 Hz, $ArCH_2$), 3.01 (dd, 1H, J=8.9, 17.9 Hz, $ArCH_2$), 2.70 (d, 1H, J=17.9 Hz, $ArCH_2$), 2.31 (s, 3H, $NCH_3$), 2.25 (s, 3H, $ArCH_3$), 2.06 (s, 3H, $ArCH_3$), 1.89 (dd, 1H, J=12.1, 15.7 Hz, $ArCH_2$), 0.90 (s, 9H, t-butyl), +3.1% nOe of ArH upon irradiation of $ArCH_3$; $^{13}$C NMR (100 MHz, CDCl$_3$) d 149.0, 147.4, 145.3, 144.3, 136.3, 135.7, 135.4, 133.2, 130.9, 130.5, 129.6, 129.5, 127.5, 125.0, 118.6, 112.5, 112.1, 105.7, 100.5, 99.8, 68.5, 61.5, 59.7, 58.8, 57.7, 56.9, 56.5, 55.4, 41.7, 26.6, 26.2, 25.5, 18.9, 15.8, 14.2, 8.7; FTIR (neat film) 3400 (w, br), 2928 (s), 2855 (s), 1459 (s), 1432 (s), 1156 (m), 1106 (s), 1061 (m), 1046 (m), 1023 (m), 967 (m), 926 (m) cm$^{-1}$; HRMS (FAB$^+$) m/z: Calcd for $C_{44}H_{51}N_3O_7SiNa$ (MNa$^+$) 784.3394, found 784.3367.

Example 30

Hydroxy Dienone 45:

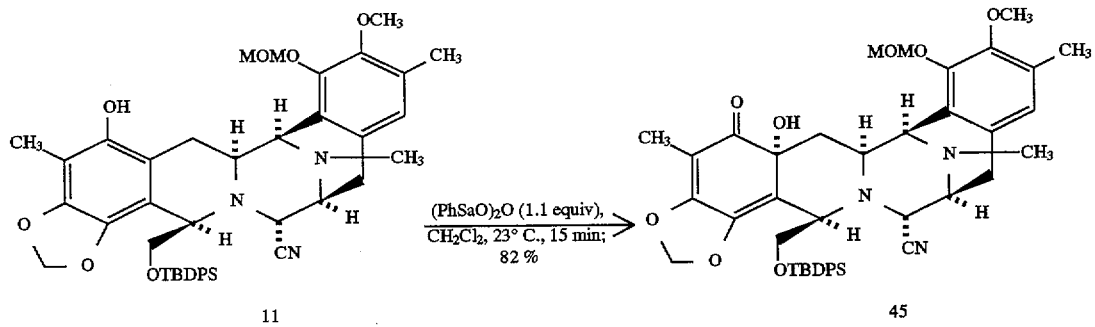

To a solution of 11 (40 mg, 0.0525 mmol, 1 equiv) in dichloromethane (6 mL) was added benzeneseleninic anhydride (21 mg, 0.0578 mmol, 1.1 equiv), and the purple solution was stirred at 23° C. for 15 min. The mixture was quenched with saturated aqueous sodium bicarbonate solution (6 mL) before it was partitioned between saturated aqueous sodium bicarbonate solution (30 mL) and dichloromethane (2×20 mL). The aqueous layer was further extracted with ethyl acetate (2×20 mL) and the combined organic layers were dried (sodium sulfate) and concentrated. The residue was purified by flash column chromatography (gradient elution: 33%→50% ethyl acetate in hexane) to afford 45 (33 mg, 82%) as a colorless film. R$_f$ 0.27 (50% ethyl acetate in hexane); [a]$_D^{23}$ +148.2 (c=0.50, CH$_2$Cl$_2$); $^1$HNMR (400 MHz, CDCl$_3$) d 7.7–7.3 (m, 10H, ArH), 6.54 (s, 1H, ArH), 5.28 (s, 1H, OCH$_2$O), 5.23 (s, 1H, OCH$_2$O), 5.02 (d, 1H, J=5.7 Hz, OCH$_2$O), 4.99 (d, 1H, J=5.7 Hz, OCH$_2$O), 4.46 (d, 1H, J=2.8 Hz), 4.35 (dd, 1H, J=2.8, 14.5 Hz), 4.05–3.95 (m, 2H), 3.88 (m, 1H), 3.79 (m, 1H), 3.63 (s, 3H, OCH$_3$), 3.31 (s, 3H, OCH$_3$), 2.90 (dd, 1H, J=8.7, 17.8 Hz, ArCH$_2$), 2.39 (d, 1H, J=17.8 Hz, ArCH$_2$), 2.23 (s, 3H, NCH$_3$), 2.21 (m, 1H, CH$_2$COH), 2.19 (s, 3H, ArCH$_3$), 2.03 (m, 1H, CH$_2$COH), 1.73 (s, 3H, CH$_3$), 1.10 (s, 9H, t-butyl); $^{13}$C NMR (100 MHz, CDCl$_3$) d 200.9, 160.2, 148.6, 148.0, 137.7, 135.8, 135.6, 133.6, 132.9, 130.5, 130.2, 129.8, 129.7, 129.6, 129.5, 127.7, 127.6, 127.5, 125.1, 124.4, 117.2, 113.5, 100.2, 99.1, 77.2, 72.9, 64.3, 60.3, 59.7, 59.6, 58.9, 57.7, 56.8, 56.5, 56.2, 55.3, 55.2, 42.6, 41.6, 41.3, 35.6, 26.9, 25.8, 25.6, 21.0, 19.4, 19.0, 15.8, 14.2, 7.0; FTIR (neat film) 3500 (w, br), 2929 (s), 1634 (s), 1428 (m), 1377 (m), 1346 (s), 1330 (s), 1232 (m), 1145 (s), 112 (s), 1065 (s), 1054 (s), 1034 (s), 1014 (s), 998 (m), 925 (s), 823 (m) cm$^{-1}$; HRMS (FAB$^+$) m/z: Calcd for $C_{44}H_{51}N_3O8SiNa$ (MNa$^+$) 800.3340, found 800.3313.

Example 31

Diol 12:

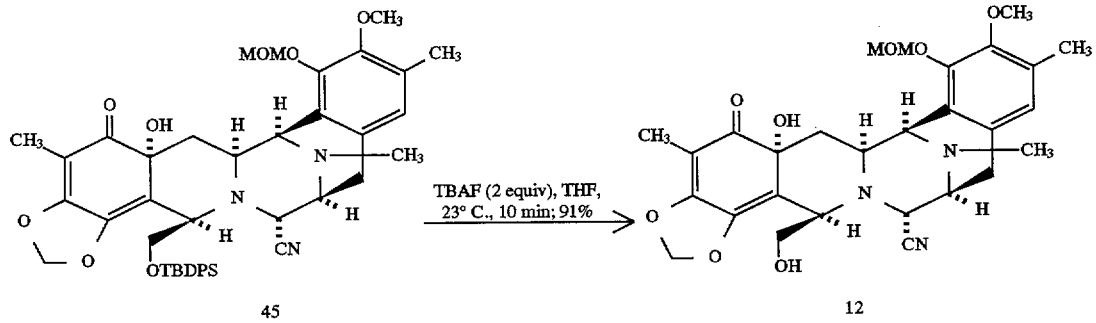

To a solution of 45 (30 mg, 0.0386 mmol, 1 equiv) in THF (4 mL) was added tetrabutylammonium fluoride (1M solution in tetrahydrofuran, 77 mL, 0.0772 mmol, 2.0 equiv), and the solution was stirred at 23° C. for 10 min. The mixture was partitioned between saturated aqueous sodium chloride solution (30 mL) and ethyl acetate (3×20 mL). The aqueous layer was further extracted with dichloromethane (2×20 mL), and combined organic layers were dried (sodium sulfate) and concentrated. The residue was purified by flash column chromatography (gradient elution: 75%→100% ethyl acetate in hexane) to afford 12 (19 mg, 91%) as a colorless film. R$_f$ 0.25 (75% ethyl acetate in hexane); [a]$_D^{23}$ +156.2 (c=0.11, CH$_2$Cl$_2$); $^1$HNMR (500 MHz, CDCl$_3$) d 6.72 (s, 1H, ArH), 5.86 (s, 2H, OCH$_2$O), 5.12 (s, 2H, OCH$_2$O), 4.10 (m, 2H), 3.92 (s, 3H, OCH$_3$), 3.88 (m, 1H), 3.80 (m, 1H), 3.62 (m, 1H), 3.52 (s, 3H, OCH$_3$), 3.34 (m, 1H), 3.04 (dd, 1H, J=7.7, 18.0 Hz, ArCH$_2$), 2.68 (m, 1H), 2.62 (d, 1H, J=18.0 Hz, ArCH$_2$), 2.32 (s, 3H, NCH$_3$), 2.24 (s, 3H, ArCH$_3$), 2.21 (m, 1H, CH$_2$COH), 2.00 (dd, 1H, J=8.5, 15.1 Hz, CH$_2$COH), 1.80 (s, 3H, CH$_3$); $^{13}$C NMR (100 MHz, CDCl$_3$) d 198.7, 158.9, 148.8, 148.4, 140.4, 131.3, 130.3, 125.4, 123.0, 116.9, 111.1, 104.3, 101.6, 99.4, 77.2, 70.3, 61.7, 60.5, 58.5, 58.0, 57.6, 57.2, 55.2, 41.6, 36.3, 25.6, 15.7, 7.2; FTIR (neat film) 3450 (w, br), 2926 (s), 1645 (s), 1417 (m), 1378 (m), 1345 (s), 1234 (m), 1157 (m), 1133 (m), 1089 (m), 1059 (m), 1038 (m), 995 (m), 970 (m), 954 (m), 924 (m) cm$^{-1}$; HRMS (FAB$^+$) m/z: Calcd for C$_{28}$H$_{33}$N$_3$O$_8$Na (MNa$^+$) 562.2165, found 562.2173.

Final Steps

Example 32

Ester 13:

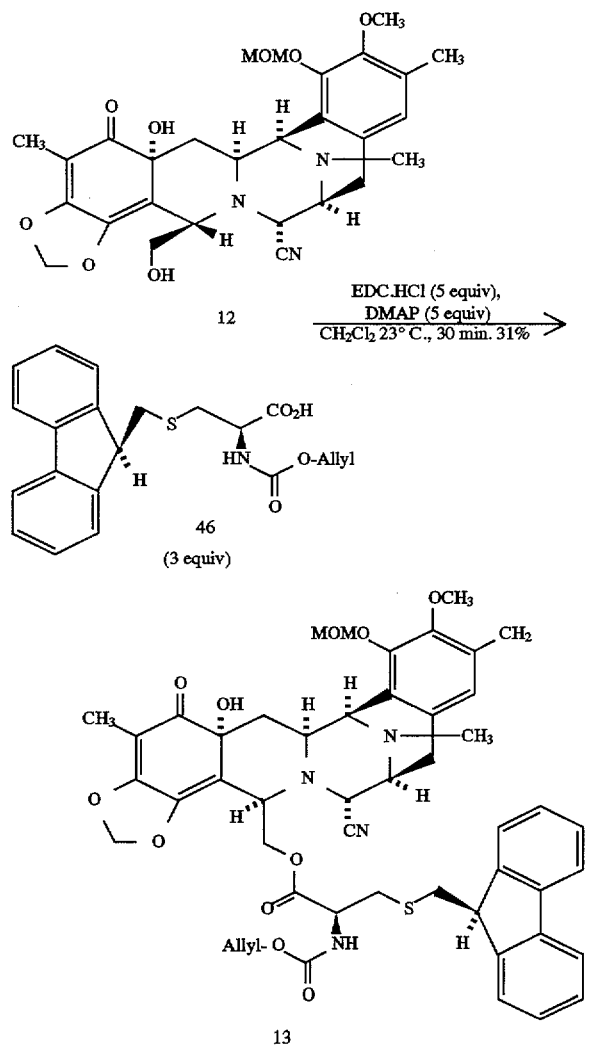

To a solution of alcohol 12 (9.0 mg, 0.0167 mmol, 1 equiv) and acid 46 (19 mg, 0.0501 mmol, 3.0 equiv) in dichloromethane (1.5 mL) was added DMAP (10 mg, 0.0835 mmol, 5.0 equiv) and 1-(3-dimethylaminopropyl)-3-ethylcarbodiimide.HCl (16 mg, 0.0835 mmol, 5.0 equiv), and the resulting solution was stirred at 23° C. for 1.5 h. The reaction mixture was partitioned between saturated aqueous sodium bicarbonate solution (30 mL) and dichloromethane (2×20 mL), and the aqueous layer was further extracted with ethyl acetate (2×20 mL). The combined organic layers were dried (sodium sulfate) and concentrated, and the residue was purified by flash column chromatography (gradient elution: 50→60% ethyl acetate in hexanes) to afford 13 (13.7 mg, 91%). R$_f$ 0.15 (50% ethyl acetate in hexanes); [a]$_D^{23}$ +200 (c=0.2, CH$_2$Cl$_2$); $^1$H NMR (400 MHz, CDCl$_3$) d 7.75 (m, 2H, ArH), 7.62 (m, 2H, ArH), 7.40 (m, 2H, ArH), 7.30 (m, 2H, ArH), 6.63 (s, 1H, ArH), 5.90 (m, 1H, vinyl H), 5.74 (s, 1H, OCH$_2$O), 5.71 (s, 1H, OCH$_2$O), 5.52 (d, 1H, J=8.3 Hz, NH), 5.32 (d, 1H, J=16.7 Hz, vinyl H), 5.22 (d, 1H, J=10.0 Hz, vinyl H), 5.10 (m, 2H, OCH$_2$O), 4.57 (m, 2H), 4.50 (m, 1H), 4.23 (dd, 1H, J=6.2, 11.2 Hz), 4.04 (m, 1H), 4.00 (dd, 1H, J=2.5, 13.3 Hz), 3.93 (m, 1H), 3.84 (m, 3H, OCH$_3$), 3.49 (m, 3H, OCH$_3$), 3.24 (m, 1H), 3.08 (m, 3H), 2.95 (m, 3H), 2.44 (d, 1H, J=18.1 Hz), 2.36 (dd, 1H, J=5.8, 15.0 Hz), 2.25 (s, 3H, NCH$_3$), 2.20 (s, 3H, ArCH$_3$), 1.83 (dd, 1H, J=9.4, 15.0 Hz, C(OH)—CH), 1.78 (s, 3H, CH$_3$); $^{13}$C NMR (100 MHz, CD$_2$Cl$_2$) d 198.7, 170.6, 158.4, 155.8, 149.0, 148.9, 146.1, 142.8, 141.4, 133.0, 131.5, 130.5, 128.0, 127.4, 125.5, 125.1, 123.4, 120.2, 118.0, 117.6, 108.5, 104.6, 102.1, 99.7, 70.9, 66.7, 66.3, 61.2, 60.4, 57.9, 57.2, 56.5, 56.0, 55.7, 54.2, 47.3, 41.5, 37.3, 35.6, 25.9, 15.9, 7.5; FTIR (neat film) 3400 (w, br), 2921 (m), 1722 (s), 1650 (s), 1448 (m), 1378 (m), 1346 (s), 1251 (m, 1234 (m), 1208 (m), 1205 (m), 1157 (m), 1133 (m), 1054 (m), 1040 (m), 1033 (m), 995 (m) cm$^{-1}$; HRMS (FAB$^+$) m/z: Calcd for C$_{49}$H$_{52}$N$_4$O$_{11}$SNa (MNa$^+$) 927.3251, found 927.3255.

Example 33

Lactone 14:

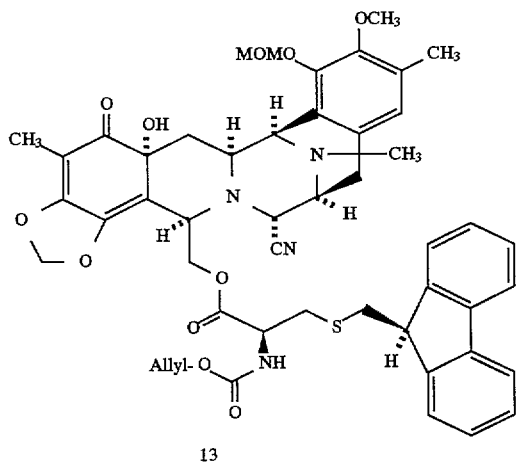

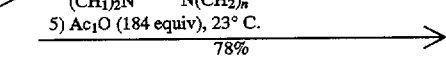

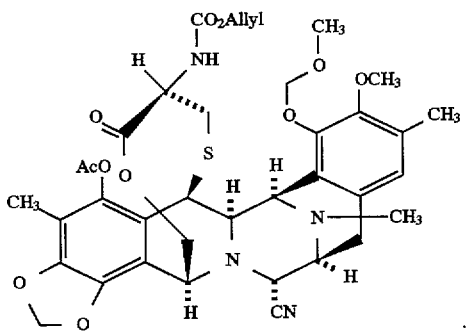

14

To a solution of triflic anhydride (8 mL, 0.0476 mmol, 16.5 equiv) in dichloromethane (2.6 mL) at −78° C. was added DMSO (18 mL, 0.254 mmol, 88 equiv), and the solution was stirred at −78° C. for 15 min. A solution of 13 (2.6 mg, 0.00287 mmol, 1 equiv) in dichloromethane (2.6 mL) was added dropwise to the reaction mixture, which was then stirred at −40° C. for 45 min. To the yellow/green reaction mixture was added diisopropyl-ethylamine (51 mL, 0.288 mmol, 100 equiv), and the yellow solution was stirred at 0° C. for 45 min before excess Swern reagent was quenched by the addition of t-butyl alcohol (13 mg, 0.176 mmol, 61 equiv) at 0° C. t-Butyl-tetramethyl guanidine (49 mL, 0.288 mmol, 100 equiv) was added to the solution which was stirred at 23° C. for 1.5 h, during which time the solution named near-colorless. Acetic anhydride (50 mL, 0.530 mmol, 184 equiv) was added, and after 1 h at 23° C., the reaction mixture was filtered through a short column of silica gel, eluting with 50% ethyl acetate in hexanes. The filtrate was concentrated, and the residue was purified by flash column chromatography (gradient elution: 25→33% ethyl acetate in hexanes) to give 14 (1.7 mg, 79%). $R_f$ 0.40 (50% ethyl acetate in hexanes); $[α]_D^{23}$ −6.0, (c=0.083, $CH_2Cl_2$); $^1$H NMR (500 MHz, $CDCl_3$) d 6.80 (s, 1H, ArH), 6.09 (d, 1H, J=1.4 Hz, $OCH_2O$), 6.00 (d, 1H, J=1.4 Hz, $OCH_2O$), 5.93 (m, 1H, vinyl H), 5.32 (dd, 1H, J=1.4, 17.0 Hz, vinyl H), 5.23 (d, 1H, J=9.9 Hz, vinyl H), 5.22 (d, 1H, J=5.2 Hz, $OCH_2O$), 5.14 (d, 1H, J=5.2 Hz, $OCH_2O$), 5.03 (d, 1H, J=13.2 Hz), 4.83 (d, 1H, J=9.3 Hz), 4.52 (m, 3H), 4.31 (m, 2H), 4.24 (s, 1H), 4.16 (m, 2H), 3.74 (s, 3H, $OCH_3$), 3.56 (s, 3H, $OCH_3$), 3.45 (m, 1H, ArCH), 3.40 (m, 1H, ArCH), 2.92 (m, 1H, ArCH), 2.29 (s, 3H, $NCH_3$), 2.28 (s, 3H, $ArCH_3$), 2.22 (s, 3H, $ArCH_3$), 2.13 (m, 1H, ArCH), 2.03 (s, 3H, AcO); $^{13}$C NMR (126 MHz, $CD_2Cl_2$) d 170.7, 168.9, 166.9, 155.6, 150.2, 148.8, 146.1, 141.5, 140.8, 133.5, 132.2, 130.7, 125.3, 120.8, 118.3, 117.9, 113.9, 102.6, 99.5, 66.1, 61.7, 61.0, 60.6, 60.0, 59.6, 59.4, 57.8, 55.4, 55.0, 54.2, 42.1, 41.4, 33.2, 30.1, 24.1, 20.6, 16.0, 14.4, 9.7; FTIR (neat film) 3450 (w, br), 2930 (m), 1760 (s), 1724 (s), 1515 (m), 1507 (m), 1488 (m), 1456 (m), 1436 (m), 1194 (s), 1089 (m), 1062 (m), 1053 (m), 997 (m), 915 (m) $cm^{-1}$; HRMS ($FAB^+$) m/z: Calcd for $C_{37}H_{42}N_4O_{11}SNa$ ($MNa^+$) 773.2469, found 773.2466.

Example 34

Amine 47:

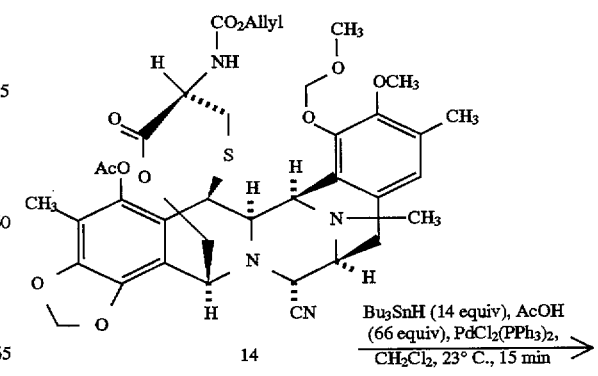

-continued

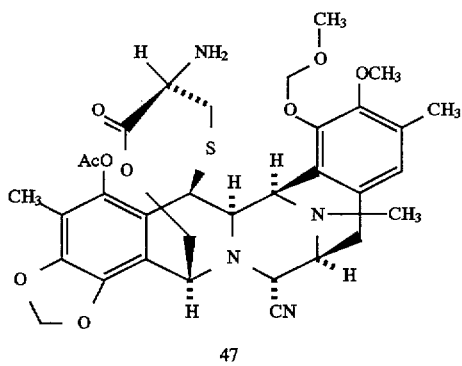

47

To a solution of 14 (5.0 mg, 0.00666 mmol, 1 equiv), PdCl$_2$(PPh$_3$)$_2$ (0.5 mg), and acetic acid (4 mL, 0.0666 mmol, 10 equiv) in dichloromethane (1 mL) was added tributyltin hydride (9 mL, 0.0333 mmol, 5.0 equiv), and the brown solution was stirred at 23° C. for 5 min. The reaction mixture was directly loaded onto a silica gel column, and the product was purified by flash column chromatography (gradient elution: ethyl acetate→4% isopropyl alcohol in ethyl acetate) to give amine 47 (3.6 mg, 84%). R$_f$ 0.25 (ethyl acetate); [a]$_D^{23}$ +10 (c=0.10, CH$_2$Cl$_2$); $^1$H NMR (500 MHz, CDCl$_3$) d 6.73 (s, 1H, ArH), 6.08 (d, 1H, J=1.0 Hz, OCH$_2$O), 5.99 (d, 1H, J=1.0 Hz, OCH$_2$O), 5.21 (d, 1H, J=3.4 Hz, OCH$_2$O), 5.14 (d, 1H, J=3.4 Hz, OCH$_2$O), 5.02 (d, 1H, J=12.0 Hz), 4.51 (m, 1H), 4.34 (d, 1H, J=4.7 Hz), 4.27 (s, 1H), 4.20 (d, 1H, J=3.0 Hz), 4.13 (d, 1H, J=12.0 Hz), 3.79 (s, 3H, OCH$_3$), 3.57 (s, 3H, OCH$_3$), 3.45 (d, 1H, J=4.7 Hz), 3.41 (m, 1H), 3.31 (m, 1H), 2.92 (m, 2H), 2.29 (s, 3H, NCH$_3$), 2.25 (s, 3H, ArCH$_3$), 2.19 (s, 3H, ArCH$_3$), 2.16 (m, 1H), 2.04 (s, 3H, AcO); $^{13}$C NMR (100 MHz, CD$_2$Cl$_2$) d 174.7, 149.8, 148.7, 141.4, 140.7, 132.7, 132.4, 132.2, 131.6, 130.8, 128.9, 128.8, 125.4, 125.2, 121.2, 118.4, 114.3, 102.5, 99.5, 61.9, 60.2, 60.1, 59.4, 59.2, 57.7, 55.4, 55.0, 54.6, 42.1, 41.5, 35.1, 30.1, 24.1, 20.6, 19.8, 15.8, 9.7; FTIR (neat film) 3100 (w), 2920 (w), 1760 (m), 1749 (m), 1462 (m), 1454 (m), 1446 (m), 1436 (m), 1423 (m), 1266 (s), 1238 (m), 1197 (m), 1160 (m), 1089 (m) cm$^{-1}$; HRMS (FAB$^+$) m/z: Calcd for C$_{33}$H$_{38}$N$_4$O$_9$SNa (MNa$^+$) 689.2257, found 689.2243.

Example 35

Ketone 15:

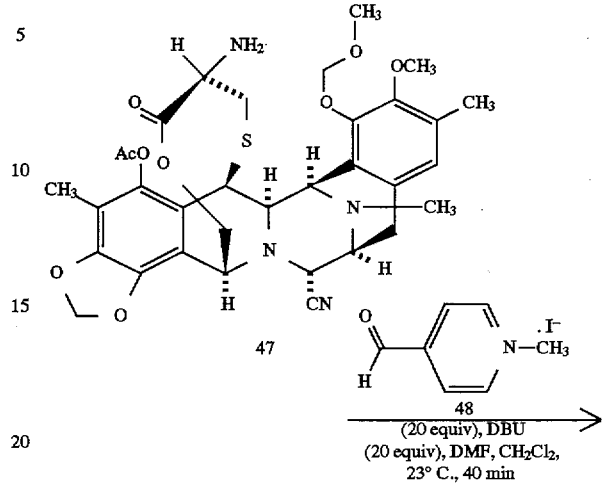

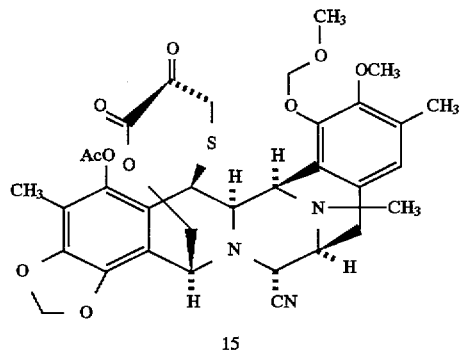

15

To a solution of amine 47 (2.9 mg, 0.00435 mmol, 1 equiv) in a mixture of DMF in dichloromethane (1:3 (v/v), 640 mL) was added solid 48 (22 mg, 0.0871 mmol, 20 equiv), and the red solution was stirred at 23° C. for 40 min. DBU (15 mL, 0.0871 mmol, 20 equiv) was added, and the black suspension was stirred at 23° C. for 15 min before saturated aqueous oxalic acid solution (0.5 mL) was added. The yellow mixture was stirred at 23° C. for 30 min before it was partitioned between saturated aqueous sodium bicarbonate solution (10 mL) and ethyl ether (30 mL). The organic layer was dried (magnesium sulfate) and concentrated, and was filtered through a short plug of silica gel with 50% ethyl acetate in hexanes to give ketone 15 (2.0 mg, 70%). R$_f$ 0.30 (50% ethyl acetate in hexanes); [a]$_D^{23}$ +102 (c=0.10, CH$_2$Cl$_2$); $^1$H NMR (400 MHz, CDCl$_3$) d 6.70 (s, 1H, ArH), 6.12 (d, 1H, J=1.7 Hz, OCH$_2$O), 6.03 (d, 1H, J=1.7 Hz, OCH$_2$O), 5.20 (d, 1H, J=5.5 Hz, OCH$_2$O), 5.13 (d, 1H, J=5.5 Hz, OCH$_2$O), 5.10 (d, 1H, J=12.0 Hz), 4.68 (m, 1H), 4.40 (s, 1H), 4.38 (dd, 1H, J=2.1, 5.1 Hz), 4.22 (dd, 1H, J=2.1, 10.9 Hz), 4.18 (d, 1H, J=2.8 Hz), 3.75 (s, 3H, OCH$_3$), 3.58 (m, 1H), 3.57 (s, 3H, OCH$_3$), 3.44 (m, 2H), 2.90 (m, 1H), 2.82 (d, 1H, J=13.3 Hz), 2.71 (d, 1H, J=17.3 Hz), 2.32 (s, 3H, NCH$_3$), 2.22 (s, 3H, ArCH$_3$), 2.17 (m, 1H), 2.16 (s, 3H, ArCH$_3$), 2.05 (s, 3H, AcO); $^{13}$C NMR (100 MHz, CD$_2$Cl$_2$) d 149.7, 149.5, 148.8, 146.8, 132.3, 130.8, 125.7, 124.6, 122.4, 120.6, 118.2, 114.0, 102.8, 99.7, 78.2, 62.1, 61.9, 60.4, 59.5, 59.1, 57.8, 55.3, 55.0, 43.8, 41.6, 37.5, 30.5, 30.1, 24.5, 20.4, 16.0, 9.8; FTIR (neat film) 2923 (s), 1764 (s), 1730 (s), 1463 (m), 1456 (s), 1447 (m), 1436 (m), 1195 (s), 1160 (m), 1089 (s) cm$^{-1}$; HRMS (FAB$^+$) m/z: Calcd for C$_{33}$H$_{36}$N$_3$O$_{10}$S (MH$^+$) 666.2121, found 666.2124.

1H, ArH), 6.52 (s, 1H, ArH), 6.51 (s, 1H, ArH), 6.12 (d, 1H, J=0.9 Hz, OCH$_2$O), 6.06 (d, 1H, J=0.9 Hz, OCH$_2$O), 5.26 (d, 1H, J=5.6 Hz, OCH$_2$O), 5.22 (d, 1H, J=5.6 Hz, OCH$_2$O), 5.06 (d, 1H, J=11.6 Hz), 4.62 (m, 1H), 4.42 (d, 1H, J=5.4 Hz), 4.36 (s, 1H), 4.25 (d, 1H, J=2.7 Hz), 4.19 (dd, 1H, J=2.3, 11.4 Hz), 3.84 (s, 3H, OCH$_3$), 3.69 (s, 3H, OCH$_3$), 3.63 (s, 3H, OCH$_3$), 3.55 (m, 1H), 3.48 (m, 1H), 3.42 (m, 1H), 3.12 (m, 1H), 3.00 (m, 2H), 2.85 (m, 1H), 2.76 (dd, 1H, J=6.9, 13.7 Hz), 2.62 (m, 2H), 2.45 (m, 2H), 2.34 (s, 3H, NCH$_3$), 2.31 (s, 3H, ArCH$_3$), 2.25 (s, 3H, ArCH$_3$), 2.09 (s, 3H, AcO); $^{13}$C NMR (100 MHz, CD$_2$Cl$_2$) d 144.8, 141.8, 131.1, 125.3, 125.1, 118.4, 114.5, 114.3, 110.3, 102.5, 99.5, 61.6; 60.3, 59.7, 59.5, 57.7, 55.6, 55.4, 55.1, 54.7, 43.0, 42.2, 41.6, 40.2, 30.1, 29.4, 24.5, 20.4, 15.9, 9.8; FTIR (neat film) 3400 (s, br), 2950 (s), 1741 (s), 1512 (s), 1462 (s), 1455 (s), 1442 (s), 1226 (s), 1194 (s), 1088 (s), 1052 (s), 1028 (s) cm$^{-1}$; HRMS (FAB$^+$) m/z: Calcd for C$_{42}$H$_{46}$N$_4$O$_{11}$SNa (MNa$^+$) 837.2782, found 837.2797.

Example 36

Tristetrahydroisoquinoline 49:

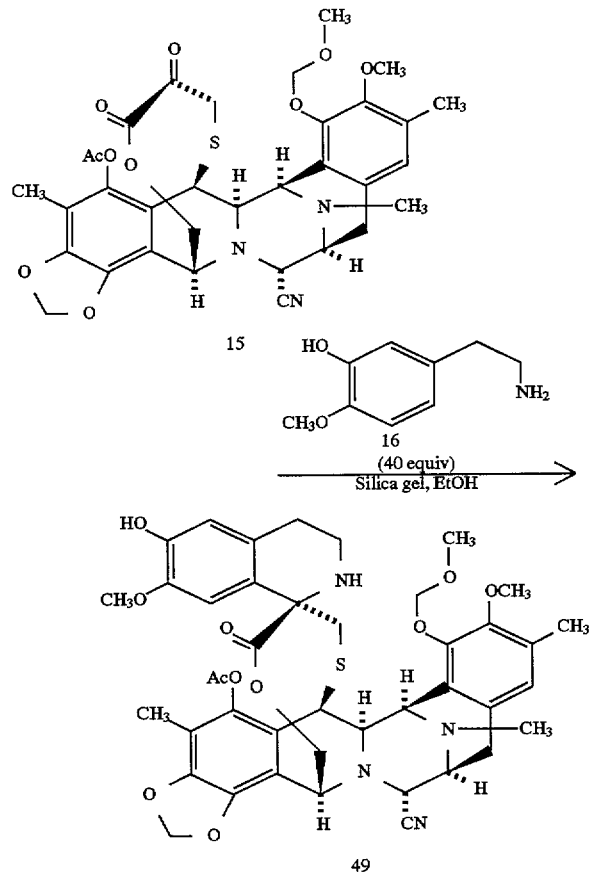

Ketone 15 (1.7 mg, 0.00256 mmol, 1 equiv), together with phenethylamine 16 (10 mg, 0.0599 mmol, 23 equiv) were dissolved in absolute ethanol (500 mL), and to this solution was added silica gel (10 mg). The suspension was stirred at 23° C. for 10 h before the mixture was diluted with ethyl acetate (5 mL) and filtered. The filtrate was concentrated, and the residue was purified by flash column chromatography (5% methanol in dichoromethane) to afford 49 (1.7 mg, 82%). R$_f$ 0.32 (5% methanol in dichoromethane); [a]$_D^{23}$ −10 (c=0.10, CH$_2$Cl$_2$); $^1$H NMR (400 MHz, CD$_2$Cl$_2$) d 6.86 (s,

Example 37

Ecteinascidin 770 (50):

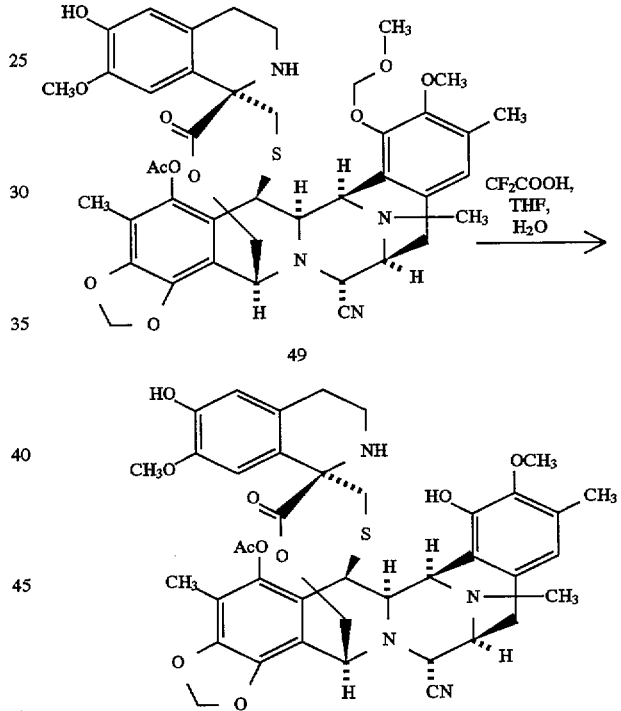

Methoxymethyl ether 49 (2.8 mg, 0.0034 mmol, 1 equiv) was dissolved in a mixture of trifluoroacetic acid:THF:water (4:1:1 (v/v), 2.8 mL), and the solution was stirred at 23° C. for 9 h. The reaction mixture was diluted with toluene (8 mL), and the solution was concentrated at 23° C. All volatiles were removed in vacuo by azeotropic removal with toluene (2×2 mL). The residue was purified by flash column chromatography (5% methanol in dichloromethane) to afford 50 (2.2 mg, 78%). R$_f$ 0.28 (5% methanol in dichloromethane); [a]$_D^{23}$ −35 (c=0.10, CH$_2$Cl$_2$); $^1$H NMR (400 MHz, CD$_2$Cl$_2$) d 6.59 (s, 1H, ArH), 6.46 (s, 1H, ArH), 6.46 (s, 1H, ArH), 6.06 (s, 1H, OCH$_2$O), 6.01 (s, 1H, OCH$_2$O), 5.84 (s, 1H), 5.47 (s, 1H), 5.02 (d, 1H, J=11.6 Hz), 4.62 (m, 1H), 4.28 (m, 2H), 4.18 (d, 1H, J=2.6 Hz), 4.14 (m, 1H), 3.79 (s, 3H, OCH$_3$), 3.63 (s, 3H, OCH$_3$), 3.46 (m, 1H), 3.41 (m, 1H), 3.08 (m, 1H), 2.92 (m, 2H), 2.79 (m, 1H), 2.56

(m, 1H), 2.3 (m, 2H), 2.28 (m, 2H), 2.32 (s, 3H, NCH$_3$), 2.26 (s, 3H, ArCH$_3$), 2.19 (s, 3H, ArCH$_3$), 2.03 (s, 3H, AcO); $^{13}$C NMR (100 MHz, CD$_2$Cl$_2$) d 168.6, 148.9, 146.7, 146.1, 131.1, 126.0, 120.7, 120.0, 118.0, 117.9, 114.5, 113.5, 109.5, 102.8, 66.2, 62.2, 61.4, 60.5, 59.8, 55.9, 54.9, 54.7, 43.4, 41.5, 40.1, 38.5, 30.0, 24.8, 24.4, 20.5, 16.0, 9:9; FTIR (neat film) 3400 (s, br), 2950 (s), 1741 (s), 1512 (s), 1462 (s), 1455 (s), 1442 (s), 1226 (s), 1194 (s), 1088 (s), 1052 (s), 1028 (s) cm$^{-1}$;

Example 38

Ecteinascidin 743 (1):

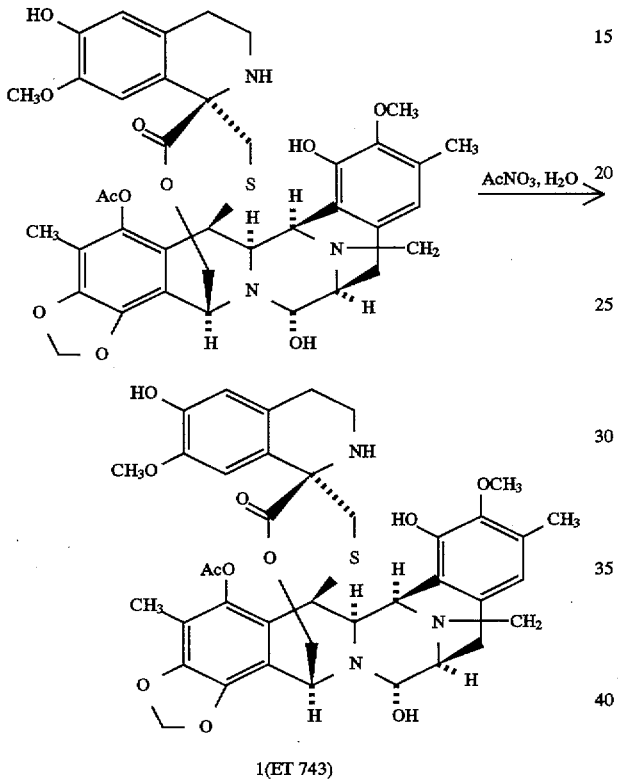

1(ET 743)

Ecteinascidin 770 (50) (2.2 mg, 0.00285 mmol, 1 equiv) was dissolved in a mixture of acetonitrile and water (3:2 (v/v), 1.0 mL), and to this solution was added solid silver nitrate (15 mg, 0.088 mmol, 30 equiv). The suspension was stirred at 23° C. for 11 h at which time a mixture of saturated aqueous sodium chloride solution and saturated aqueous sodium bicarbonate solution (1:1 (v/v), 2.0 mL) was added. The mixture was stirred vigorously at 23° C. for 15 min before it was partitioned between a mixture of saturated aqueous sodium chloride solution and saturated aqueous sodium bicarbonate solution (1:1 (v/v), 15 mL) and dichloromethane (3×10 mL). The combined organic layers were dried (sodium sulfate) and filtered through a pad of celite. The filtrate was concentrated to give clean 1 (2.0 mg, 95%), identical in all respects to that of an authentic sample. HPLC (Zorbax ODS, C$_{18}$, 4.6 mm×25 cm, flow rate: 1.0 mL/min) R$_T$ 11.28 min (co-injection, 25% CH$_3$CN in H$_2$O with 0.2% TFA); [a]$_D^{23}$ −34 (c=0.10, CH$_2$Cl$_2$); $^1$H NMR (500 MHz, CDCl$_3$) d 6.59 (s, 1H, ArH), 6.47 (s, 1H, ArH), 6.46 (s, 1H, ArH), 6.03 (d, 1H, J=1.1 Hz, OCH$_2$O), 5.98 (d, 1H, J=1.1 Hz, OCH$_2$O), 5.80 (s, 1H), 5.09 (d, 1H, J=10.9 Hz), 4.77 (s (br), 1H), 4.43 (d, 1H, J=2.8 Hz), 4.36 (m, 1H), 4.05 (dd, 1H, J=2.4, 11.2 Hz), 3.79 (s, 3H, OCH$_3$), 3.61 (s, 3H, OCH$_3$), 3.54 (d, 1H, J=4.5 Hz), 3.20 (m, 1H), 3.10 (m, 1H), 2.84 (m, 2H), 2.78 (m, 1H), 2.57 (m, 1H), 2.40 (dt, 1H, J=15.9, 3.3 Hz), 2.32 (s, 3H, NCH$_3$), 2.26 (s, 3H, ArCH$_3$), 2.17 (s, 3H, ArCH$_3$), 2.02 (s, 3H, AcO); $^{13}$C NMR (100 MHz, CD$_2$Cl$_2$) d 162.2, 141.0, 121.1, 114.4, 109.7, 102.7, 82.1, 65.3, 62.5, 61.2, 60.6, 59.7, 56.4, 55.7, 55.5, 42.9, 40.6, 40.3, 30.1, 24.7, 20.5, 16.1, 9.9; FTR (neat film) 3400 (m, br), 2933 (s), 1760 (m), 1741 (s), 1456 (s), 1448 (s), 1430 (s), 1235 (s), 1195 (s), 1088 (s) cm$^{-1}$; Exact Mass (ES$^+$) m/z: Calcd for C$_{39}$H$_{44}$N$_3$O$_{11}$S (MH$^+$) 762.2697, found 762.2683.

FOOTNOTES AND INFORMATION DISCLOSURE

The following footnotes and/or reference notes have been referred to above. The inventors accordingly wish to cite the publications which follow as potential prior art to the invention claimed herein. In addition, the publications cited below are hereby incorporated herein by reference.

(1) The pioneering research in this area is due to Prof. Kenneth L. Rinehart and his group. See, (a) Rinehart, K. L.; Shield, L. S. in *Topics in Pharmaceutical Sciences*, eds. Breimer, D. D.; Crommelin, D. J. A.; Midha, K. K. (Amsterdam Medical Press, Noordwijk, The Netherlands), 1989, pp. 613. (b) Rinehart, K. L.; Holt, T. G.; Fregeau, N. L.; Keifer, P. A.; Wilson, G. R.; Perun, T. J., Jr.; Sakai, R.; Thompson, A. G.; Stroh, J. G.; Shield, L. S.; Seigler, D. S.; Li, L. H.; Martin, D. G.; Grimmelikhuijzen, C. J. P.; Gäde, G. *J. Nat. Prod.* 1990, 53, 771. (c) Rinehart, K. L.; Sakai, R. Holt, T; G.; Fregeau, N. L.; Perun, T. J., Jr.; Seigler, D. S.; Wilson, G. R.; Shield, L. S. *Pure Appl. Chem.* 1990, 62, 1277. (d) Rinehart, K. L.; Holt, T. G.; Fregeau, N. L.; Stroh, J. G.; Keifer, P. A.; Sun, F.; Li, L. H.; Martin, D. G. *J. Org. Chem.* 1990, 55, 4512. (e) Wright, A. E.; Forleo, D. A.; Gunawardana, G. P.; Gunasekera, S. P.; Koehn, F. E.; McConnell, O. J. *J. Org. Chem.* 1990, 55, 4508. (f) Sakai, R.; Rinehart, K. L.; Guan, Y.; Wang, H.-J. *Proc. Natl. Acad. Sci. USA* 1992, 89, 11456. See also, U.S. Pat. Nos. 5,089,273; 5,149,804; 5,256,663; and 5,478,932, each incorporated herein by reference.

(2) *Science* 1994, 266, 1324.

(3) The current clinical plan calls for the administration of three 0.5 mg doses of 1 per patient; personal communication from Dr. Glynn Faircloth, PharmaMar U.S.A., Cambridge, Mass.

(4) (a) Prepared from 3,4-methylenedioxyphenyl methoxymethyl ether by the sequence: (1) lithiation at C-2 (3 equiv of BuLi, 3 equiv of tetramethylethylene diamine in hexane at 0° C. for 4 h) and reaction with CH$_3$I (6 equiv at −78°→23° C. over 15 min) to afford exclusively the 2-methyl derivative (87%); (2) ortho lithiation (2 equiv of BuLi in THF at −30° C. for 13 h) and subsequent formylation with 4 equiv of DMF (64% yield); (3) cleavage of the MeOCH$_2$ protecting group (0.55 equiv CH$_3$SO$_3$H in CH$_2$Cl$_2$ at 0° C.) and (4) treatment of the resulting 3-methyl-4,5-methylenedioxy salicylaldehyde with 1.5 equiv of NaH in DMF at 0° C. for 5 min and 2 equiv of benzyl bromide at 23° C. for 40 min (86% overall). (b) Prepared from the monoallyl ester of malonic acid by conversion to the mixed anhydride with BOP chloride (Aldrich) and reaction with 2,2-dimethoxyethanol.

(5) This step, which involves complete isomerization to the thermodynamically more stable Z-α-acylaminoacrylic ester, represents a generally useful process for the stereospecific synthesis of such compounds.

(6) Koenig, K. E. in *Asymmetric Synthesis*; Morrison, J. D., Ed., Academic Press, Inc., Orlando, Fla., Vol. 5, 1985, p. 71.

(7) The conversion 4→5 demonstrates a useful method for control of stereochemistry in the tetrahydroisoquinoline series.

(8) (a) This step converts the tertiary hydroxyl group of 13 to the O-dimethylsulfonium derivative. The use of oxalyl chloride-DMSO as reagent is unsatisfactory due to interference by chloride in the subsequent steps of quinone methide formation and addition. (b) This step generates the quinone methide probably by cycloelimination of the Swern type oxosulfonium ylide intermediate.

(9) Barton, D. H. R.; Elliott, J. D.; Géro, S. D. *J. Chem. Soc. Perkin Trans.* 1, 1982, 2085.

(10) Obtained from Prof. K. L. Rinehart and PharmaMar, U.S.A.

(11) For previous work on the synthesis of the saframycins see: (a) Fukuyama, T.; Sachleben, R. A. *J. Am. Chem. Soc.* 1982, 104, 4957. (b) Fukuyama, T.; Yang, L.; Ajeck, K. L.; Sachleben, R. A. *J. Am. Chem. Soc.* 1990, 112, 3712. (c) Saito, N.; Yamauchi, R.; Nishioka, H.; Ida, S.; Kubo, A. *J. Org. Chem.* 1989, 54, 5391.

(12) Still, W. C.; Kahn, M.; Mitra, A. *J. Org. Chem.*, 1978, 43 2923.

(13) Kofron, W. G.; Baclawski, L. M. *J. Org. Chem.*, 1976, 41, 1979.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. An enantio- and stereocontrolled process for the preparation of ecteinascidin 743 comprising the steps of:

(a) forming an α,β-unsaturated malonic ester of Formula 2, having the following structure:

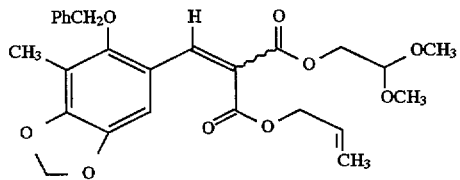

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

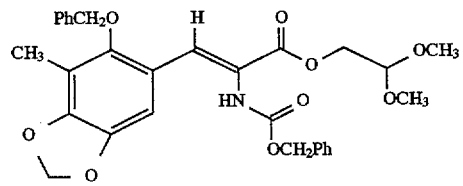

by selective allyl ester cleavage, Curtius rearrangement, and reaction of the intermediate isocyanate with benzyl alcohol;

(c) converting the compound of Formula 3 into the compound of Formula 4 having the following structure:

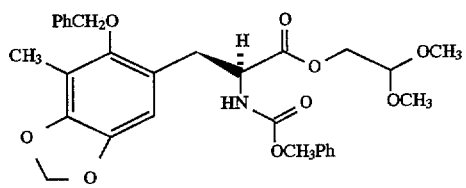

by catalytic hydrogenation over Rh[(COD)R,R-DIPAMP]$^+$BF$_4^-$;

(d) converting the compound of Formula 4 into the compound of Formula 5 having the following structure:

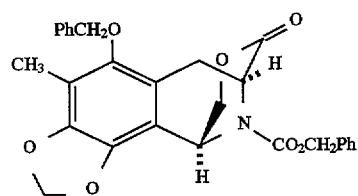

by acetal cleavage, wherein isolation and exposure of the resulting aldehyde to BF$_3$.Et$_2$O and 4 Å mol sieves yields the bridged lactone compound of Formula 5;

(e) converting the bridged lactone compound of Formula 5 to the free amino phenol compound of Formula 6 having the following structure:

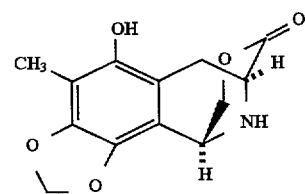

by hydrogenolysis over 10% Pd—C;

(f) forming the protected α-amino ester compound of Formula 7 having the following structure:

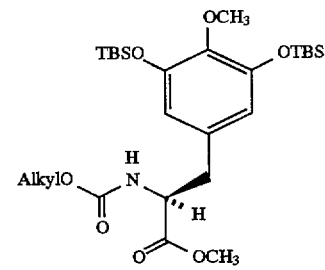

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

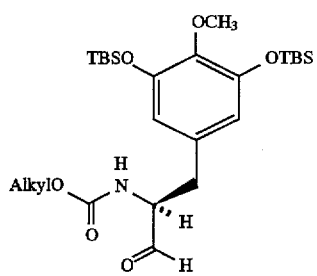

by reduction;

(h) combining the compounds of Formulae 6 and 8 to afford the monobridged pentacyclic intermediate of Formula 10, having the following structure:

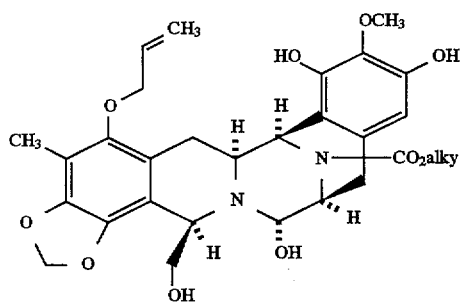

as follows:

reacting the compounds of Formulae 6 and 8 to give a coupled phenolic α-amino nitrile, followed by O-allylation to give the allyl ether compound of Formula 9; having the following structure:

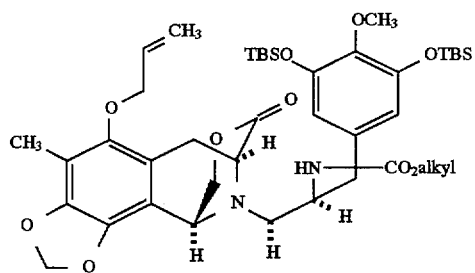

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 by an internal Mannich bisannulation;

(i) converting the pentacycle compound of Formula 10 to the compound of Formula 11 having the following structure:

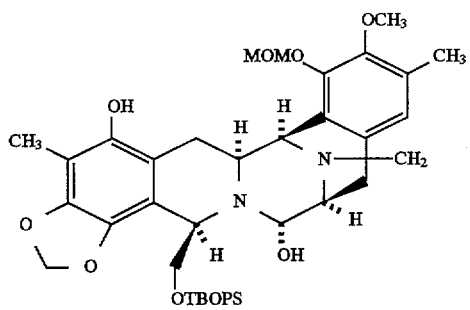

by the selective trifluoromethane-sulfonation of the least hindered phenolic hydroxyl; followed by (1) selective silylation of the primary hydroxyl; (2) protection of the remaining phenolic group as the methoxymethyl ether; (3) double deallylation; (4) reductive N-methylation; and (5) replacement of $CF_3SO_3$ by $CH_3$;

(j) oxidizing the phenol compound of Formula 11 effected position-selective angular hydroxylation to give after desilylation the dihydroxy dienone compound of Formula 12 having the following structure:

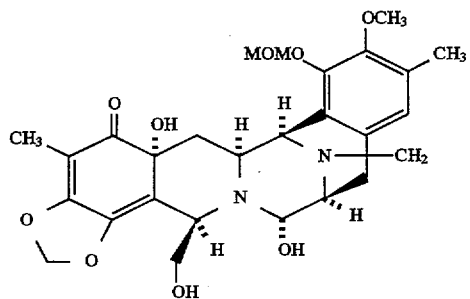

(k) forming the compound of Formula 13 having the following structure:

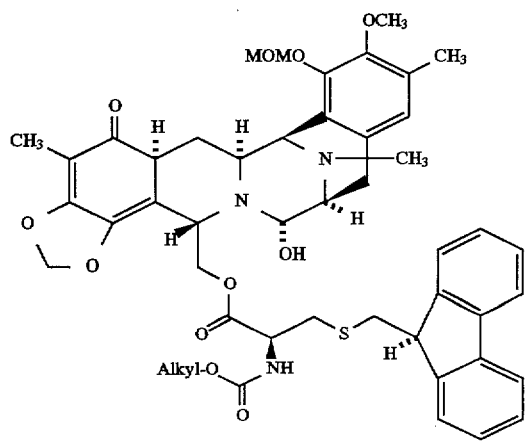

by esterifying the primary hydroxyl function of the compound of Formula 12 with (S)-N-allyloxycarbonyl-S-(9-fluorenylmethyl)cysteine;

(l) transforming the compound of Formula 13 to the bridged lactone compound of Formula 14 having the following structure:

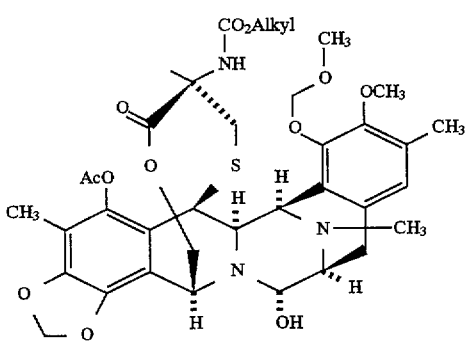

by;

(l) first reacting the compound of Formula 13 with an in situ generated Swern reagent; (2) followed by the formation of the exendo quinone methide, (3) destruction of the excess Swern reagent; (4) addition of excess N-tert-butyl-N',N"-tetramethylguanidine to generate the 10-membered lactone bridge; and (5) addition of excess Ac$_2$O to acetylate the resulting phenoxide group;

(m) cleaving the N-allyloxycarbonyl group of the compound of Formula 14 and oxidizing the resulting α-amino lactone to the corresponding α-keto lactone by transamination thereby forming the compound of Formula 15 having the following structure:

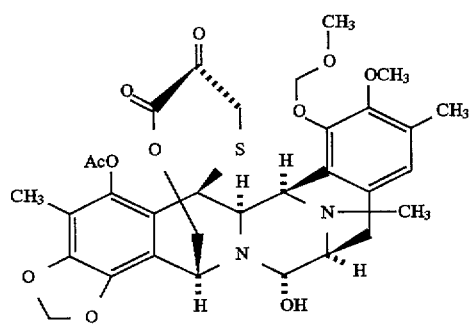

(n) stereospecifically forming spiro tetrahydroisoquinoline compound by reacting the compound of Formula 15 with 2-[3-hydroxy-4-methoxy-phenyl]ethylamine;

(o) followed by methoxymethyl cleavage and replacement of CN by HO to form the compound of Formula 1, ecteinascidin 743, having the following structure:

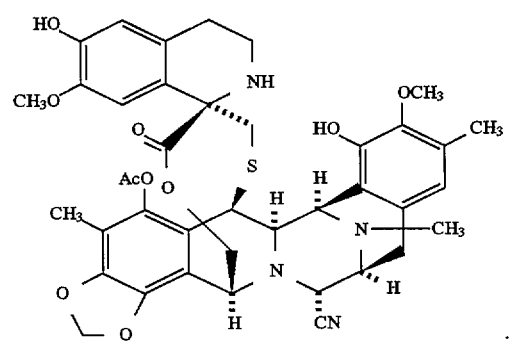

2. An enantio- and stereocontrolled process for the preparation of ecteinascidin 770 comprising the steps of:

(a) forming an α,β-unsaturated malonic ester of Formula 2, having the following structure:

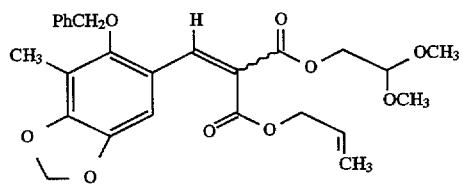

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

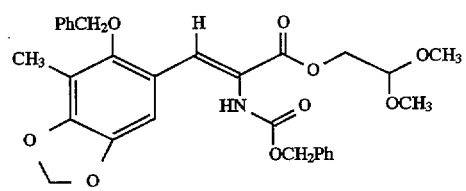

by selective allyl ester cleavage, Curtius rearrangement, and reaction of the intermediate isocyanate with benzyl alcohol;

(c) converting the compound of Formula 3 into the compound of Formula 4 having the following structure:

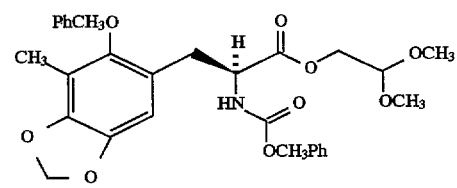

by catalytic hydrogenation over Rh[(COD)R,R-DIPAMP]$^+$BF$_4^-$;

(d) converting the compound of Formula 4 into the compound of Formula 5 having the following structure:

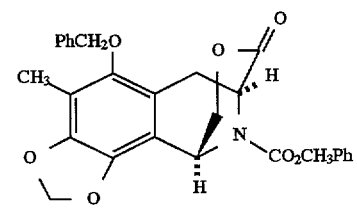

by acetal cleavage, wherein isolation and exposure of the resulting aldehyde to BF$_3$.Et$_2$O and 4 Å mol sieves yields the bridged lactone compound of Formula 5;

(e) converting the bridged lactone compound of Formula 5 to the free amino phenol compound of Formula 6 having the following structure:

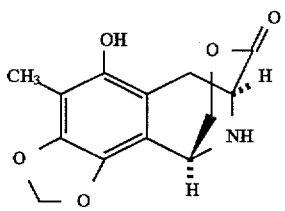

by hydrogenolysis over 10% Pd—C;

(f) forming the protected α-amino ester compound of Formula 7 having the following structure:

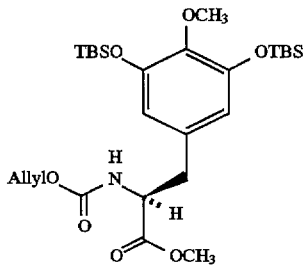

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

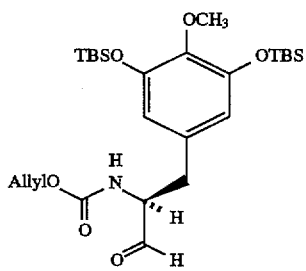

by reduction;

(h) combining the compounds of Formulae 6 and 8 to afford the monobridged pentacyclic intermediate of Formula 10, having the following structure:

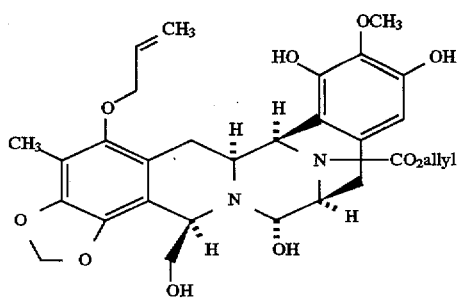

as follows:

reacting the compounds of Formulae 6 and 8 to give a coupled phenolic α-amino nitrile, followed by O-allylation to give the allyl ether compound of Formula 9 having the following structure:

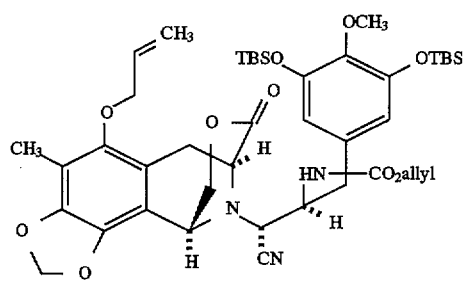

selectively converting the lactone function in the compound of Formula 9 to a lactol by reacting the compound of Formula 9 with diisobutylaluminum hydride; desilylating the lactol compound; and cyclizing the desilylated compound to afford the pentacycle compound of Formula 10 having the following structure;

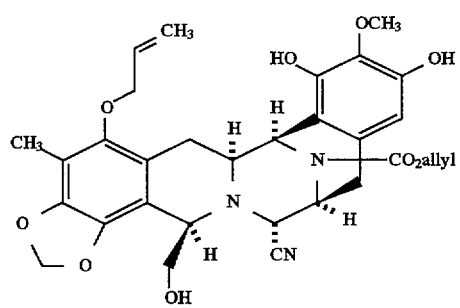

by an internal Mannich bisannulation;

(i) converting the pentacycle compound of Formula 10 to the compound of Formula 11 having the following structure:

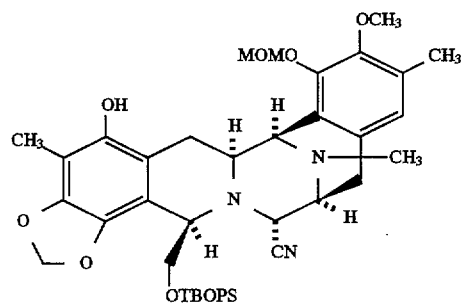

by the selective trifluoromethane-sulfonation of the least hindered phenolic hydroxyl; followed by (1) selective silylation of the primary hydroxyl; (2) protection of the remaining phenolic group as the methoxymethyl ether; (3) double deallylation; (4) reductive N-methylation; and (5) replacement of $CF_3SO_3$ by $CH_3$;

(j) oxidizing the phenol compound of Formula 11 effected position-selective angular hydroxylation to give after desilylation the dihydroxy dienone compound of Formula 12 having the following structure:

(k) forming the compound of Formula 13 having the following structure:

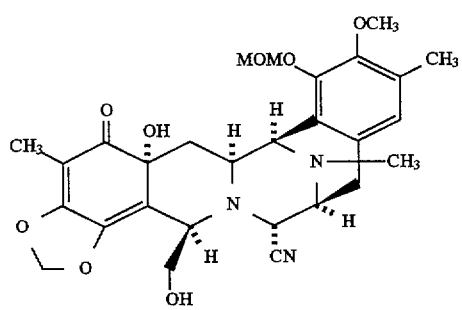

by esterifying the primary hydroxyl function of the compound of Formula 12 with (S)-N-allyloxycarbonyl-S-(9-fluorenylmethyl)cysteine;

(l) transforming the compound of Formula 13 to the bridged lactone compound of Formula 14 having the following structure:

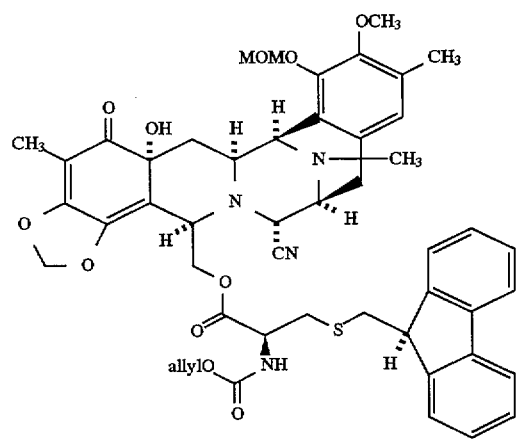

by;
(1) first reacting the compound of Formula 13 with an in situ generated Swern reagent; (2) followed by the formation of the exendo quinone methide, (3) destruction of the excess Swern reagent; (4) addition of excess N-tert-butyl-N',N''-tetramethylguanidine to generate the 10-membered lactone bridge; and (5) addition of excess Ac₂O to acetylate the resulting phenoxide group;

(m) cleaving the N-allyloxycarbonyl group of the compound of Formula 14 and oxidizing the resulting α-amino lactone to the corresponding α-keto lactone by transamination thereby forming the compound of Formula 15 having the following structure:

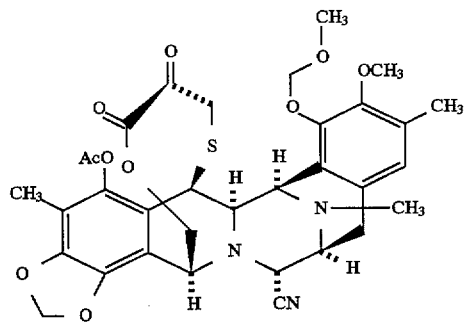

(n) stereospecifically forming spiro tetrahydro-isoquinoline compound by reacting the compound of Formula 15 with 2-[3-hydroxy-4-methoxy-phenyl] ethylamine; and (o) methoxymethyl cleavage to form the compound of Formula 50, ecteinascidin 770 having the following structure:

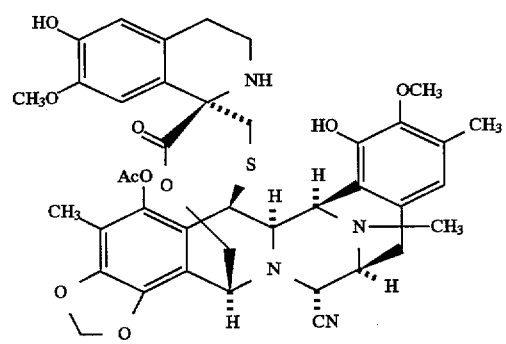

3. An enantio- and stereocontrolled process for the preparation of the spiro tetrahydro-isoquinoline ecteinascidin synthetic intermediate compound of Formula 49 having the following structure:

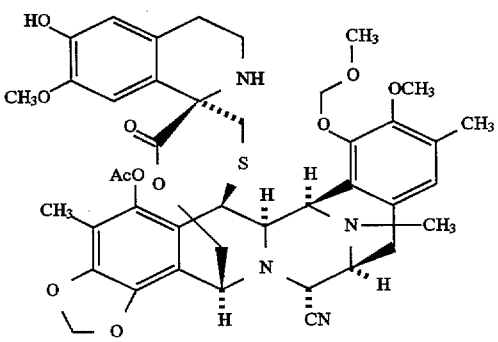

comprising the steps of:

(a) forming an α,β-unsaturated malonic ester of Formula 2, having the following structure:

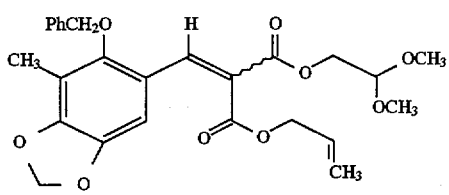

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

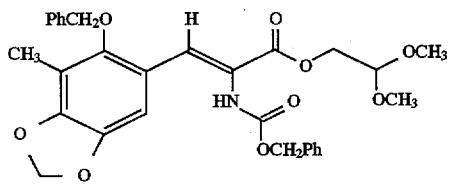

by selective allyl ester cleavage, Curtius rearrangement, and reaction of the intermediate isocyanate with benzyl alcohol;

(c) converting the compound of Formula 3 into the compound of Formula 4 having the following structure:

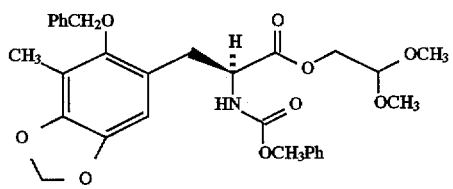

by catalytic hydrogenation over Rh[(COD)R,R-DIPAMP]$^+$BF$_4^-$;

(d) converting the compound of Formula 4 into the compound of Formula 5 having the following structure:

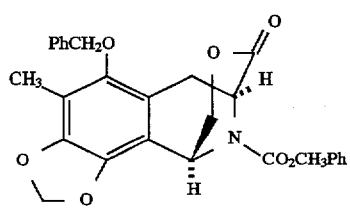

by acetal cleavage, wherein isolation and exposure of the resulting aldehyde to BF$_3$.Et$_2$O and 4 Å mol sieves yields the bridged lactone compound of Formula 5;

(e) converting the bridged lactone compound of Formula 5 to the free amino phenol compound of Formula 6 having the following structure:

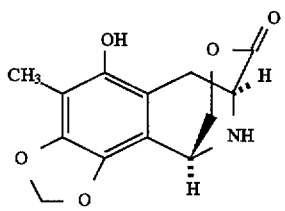

by hydrogenolysis over 10% Pd—C;

(f) forming the protected α-amino ester compound of Formula 7 having the following structure:

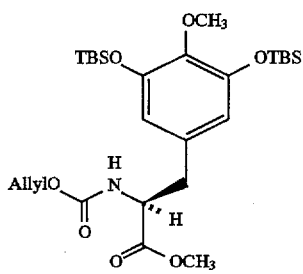

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

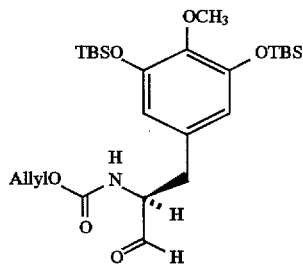

by reduction;

(h) combining the compounds of Formulae 6 and 8 to afford the monobridged pentacyclic intermediate of Formula 10, having the following structure:

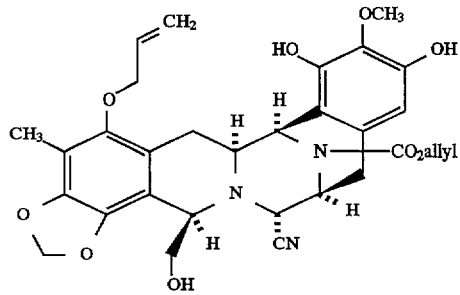

as follows;

reacting the compounds of Formulae 6 and 8 to give a coupled phenolic α-amino nitrile, followed by O-allylation to give the allyl ether compound of Formula 9 having the following structure:

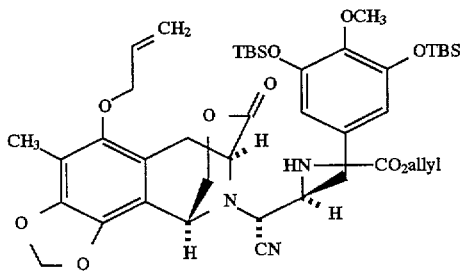

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 having the following structure:

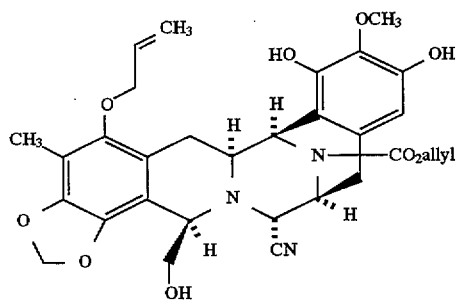

by an internal Mannich bisannulation;

(i) converting the pentacycle compound of Formula 10 to the compound of Formula 11 having the following structure:

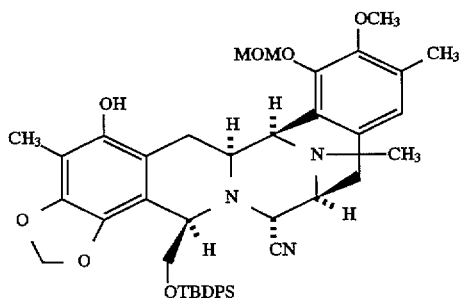

by the selective trifluoromethane-sulfonation of the least hindered phenolic hydroxyl; followed by (1) selective silylation of the primary hydroxyl; (2) protection of the remaining phenolic group as the methoxymethyl ether; (3) double deallylation; (4) reductive N-methylation; and (5) replacement of $CF_3SO_3$ by $CH_3$;

(j) oxidizing the phenol compound of Formula 11 effected position-selective angular hydroxylation to give after desilylation the dihydroxy dienone compound of Formula 12 having the following structure:

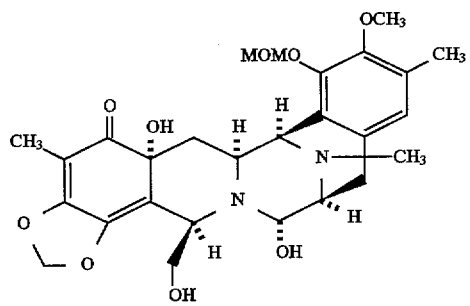

(k) forming the compound of Formula 13 having the following structure:

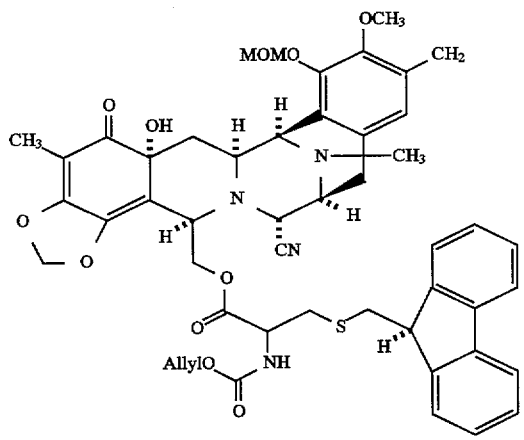

by esterifying the primary hydroxyl function of the compound of Formula 12 with (S)-N-allyloxycarbonyl-S-(9-fluorenylmethyl)cysteine;

(l) transforming the compound of Formula 13 to the bridged lactone compound of Formula 14 having the following structure:

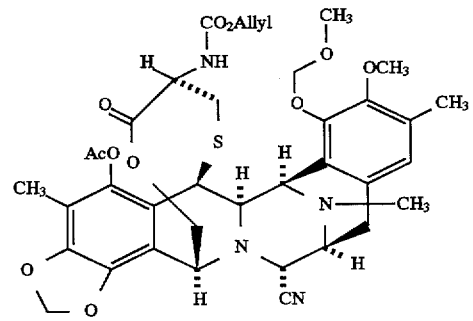

(1) first reacting the compound of Formula 13 with an in situ generated Swern reagent; (2) followed by the formation of the exendo quinone methide, (3) destruction of the excess Swern reagent; (4) addition of excess N-tert-butyl-N',N"-tetramethylguanidine to generate the 10-membered lactone bridge; and (5) addition of excess $Ac_2O$ to acetylate the resulting phenoxide group;

(m) cleaving the N-allyloxycarbonyl group of the compound of Formula 14 and oxidizing the resulting α-amino lactone to the corresponding α-keto lactone by transamination thereby forming the compound of Formula 15 having the following structure:

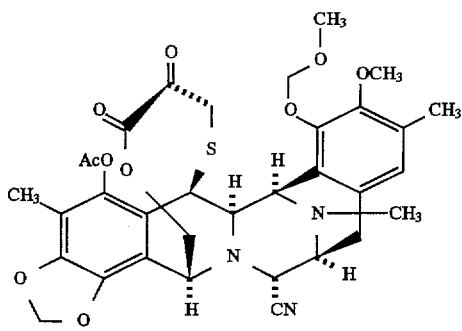

and (n) stereospecifically forming the spiro tetrahydro-isoquinoline compound of Formula 49 by reacting the compound of Formula 15 with 2[-3-hydroxy-4-methoxy-phenyl]ethylamine.

4. An enantio- and stereocontrolled process for the preparation of the ecteinascidin synthetic intermediate of Formula 15, having the following structure:

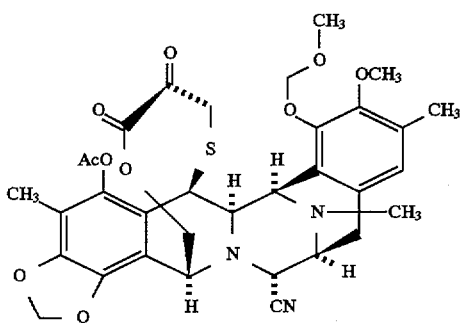

comprising the steps of:

(a) forming an α,β-unsaturated malonic ester of Formula 2, having the following structure:

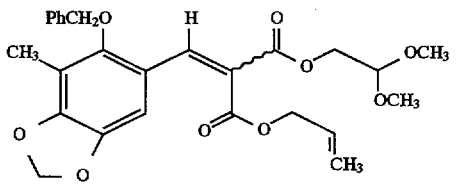

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

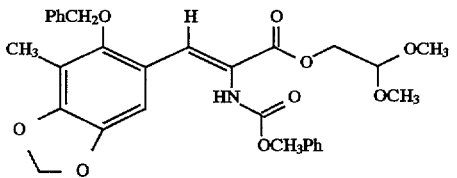

by selective allyl ester cleavage, Curtius rearrangement, and reaction of the intermediate isocyanate with benzyl alcohol;

(c) converting the compound of Formula 3 into the compound of Formula 4 having the following structure:

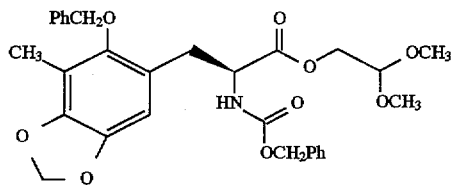

by catalytic hydrogenation over Rh[(COD)R,R-DIPAMP]$^+$BF$_4^-$;

(d) converting the compound of Formula 4 into the compound of Formula 5 having the following structure:

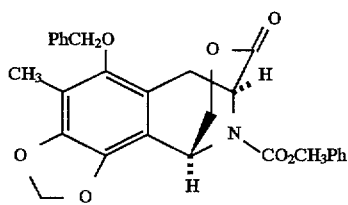

by acetal cleavage, wherein isolation and exposure of the resulting aldehyde to BF$_3$.Et$_2$O and 4 Å mol sieves yields the bridged lactone compound of Formula 5;

(e) converting the bridged lactone compound of Formula 5 to the free amino phenol compound of Formula 6 having the following structure:

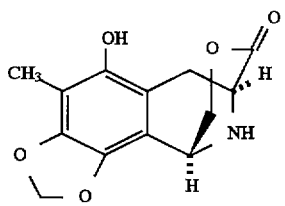

by hydrogenolysis over 10% Pd—C;

(f) forming the protected amino ester compound of Formula 7 having the following structure:

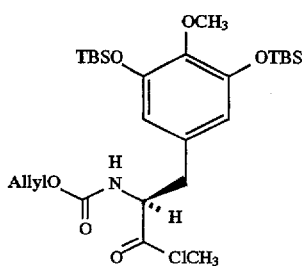

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

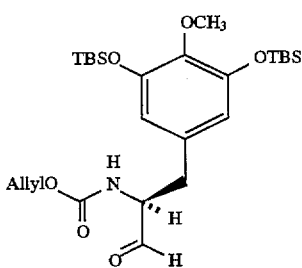

by reduction;

(h) combining the compounds of Formulae 6 and 8 to afford the monobridged pentacyclic intermediate of Formula 10, having the following structure:

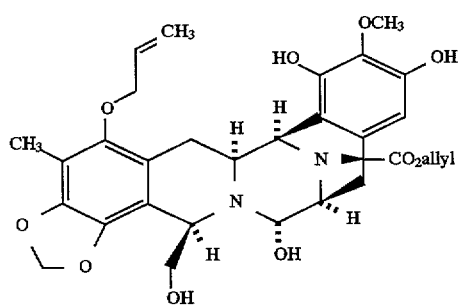

as follows:

reacting the compounds of Formulae 6 and 8 to give a coupled phenolic α-amino nitrile, followed by O-allylation to give the allyl ether compound of Formula 9 having the following structure:

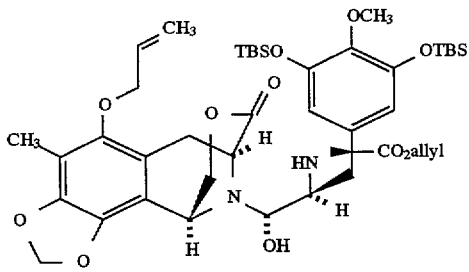

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 having the following structure:

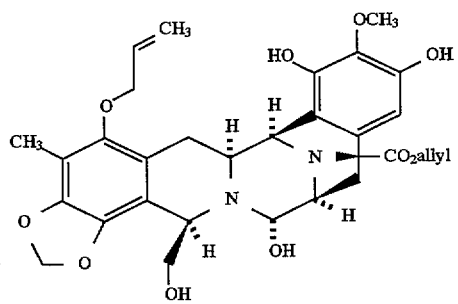

by an internal Mannich bisannulation;

(i) converting the pentacycle compound of Formula 10 to the compound of Formula 11 having the following structure:

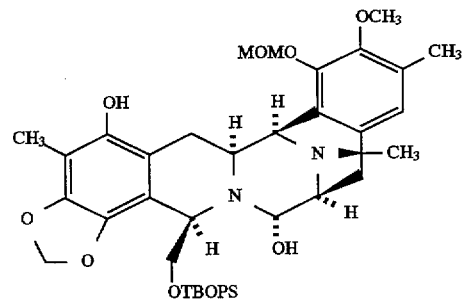

by the selective trifluoromethane-sulfonation of the least hindered phenolic hydroxyl; followed by (1) selective silylation of the primary hydroxyl; (2) protection of the remaining phenolic group as the methoxymethyl ether (3) double deallylation; (4) reductive N-methylation; and (5) replacement of $CF_3SO_3$ by $CH_3$;

(j) oxidizing the phenol compound of Formula 11 effected position-selective angular hydroxylation to give after desilylation the dihydroxy dienone compound of Formula 12 having the following structure:

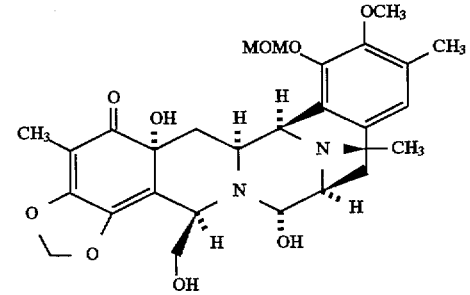

(k) forming the compound of Formula 13 having the following structure:

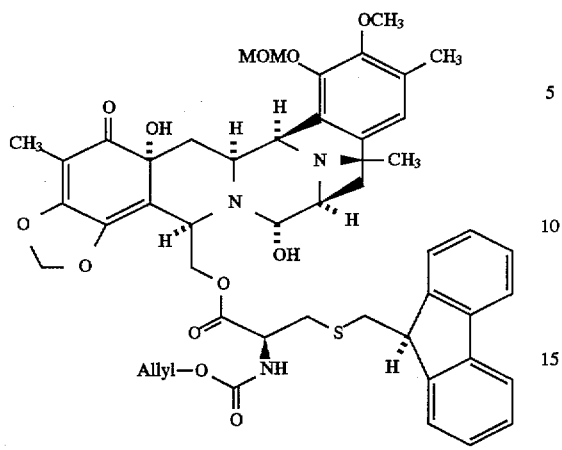

by esterifying the primary hydroxyl function of the compound of Formula 12 with (S)-N-allyloxycarbonyl-S-(9-fluorenylmethyl)cysteine;

(l) transforming the compound of Formula 13 to the bridged lactone compound of Formula 14 having the following structure:

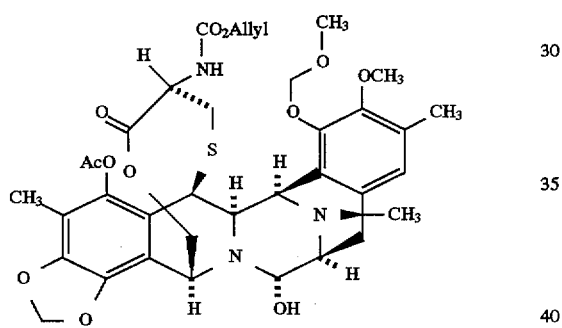

by;

(1) first reading the compound of Formula 13 with an in situ generated Swern reagent; (2) followed by the formation of the exendo quinone methide, (3) destruction of the excess Swern reagent; (4) addition of excess N-tert-butyl-N',N"-tetramethylguanidine to generate the 10-membered lactone bridge; and (5) addition of excess Ac$_2$O to acetylate the resulting phenoxide group; and (m) cleaving the N-allyloxycarbonyl group of the compound of Formula 14 and oxidizing the resulting α-amino lactone to the corresponding α-keto lactone by transamination thereby forming the compound of Formula 15.

5. An enantio- and stereocontrolled process for the preparation of the ecteinascidin synthetic intermediate of Formula 14, having the following structure:

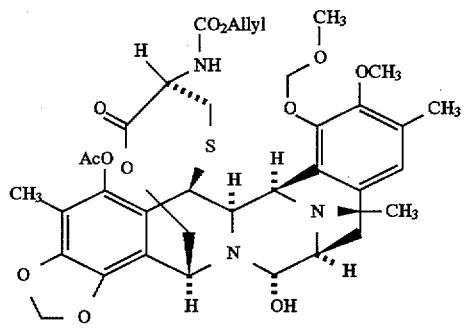

comprising the steps of:

(a) forming an α,β-unsaturated malonic ester of Formula 2, having the following structure:

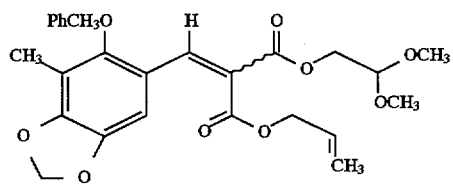

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

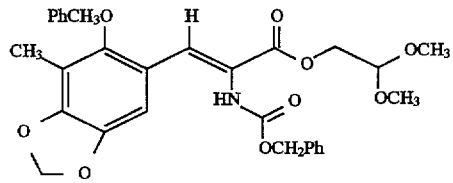

by selective allyl ester cleavage, Curtius rearrangement, and reaction of the intermediate isocyanate with benzyl alcohol;

(c) converting the compound of Formula 3 into the compound of Formula 4 having the following structure:

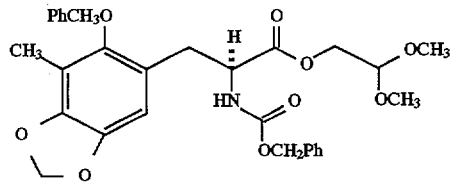

by catalytic hydrogenation over Rh[(COD)R,R-DIPAMP]$^+$BF$_4^-$;

(d) converting the compound of Formula 4 into the compound of Formula 5 having the following structure:

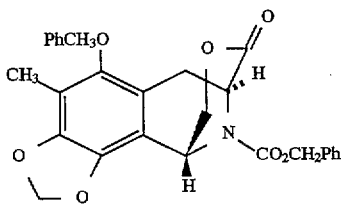

by acetal cleavage, wherein isolation and exposure of the resulting aldehyde to $BF_3.Et_2O$ and 4 Å mol sieves yields the bridged lactone compound of Formula 5;

(e) converting the bridged lactone compound of Formula 5 to the free amino phenol compound of Formula 6 having the following structure:

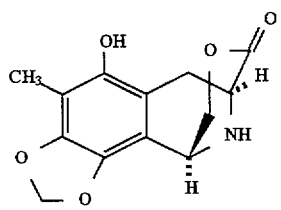

by hydrogenolysis over 10% Pd—C;

(f) forming the protected α-amino ester compound of Formula 7 having the following structure:

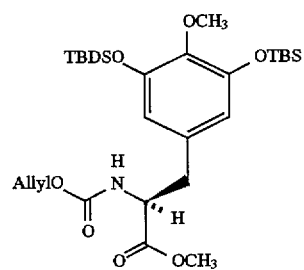

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

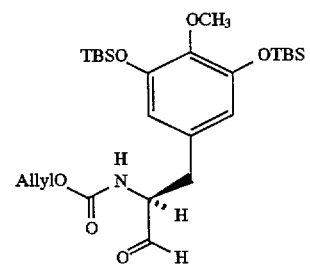

by reduction;

(h) combining the compounds of Formulae 6 and 8 to afford the monobridged pentacyclic intermediate of Formula 10, having the following structure:

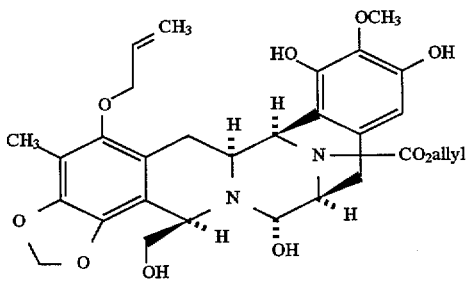

as follows:

reacting the compounds of Formulae 6 and 8 to give a coupled phenolic α-amino nitrile, followed by O-allylation to give the allyl ether compound of Formula 9 having the following structure:

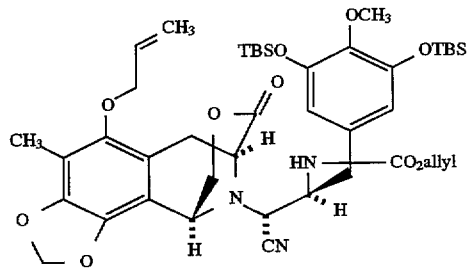

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 having the following structure:

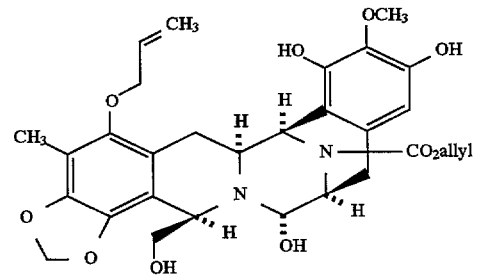

by a internal Mannich bisannulation;

(i) converting the pentacycle compound of Formula 10 to the compound of Formula 11 having the following structure:

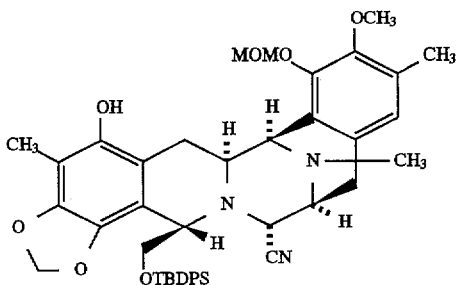

by the selective trifluoromethane-sulfonation of the least hindered phenolic hydroxyl; followed by
(1) selective silylation of the primary hydroxy; (2) protection of the remaining phenolic group as the methoxymethyl ether; (3) double deallylation; (4) reductive N-methylation; and (5) replacement of $CF_3SO_3$ by $CH_3$;

(j) oxidizing the phenol compound of Formula 11 effected position-selective angular hydroxylation to give after desilylation the dihydroxy dienone compound of Formula 12 having the following structure:

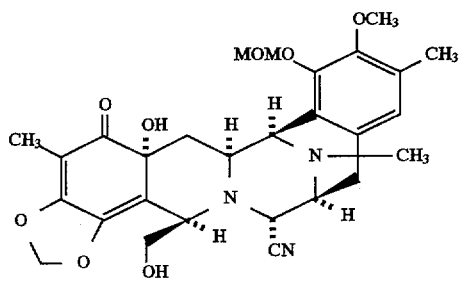

(k) forming the compound of Formula 13 having the following structure:

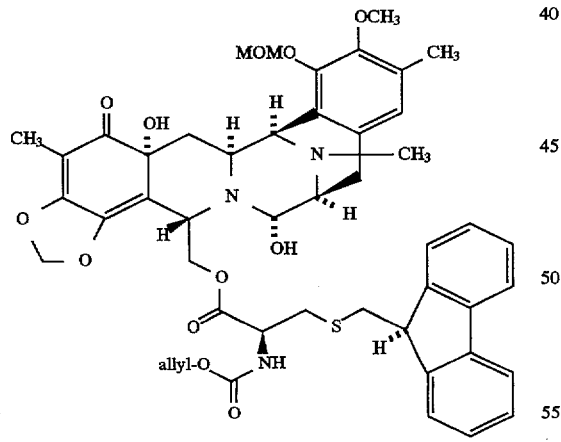

by esterifying the primary hydroxyl function of the compound of Formula 12 with (S)-N-allyloxycarbonyl-S-(9-fluorenylmethyl)cysteine; and (l) transforming the compound of Formula 13 to the bridged lactone compound of Formula 14 by;
(1) first reacting the compound of Formula 13 with an in situ generated Swern reagent; (2) followed by the formation of the exendo quinone methide, (3) destruction of the excess Swern reagent; (4) addition of excess N-tert-butyl-N',N"-tetramethylguanidine to generate the 10-membered lactone bridge; and (5) addition of excess $Ac_2O$ to acetylate the resulting phenoxy group.

6. An enantio- and stereocontrolled process for the preparation of the ecteinascidin synthetic intermediate of Formula 13, having the following structure:

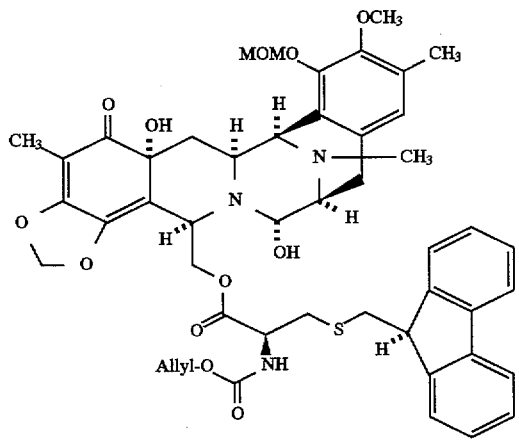

comprising the steps of:

(a) forming an α,β-unsaturated malonic ester of Formula 2, having the following structure:

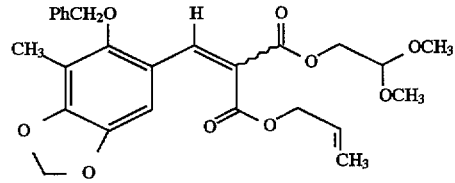

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

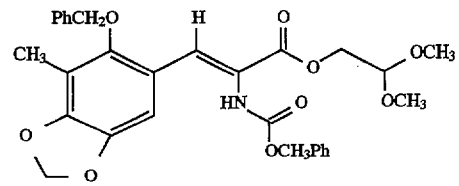

by selective allyl ester cleavage, Curtius rearrangement, and reaction of the intermediate isocyanate with benzyl alcohol;

(c) converting the compound of Formula 3 into the compound of Formula 4 having the following structure:

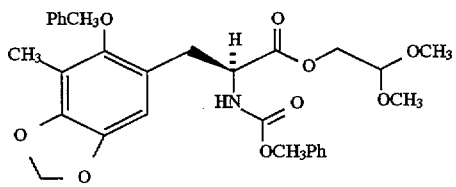

by catalytic hydrogenation over Rh[(COD)R,R-DIPAMP]⁺BF₄⁻;

(d) converting the compound of Formula 4 into the compound of Formula 5 having the following, structure:

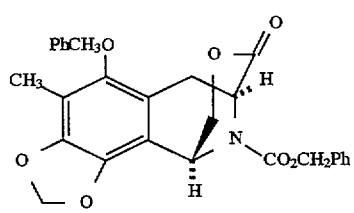

by acetal cleavage, wherein isolation and exposure of the resulting aldehyde to $BF_3 \cdot Et_2O$ and 4 Å mol sieves yields the bridged lactone compound of Formula 5;

(e) converting the bridged lactone compound of Formula 5 to the free amino phenol compound of Formula 6 having the following structure:

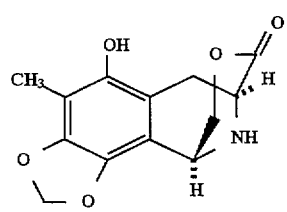

by hydrogenolysis over 10% Pd—C;

(f) forming the protected α-amino ester compound of Formula 7 having the following structure:

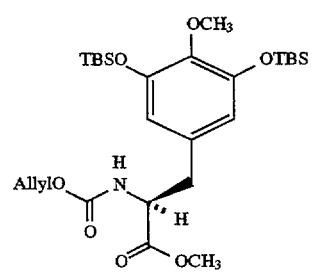

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

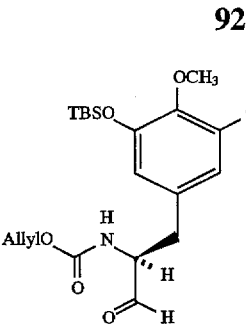

by reduction;

(h) combining the compounds of Formulae 6 and 8 to afford the monobridged pentacyclic intermediate of Formula 10, having the following structure:

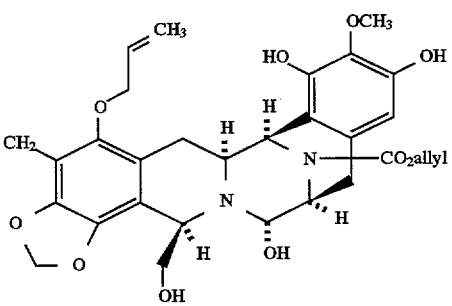

as follows:

reacting the compounds of Formulae 6 and 8 to give a coupled phenolic α-amino nitrile, followed by O-allylation to give the ally ether compound of Formula 9 having the following structure:

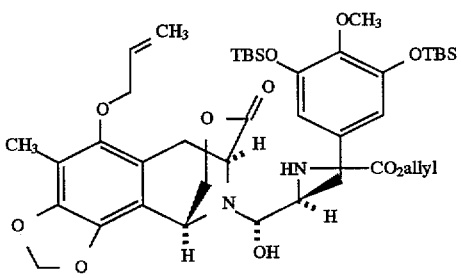

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 by an internal Mannich bisannulation;

(i) converting the pentacycle compound of Formula 10 to the compound of Formula 11 having the following structure:

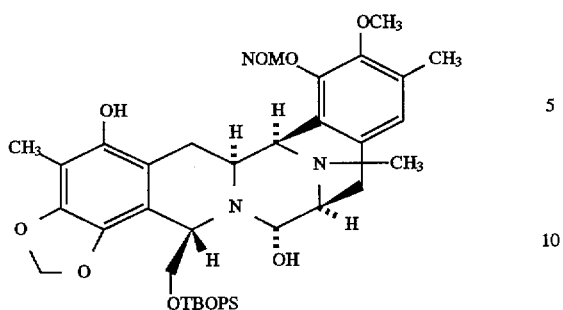

by the selective trifluoromethane-sulfonation the least hindered phenolic hydroxyl; followed by
(1) selective silylation of the primary hydroxyl; (2) protection of the remaining phenolic group as the methoxymethyl ether; (3) double deallylation; (4) reductive N-methylation, and (5) replacement of $CF_3SO_3$ by $CH_3$;

(j) oxidizing the phenol compound of Formula 11 effected position-selective angular hydroxylation to give after desilylation the dihydroxy dienone compound of Formula 12 having the following structure:

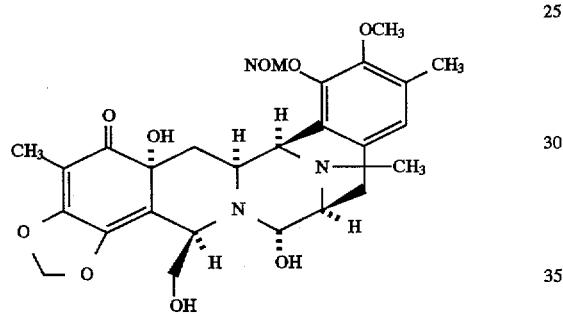

and (k) forming the compound of Formula 13 by esterifying the primary hydroxyl function of the compound of Formula 12 with (S)-N-allyloxycarbonyl-S-(9-fluorenylmethyl)cysteine.

7. An enantio- and stereocontrolled process for the preparation of the ecteinascidin synthetic intermediate of Formula 12, comprising the steps of:

(a) forming an α,β-unsaturated malonic ester of Formula 2, having the following structure:

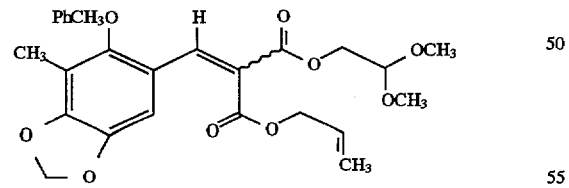

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

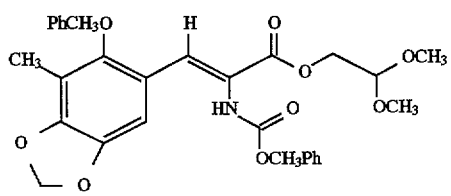

by selective allyl ester cleavage, Curtius rearrangement, and reaction of the intermediate isocyanate with benzyl alcohol;

(c) converting the compound of Formula 3 into the compound of Formula 4 having the following structure:

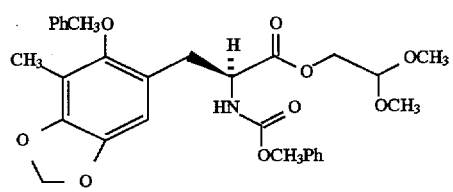

by catalytic hydrogenation over $Rh[(COD)R,R-DIPAMP]^+BF_4^-$;

(d) converting the compound of Formula 4 into the compound of Formula 5 having the following structure:

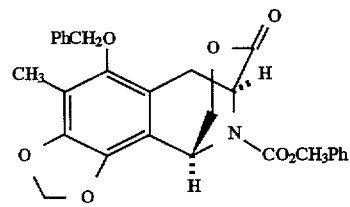

by acetal cleavage, wherein isolation and exposure of the resulting aldehyde to $BF_3.Et_2O$ and 4 Å mol sieves yields the bridged lactone compound of Formula 5;

(e) converting the bridged lactone compound of Formula 5 to the free amino phenol compound of Formula 6 having the following structure:

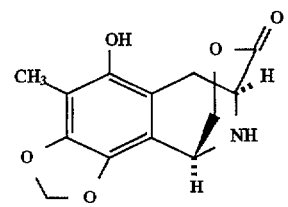

by hydrogenolysis over 10% Pd—C;

(f) forming the protected α-amino ester compound of Formula 7 having the following structure:

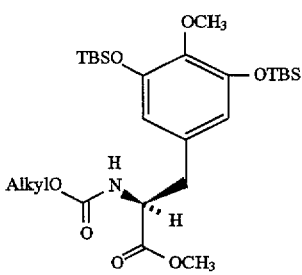

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

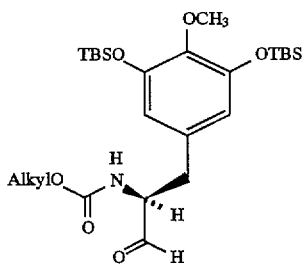

by reduction;

(h) combining the compounds of Formulae 6 and 8 to afford the monobridged pentacyclic intermediate of Formula 10, having the following structure:

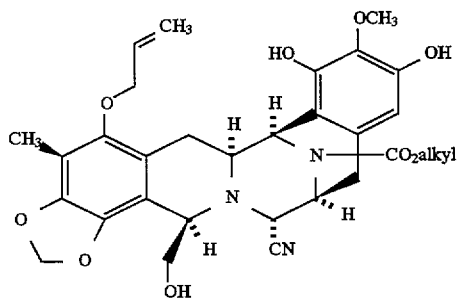

as follows:
reacting the compounds of Formulae 6 and 8 to give a coupled phenolic α-amino nitrile, followed by O-allylation to give the allyl ether compound of Formula 9 having the following structure:

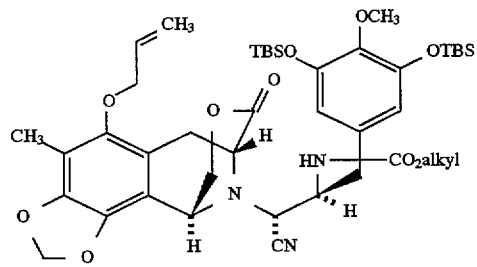

selectively converting the lactone function in the compound of Formula 9 to a lactol by reacting the compound of Formula 9 with diisobutylaluminum hydride;
desilylating the lactol compound; and
cyclizing the desilylated compound to afford the pentacycle compound of Formula 10 by an internal Mannich bisannulation;

(i) converting the pentacycle compound of Formula 10 to the compound of Formula 11 having the following structure:

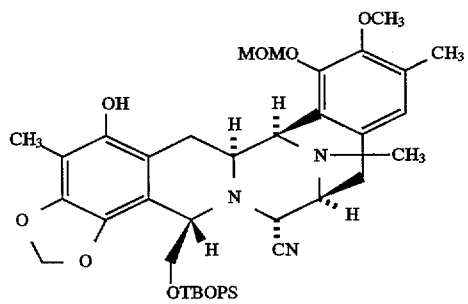

by the selective trifluoromethane-sulfonation of the least hindered phenolic hydroxyl; followed by (1) selective silylation of the primary hydroxyl; (2) protection of the remaining phenolic group as the methoxymethyl ether; (3) double deallylation; (4) reductive N-methylation; and (5) replacement of $CF_3SO_3$ by $CH_3$; and (j) oxidizing the phenol compound of Formula 11 effected position-selective angular hydroxylation to give after desilylation the dihydroxy dienone compound of Formula 12 having the following structure:

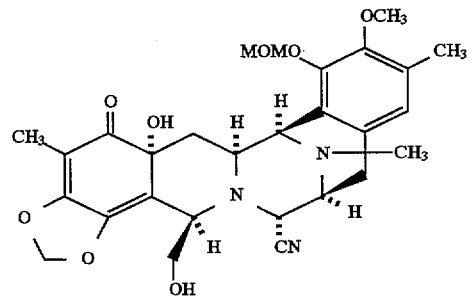

8. An enantio- and stereocontrolled process for the preparation of the ecteinascidin synthetic intermediate of Formula 11, having the following structure;

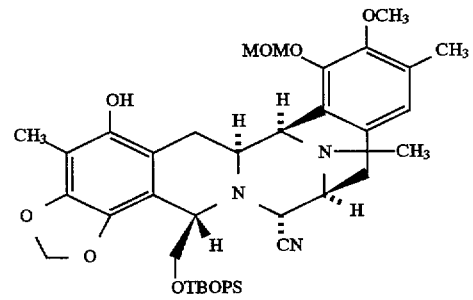

comprising the steps of:

(a) forming an α,β-unsaturated malonic ester of Formula 2, having the following structure:

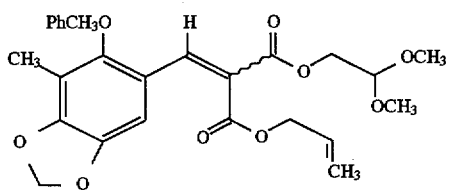

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

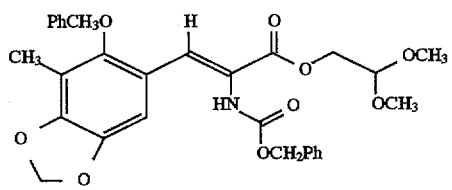

by selective allyl ester cleavage, Curtius rearrangement, and reaction of the intermediate isocyanate with benzyl alcohol;

(c) converting the compound of Formula 3 into the compound of Formula 4 having the following structure:

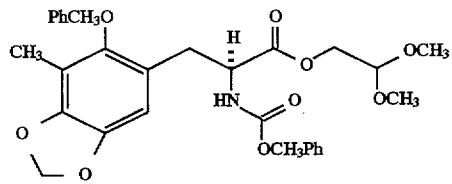

by catalytic hydrogenation over Rh[(COD)R,R-DIPAMP]⁺BF₄⁻;

(d) converting the compound of Formula 4 into the compound of Formula 5 having the following structure:

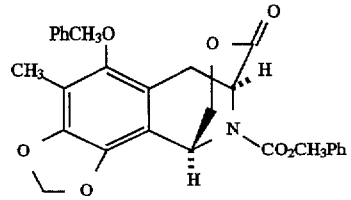

by acetal cleavage, wherein isolation and exposure of the resulting aldehyde to BF₃·Et₂O and 4 Å mol sieves yields the bridged lactone compound of Formula 5;

(e) converting the bridged lactone compound of Formula 5 to the free amino phenol compound of Formula 6 having the following structure:

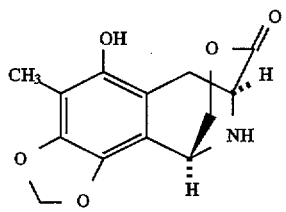

by hydrogenolysis over 10% Pd—C;

(f) forming the protected α-amino ester compound of Formula 7 having the following structure:

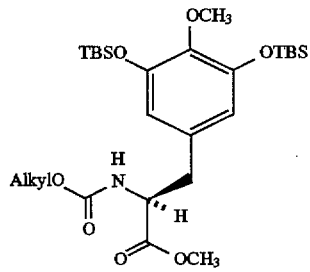

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

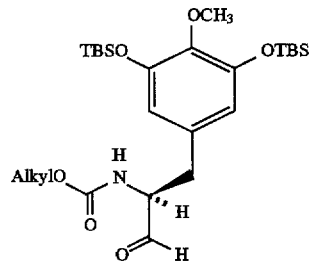

by reduction;

(h) combining the compounds of Formulae 6 and 8 to afford the monobridged pentacyclic intermediate of Formula 10, having the following structure:

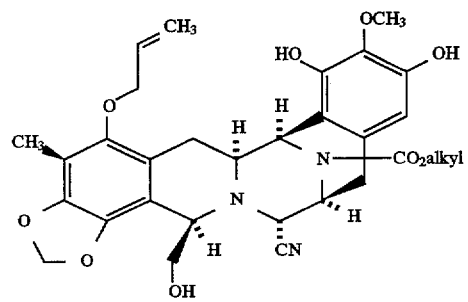

as follows:
reacting the compounds of Formulae 6 and 8 to give a coupled phenolic α-amino nitrile, followed by O-allylation to give the allyl ether compound of Formula 9 having the following structure:

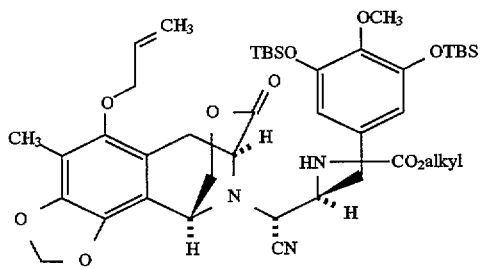

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 by an internal Mannich bisannulation; and (i) converting the pentacycle compound of Formula 10 to the compound of Formula 11 by the selective trifluoromethane-sulfonation of the least hindered phenolic hydroxyl; followed by (1) selective silylation of the primary hydroxyl; (2) protection of the remaining phenolic group as the methoxymethyl ether; (3) double deallylation; (4) reductive N-methylation; and (5) replacement of $CF_3SO_3$ by $CH_3$.

9. An enantio- and stereocontrolled process for the preparation of the ecteinascidin synthetic intermediate of Formula 10, having the following structure:

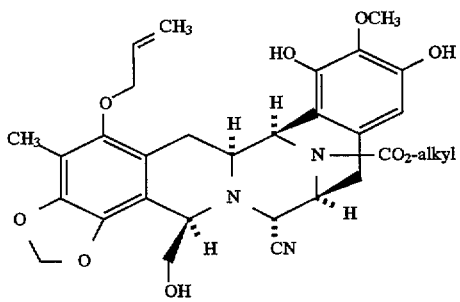

comprising the steps of:

(a) forming α,β-unsaturated malonic ester of Formula 2, having the following structure:

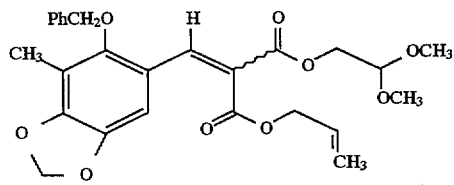

as a mixture of E and Z isomers from 2-benzyloxy-3-methyl-4,5-methylenedioxybenzaldehyde and allyl 2,2-dimethoxyethyl malonate;

(b) stereospecifically converting the compound of Formula 2 to the compound of Formula 3, having the following structure:

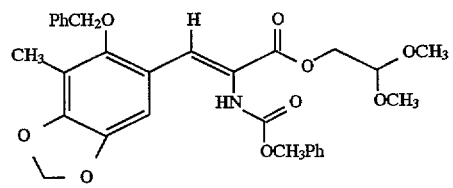

by selective allyl ester cleavage, Curtius rearrangement, and reaction of the intermediate isocyanate with benzyl alcohol;

(c) converting the compound of Formula 3 into the compound of Formula 4 having the following structure:

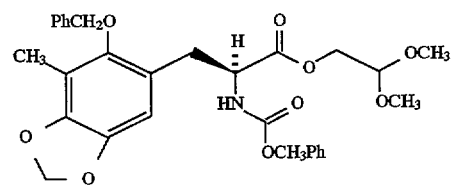

by catalytic hydrogenation over $Rh[(COD)R,R\text{-}DIPAMP]^+BF_4^-$;

(d) converting the compound of Formula 4 into the compound of Formula 5 having the following structure:

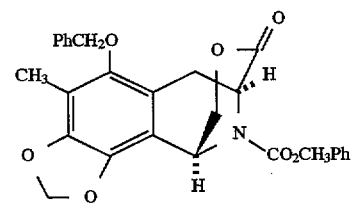

by acetal cleavage, wherein isolation and exposure of the resulting aldehyde to $BF_3.Et_2O$ and 4 Å mol sieves yields the bridged lactone compound of Formula 5;

(e) converting the bridged lactone compound of Formula 5 to the free amino phenol compound of Formula 6 having the following structure:

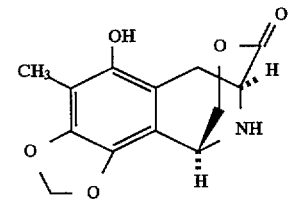

by hydrogenolysis over 10% Pd—C;

(f) forming the protected α-amino ester compound of Formula 7 having the following structure:

101

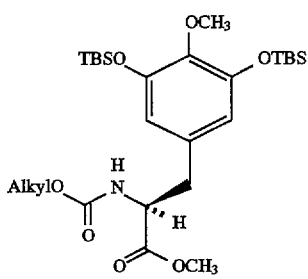

by reacting 3,5-bis-tert-butyl-dimethyl-silyloxy-4-methoxybenzaldehyde and methyl hydrogen malonate;

(g) converting the protected α-amino ester compound of Formula 7 to the chiral aldehyde 8 having the following structure:

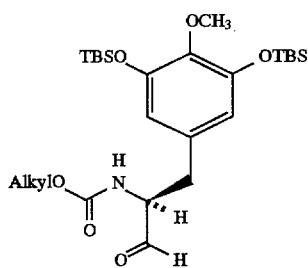

by reduction; and (h) combining the compounds of Formulae 6 and 8 to afford the monobridged pentacyclic intermediate of Formula 10, as follows:

reacting the compounds of Formulae 6 and 8 to give a coupled phenolic α-amino nitrile, followed by O-allylation to give the allyl ether compound of Formula 9 having the following structure:

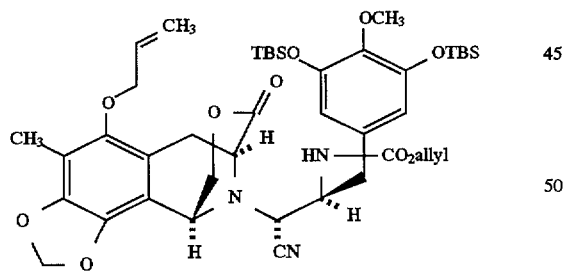

selectively converting the lactone function in the compound of Formula 9 to a lactol by reacting the compound of Formula 9 with diisobutylaluminum hydride;

desilylating the lactol compound; and cyclizing the desilylated compound to afford the pentacycle compound of Formula 10 by an internal Mannich bisannulation.

102

10. The α,β-unsaturated diester compound of Formula 2:

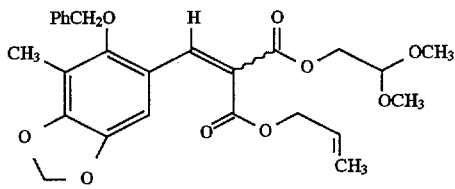

11. The benzyl carbamate compound of Formula 3:

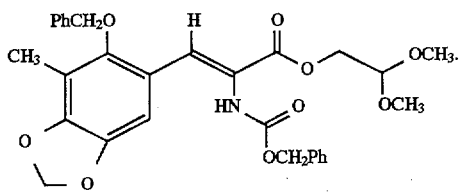

12. The protected amino acid compound of Formula 4:

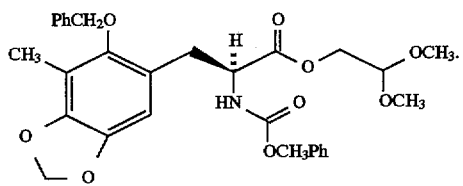

13. The lactone compound of Formula 5:

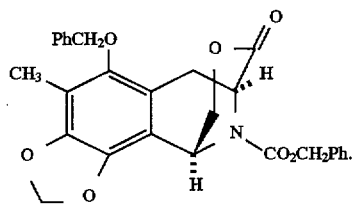

14. The aminophenol compound of Formula 6:

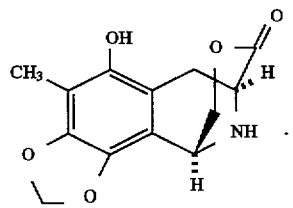

15. The aminonitrile compound of Formula 37:

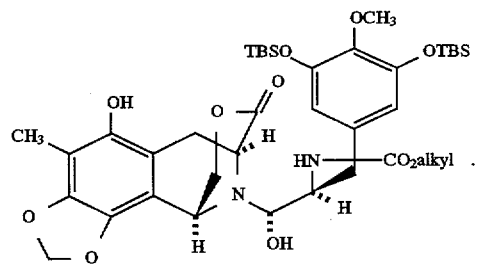

16. The allyl ether compound of Formula 9:
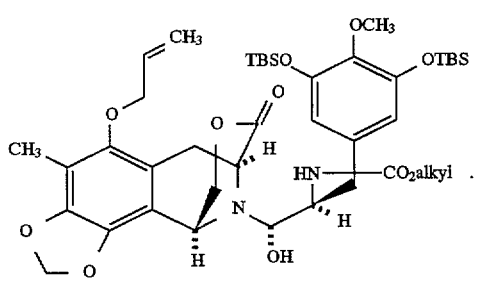
17. The compound of Formula 38:
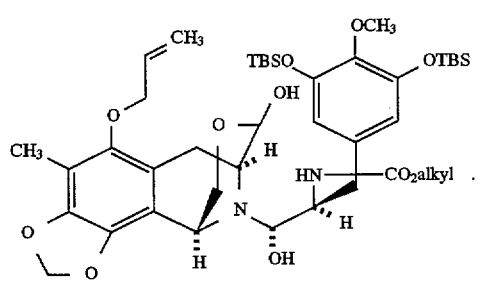
18. The compound of Formula 39:
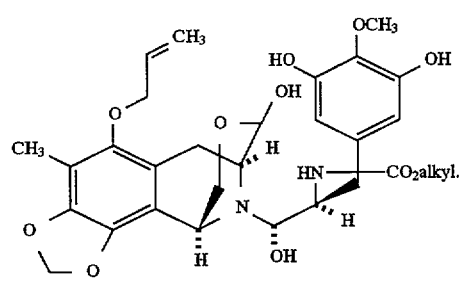
19. The triol compound of Formula 10:
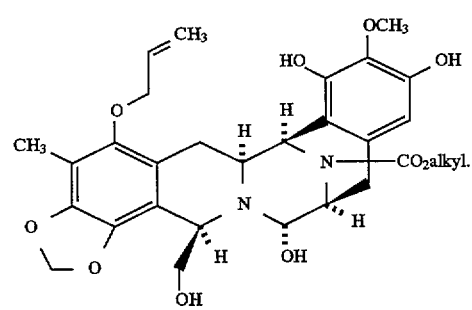
20. The aryl triflate compound of Formula 40:
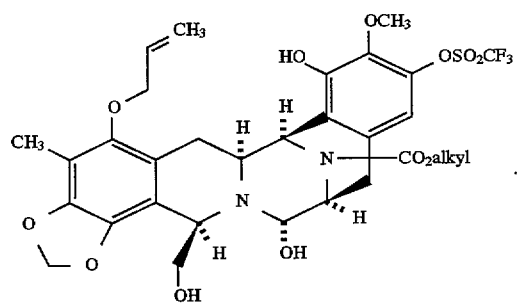
21. The silyl ether compound of Formula 41:
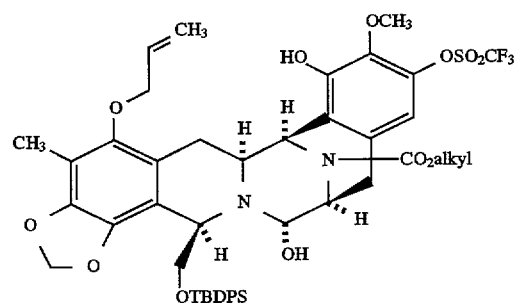
22. The methoxymethyl ether compound of formula 42:
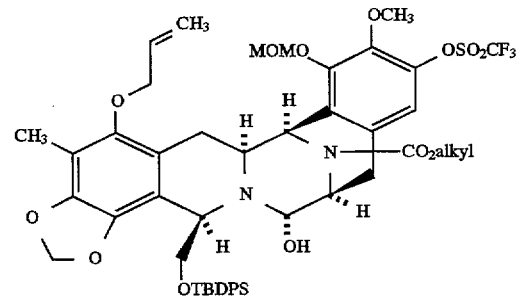
23. The aminophenol compound of Formula 43:
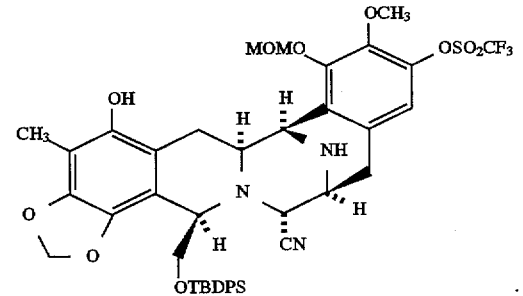

24. The phenol compound of Formula 44:
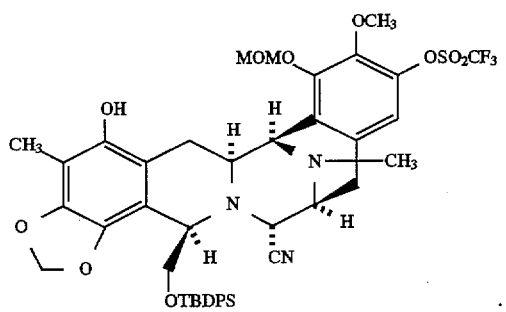
25. The phenol compound of Formula 11:
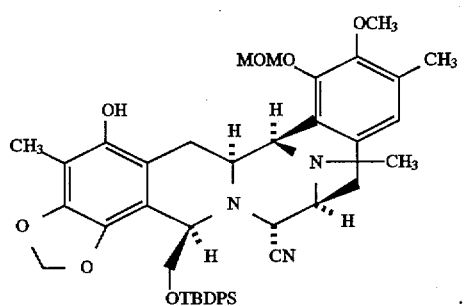
26. The hydroxy dienone compound of Formula 45:
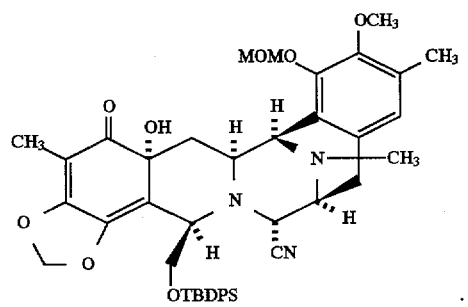
27. The diol compound of Formula 12:
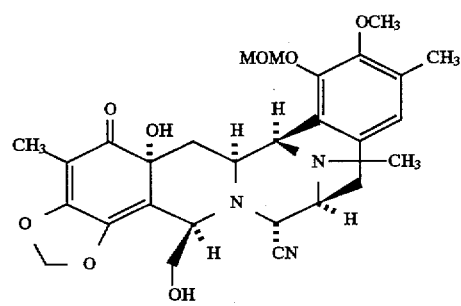
28. The ester compound of Formula 13:
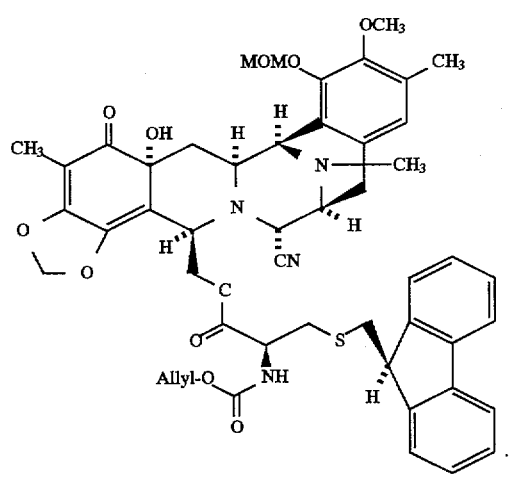
29. The lactone compound of Formula 14:
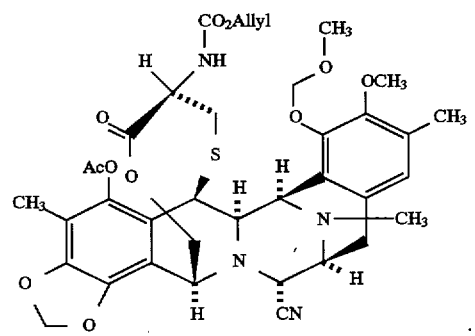
30. The amine compound of Formula 47:
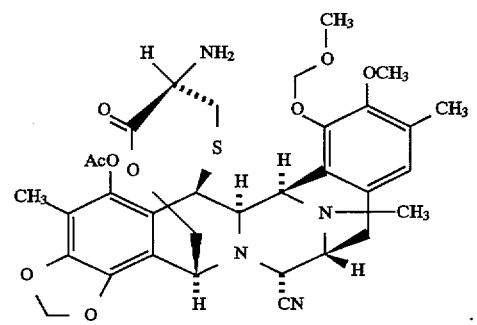

31. The ketone compound of Formula 15:
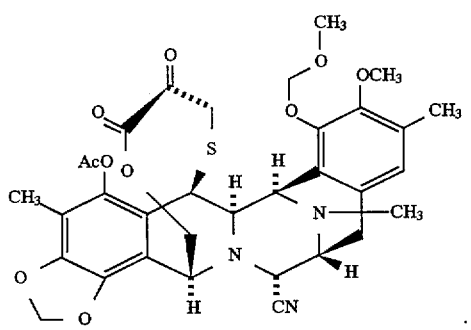
32. The tristetrahydroisoquinoline compound of Formula 48:
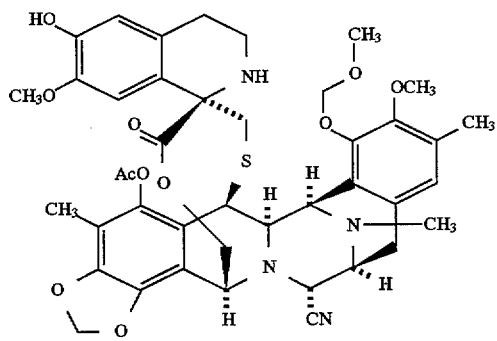
* * * * *

UNITED STATES PATENT AND TRADEMARK OFFICE
CERTIFICATE OF CORRECTION

PATENT NO. : 5,721,362  
APPLICATION NO. : 08/715541  
DATED : February 24, 1998  
INVENTOR(S) : Elias Corey and David Gin It is certified that error appears in the above-identified patent and that said Letters Patent is hereby corrected as shown below:

IN THE ABSTRACT

Kindly replace

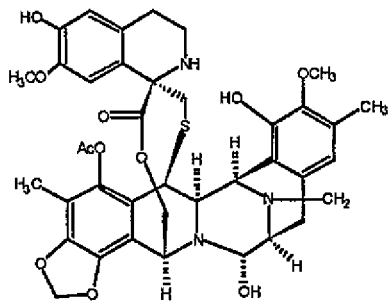  with  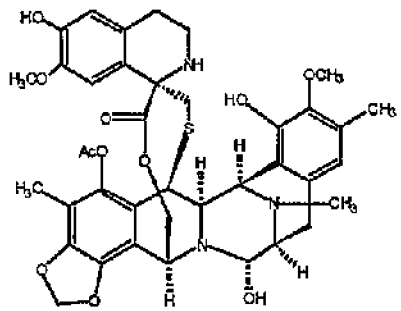

IN THE SPECIFICATION

In column 2, kindly replace

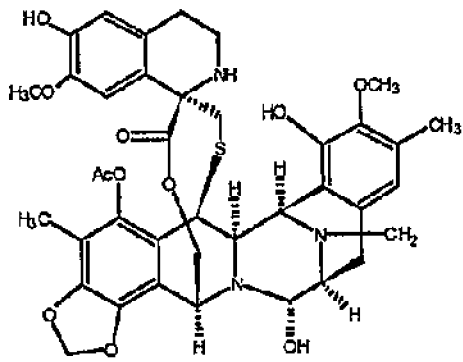  with  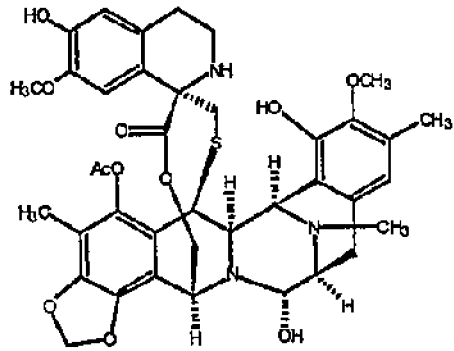

UNITED STATES PATENT AND TRADEMARK OFFICE
CERTIFICATE OF CORRECTION

PATENT NO. : 5,721,362  Page 2 of 43
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 3, Scheme I, compound 4, kindly replace

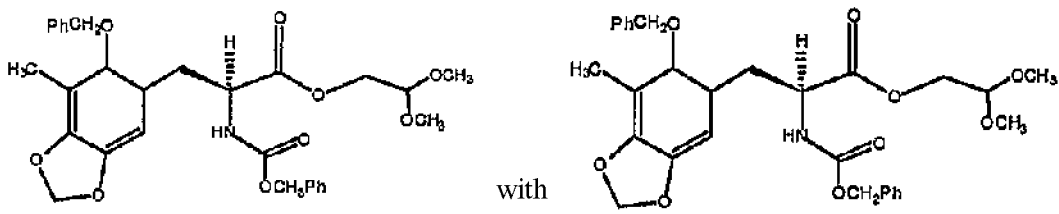

In column 3, Scheme I, compounds 5 and 6, kindly replace

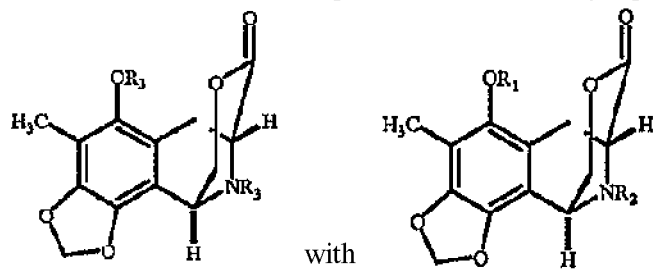

In column 3, Scheme I, compounds 7 and 8, kindly replace

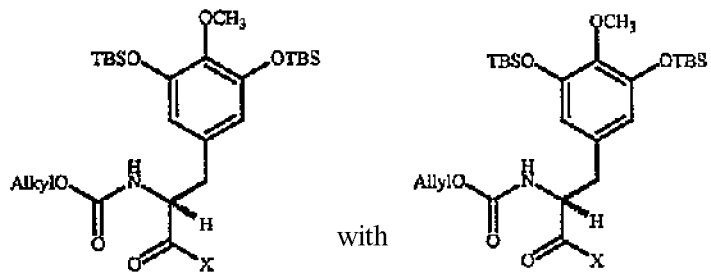

In column 4, Scheme I, compound 10, kindly replace

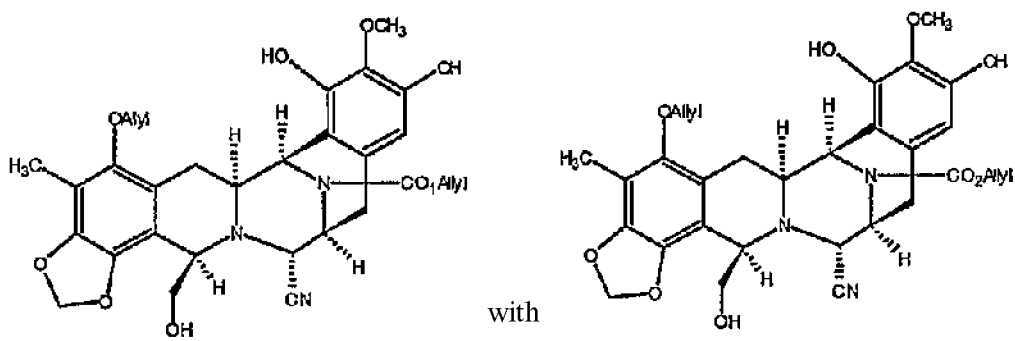

UNITED STATES PATENT AND TRADEMARK OFFICE
CERTIFICATE OF CORRECTION

PATENT NO.        : 5,721,362
APPLICATION NO.   : 08/715541
DATED             : February 24, 1998
INVENTOR(S)       : Elias Corey and David Gin It is certified that error appears in the above-identified patent and that said Letters Patent is hereby corrected as shown below:

In column 5, Scheme I, kindly replace the label "72" for the first compound with the label --12--.

In column 6, Scheme I, compound 16, kindly replace

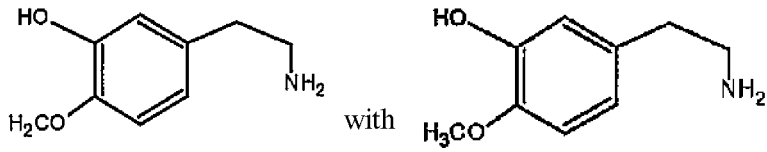

In column 9, lines 1-20, compounds 5 and 6, kindly replace

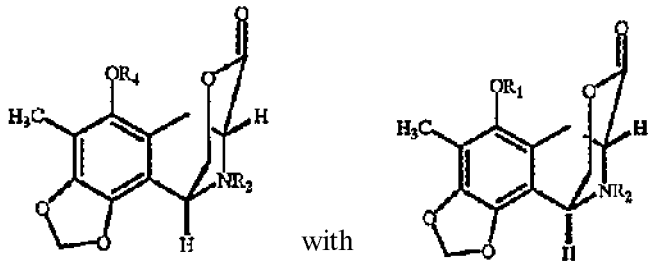

In column 9, lines 50-60, compound 38, kindly replace

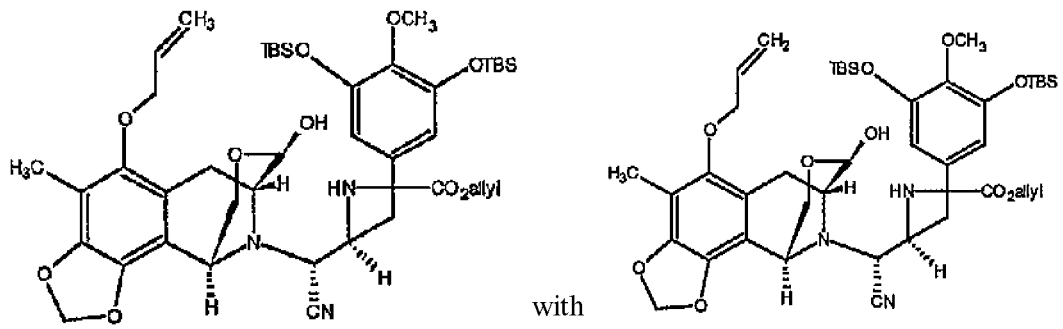

UNITED STATES PATENT AND TRADEMARK OFFICE
CERTIFICATE OF CORRECTION

PATENT NO. : 5,721,362  
APPLICATION NO. : 08/715541  
DATED : February 24, 1998  
INVENTOR(S) : Elias Corey and David Gin It is certified that error appears in the above-identified patent and that said Letters Patent is hereby corrected as shown below:

In column 10, lines 1-15, compound 39, kindly replace

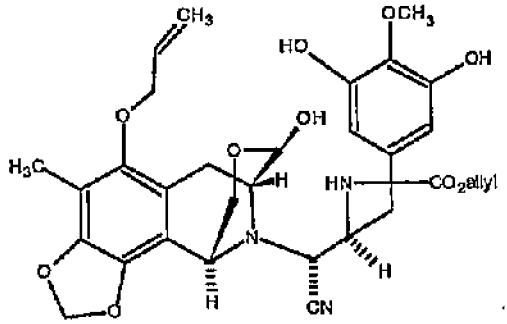 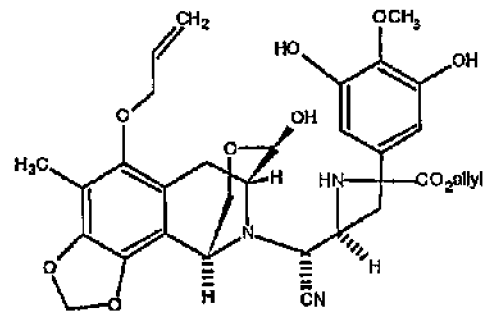 .with

In column 11, lines 40-50, compound 45, kindly replace

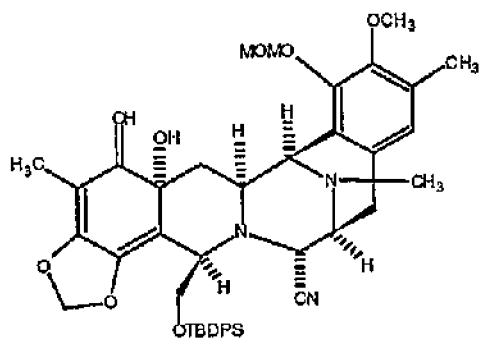 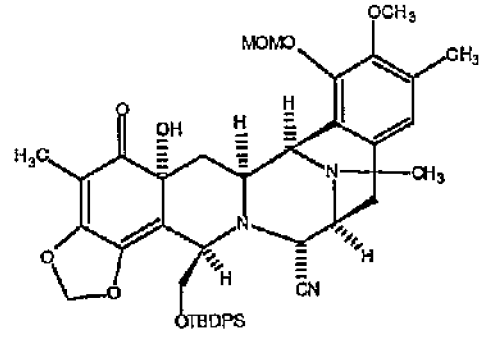 with

In column 11, lines 50-65, compound 12, kindly replace

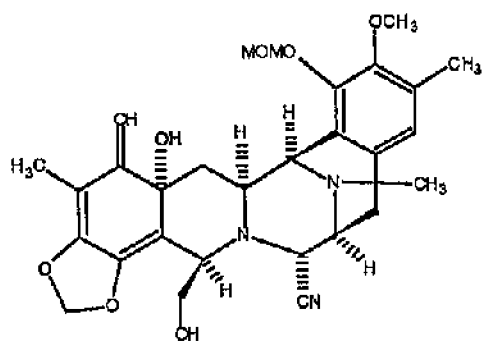 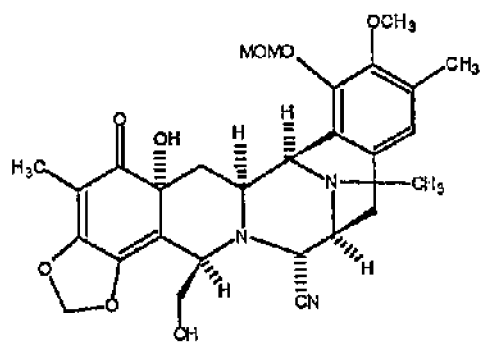 with

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 12, lines 1-15, compound 13, kindly replace

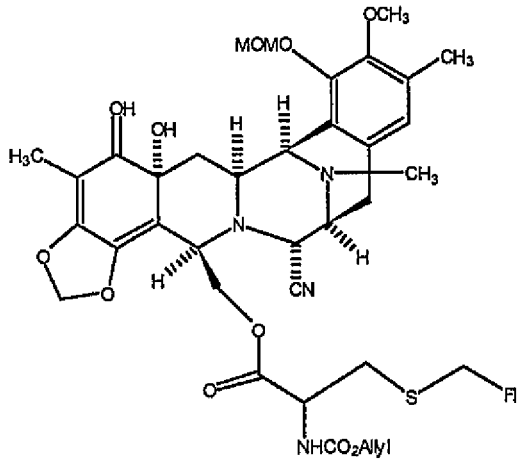 with 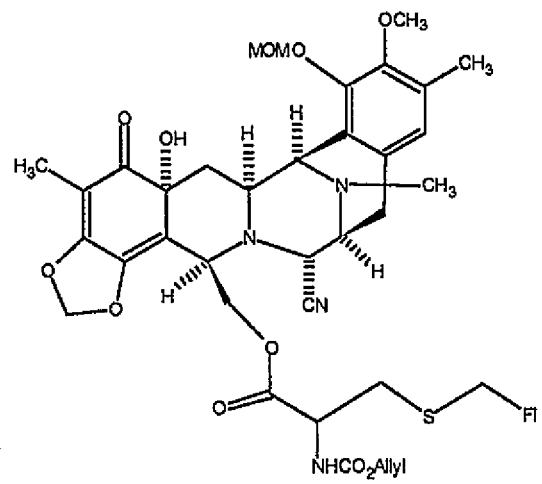

In column 12, lines 20-35, compound 14, kindly replace

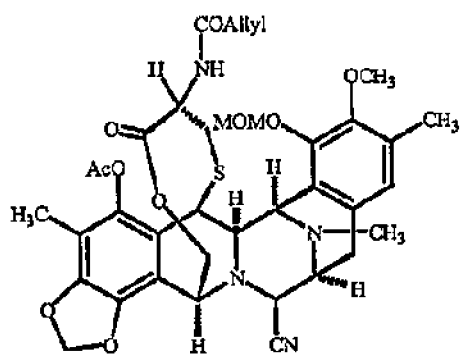 with 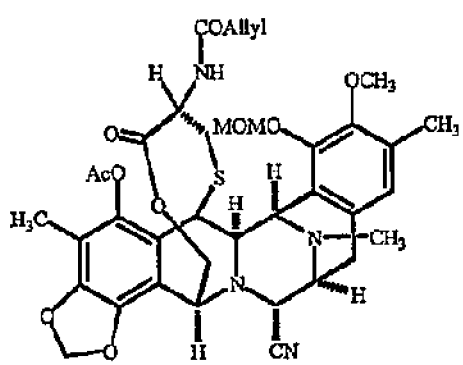

In column 12, lines 50-65, compound 15, kindly replace

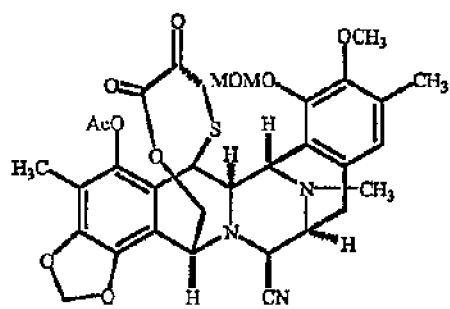 with 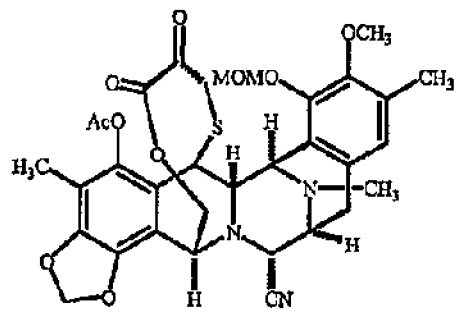

UNITED STATES PATENT AND TRADEMARK OFFICE
CERTIFICATE OF CORRECTION

PATENT NO.        : 5,721,362                                    Page 6 of 43
APPLICATION NO. : 08/715541
DATED              : February 24, 1998
INVENTOR(S)      : Elias Corey and David Gin It is certified that error appears in the above-identified patent and that said Letters Patent is hereby corrected as shown below:

In column 13, lines 1-14, compound 48, kindly replace

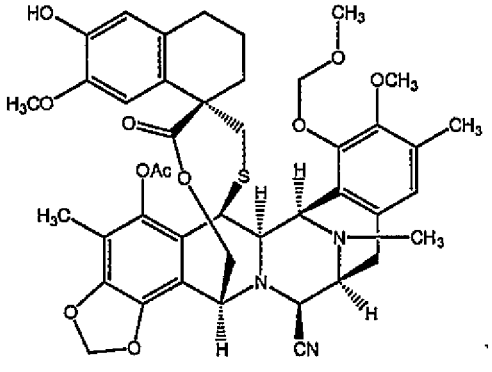 with 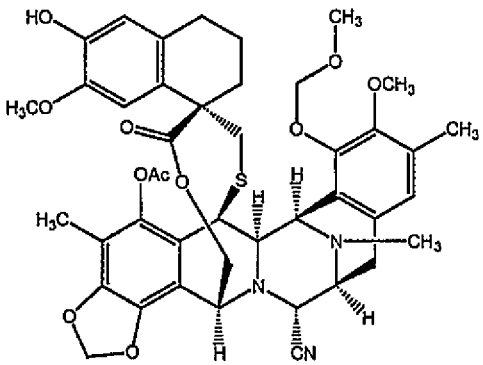

In column 15, Scheme 2, compound 23, kindly replace

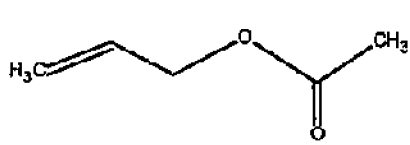 with 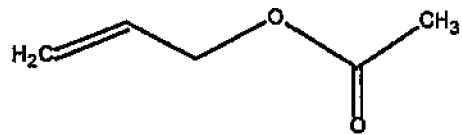

In column 16, Scheme 2, compound 20, kindly replace

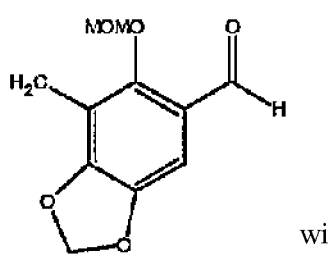 with 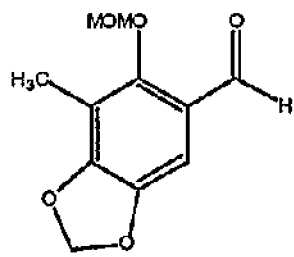

In column 17, Scheme 2, compound 24, kindly replace

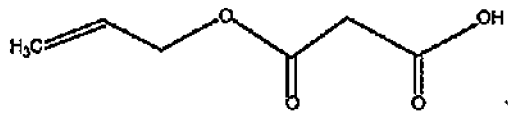 with 

UNITED STATES PATENT AND TRADEMARK OFFICE
CERTIFICATE OF CORRECTION

PATENT NO.         : 5,721,362
APPLICATION NO. : 08/715541
DATED                  : February 24, 1998
INVENTOR(S)        : Elias Corey and David Gin It is certified that error appears in the above-identified patent and that said Letters Patent is hereby corrected as shown below:

In column 18, Scheme 2, compound 25, kindly replace

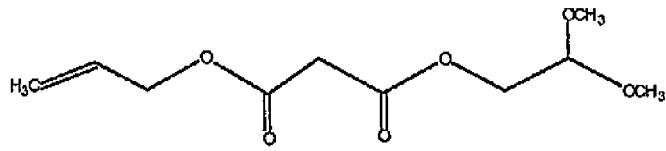

with

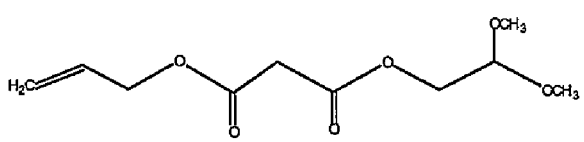

In column 17, Scheme 2, kindly delete the number "25" underneath the structure of 2,2-dimethoxyethanol by replacing

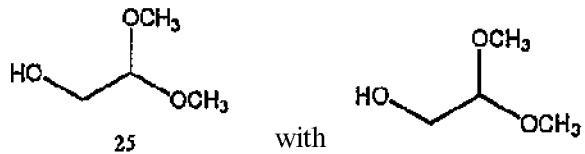

In column 17, Scheme 3, compound 26, kindly replace

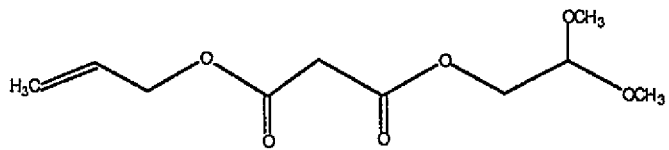

with

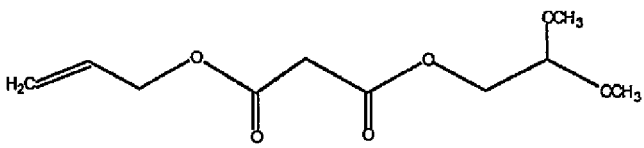

In column 19, Scheme 4, compound 29, kindly replace

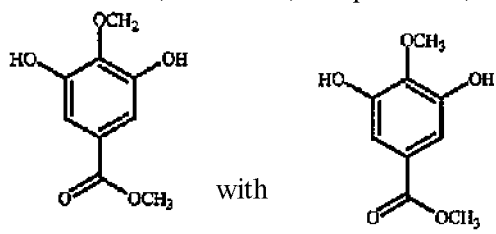

UNITED STATES PATENT AND TRADEMARK OFFICE
CERTIFICATE OF CORRECTION

PATENT NO.        : 5,721,362
APPLICATION NO. : 08/715541
DATED              : February 24, 1998
INVENTOR(S)       : Elias Corey and David Gin It is certified that error appears in the above-identified patent and that said Letters Patent is hereby corrected as shown below:

In column 19, Scheme 4, compound 34 kindly replace

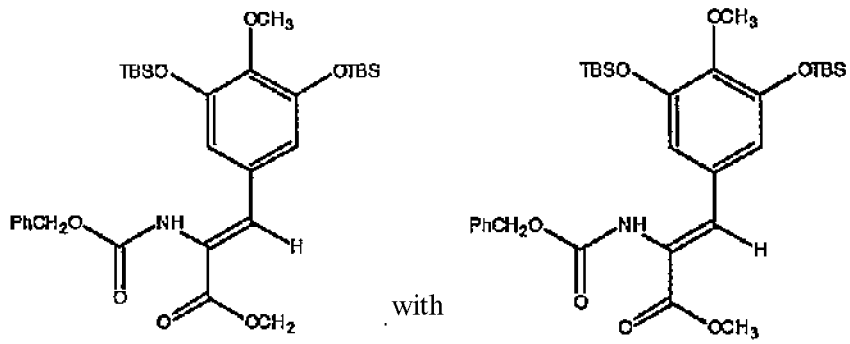

In columns 19 and 20, Scheme 4, compound 36, kindly replace

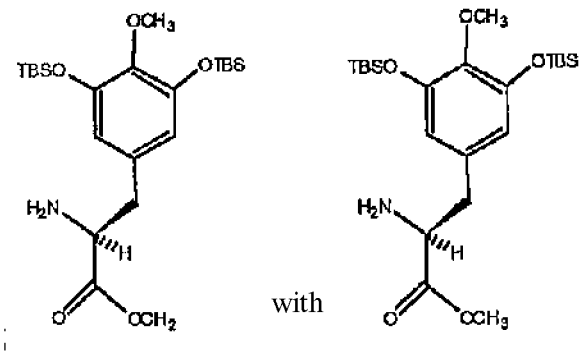

In column 23, Scheme 5, compound 41, kindly replace

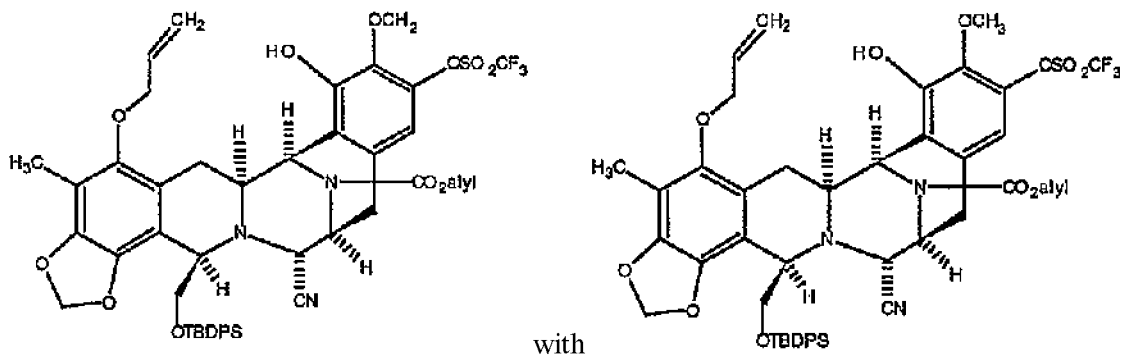

UNITED STATES PATENT AND TRADEMARK OFFICE
CERTIFICATE OF CORRECTION

PATENT NO.         : 5,721,362                              Page 9 of 43
APPLICATION NO. : 08/715541
DATED                 : February 24, 1998
INVENTOR(S)        : Elias Corey and David Gin It is certified that error appears in the above-identified patent and that said Letters Patent is hereby corrected as shown below:

In column 23, Scheme 6, compound 41, kindly replace

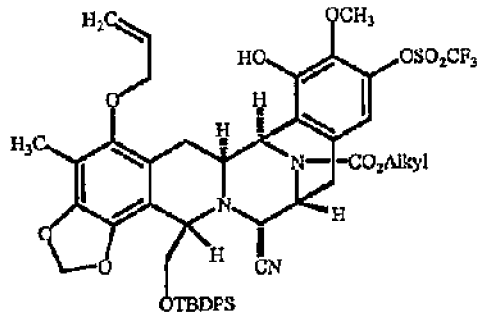 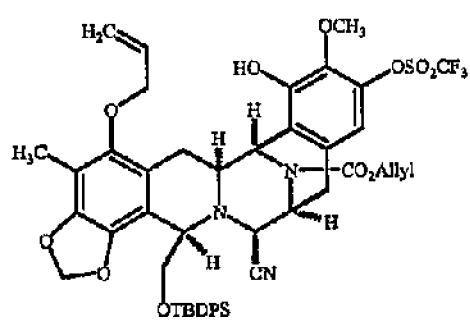

with

In column 24, Scheme 6, compound 42, kindly replace

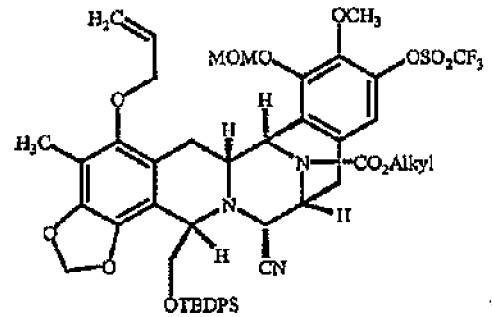 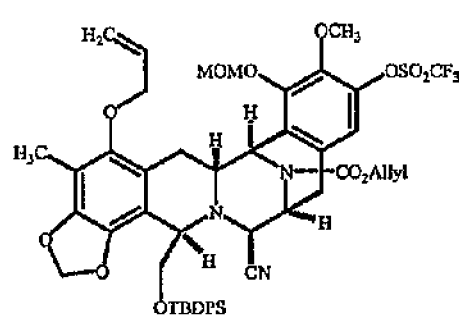

with

In column 23, Scheme 6, compound 44, kindly replace

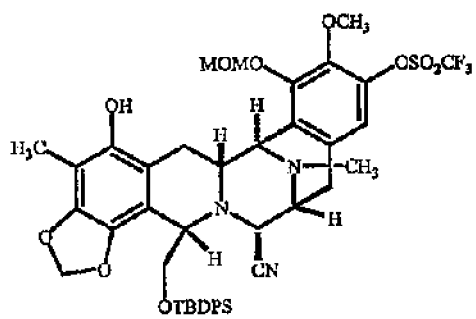 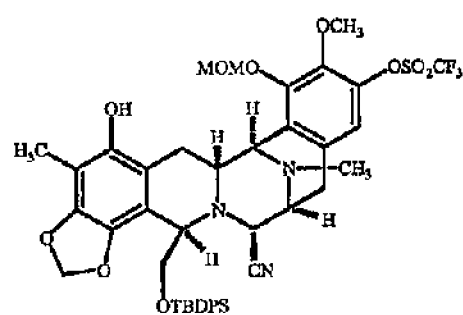

with

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 24, Scheme 6, compound 43, kindly replace

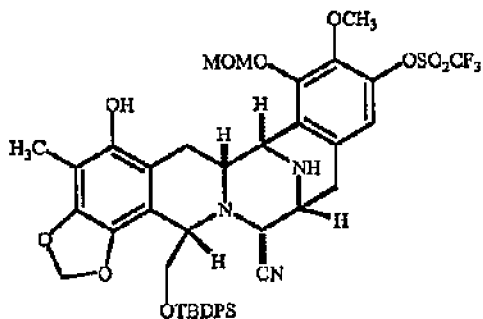 with 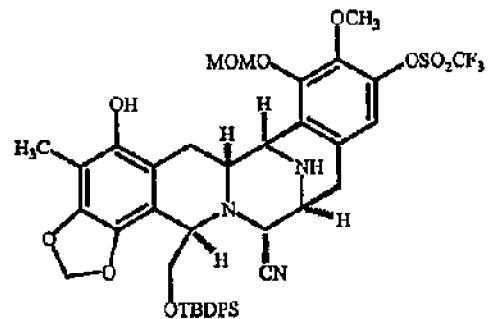

In column 25, Scheme 6, compound 11, kindly replace

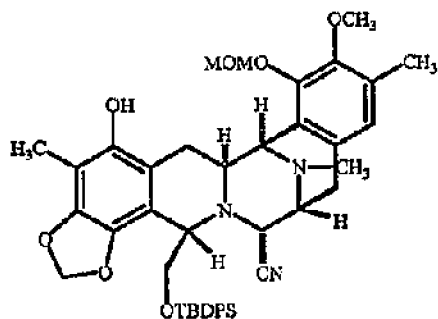 with 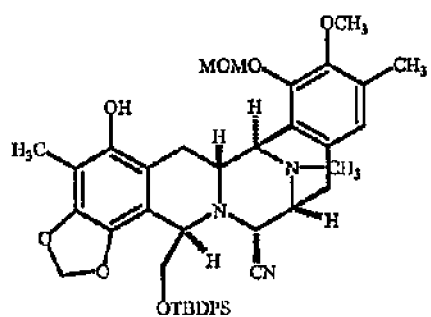

In column 26, Scheme 6, compound 45, kindly replace

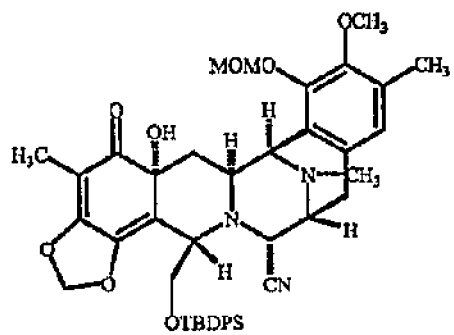 with 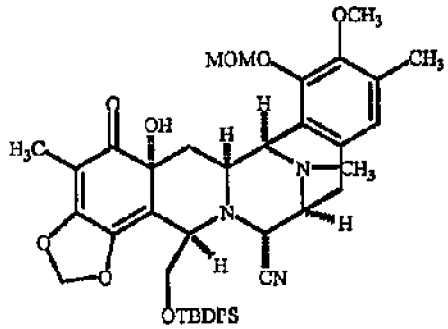

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In columns 25 and 26, Scheme 6, compound 12, kindly replace

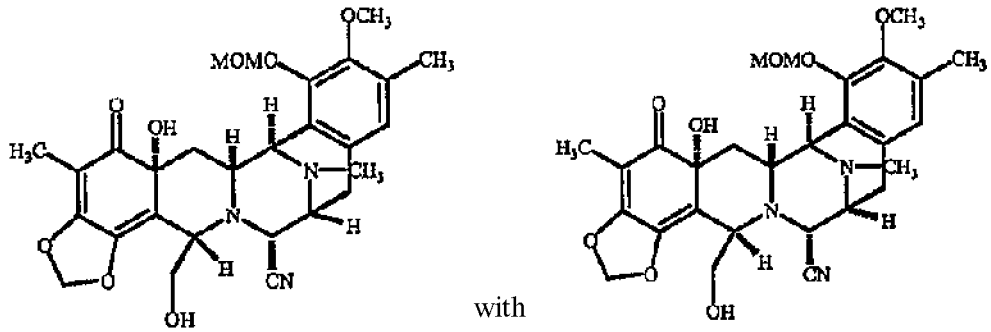

with

In column 25, Scheme 7, compound 12, kindly replace

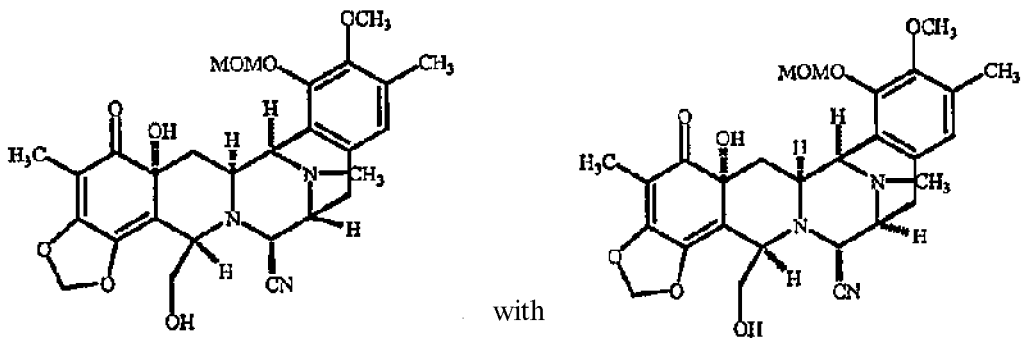

with

In column 26, Scheme 7, compound 13, kindly replace

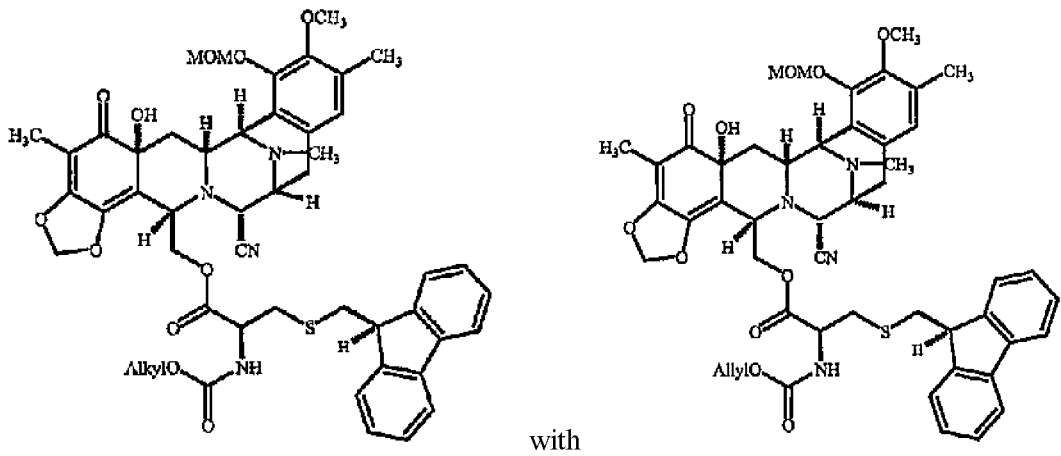

with

UNITED STATES PATENT AND TRADEMARK OFFICE
CERTIFICATE OF CORRECTION

PATENT NO.        : 5,721,362
APPLICATION NO.   : 08/715541
DATED             : February 24, 1998
INVENTOR(S)       : Elias Corey and David Gin It is certified that error appears in the above-identified patent and that said Letters Patent is hereby corrected as shown below:

In column 25, Scheme 7, compound 46, kindly replace

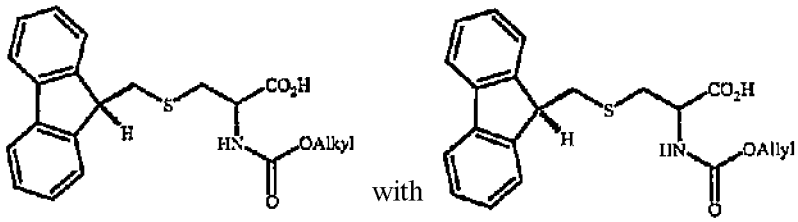 with

In column 27, Scheme 7, compound 47, kindly replace

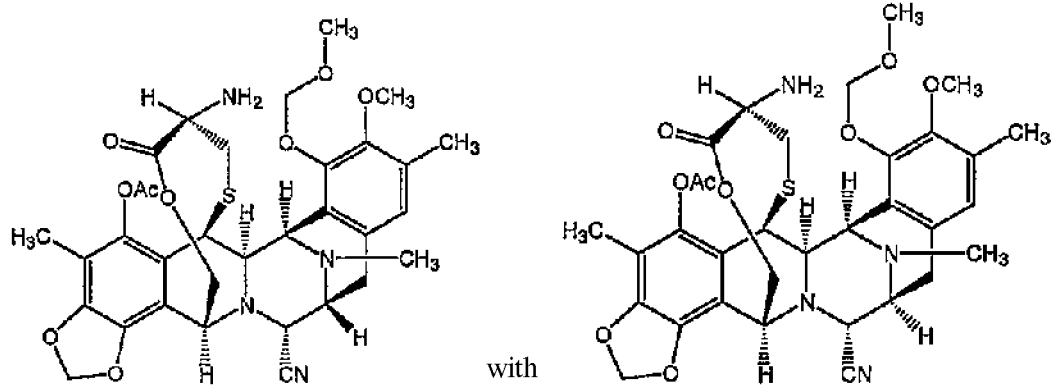 with

In column 28, Scheme 7, compound 14, kindly replace

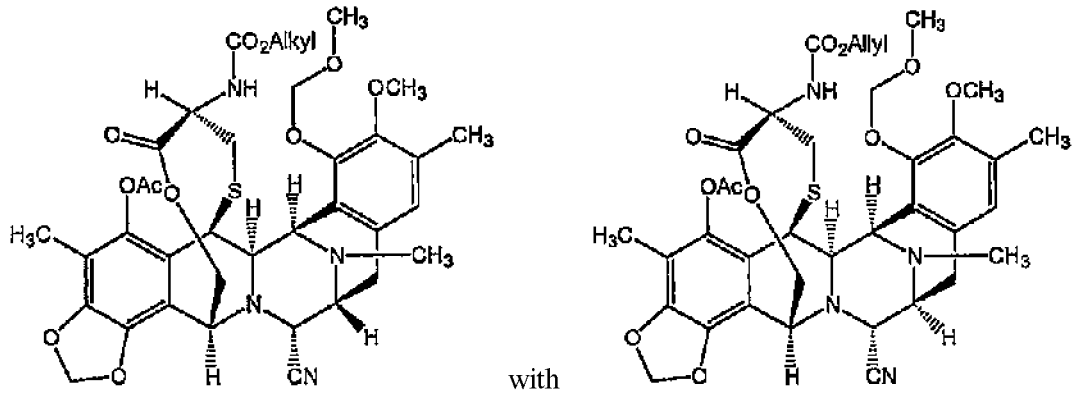 with

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 27, scheme 7, Scheme 7, compound 15, kindly replace

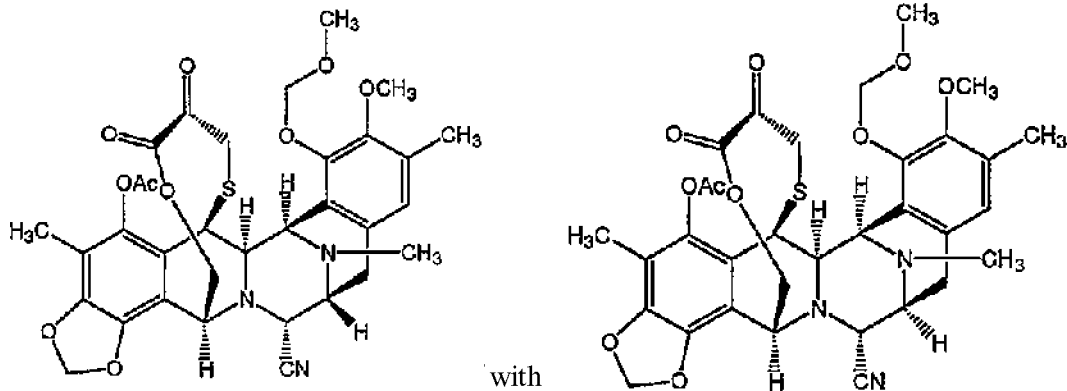

with

In column 28, Scheme 7, compound 49, kindly replace

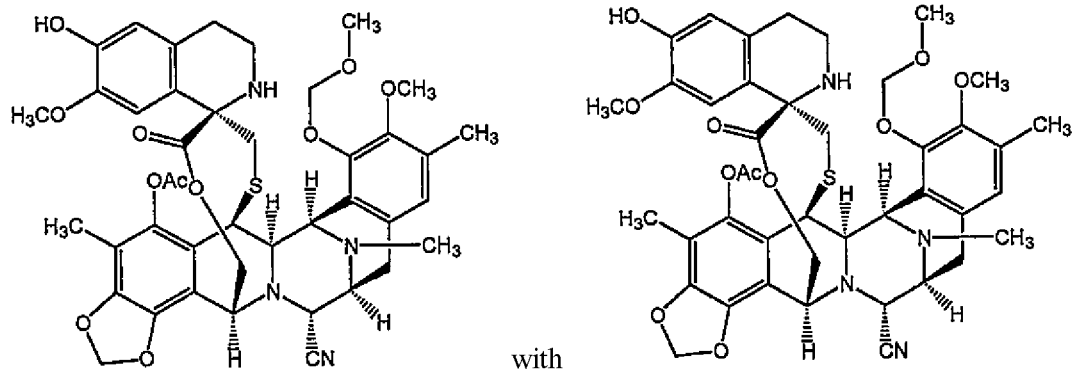

with

In columns 27 and 28, Scheme 7, compound 1 (ET-743), kindly replace

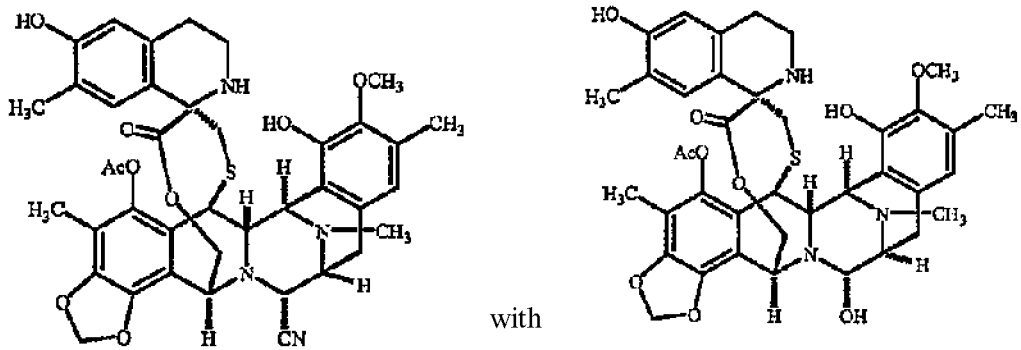

with

UNITED STATES PATENT AND TRADEMARK OFFICE
CERTIFICATE OF CORRECTION

PATENT NO.        : 5,721,362
APPLICATION NO. : 08/715541
DATED             : February 24, 1998
INVENTOR(S)       : Elias Corey and David Gin It is certified that error appears in the above-identified patent and that said Letters Patent is hereby corrected as shown below:

In column 32, lines 25-30, compound 23, kindly replace

In column 32, lines 30-35 and lines 63-67, compound 24, kindly replace

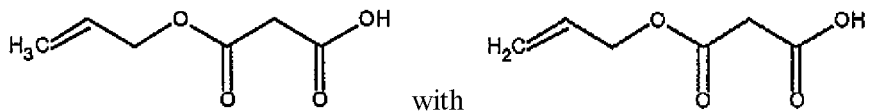

In column 33, lines 7-13, compound 25, kindly replace

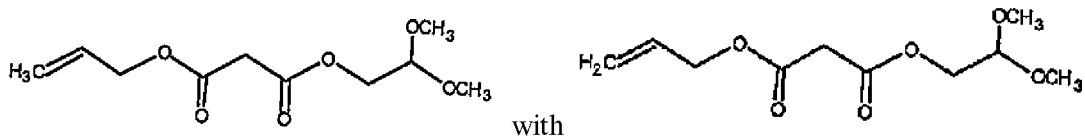

In column 33, lines 1-6, kindly delete the number "25" underneath the structure of 2,2-dimethoxyethanol by replacing

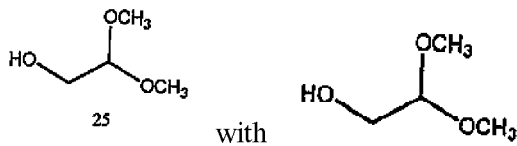

In column 40, lines 52-65, compound 35, kindly replace

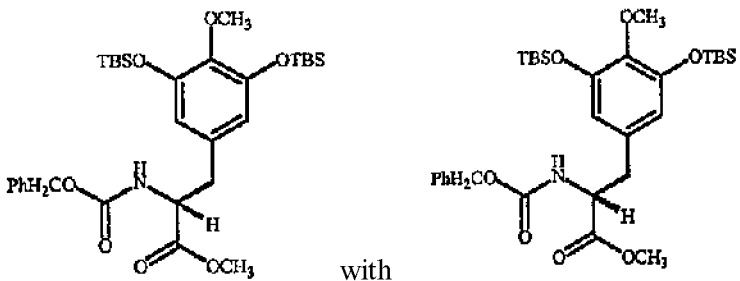

UNITED STATES PATENT AND TRADEMARK OFFICE
CERTIFICATE OF CORRECTION

PATENT NO. : 5,721,362　　　　　　　　　　　　　　　　　　　　　Page 15 of 43
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 41, lines 25-37, compound 35, kindly replace

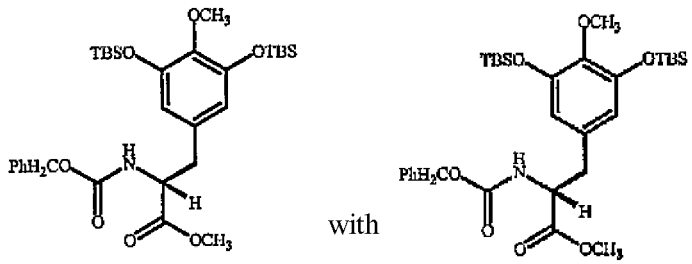

with

In column 57, lines 15-25, compound 12, kindly replace

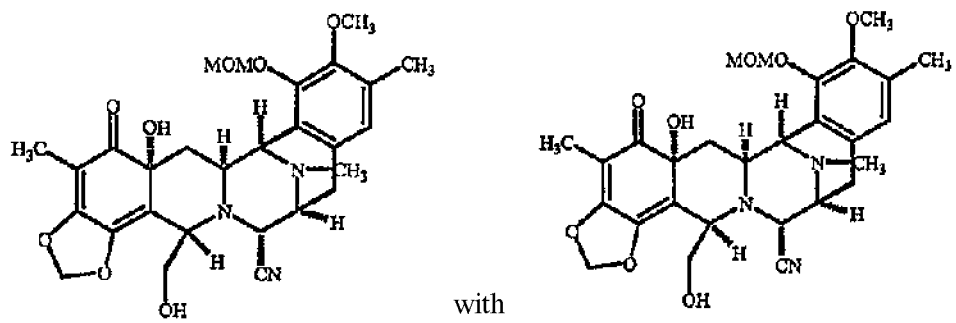

with

In column 57, lines 35-55, compound 13, kindly replace

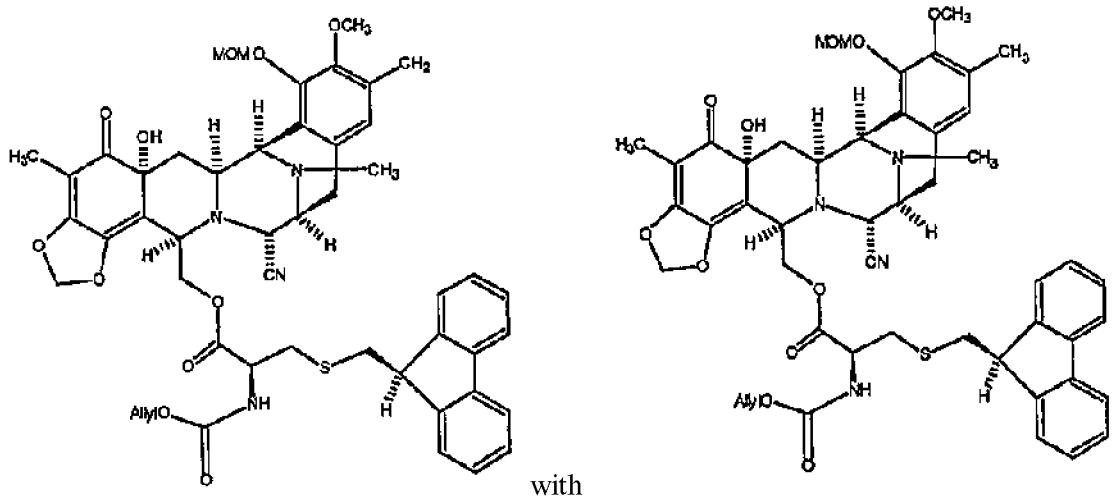

with

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 65, lines 13-27, kindly replace

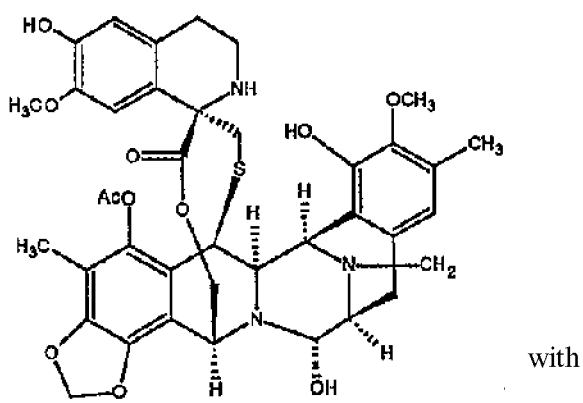 with 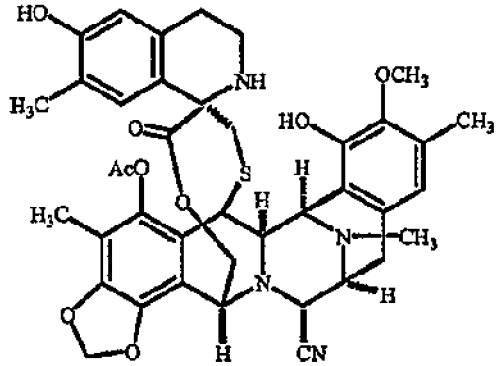

In column 65, lines 27-44, kindly replace

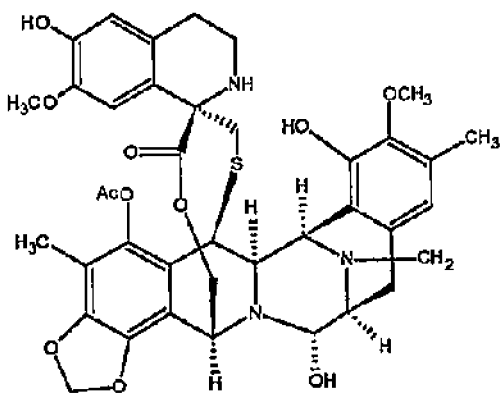 with 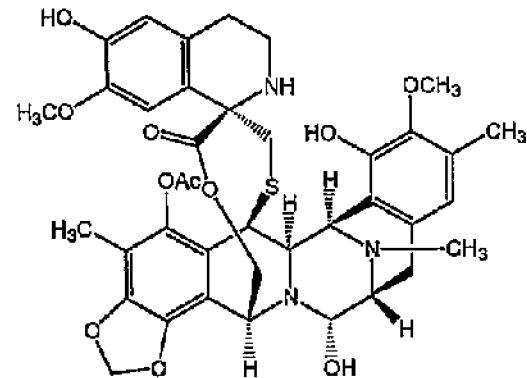

IN THE CLAIMS

In column 67, claim 1 step (a), lines 36-44, kindly replace

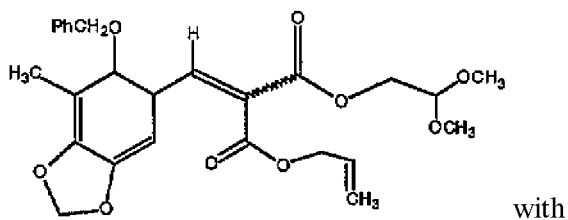 with 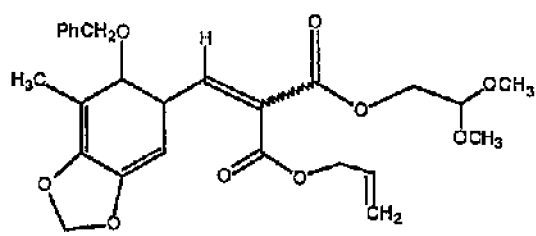

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 68, claim 1 step (c), lines 1-10, kindly replace

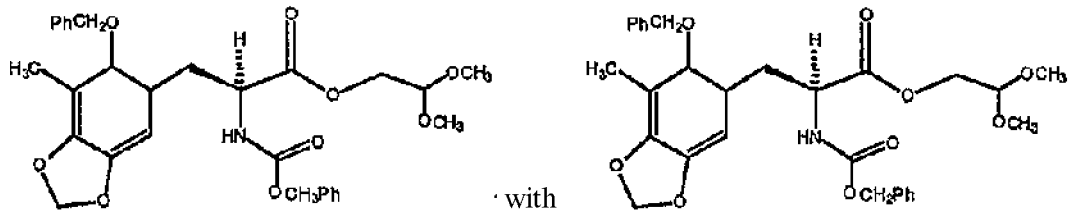 · with

In column 68, claim 1 step (f), lines 46-59, kindly replace

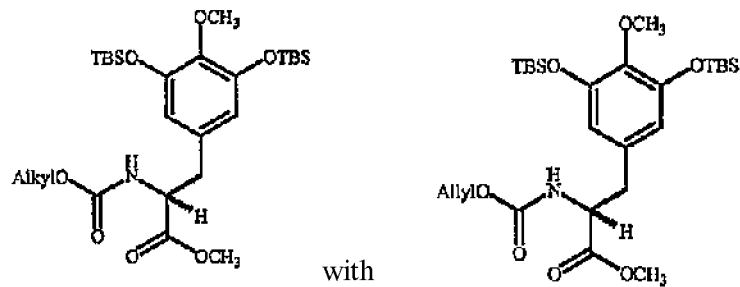 with

In column 69, claim 1 step (f), lines 1-15, kindly replace

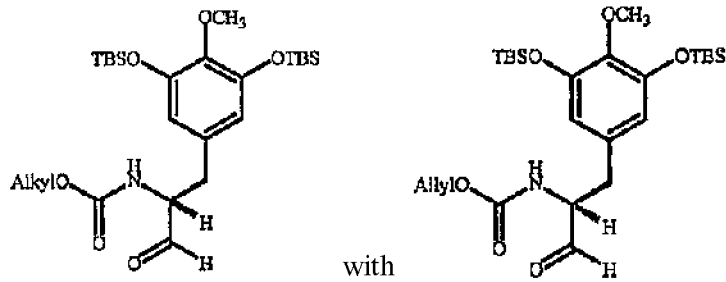 with

In column 69, claim 1 step (h), lines 19-33, kindly replace

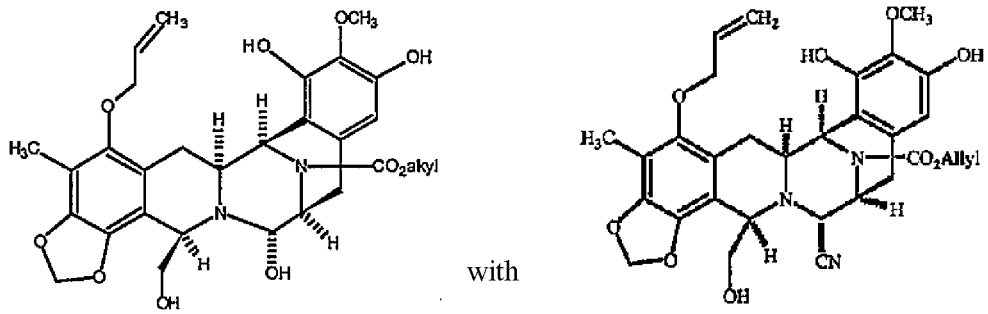 with

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 69, claim 1, step (h), lines 39-50, kindly replace

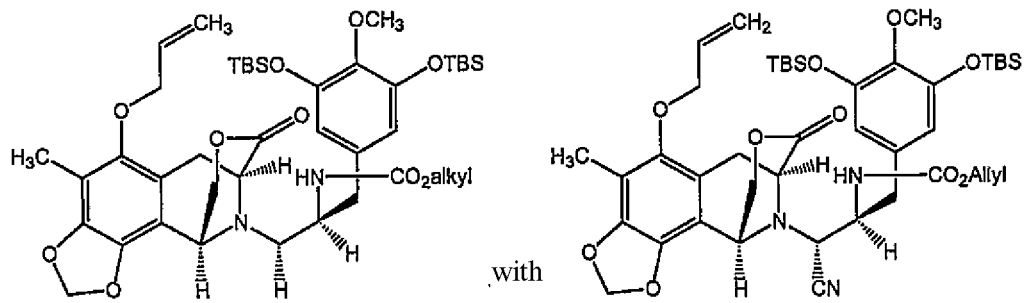

with

In column 70, claim 1 step (i), lines 1-14, kindly replace

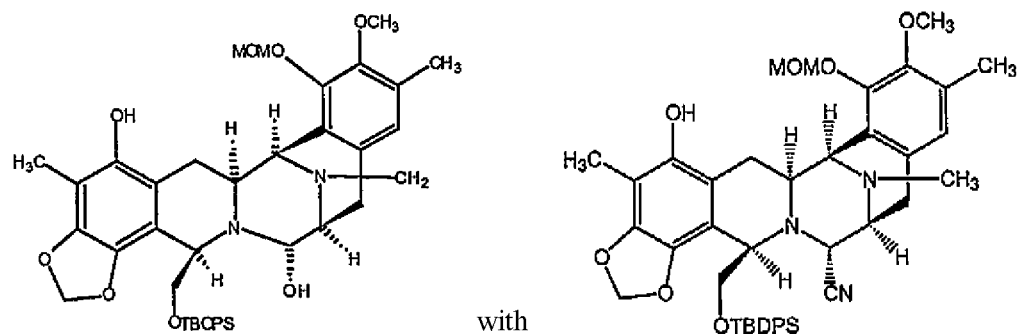

with

In column 70, claim 1 step (j), lines 26-39, kindly replace

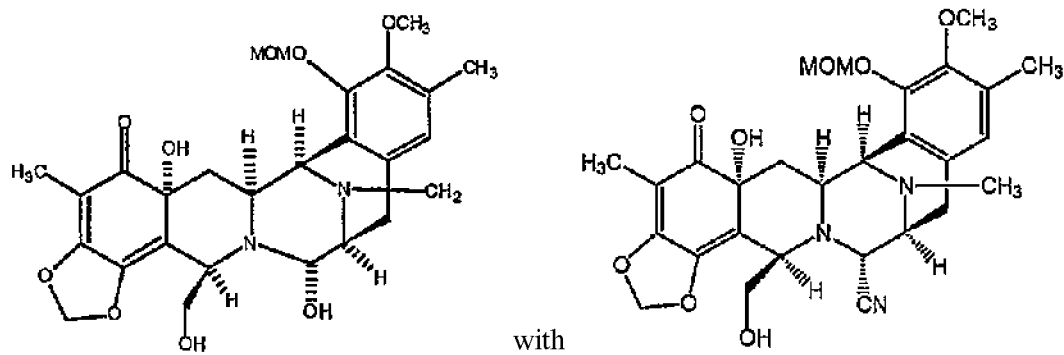

with

UNITED STATES PATENT AND TRADEMARK OFFICE
CERTIFICATE OF CORRECTION

PATENT NO.        : 5,721,362
APPLICATION NO.   : 08/715541
DATED             : February 24, 1998
INVENTOR(S)       : Elias Corey and David Gin It is certified that error appears in the above-identified patent and that said Letters Patent is hereby corrected as shown below:

In column 70, claim 1 step (k), lines 42-60, kindly replace

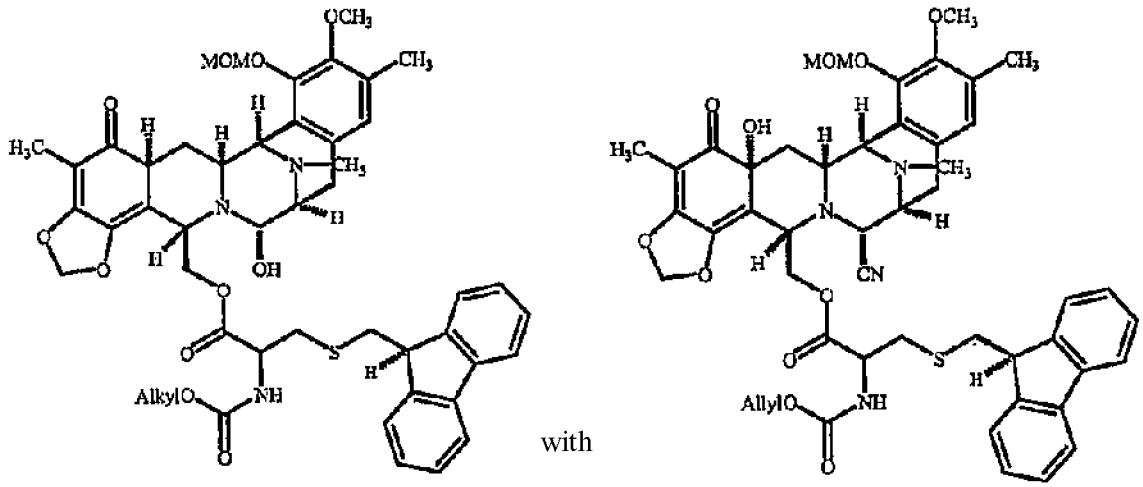

with

In column 71, claim 1 step (l), lines 1-15, kindly replace

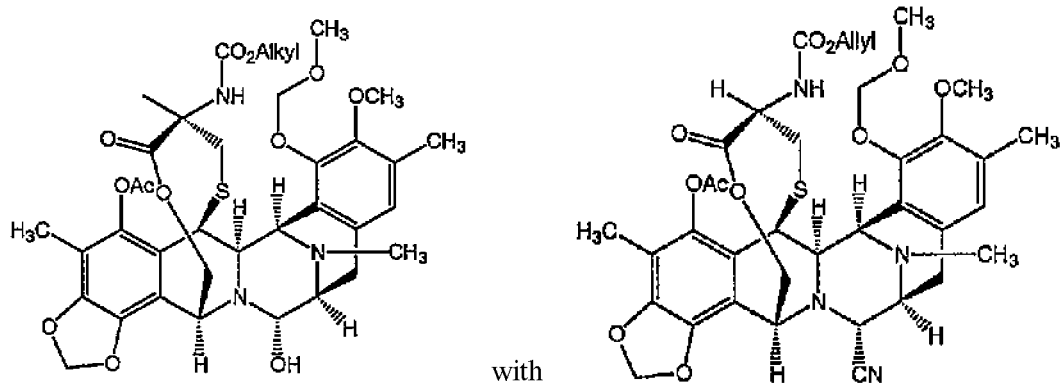

with

In column 71, claim 1 step (m), line 30-43, kindly replace

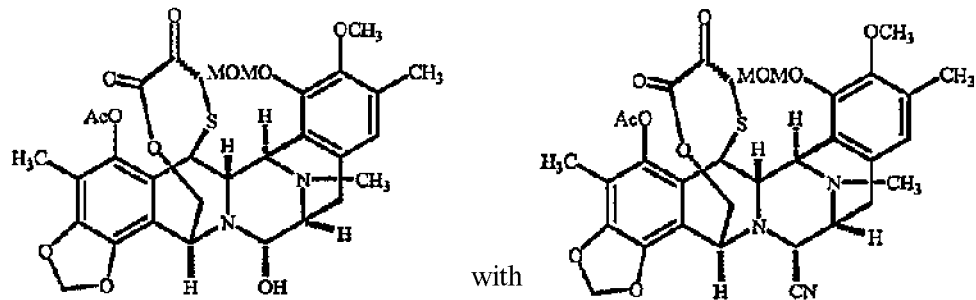

with

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 71, claim 1 step (o), lines 51-65, kindly replace

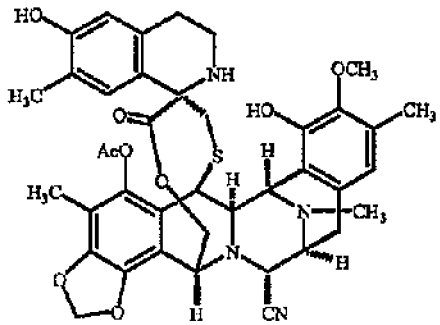 with 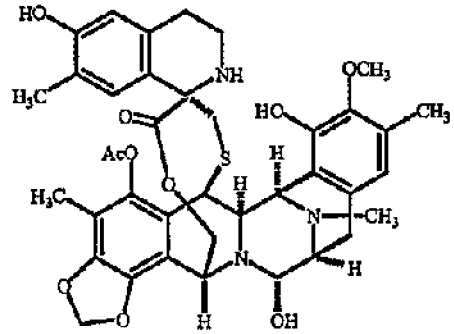

In column 72, claim 2 step (a), lines 3-12, kindly replace

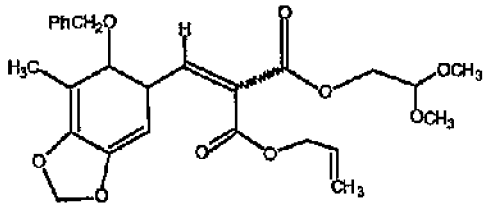 with 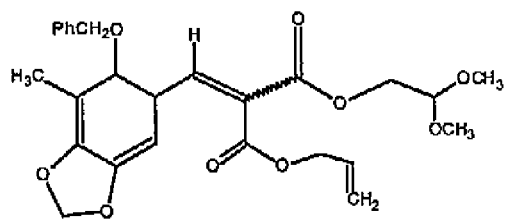

In column 72, claim 2 step (c), lines 36-45, kindly replace

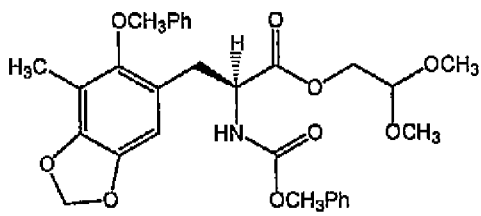 with 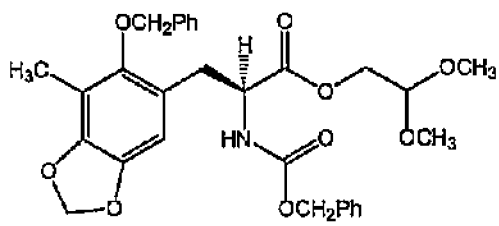

In column 72, claim 2 step (d), lines 50-60, kindly replace

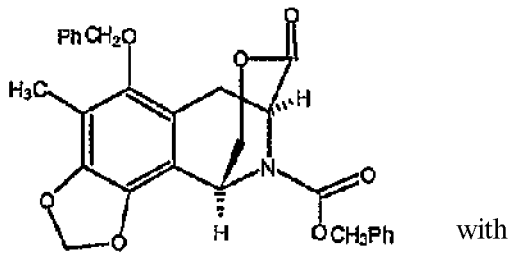 with 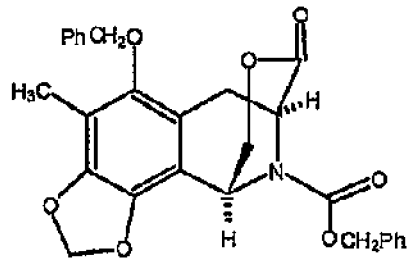

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 73, claim 2 step (h), lines 50-60, kindly replace

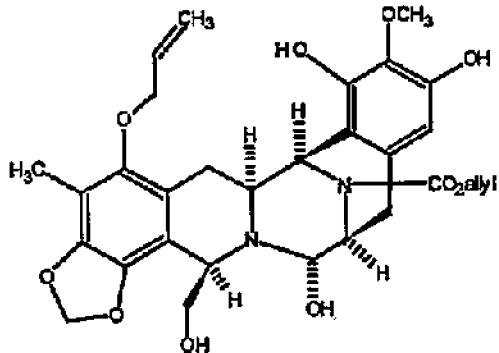 with 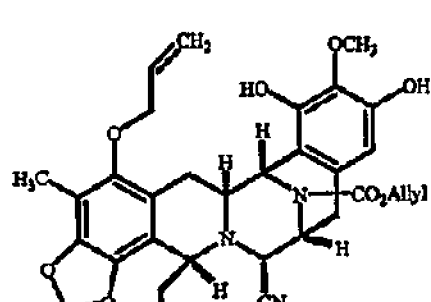

In column 74, claim 2 step (h), lines 1-13, kindly replace

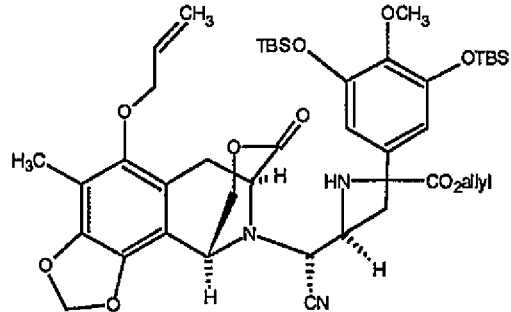 with 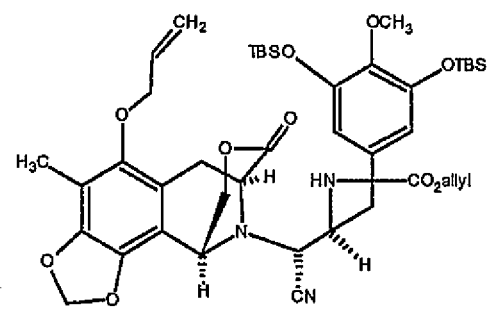

In Column 74, claim 2 step (h), lines 22-35, kindly replace

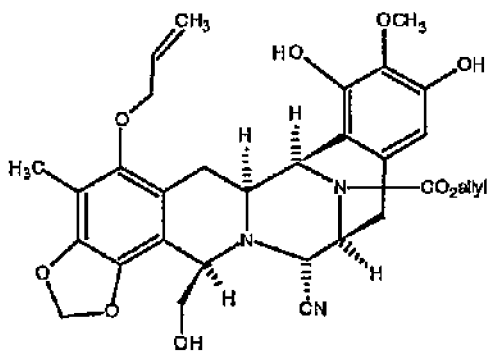 with 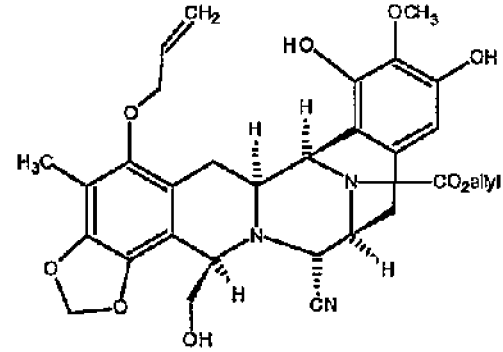

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 77, claim 3 step (a), lines 1-10, kindly replace

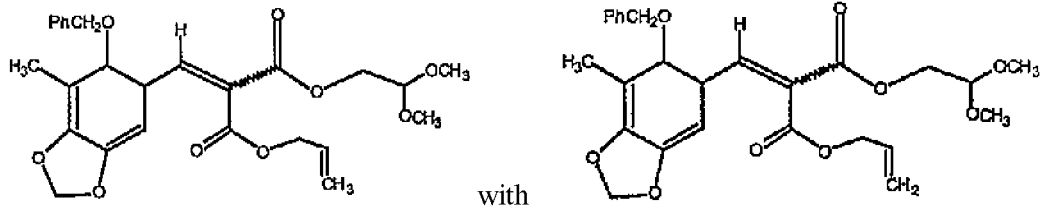

In column 77, claim 3 step (c), lines 35-43, kindly replace

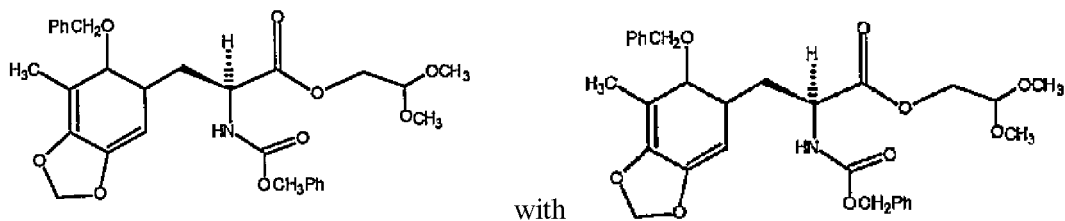

In column 77, claim 3 step (d), lines 50-58, kindly replace

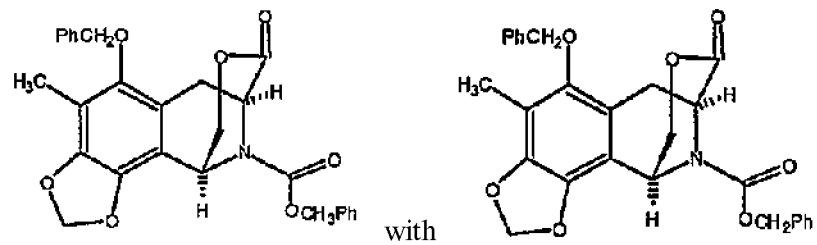

In column 79, claim 3 step (h), lines 23-25, kindly replace

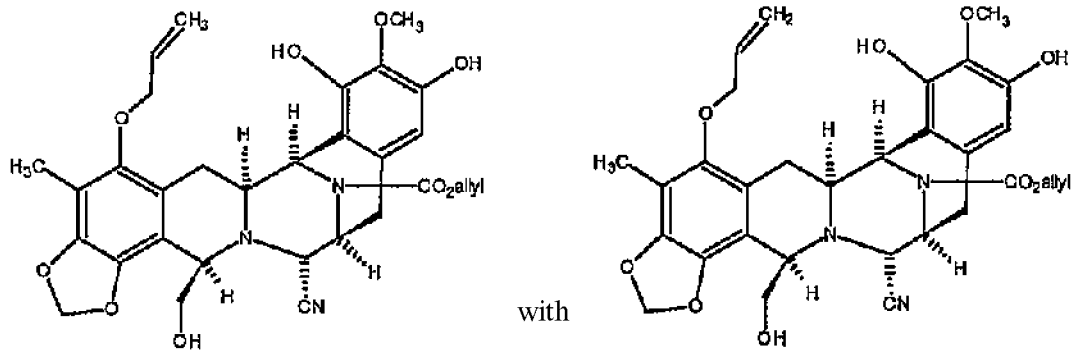

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 80, claim 3 step (j), lines 1-13, kindly replace

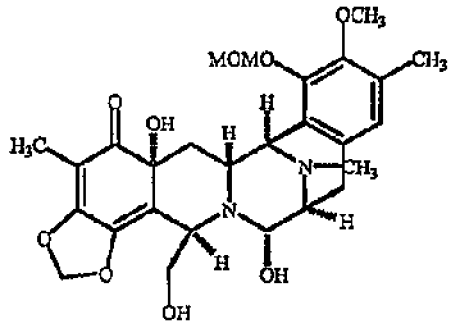 with 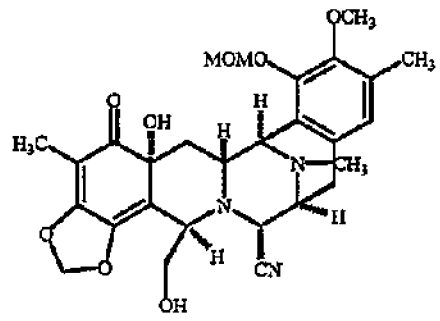

In column 80, claim 3 step (k), lines 17-35, kindly replace

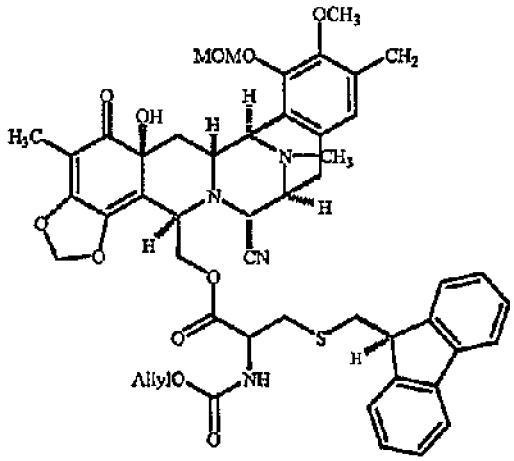 with 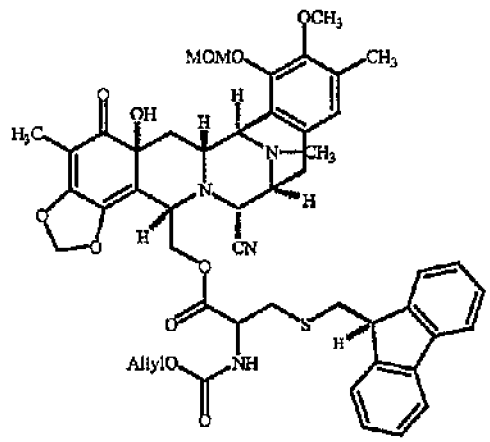

In column 81, claim 4 step (a), lines 41-49, kindly replace

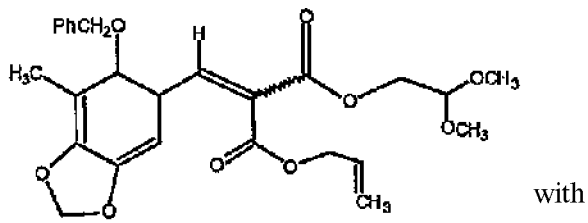 with 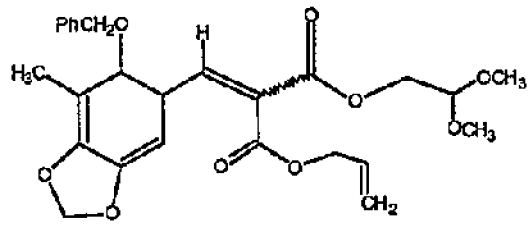

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 81, claim 1 step (b), lines 56-64 kindly replace

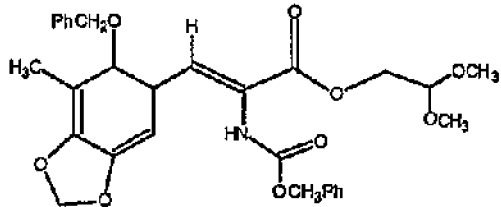 with 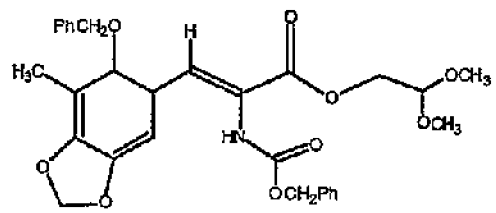

In column 82, claim 4 step (d), lines 19-28, kindly replace

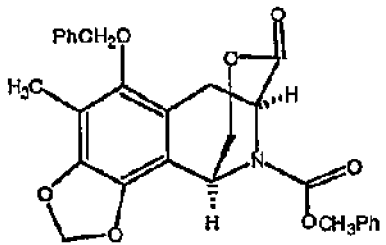 with 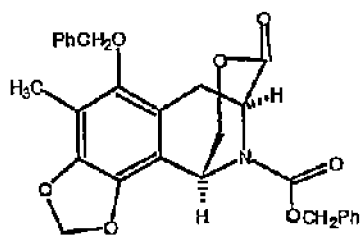

In column 82, claim 4 step (f), lines 50-60, kindly replace

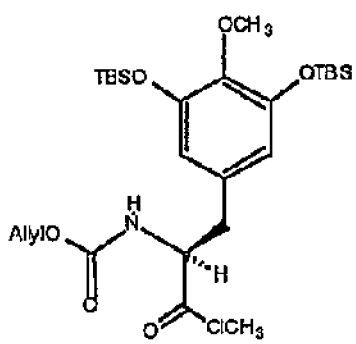 with 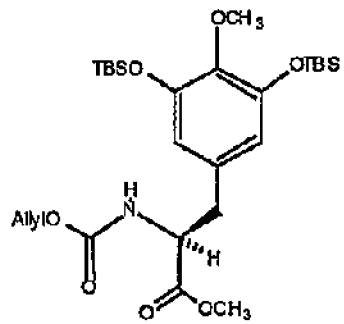

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 83, claim 4 step (h), lines 29-31, kindly replace

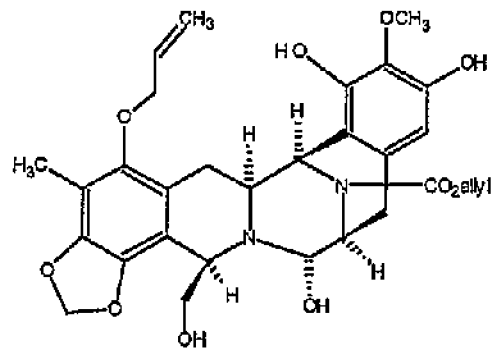 with 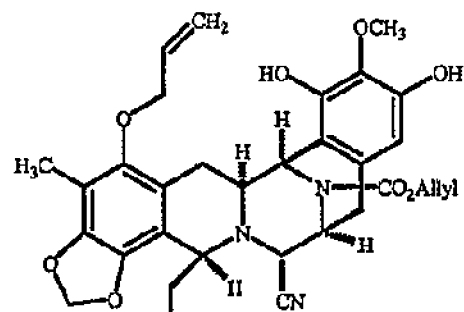

In column 83, claim 4 step (h), lines 39-50, kindly replace

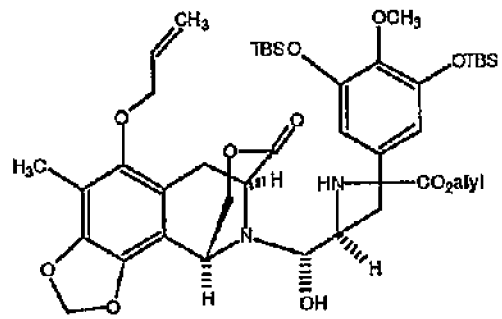 with 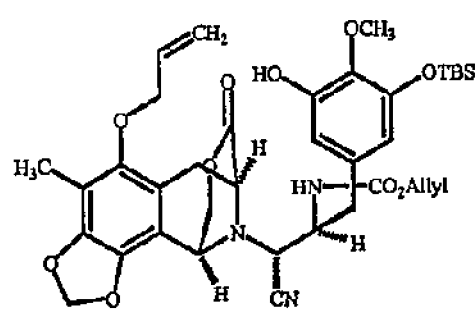

In column 84, claim 4 step (h), lines 1-13, kindly replace

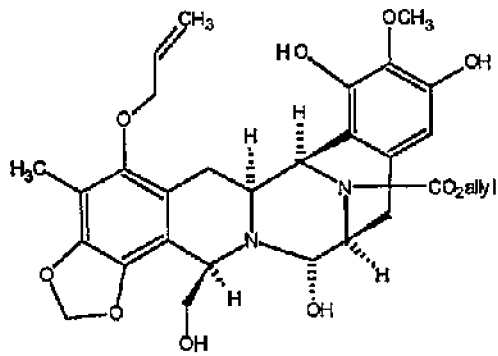 with 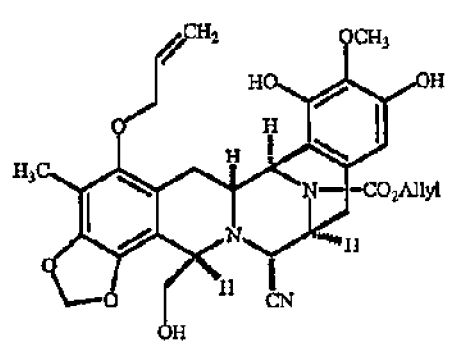

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In colummn 84, claim 4 step (h), lines 20-32, kindly replace

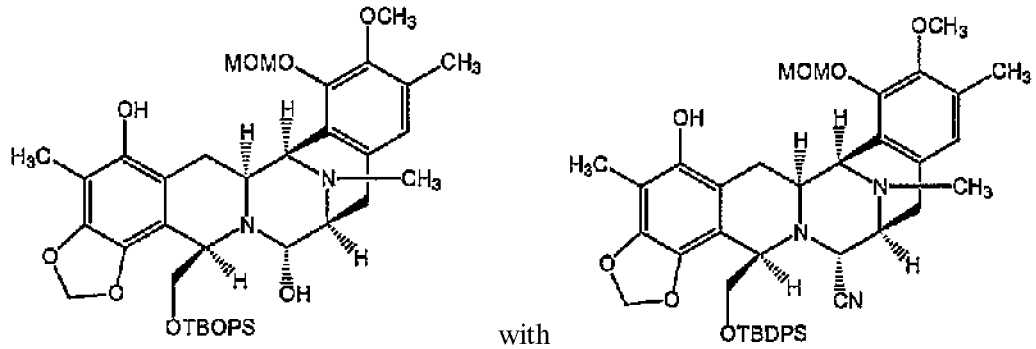

with

In column 84, claim 4 step (j), lines 45-57, kindly replace

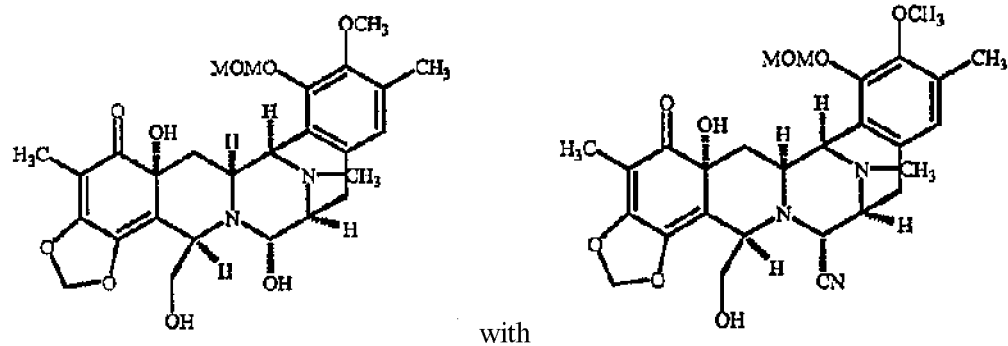

with

In column 85, claim 4 step (k), lines 1-20, kindly replace

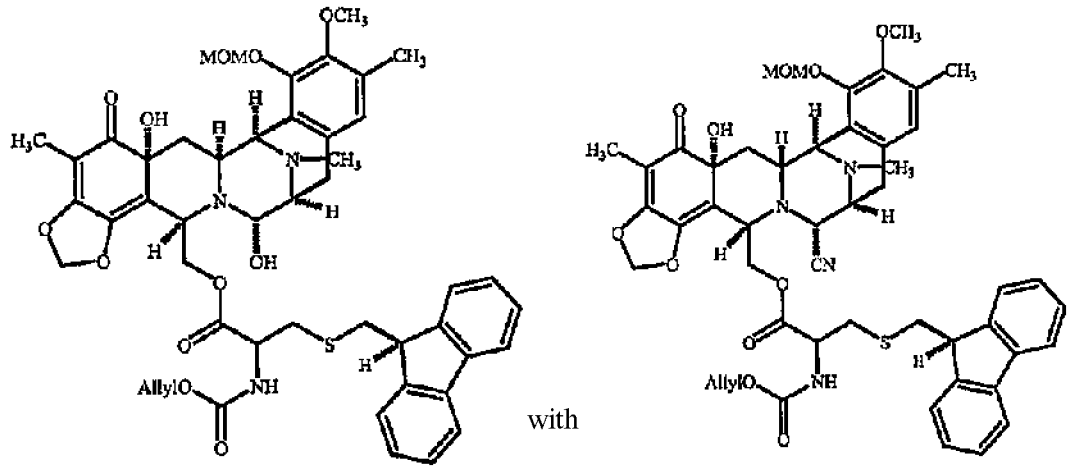

with

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 85, claim 4 step (i), lines 27-41, kindly replace

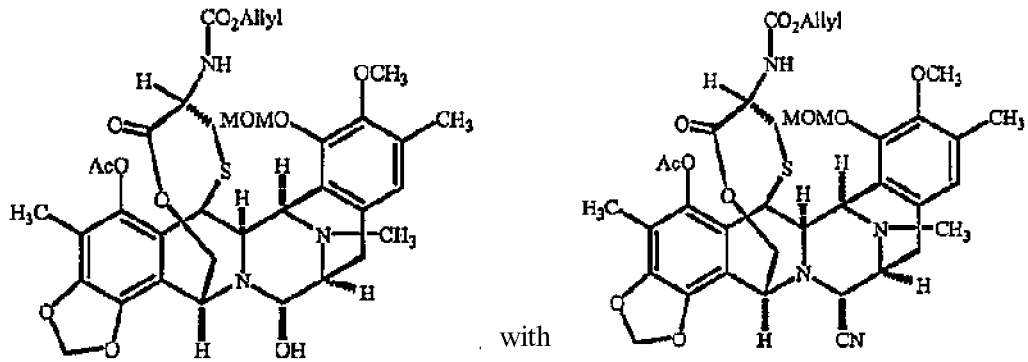

with

In column 86, claim 5, lines 1-15, kindly replace

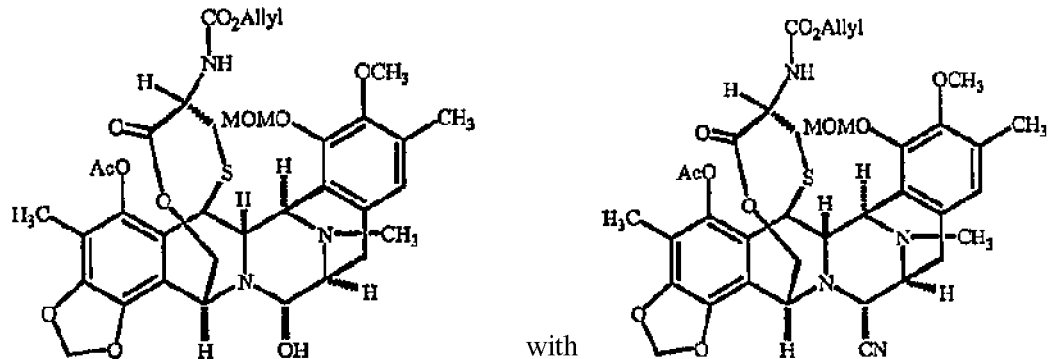

with

In column 86, claim 5 step (a), lines 18-27, kindly replace

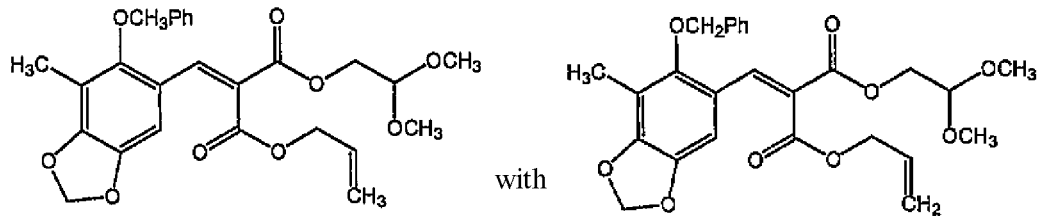

with

In column 86, claim 5 step (b), lines 35-42, kindly replace

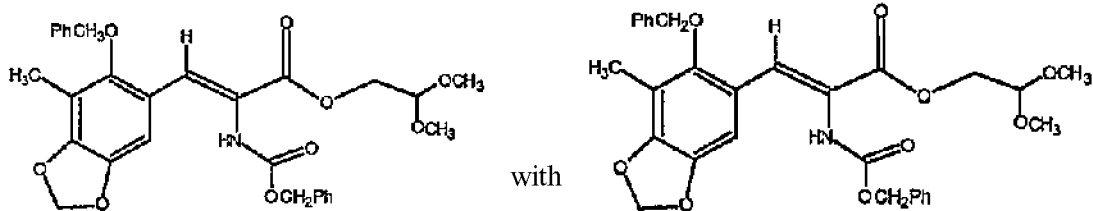

with

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 86, claim 5 step (c), lines 49-57, kindly replace

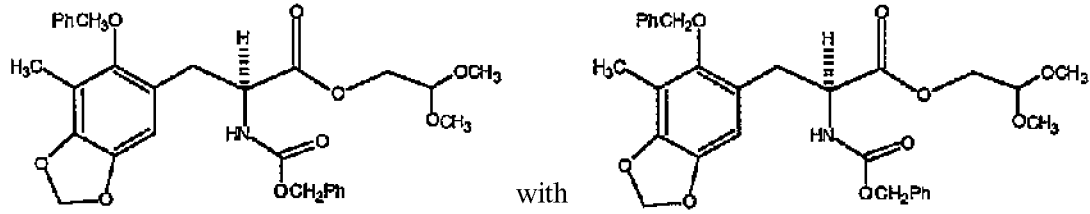

with

In column 87, claim 5 step (d), lines 1-10, kindly replace

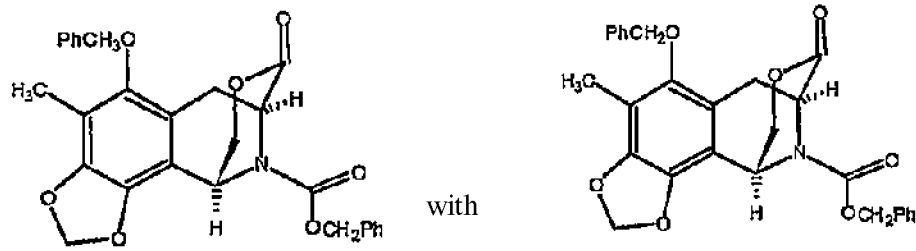

with

In column 88, claim 5 step (h), lines 5-15, kindly replace

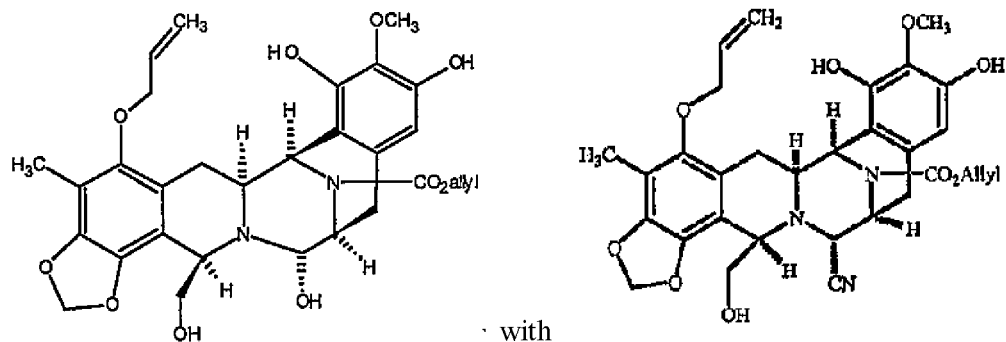

with

In column 88, claim 5 step (h), lines 24-35, kindly replace

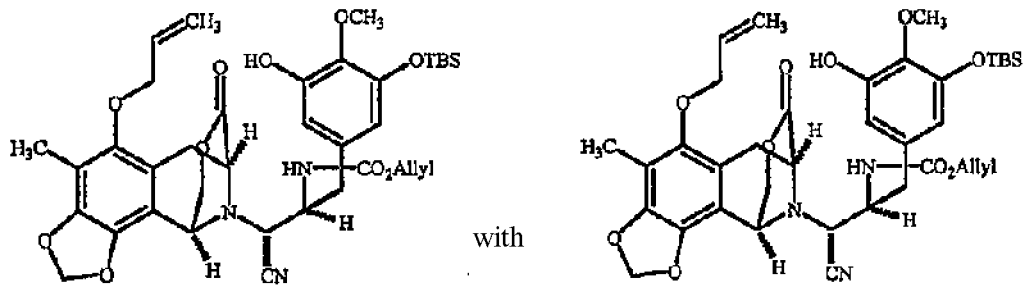

with

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 88, claim 5 step (h), after line 45 kindly replace

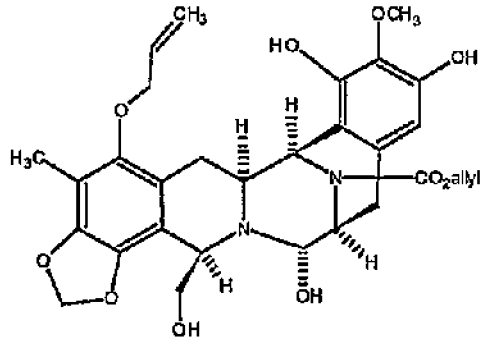 with 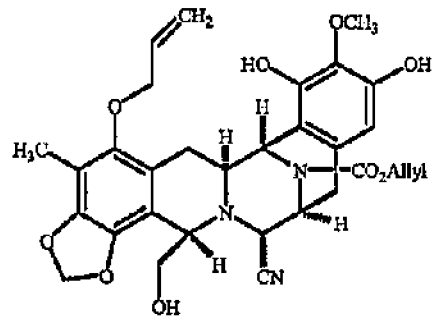

In column 89, claim 5 step (k), lines 40-57, kindly replace

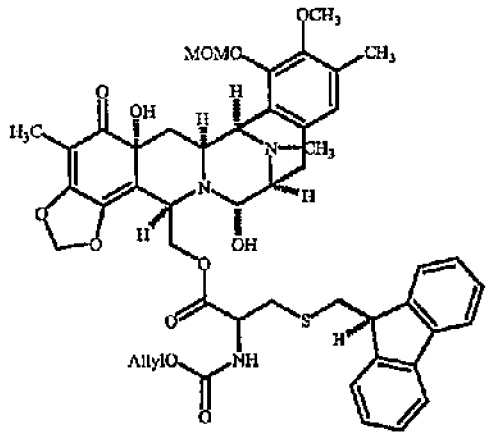 with 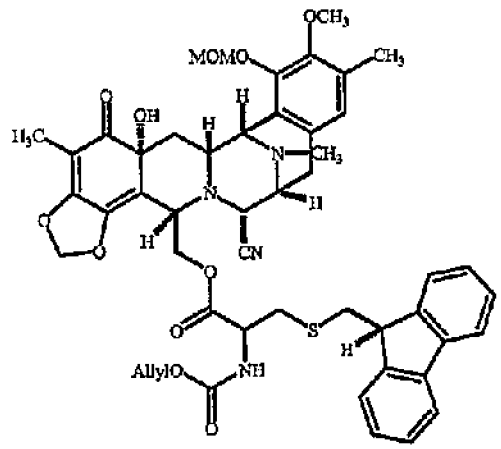

In column 90, claim 6, lines 11-29, kindly replace

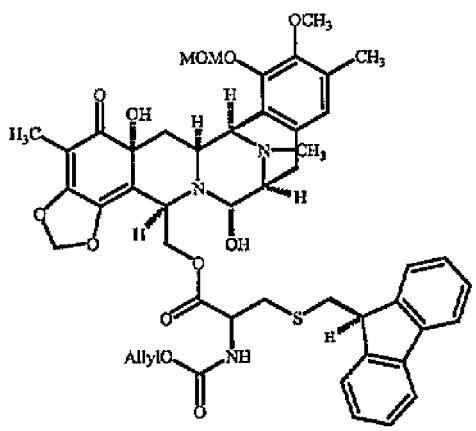 with 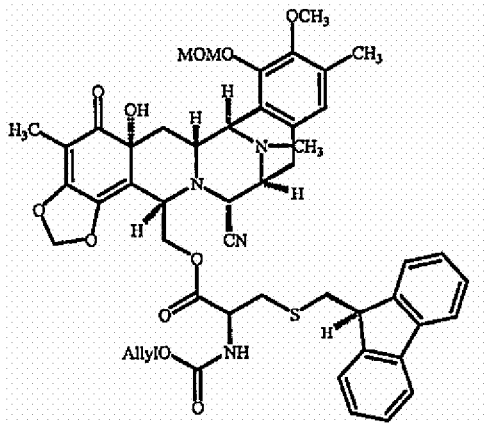

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 90, claim 6 step (a), lines 34-43, kindly replace

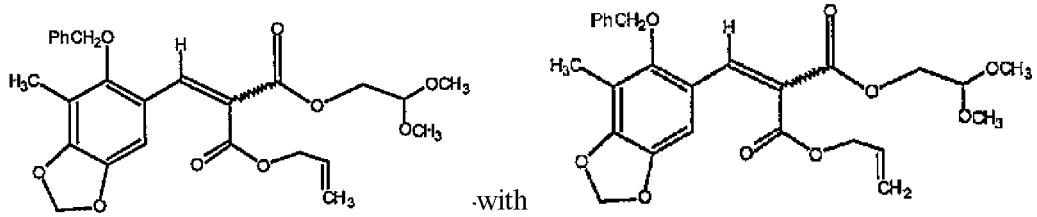

In column 90, claim 6 step (b), lines 50-58, kindly replace

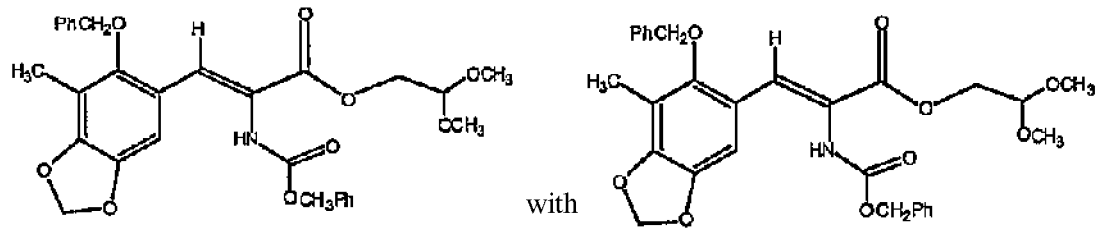

In column 91, claim 6 step (c), lines 1-9, kindly replace

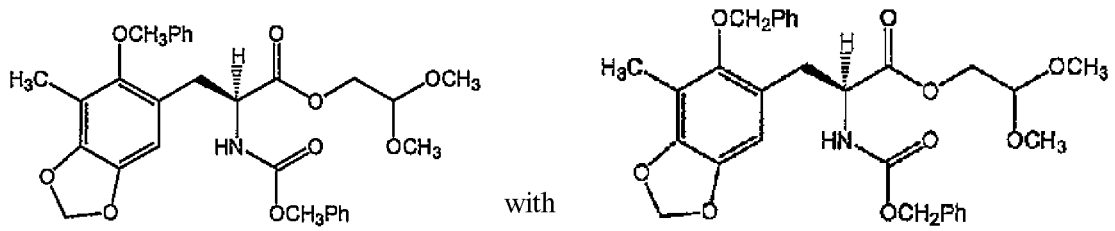

In column 91, claim 6 step (d), lines 15-25, kindly replace

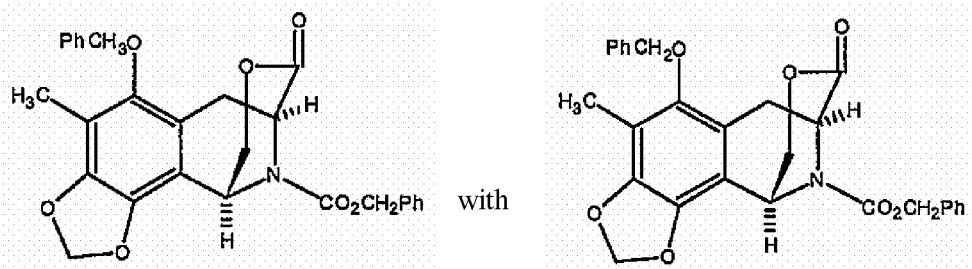

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 92, claim 6 step (h), lines 18-30, kindly replace

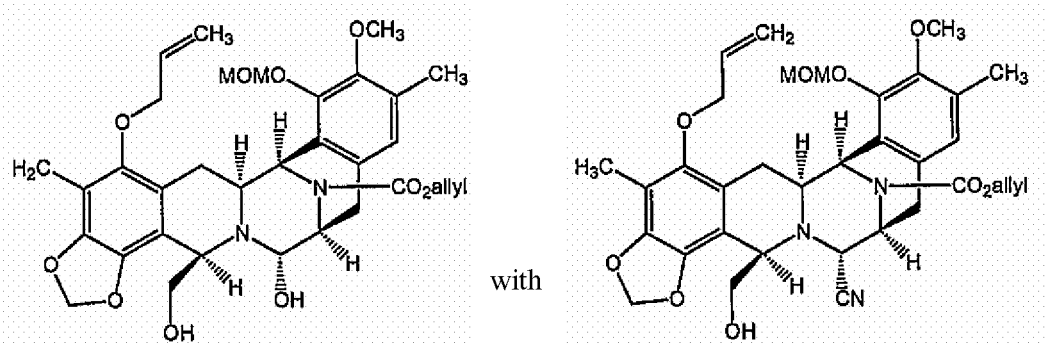

with

In column 92, claim 6 step (h), lines 37 to 49, kindly replace

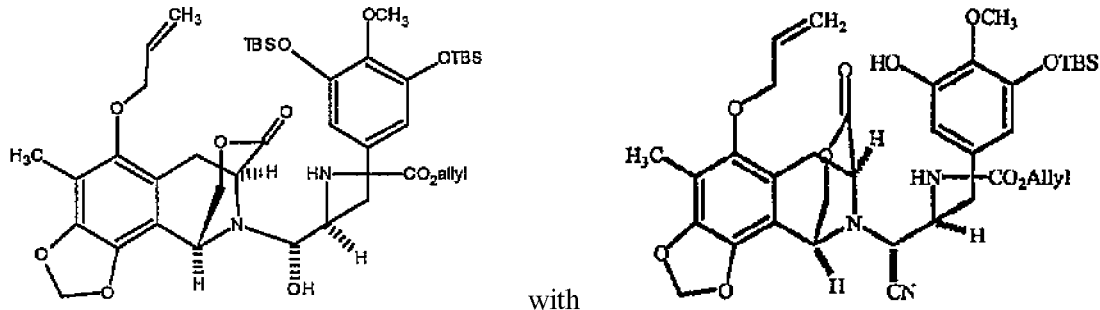

with

In colum 93, claim 6 step (i), lines 1-13, kindly replace

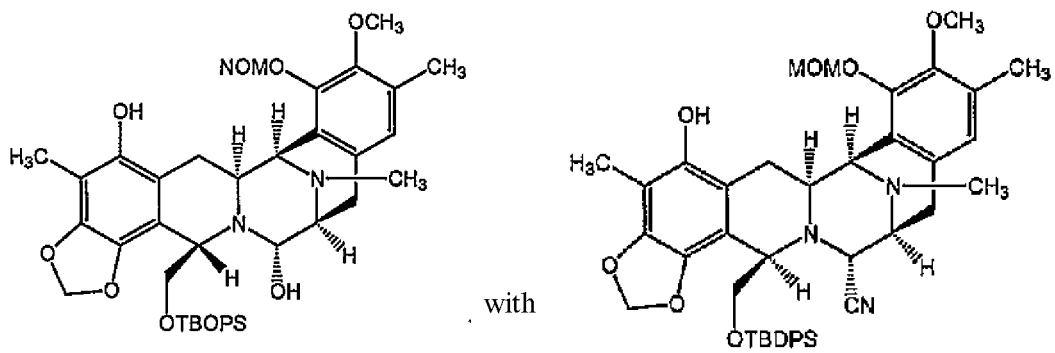

with

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 93, claim 6 step (j), lines 25-38, kindly replace

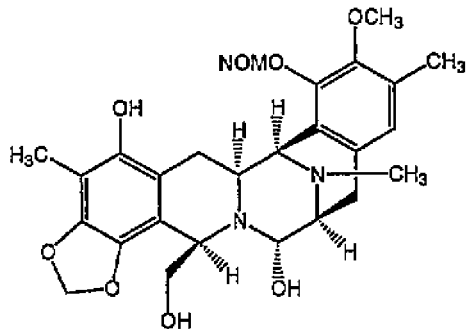   with   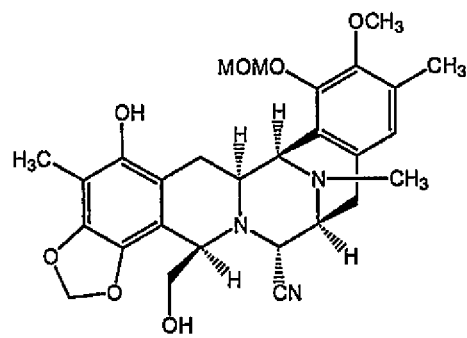

In column 93, claim 7 step (a), lines 49-55, kindly replace

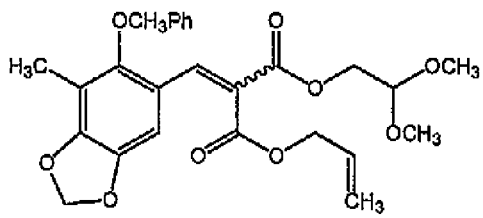   with   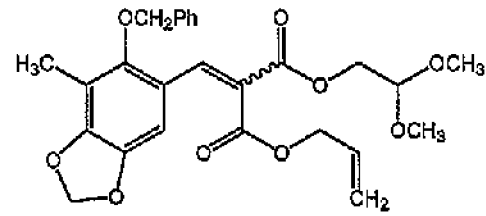

In column 94, claim 7 step (b), lines 1-10, kindly replace

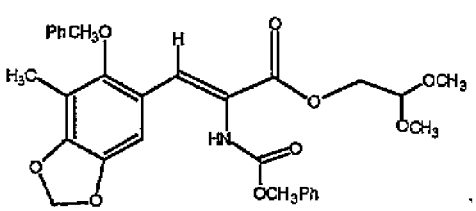   , with   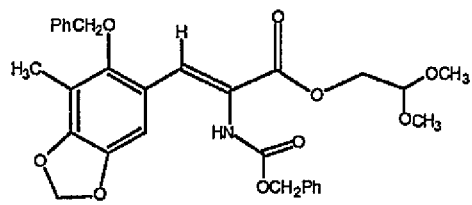

In column 94, claim 7 step (c), lines 17-25, kindly replace

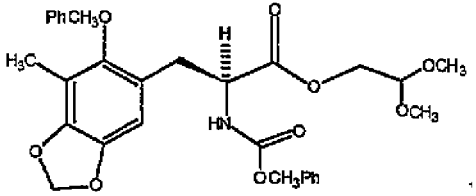   with   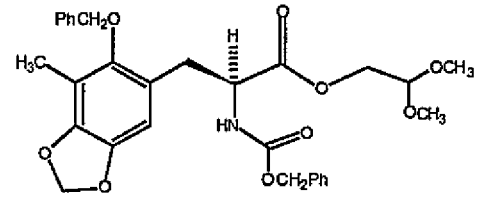

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 94, claim 7 step (d), lines 32-40, kindly replace

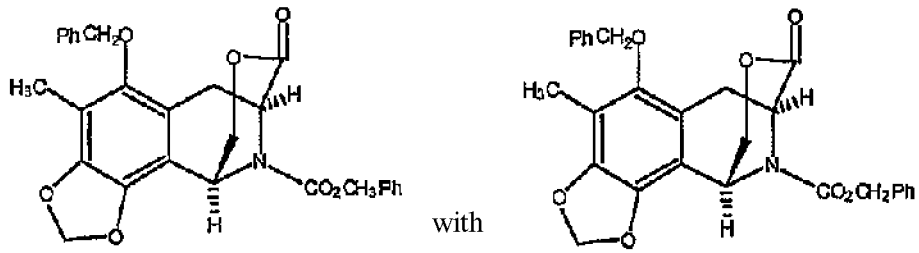

with

In column 95, claim 7 step (f), lines 1-13, kindly replace

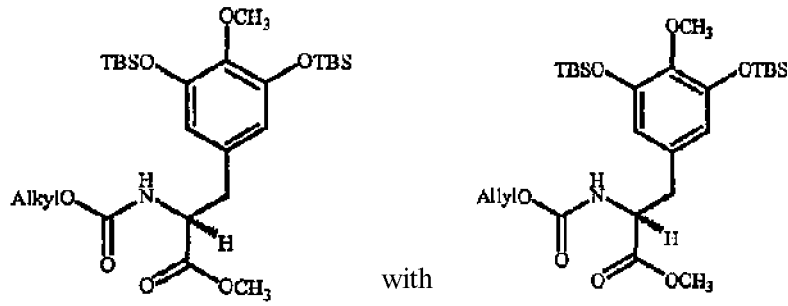

with

In column 95, claim 7 step (g), lines 20-30, kindly replace

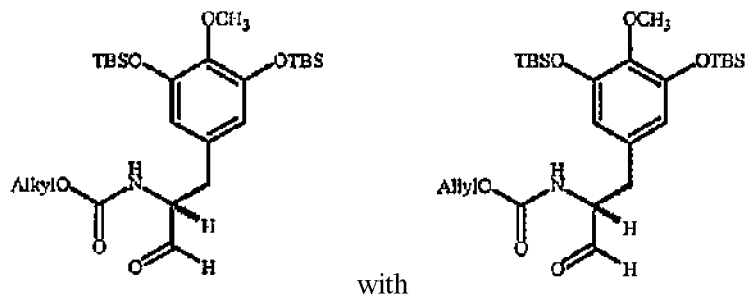

with

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 95, claim 7 step (h), lines 37-49, kindly replace

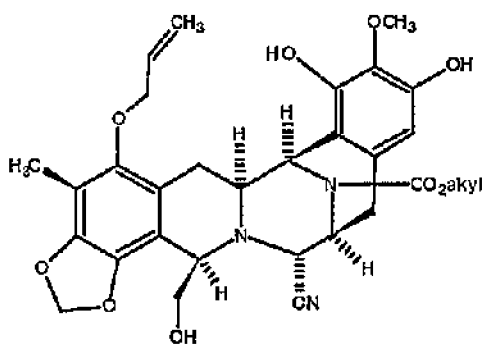 with 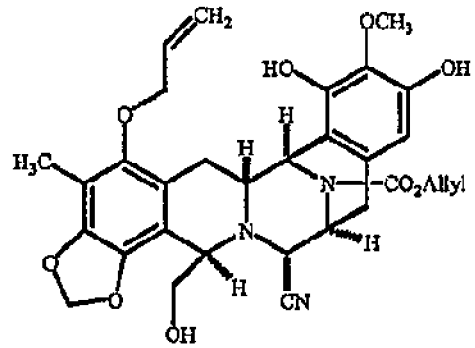

In column 95, claim 7 step (h), lines 55-65, kindly replace

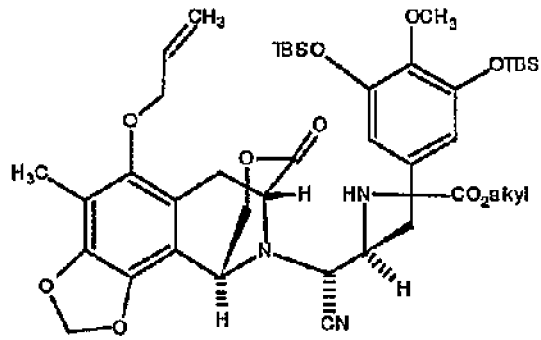 with 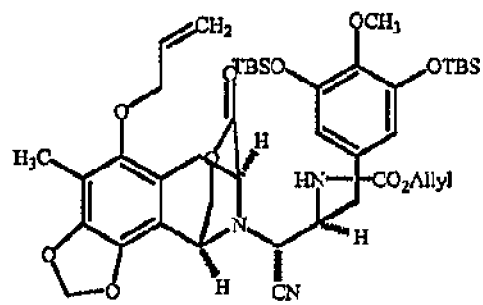

In column 97, claim 8 step (a), lines 3-12, kindly replace

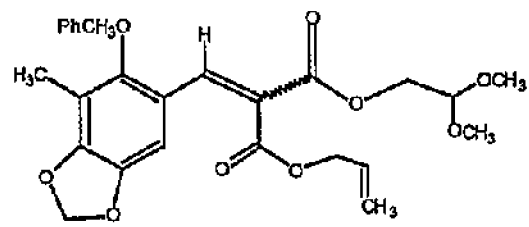 with 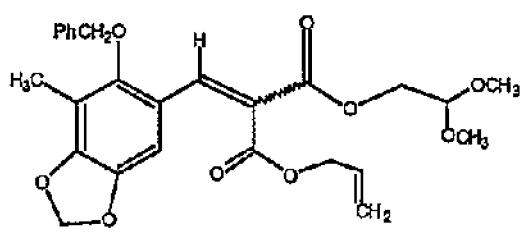

UNITED STATES PATENT AND TRADEMARK OFFICE
CERTIFICATE OF CORRECTION

PATENT NO.       : 5,721,362
APPLICATION NO.  : 08/715541
DATED            : February 24, 1998
INVENTOR(S)      : Elias Corey and David Gin It is certified that error appears in the above-identified patent and that said Letters Patent is hereby corrected as shown below:

In column 97, claim 8 step (b), lines 20-29, kindly replace

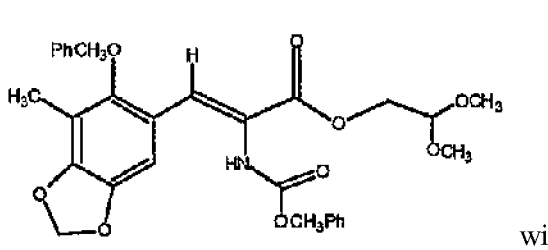 with 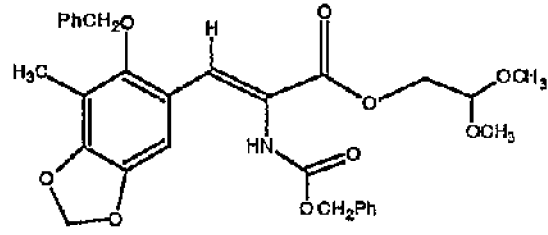

In column 97, claim 8 step (c), lines 36-45, kindly replace

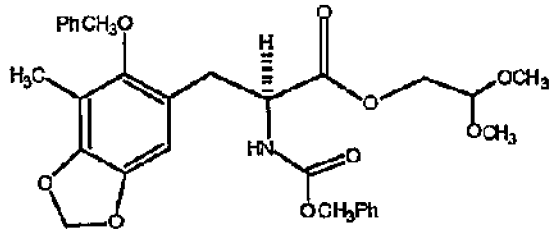 with 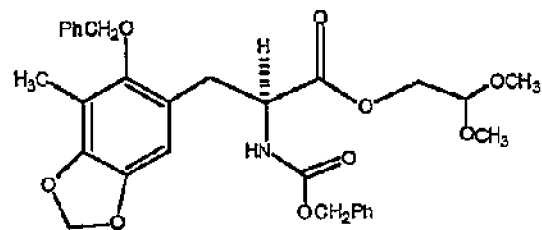

In column 97, claim 8 step (d), lines 51-60, kindly replace

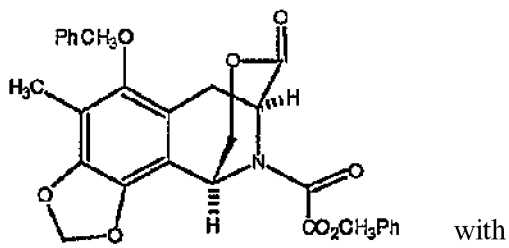 with 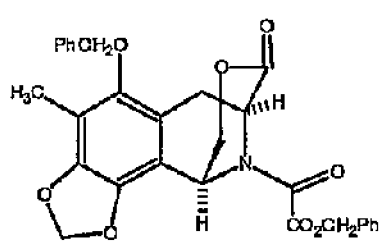

In column 98, claim 8 step (f), lines 15-25, kindly replace

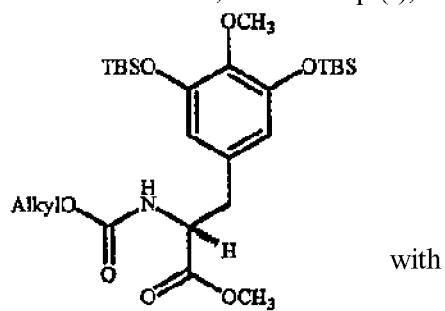 with 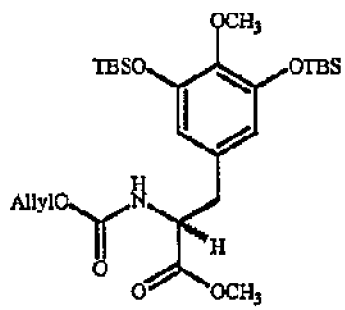

UNITED STATES PATENT AND TRADEMARK OFFICE
CERTIFICATE OF CORRECTION

PATENT NO.        : 5,721,362
APPLICATION NO.   : 08/715541
DATED             : February 24, 1998
INVENTOR(S)       : Elias Corey and David Gin It is certified that error appears in the above-identified patent and that said Letters Patent is hereby corrected as shown below:

In column 98, claim 8 step (g), lines 32-44, kindly replace

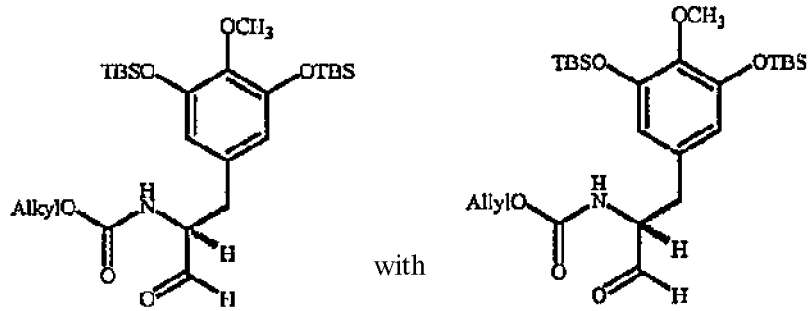

with

In column 98, claim 8 step (h), lines 49-62, kindly replace

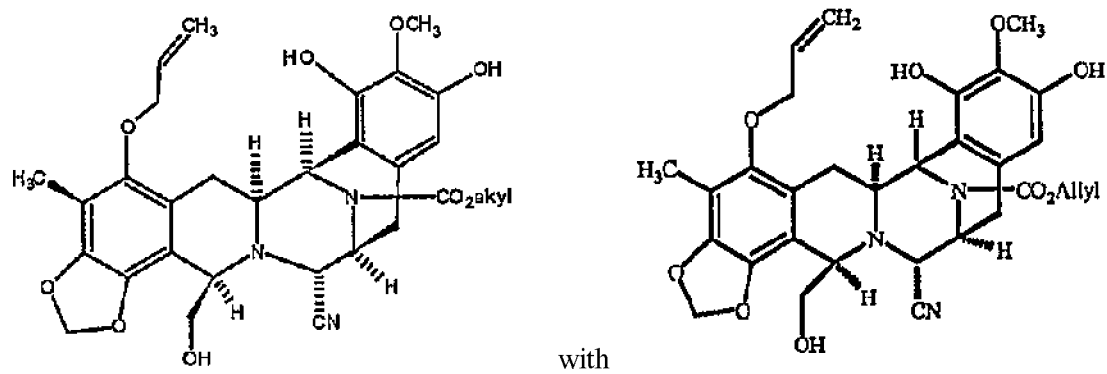

with

In column 99, claim 8 step (h), lines 1-12, kindly replace

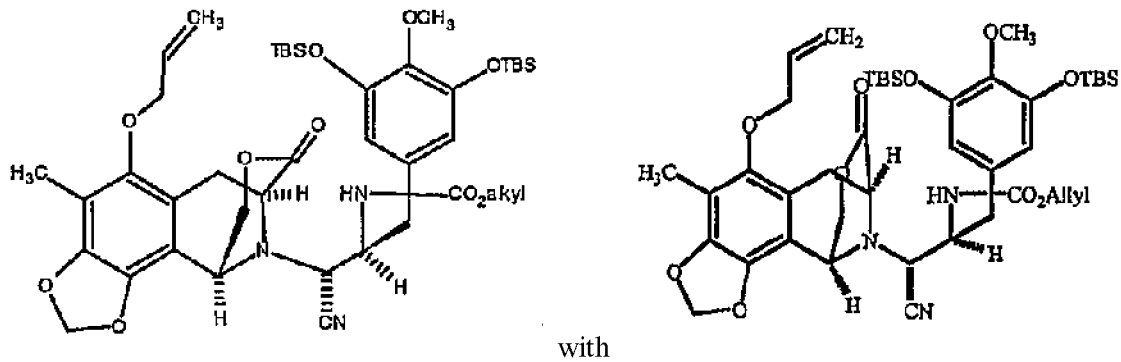

with

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 99, claim 9, lines 32-45, kindly replace

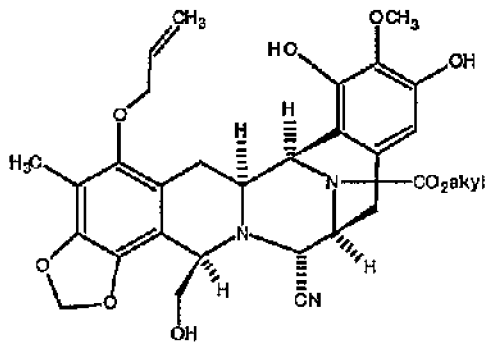
with
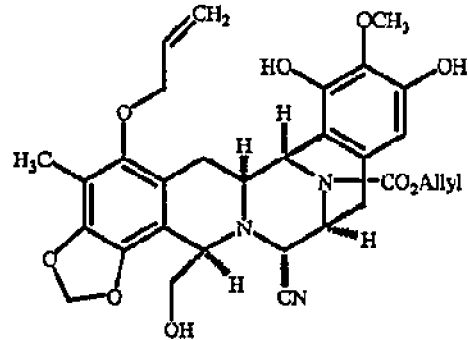

In column 99, claim 9 step (a), lines 48-57, kindly replace

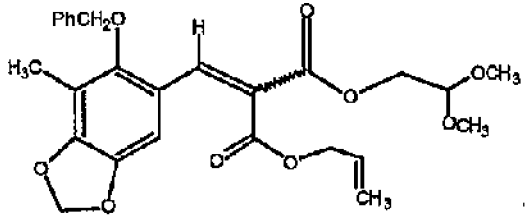
with
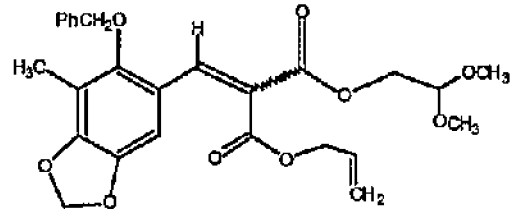

In column 100, claim 9 step (b), lines 1-10, kindly replace

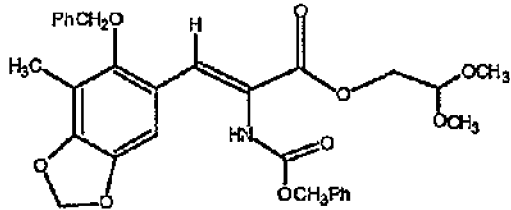
with
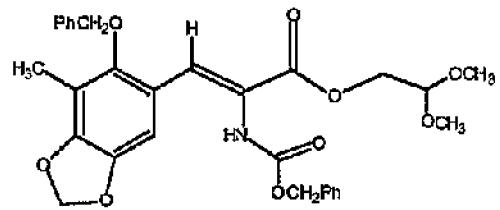

In column 100, claim 9 step (c), lines 17-25, kindly replace

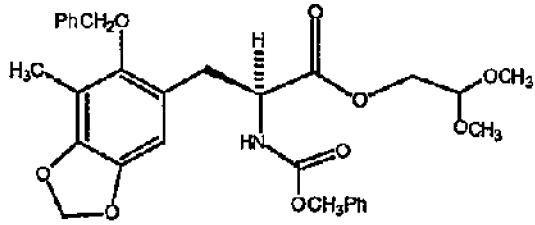
with
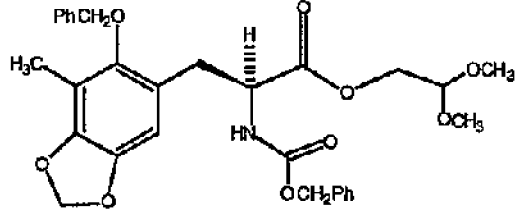

UNITED STATES PATENT AND TRADEMARK OFFICE
CERTIFICATE OF CORRECTION

PATENT NO.       : 5,721,362
APPLICATION NO. : 08/715541
DATED            : February 24, 1998
INVENTOR(S)      : Elias Corey and David Gin It is certified that error appears in the above-identified patent and that said Letters Patent is hereby corrected as shown below:

In column 100, claim 9 step (d), lines 33-41, kindly replace

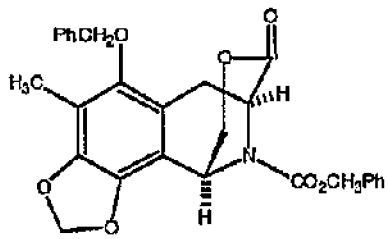 with 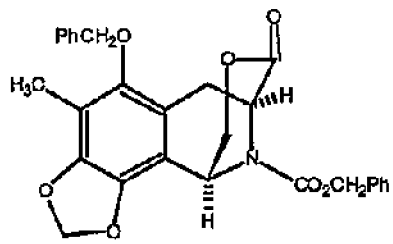

In column 101, claim 9 step (f), lines 1-13, kindly replace

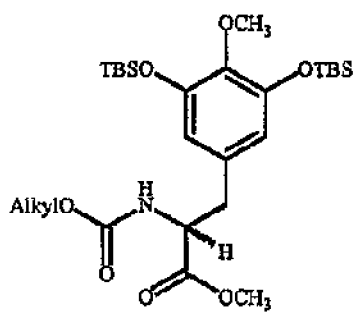 with 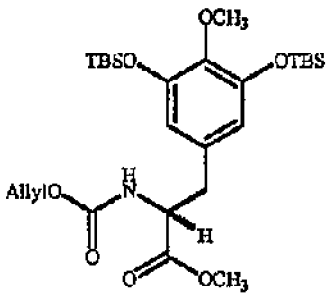

In column 101, claim 9 step (g), lines 22-32, kindly replace

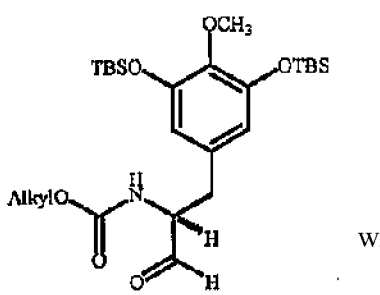 with 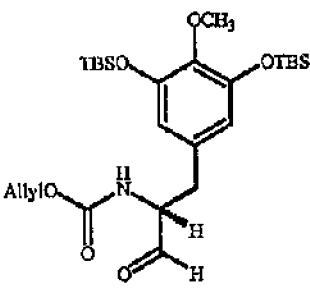

UNITED STATES PATENT AND TRADEMARK OFFICE
CERTIFICATE OF CORRECTION

PATENT NO.      : 5,721,362
APPLICATION NO. : 08/715541
DATED           : February 24, 1998
INVENTOR(S)     : Elias Corey and David Gin It is certified that error appears in the above-identified patent and that said Letters Patent is hereby corrected as shown below:

In column 101, claim 9 step (h), lines 43-54, kindly replace

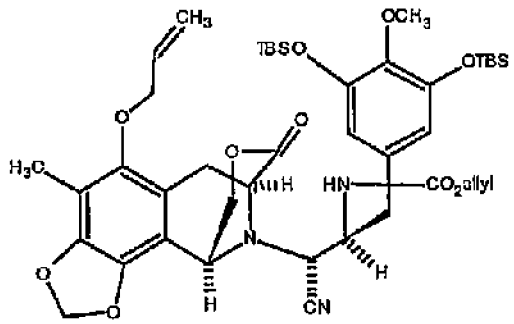 with 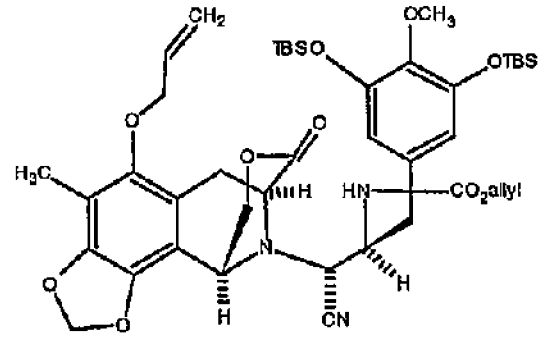

In column 102, claim 10, lines 2-10, kindly replace

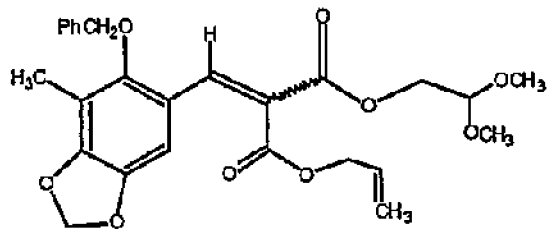 with 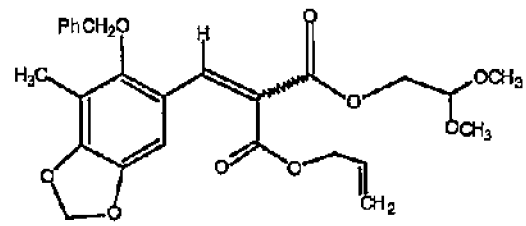

In column 102, claim 12, lines 23-30, kindly replace

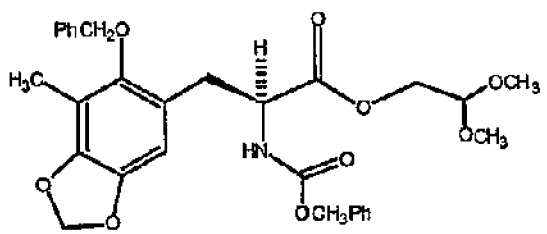 with 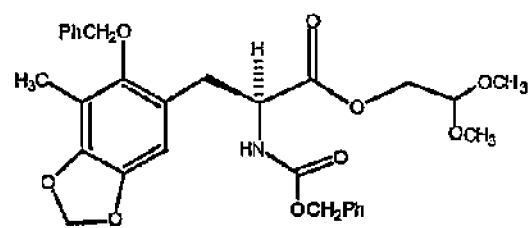

In column 102, claim 15, lines 55-65, kindly replace

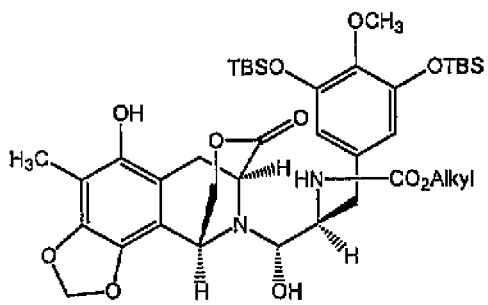 with 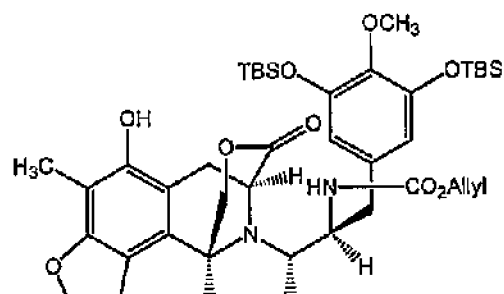

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 103, claim 16, lines 1-15, kindly replace

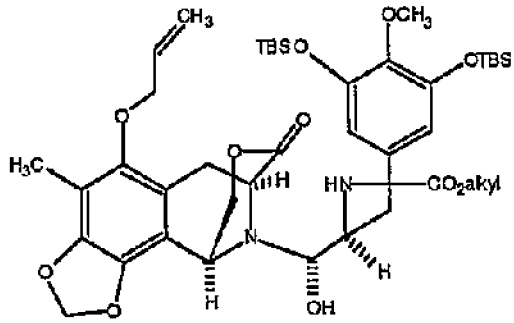 with 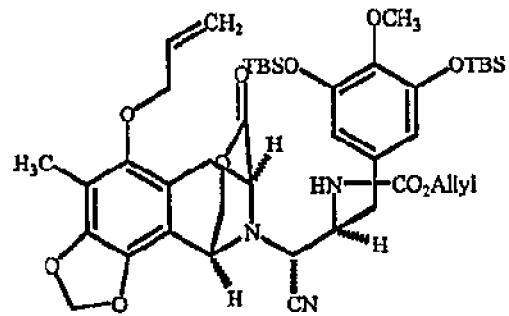

In column 103, claim 17, lines 16-28, kindly replace

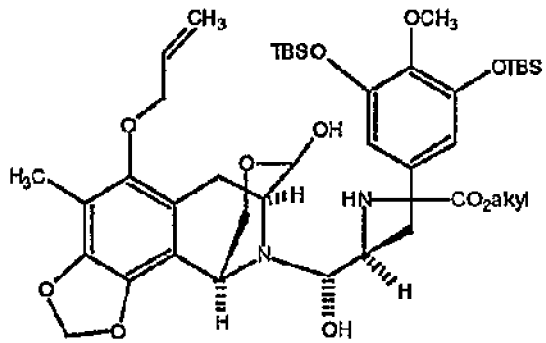 with 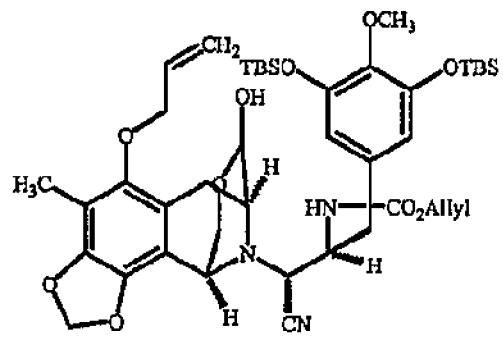

In column 103, claim 18, lines 30-42, kindly replace

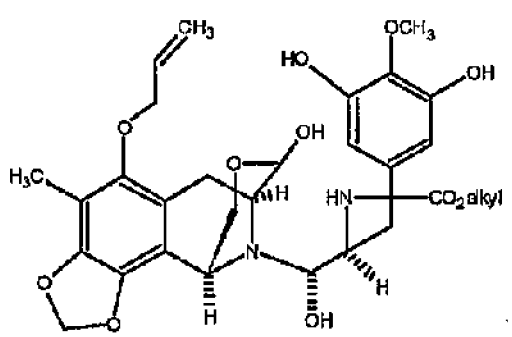 with 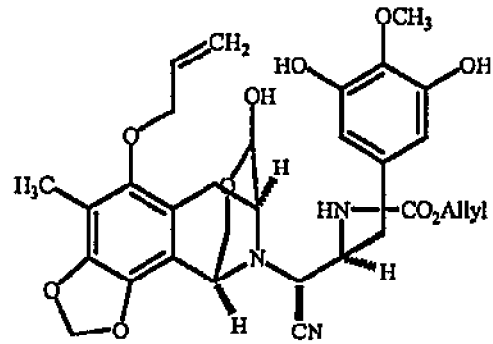

UNITED STATES PATENT AND TRADEMARK OFFICE
CERTIFICATE OF CORRECTION

PATENT NO.        : 5,721,362                                 Page 41 of 43
APPLICATION NO.   : 08/715541
DATED             : February 24, 1998
INVENTOR(S)       : Elias Corey and David Gin It is certified that error appears in the above-identified patent and that said Letters Patent is hereby corrected as shown below:

In column 103, claim 19, lines 45-57, kindly replace

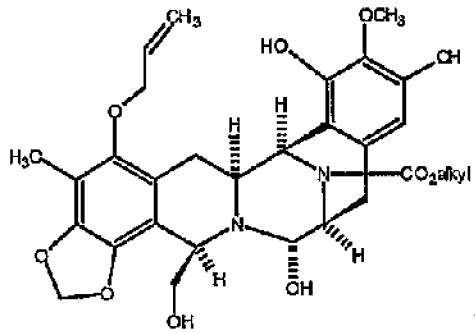

with

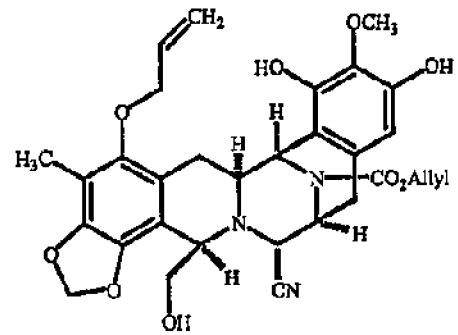

In column 104, claim 20, lines 2-14, kindly replace

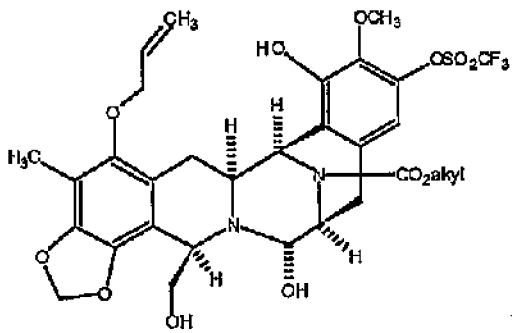

with

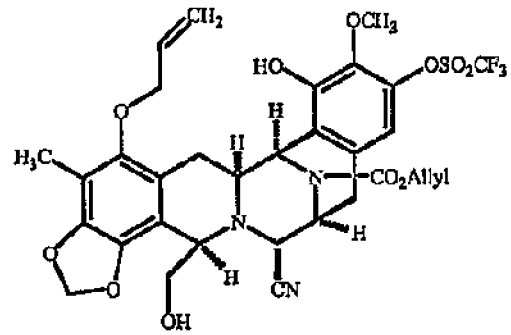

In column 104, claim 21, lines 17-28, kindly replace

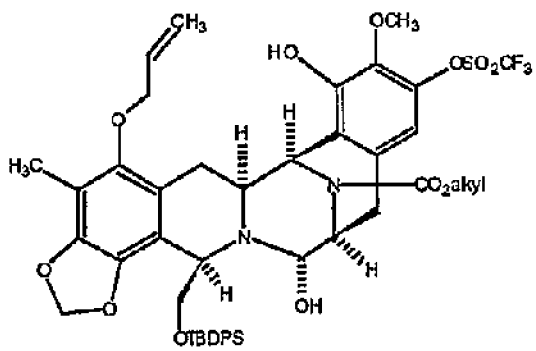

with

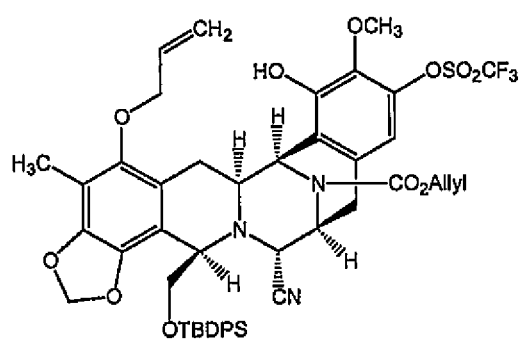

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 104, claim 22, lines 31-43, kindly replace

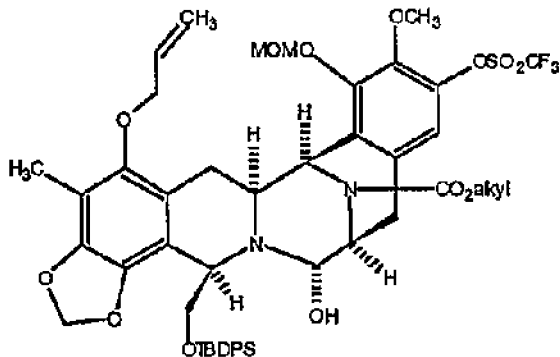 with 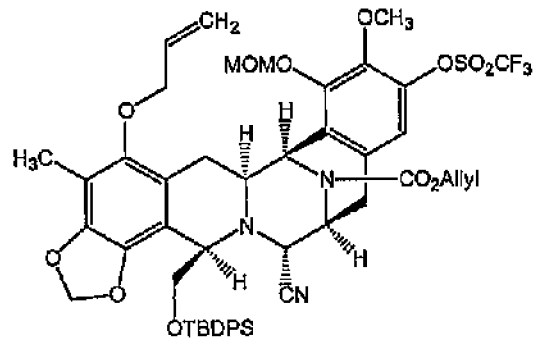

In column 106, claim 28, lines 5-23, kindly replace

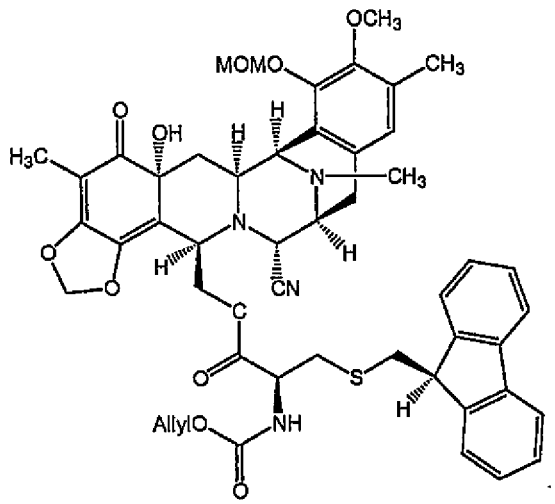 with 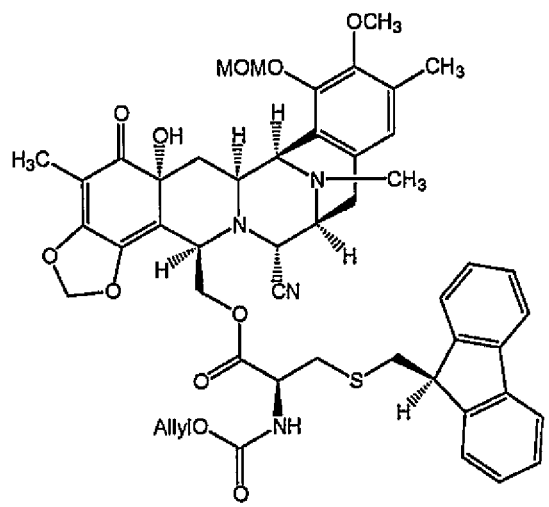

In column 106, claim 30, lines 47-60, kindly replace

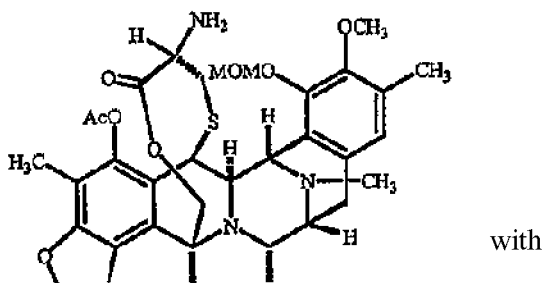 with 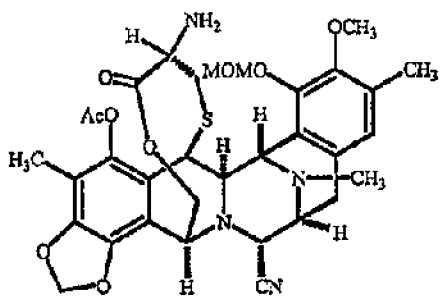

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Elias Corey and David Gin It is certified that error appears in the above-identified patent and that said Letters Patent is hereby corrected as shown below:

In column 107, claim 31, lines 2-15, kindly replace

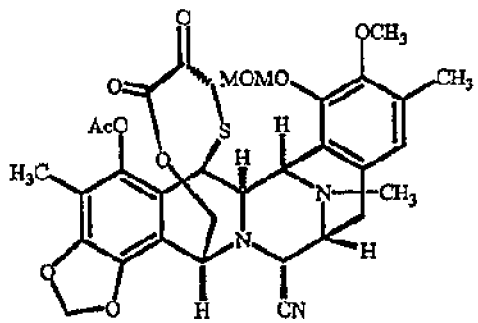 with 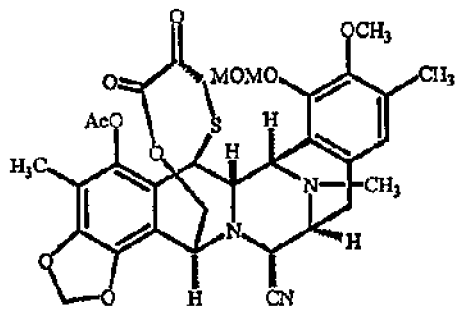

In column 107, claim 32, line 16-18, kindly replace "Formula 48" with --Formula 49--.

Signed and Sealed this

Twenty-fifth Day of September, 2007

JON W. DUDAS
*Director of the United States Patent and Trademark Office*

UNITED STATES PATENT AND TRADEMARK OFFICE
CERTIFICATE OF CORRECTION

PATENT NO. : 5,721,362
APPLICATION NO. : 08/715541
DATED : February 24, 1998
INVENTOR(S) : Corey et al.

Page 1 of 1

It is certified that error appears in the above-identified patent and that said Letters Patent is hereby corrected as shown below:

In the Specification

Column 1, under STATEMENT OF GOVERNMENT SUPPORT, Line 8-11:
Please delete "This invention was supported in part by funding from the National Institutes of Health and the National Science Foundation. Accordingly, the Government of the United States may have certain rights in this invention."
And insert --This invention was made with government support under GM034167 awarded by National Institutes of Health (NIH). The government has certain rights in this invention.--

Signed and Sealed this
Fourth Day of October, 2022

Katherine Kelly Vidal
*Director of the United States Patent and Trademark Office*